United States Patent
Hagihara et al.

(10) Patent No.: US 8,685,986 B2
(45) Date of Patent: *Apr. 1, 2014

(54) MEDICAL COMPOSITION FOR TREATMENT OR PROPHYLAXIS OF GLAUCOMA

(75) Inventors: Masahiko Hagihara, Ube (JP); Kenji Yoneda, Ube (JP); Eiji Okanari, Ube (JP); Manabu Shigetomi, Ube (JP)

(73) Assignee: Ube Industries, Ltd., Ube-Shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/260,946

(22) PCT Filed: Mar. 30, 2010

(86) PCT No.: PCT/JP2010/055719
§ 371 (c)(1),
(2), (4) Date: Dec. 22, 2011

(87) PCT Pub. No.: WO2010/113957
PCT Pub. Date: Oct. 7, 2010

(65) Prior Publication Data
US 2012/0190852 A1    Jul. 26, 2012

(30) Foreign Application Priority Data

Mar. 30, 2009  (JP) ................................. 2009-082725

(51) Int. Cl.
*C07D 401/12* (2006.01)
*A61K 31/44* (2006.01)

(52) U.S. Cl.
USPC ............ 514/256; 514/333; 544/333; 546/256

(58) Field of Classification Search
None
See application file for complete search history.

(56) References Cited

U.S. PATENT DOCUMENTS

| | | | |
|---|---|---|---|
| 6,448,290 B1 | 9/2002 | Ohuchida et al. | |
| 6,498,172 B1 | 12/2002 | Cameron et al. | |
| 7,491,748 B2 | 2/2009 | Tani et al. | |
| 2003/0216445 A1 | 11/2003 | Cameron et al. | |
| 2006/0258728 A1 | 11/2006 | Tani et al. | |
| 2007/0049625 A1 | 3/2007 | Woodward et al. | |
| 2008/0045545 A1 | 2/2008 | Prasanna et al. | |
| 2008/0114002 A1 | 5/2008 | Bonnert et al. | |
| 2010/0113388 A1 | 5/2010 | Tani et al. | |
| 2011/0054172 A1 | 3/2011 | Iwamura et al. | |

FOREIGN PATENT DOCUMENTS

| | | |
|---|---|---|
| EP | 2 264 009 A1 | 12/2010 |
| EP | 2415763 A1 | 2/2012 |
| JP | 2001-519414 A | 10/2001 |
| JP | 2005-521668 A | 7/2005 |
| JP | 2006-519250 A | 8/2006 |
| JP | 2007-515467 A | 6/2007 |
| JP | 2007-186424 A | 7/2007 |
| JP | 2008-503490 A | 2/2008 |
| JP | 2008-505874 A | 2/2008 |
| JP | 2009-502982 A | 1/2009 |
| WO | WO 98/27053 A1 | 6/1998 |
| WO | WO 98/28264 A1 | 7/1998 |
| WO | WO 99/19300 A1 | 4/1999 |
| WO | WO 02/24647 A1 | 3/2002 |
| WO | WO 03/016254 A1 | 2/2003 |
| WO | WO 03/037433 A1 | 5/2003 |
| WO | WO 03/074483 A1 | 9/2003 |
| WO | WO 2004/078169 A1 | 9/2004 |
| WO | WO 2005/061449 A1 | 7/2005 |
| WO | WO 2005/072743 A1 | 8/2005 |
| WO | WO 2006/005909 A1 | 1/2006 |
| WO | WO 2006/009876 A2 | 1/2006 |
| WO | WO 2007/014462 A1 | 2/2007 |
| WO | WO 2007/017687 A2 | 2/2007 |
| WO | WO 2007/027468 A1 | 3/2007 |
| WO | WO 2008/015517 A2 | 2/2008 |
| WO | WO 2009/113600 A1 | 9/2009 |
| WO | WO 2010/113957 A1 | 10/2010 |

OTHER PUBLICATIONS

Supplementary European Search Report for corresponding European Patent Application No. 10758728.9, dated Jul. 17, 2012.
Non-Final Office Action for related U.S. Appl. No. 12/922,028, dated Jan. 25, 2013.
International Search Report, dated Apr. 28, 2009 for International Application No. PCT/JP2009/054713.
Supplementary European Search Report dated Jun. 22, 2012 for European Patent Application No. 09721163.
Biswas et al., "Prostaglandin E2 receptor subtypes, EP1, EP2, EP3 and EP4 in human and mouse ocular tissues—a comparative immunohistochemical study", Prostaglandins, Leukotrienes and Essential Fatty Acids, vol. 71, 2004, pp. 277-288.
Bito et al., "Long-term Maintenance of Reduced Intraocular Pressure by Daily or Twice Daily Topical Application of Prostaglandins to Cat or Rhesus Monkey Eyes", Investigative Ophthalmology & Visual Science, vol. 24, No. 3, Mar. 1983, pp. 312-319.
Holmes et al., "PTP1B inhibitors: Synthesis and evaluation of difluoro-methylenephosphonate bioisosteres on a sulfonamide scaffold", Bioorganic & Medicinal Chemistry Letters, vol. 18, 2008, pp. 2719-2724.

(Continued)

*Primary Examiner* — Zinna Northington Davis
(74) *Attorney, Agent, or Firm* — Birch, Stewart, Kolasch & Birch, LLP

(57) ABSTRACT

The present invention is to provide a medical composition for the treatment or prophylaxis of glaucoma which comprises a pyridylaminoacetic acid compound represented by the formula (1):

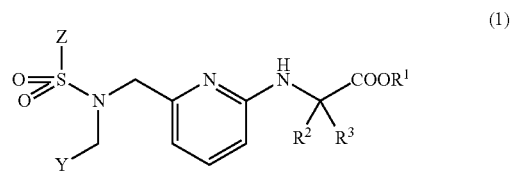

(1)

wherein $R^1$, $R^2$, $R^3$, Y, and Z are defined in the specification.

18 Claims, No Drawings

(56) References Cited

OTHER PUBLICATIONS

International Search Report dated Jun. 8, 2010 for International Application No. PCT/JP2010/055719.

Schlotzer-Schrehardt et al., "Expression and Localization of FP and EP Prostanoid Receptor Subtypes in Human Ocular Tissues", Investigative Ophthalmology & Visual Science, vol. 43, No. 5, May 2002, pp. 1475-1487.

Cameron et al., "Discovery of CP-533536: An EP2 receptor selective prostaglandin E2 (PGE2) agonist that induces local bone formation", Bioorganic & Medicinal Chemistry Letters, vol. 19, 2009 (available online Jan. 23, 2009), pp. 2075-2078.

Carey, "Organic Chemistry," 6th Edition, Chapter 1, 2006, pp. 9-10 (9 pages total).

Cornelison, "Human papillomavirus genotype 16 vaccines for cervical cancer prophylaxis and treatment," Current Opinion in Oncology, vol. 12, 2000, pp. 466-473.

Dermer, "Another Anniversary for the War on Cancer," Bio/Technology, vol. 12, Mar. 1994, p. 320.

Extended European Search Report dated Dec. 18, 2012 for European Patent Application No. 10815458.4.

Extended European Search Report dated Jan. 17, 2013 for European Patent Application No. 10815462.6.

Extended European Search Report dated Jun. 18, 2013 for European Application No. 10839533.6.

Freshney, "Culture of Animal Cells: A Manual of Basic Technique and Specialized Applications," Fifth Edition, 2005, pp. 7-9.

Gauvreau et al., "Protective Effects of Inhaled PGE2 on Allergen-induced Airway Responses and Airway Inflammation", American Journal of Respiratory and Critical Care Medicine, vol. 159, 1999, pp. 31-36.

International Preliminary Report on Patentability, and Translation of Written Opinion of the International Searching Authority, dated Apr. 19, 2012, for International Application No. PCT/JP2010/065649 (Forms PCT/IB/338, PCT/IB/373 and PCT/ISA/237).

International Preliminary Report on Patentability, and Translation of Written Opinion of the International Searching Authority, dated Apr. 19, 2012, for International Application No. PCT/JP2010/065654 (Forms PCT/IB/338, PCT/IB/373 and PCT/ISA/237).

International Preliminary Report on Patentability, and Translation of Written Opinion of the International Searching Authority, dated Aug. 23, 2012, for International Application No. PCT/JP2010/073274 (Forms PCT/IB/338, PCT/IB/373 and PCT/ISA/237).

International Search Report dated Mar. 15, 2011 for International Application No. PCT/JP2010/073274.

International Search Report dated Oct. 26, 2010 for International Application No. PCT/JP2010/065649.

International Search Report dated Oct. 5, 2010 for International Application No. PCT/JP2010/065654.

Linden et al., "Prostaglandin Analogues in the Treatment of Glaucoma," Drugs and Aging, May 1999, vol. 14, No. 5, pp. 387-398, XP009014535.

Paralkar et al., "An EP2 receptor-selective prostaglandin E2 agonist induces bone healing", PNAS, vol. 100, No, 11, May 27, 2003, pp. 6736-6740.

Tilley et al., "Receptors and pathways mediating the effects of prostaglandin E2 on airway tone", American Journal of Physiology—Lung Cellular and Molecular Physiology, vol. 284, 2003, L599-L606.

Tsuji et al., "A systemically administered EP2 receptor agonist stimulates pulmonary angiogenesis in a murine model of emphysema," Prostaglandins & Other Lipid Mediators, vol. 90, 2009 (available online Sep. 16, 2009), pp. 85-88.

U.S. Final Rejection dated Jul. 24, 2013 for U.S. Appl. No. 12/922,028.

U.S. Office Action dated Mar. 14, 2013 for U.S. Appl. No. 13/518,824.

U.S. Office Action dated May 13, 2013 for U.S. Appl. No. 13/395,303.

U.S. Office Action dated May 28, 2013 for U.S. Appl. No. 13/395,370.

MEDICAL COMPOSITION FOR TREATMENT OR PROPHYLAXIS OF GLAUCOMA

CROSS REFERENCE TO RELATED APPLICATIONS

This application is a National Phase application of PCT/JP2010/055719 filed on Mar. 30, 2010, which claims the benefit under 35 U.S.C. §119(a) to Patent Application No. 2009-082725 filed in Japan, on Mar. 30, 2009. The entire contents of all of the above applications are hereby incorporated by reference.

TECHNICAL FIELD

The present invention relates to a medical composition containing a pyridylaminoacetic acid compound or a pharmaceutically acceptable salt thereof as an effective ingredient, which is expected to have an excellent ocular hypotensive effect due to high EP2 receptor selectivity and potent EP2 agonistic action, and useful as a medicine for the treatment and/or prophylaxis of glaucoma.

BACKGROUND ART

Glaucoma is an eye disease which is an eye function disorder characterized in that aqueous humor is accumulated due to circulatory disorder of aqueous humor, an intraocular pressure is continuously increased, optic nerve is pressed, whereby it causes temporal or permanent visual field defect or low vision. The pathogenesis is said to be increase in the intraocular pressure, but there have been also known low intraocular pressure glaucoma which causes optic nerve disorder even when the intraocular pressure is in a normal value, and ocular hypertension which causes no optic nerve disorder even when the intraocular pressure is high. It is effective to lower the intraocular pressure for the treatment of the above-mentioned glaucoma and ocular hypertension. For the treatment of glaucoma and ocular hypertension, there may be mentioned, for example, drug therapy, laser therapy and surgical repair, and in the drug therapy, ophthalmic solutions which are local administration to avoid side reaction are currently the main stream.

In therapeutic agents for glaucoma or ocular hypertension presently used for clinical purposes, there are symphathetic drugs ($\alpha_2$ agonist, non-selective adrenergic drug, etc.), parasymphathetic drugs, sympathetic inhibitors ($\alpha_1$ blocker, $\beta$ blocker, $\alpha_1\beta$ blocker, etc.), carbonic anhydrase inhibitors, hyperosmotic agent, etc. However, in recent years, prostaglandin-like (hereinafter abbreviated to as "PG") drugs which have potent ocular hypotensive effects and have less side effect are leapsed into the firstly selecting drugs. A function and mechanism of the drugs for reducing the intraocular pressure are to restrain formation of aqueous humor and to promote drainage of aqueous humor. In the pathway of the aqueous humor, there are a trabecular meshwork pathway and an uveoscleral pathway and a FP agonist which is a PG series drug has been reported to promote drainage of the aqueous humor through the uveoscleral pathway.

The FP agonist presently used in clinical therapy is $PGF_{2\alpha}$ derivatives (Latanoprost and Isopropyl unoprostone), which is less causing allergy, and causes substantially no systemic side effect, but as a main side effect, there have been reported that it strengthens chromatosis in the iris, particularly in the iris with pale brown color, etc., and worsening in uveites, etc.

Also, as the other PG receptor agonists, it has been considered that $PGF_{1\alpha}$ and $PGE_2$ derivatives are promising.

In the researches in recent years, it has been known that there exist subtypes in the $PGE_2$ receptor each having different roles. The subtypes known at present are roughly classified into 4 types, and they are classified into EP1, EP2, EP3 and EP4, respectively. In the eye tissue of human, these 4 subtypes are expressed together (see Non-Patent Literatures 1 and 2), but each role has not yet been clarified. However, it has been clarified that the EP2 agonist has ocular hypotensive effects (see Non-Patent Literature 3), and at least a part of the ocular hypotensive effects of $PGE_2$ is considered to be through EP2. The EP2 agonist has functions not only to promote drainage of the aqueous humor through the uveoscleral pathway, but also to promote drainage of the aqueous humor through the trabecular meshwork pathway. Moreover, the EP2 agonist does not act on melanocytes, so that the above-mentioned side effect appeared in the FP agonist can be avoided. Accordingly, it has been desired to develop an agonist which has high selectivity to the EP2 receptor in the points of medical effects and safety.

Heretofore, a number of derivatives having the $PGE_2$ skeleton have been disclosed, and it has been known that they are effective for the treatment of various diseases (for example, asthma, bone diseases, immune diseases, etc.) (see Patent Literatures 1 to 3). Also, some EP2 agonists having no $PGE_2$-like skeleton have been disclosed (see Patent Literatures 4 to 8), and it has been reported to shown ocular hypotensive effects (see Patent Literatures 7 and 9). However, it has never been disclosed that the sulfoneamide compounds having a specific structure of the present invention are useful for glaucoma due to ocular hypotensive effects based on the excellent EP2 receptor selectivity and potent EP2 agonistic action.

[Non-Patent Literature 1] Prostaglandins, Leukotrienes and Essential Fatty Acids, 71, 277 (2004)
[Non-Patent Literature 2] Invest. Ophthalmol. Vis. Sci., 43, 1475 (2002)
[Non-Patent Literature 3] Invest. Ophthalmol. Vis. Sci., 24, 312 (1983)
[Patent Literature 1] WO 03/37433
[Patent Literature 2] WO 02/24647
[Patent Literature 3] WO 03/74483
[Patent Literature 4] WO 98/28264
[Patent Literature 5] WO 99/19300
[Patent Literature 6] WO 2004/078169
[Patent Literature 7] WO 2008/015517
[Patent Literature 8] WO 2007/017687
[Patent Literature 9] WO 2007/027468

DISCLOSURE OF THE INVENTION

Problems to be Solved by the Invention

The present inventors have researched for the purpose of providing a medical composition containing a specific sulfoneamide compound which is useful for treatment and/or prophylaxis of glaucoma with less side reaction, whereby they have accomplished the present invention. That is, the present invention is to provide a medical composition containing a novel pyridylaminoacetic acid compound or a pharmaceutically acceptable salt thereof having an ocular hypotensive effect due to high EP2 receptor selectivity and potent EP2 agonistic action.

Means to Solve the Problems

The present inventors have earnestly investigated on a sulfoneamide compound, and as a result, they have found that a group of sulfoneamide compounds having pyridylaminoacetic acid as a partial structure thereof has an ocular hypotensive effect due to high EP2 receptor selectivity and potent EP2 agonistic action, whereby they have accomplished the present invention.

The present invention relates to (1) a medical composition for the treatment or prophylaxis of glaucoma which comprises a compound represented by the following formula (1)

[Formula 1]

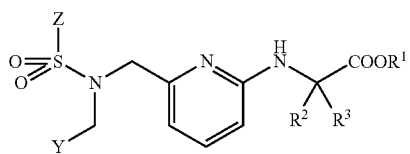

(1)

wherein $R^1$, $R^2$ and $R^3$ each independently represent a hydrogen atom or $C_1$-$C_6$ alkyl group, Y represents a bicyclic heteroaromatic ring group which may be substituted by a group(s) selected from the group consisting of a halogen atom, $C_1$-$C_6$ alkyl group, halogeno $C_1$-$C_6$ alkyl group, $C_1$-$C_6$ alkoxyl group, halogeno $C_1$-$C_6$ alkoxyl group and $C_1$-$C_6$ alkylthio group, or a group -$Q^1$-$Q^2$ wherein $Q^1$ represents an arylene group or 5- to 6-membered heteroarylene group, $Q^2$ represents an aromatic group or 5- to 6-membered ring heterocyclic group each of which may be substituted by a group(s) selected from the group consisting of a halogen atom, hydroxyl group, $C_1$-$C_6$ alkyl group, halogeno $C_1$-$C_6$ alkyl group, $C_1$-$C_6$ alkoxyl group and halogeno $C_1$-$C_6$ alkoxyl group, Z represents an aromatic group or a 5- to 6-membered heteroaromatic ring group each of which may be substituted by a group(s) selected from the group consisting of a halogen atom, $C_1$-$C_6$ alkyl group, halogeno $C_1$-$C_6$ alkyl group, $C_1$-$C_6$ alkoxyl group and halogeno $C_1$-$C_6$ alkoxyl group, or a pharmaceutically acceptable salt thereof as an effective ingredient, (2) the medical composition described in the above-mentioned (1), wherein $R^2$ and $R^3$ each independently represent a hydrogen atom or $C_1$-$C_4$ alkyl group, (3) the medical composition described in the above-mentioned (1) or (2), wherein Y represents a bicyclic heteroaromatic ring group which may be substituted by a group(s) selected from the group consisting of a halogen atom, $C_1$-$C_4$ alkyl group, halogeno $C_1$-$C_4$ alkyl group, $C_1$-$C_4$ alkoxyl group, halogeno $C_1$-$C_4$ alkoxyl group and $C_1$-$C_4$ alkylthio group, or a group -$Q^1$-$Q^2$ wherein $Q^1$ represents an arylene group or 5- to 6-membered heteroarylene group, $Q^2$ represents an aromatic group or a 5- to 6-membered ring heterocyclic group each of which may be substituted by a group(s) selected from the group consisting of a halogen atom, hydroxyl group, $C_1$-$C_4$ alkyl group, halogeno $C_1$-$C_4$ alkyl group, $C_1$-$C_4$ alkoxyl group and halogen $C_1$-$C_4$ alkoxyl group, (4) the medical composition described in any of the above-mentioned (1) to (3), wherein Z represents an aromatic group or a completely unsaturated 5- to 6-membered heteroaromatic ring group each of which may be substituted by a group(s) selected from the group consisting of a halogen atom, $C_1$-$C_4$ alkyl group, halogeno $C_1$-$C_4$ alkyl group, $C_1$-$C_4$ alkoxyl group and halogeno $C_1$-$C_4$ alkoxyl group, (5) the medical composition described in any of the above-mentioned (1) to (4), wherein Y represents a benzofuryl group, benzothienyl group, benzoxazolyl group or benzothiazolyl group each of which may be substituted by a group(s) selected from the group consisting of a halogen atom, $C_1$-$C_4$ alkyl group, halogeno $C_1$-$C_4$ alkyl group, $C_1$-$C_4$ alkoxyl group, halogeno $C_1$-$C_4$ alkoxyl group and $C_1$-$C_4$ alkylthio group, or a group -$Q^1$-$Q^2$ wherein $Q^1$ represents a phenylene group, thienylene group, pyridazinylene group or pyrimidinylene group, $Q^2$ represents a phenyl group, thienyl group, pyrazolyl group, oxazolyl group, thiazolyl group, 1,2,4-triazolyl group, pyridyl group, pyridazinyl group, pyrimidinyl group, 4,5-dihydrothiazolyl group, pyrrolidinyl group or piperidinyl group each of which may be substituted by a group(s) selected from the group consisting of a halogen atom, hydroxyl group, $C_1$-$C_4$ alkyl group, halogeno $C_1$-$C_4$ alkyl group, $C_1$-$C_4$ alkoxyl group and halogeno $C_1$-$C_4$ alkoxyl group, (6) the medical composition described in the above-mentioned (5), wherein Y represents a benzofuryl group, benzothienyl group, benzoxazolyl group or benzothiazolyl group each of which may be substituted by a group(s) selected from the group consisting of a fluorine atom, chlorine atom, bromine atom, methyl group, ethyl group, propyl group, isopropyl group, tert-butyl group, trifluoromethyl group, difluoromethyl group, trichloromethyl group, dichloromethyl group, 2,2,2-trifluoroethyl group, 2,2,2-trichloroethyl group, methoxy group, ethoxy group, propoxy group, isopropoxy group, tert-butoxy group, trifluoromethoxy group, difluoromethoxy group, trichloromethoxy group, dichloromethoxy group, methylthio group, ethylthio group, propylthio group, isopropylthio group and tert-butylthio group, (7) the medical composition described in the above-mentioned (5), wherein Y represents a group -$Q^1$-$Q^2$ wherein $Q^1$ represents a phenylene group, thienylene group, pyridazinylene group or pyrimidinylene group, $Q^2$ represents a phenyl group, thienyl group, pyrazolyl group, oxazolyl group, thiazolyl group, 1,2,4-triazolyl group, pyridyl group, pyridazinyl group, pyrimidinyl group, 4,5-dihydrothiazolyl group, pyrrolidinyl group or piperidinyl group each of which may be substituted by a group(s) selected from the group consisting of a fluorine atom, chlorine atom, bromine atom, hydroxyl group, methyl group, ethyl group, propyl group, isopropyl group, tert-butyl group, trifluoromethyl group, difluoromethyl group, trichloromethyl group, dichloromethyl group, 2,2,2-trifluoroethyl group, 2,2,2-trichloroethyl group, methoxy group, ethoxy group, propoxy group, isopropoxy group, tert-butoxy group, trifluoromethoxy group, difluoromethoxy group, trichloromethoxy group and dichloromethoxy group, (8) the medical composition described in any of the above-mentioned (1) to (7), wherein Z represents a phenyl group, thienyl group, imidazolyl group, thiazolyl group, pyridyl group or pyrimidinyl group each of which may be substituted by a group(s) selected from the group consisting of a halogen atom, $C_1$-$C_4$ alkyl group, halogeno $C_1$-$C_4$ alkyl group, $C_1$-$C_4$ alkoxyl group and halogeno $C_1$-$C_4$ alkoxyl group, (9) the medical composition described in the above-mentioned (8), wherein Z represents a phenyl group, thienyl group, imidazolyl group, thiazolyl group, pyridyl group or pyrimidinyl group each of which may be substituted by a group(s) selected from the group consisting of a fluorine atom, chlorine atom, bromine atom, methyl group, ethyl group, propyl group, isopropyl group, tert-butyl group, trifluoromethyl group, difluoromethyl group, trichloromethyl group, dichloromethyl group, 2,2,2-trifluoroethyl group, 2,2,2-trichloroethyl group, methoxy group, ethoxy group, propoxy group, isopropoxy group, tert-butoxy group, trifluoromethoxy group, difluoromethoxy group, trichloromethoxy group and dichloromethoxy group,

(10) the medical composition described in any of the above-mentioned (1) to (9), wherein $R^2$ and $R^3$ each independently represent a hydrogen atom or methyl group,

(11) the medical composition described in any of the above-mentioned (1) to (5), (8) to (10), wherein Y represents a benzofuryl group or benzothienyl group each of which may be substituted by a group(s) selected from the group consisting of a halogen atom and $C_1$-$C_4$ alkoxyl group,

(12) the medical composition described in any of the above-mentioned (1) to (5), (8) to (10), wherein Y represents a group -$Q^1$-$Q^2$ wherein $Q^1$ represents a phenylene group or pyridazinylene group, $Q^2$ represents a phenyl group, pyrazolyl group, thiazolyl group, 1,2,4-triazolyl group, pyridyl group, pyridazinyl group, pyrimidinyl group or 4,5-dihydrothiazolyl group each of which may be substituted by a group(s) selected from the group consisting of a halogen atom, $C_1$-$C_4$ alkyl group and halogen $C_1$-$C_4$ alkyl group,

(13) the medical composition described in any of the above-mentioned (1) to (8), (10) to (12), wherein Z represents a phenyl group or pyridyl group each of which may be substituted by a group(s) selected from the group consisting of a halogen atom and $C_1$-$C_4$ alkoxyl group,

(14) the medical composition described in the above-mentioned (1), wherein $R^1$ represents a hydrogen atom, methyl group, ethyl group, propyl group, isopropyl group, butyl group, isobutyl group, sec-butyl group, tert-butyl group, pentyl group or hexyl group, $R^2$ and $R^3$ each independently represent a hydrogen atom or methyl group, Y represents a benzofuran-2-yl group, 6-fluorobenzofuran-2-yl group, 6-chlorobenzofuran-2-yl group, 6-methoxybenzofuran-2-yl group, benzo[b]thiophen-2-yl group, 6-fluorobenzo[b]thiophen-2-yl group, 5,6-difluorobenzo[b]thiophen-2-yl group, 6-chlorobenzo[b]thiophen-2-yl group, 6-chloro-5-fluorobenzo[b]thiophen-2-yl group, 6-methylbenzo[b]thiophen-2-yl group, 5-fluoro-6-methylbenzo[b]thiophen-2-yl group, 6-ethylbenzo[b]thiophen-2-yl group, 6-ethyl-5-fluorobenzo[b]thiophen-2-yl group, 6-trifluoromethylbenzo[b]thiophen-2-yl group, 5-fluoro-6-trifluoromethylbenzo[b]thiophen-2-yl group, 6-methoxybenzo[b]thiophen-2-yl group, 5-fluoro-6-methoxybenzo[b]thiophen-2-yl group, 6-difluoromethoxybenzo[b]thiophen-2-yl group, 6-difluoromethoxy-5-fluorobenzo[b]thiophen-2-yl group, 6-methylthiobenzo[b]thiophen-2-yl group, 5-fluoro-6-methylthiobenzo[b]thiophen-2-yl group, biphenyl-4-yl group, 2'-fluorobiphenyl-4-yl group, 3'-fluorobiphenyl-4-yl group, 4'-fluorobiphenyl-4-yl group, 2',4'-difluorobiphenyl-4-yl group, 3',4'-difluorobiphenyl-4-yl group, 2'-chlorobiphenyl-4-yl group, 3'-chlorobiphenyl-4-yl group, 4'-chlorobiphenyl-4-yl group, 4'-chloro-2'-fluorobiphenyl-4-yl group, 4'-chloro-3'-fluorobiphenyl-4-yl group, 4'-hydroxybiphenyl-4-yl group, 3'-methylbiphenyl-4-yl group, 3'-ethylbiphenyl-4-yl group, 3'-trifluoromethylbiphenyl-4-yl group, 3'-methoxybiphenyl-4-yl group, 3'-difluoromethoxybiphenyl-4-yl group, 4-(thiophen-2-yl)phenyl group, 4-(thiophen-3-yl)phenyl group, 4-(pyrazol-1-yl)phenyl group, 4-(oxazol-2-yl)phenyl group, 4-(oxazol-4-yl)phenyl group, 4-(thiazol-2-yl)phenyl group, 4-(4-fluorothiazol-2-yl)phenyl group, 4-(4-chlorothiazol-2-yl)phenyl group, 4-(5-chlorothiazol-2-yl)phenyl group, 4-(5-methylthiazol-2-yl)phenyl group, 4-(4,5-dimethylthiazol-2-yl)phenyl group, 4-(4-trifluoromethylthiazol-2-yl)phenyl group, 4-(thiazol-4-yl)phenyl group, 4-(2-fluorothiazol-4-yl)phenyl group, 4-(2-chlorothiazol-4-yl)phenyl group, 4-(thiazol-5-yl)phenyl group, 4-(1,2,4-triazol-1-yl)phenyl group, 4-(pyridin-2-yl)phenyl group, 4-(pyridazin-3-yl)phenyl group, 4-(pyridazin-4-yl)phenyl group, 4-(pyrimidin-2-yl)phenyl group, 4-(5-hydroxypyrimidin-2-yl)phenyl group, 4-(pyrimidin-4-yl)phenyl group, 4-(pyrimidin-5-yl)phenyl group, 4-(4,5-dihydrothiazol-2-yl)phenyl group, 6-phenylpyridazin-3-yl group, 6-(thiazol-2-yl)pyridazin-3-yl group or 6-(thiazol-4-yl)pyridazin-3-yl group, and Z represents a phenyl group, 2-fluorophenyl group, 3-fluorophenyl group, 4-fluorophenyl group, 3,4-difluorophenyl group, 3,5-difluorophenyl group, 3,4,5-trifluorophenyl group, 2-chlorophenyl group, 3-chlorophenyl group, 4-chlorophenyl group, 2,6-dichlorophenyl group, 4-chloro-3-fluorophenyl group, 4-chloro-3,5-difluorophenyl group, 4-bromophenyl group, 4-methylphenyl group, 3-fluoro-4-methylphenyl group, 4-ethylphenyl group, 4-ethyl-3-fluorophenyl group, 4-propylphenyl group, 4-isopropylphenyl group, 4-tert-butylphenyl group, 4-trifluoromethylphenyl group, 3-fluoro-4-trifluoromethylphenyl group, 4-difluoromethylphenyl group, 4-trichloromethylphenyl group, 4-dichloromethylphenyl group, 4-(2,2,2-trifluoroethyl)phenyl group, 4-(2,2,2-trichloroethyl)phenyl group, 4-methoxyphenyl group, 3-fluoro-4-methoxyphenyl group, 4-ethoxyphenyl group, 4-propoxyphenyl group, 4-isopropoxyphenyl group, 4-tert-butoxyphenyl group, 4-trifluoromethoxyphenyl group, 4-difluoromethoxyphenyl group, 4-difluoromethoxy-3-fluorophenyl group, 4-trichloromethoxyphenyl group, 4-dichloromethoxyphenyl group, thiophen-2-yl group, thiophen-3-yl group, 5-chlorothiophen-2-yl group, 1-methyl-1H-imidazol-4-yl group, thiazol-2-yl group, pyridine-2-yl group, 5-fluoropyridin-2-yl group, 5-chloropyridin-2-yl group, 5-methylpyridin-2-yl group, 5-ethylpyridin-2-yl group, 5-trifluoromethylpyridin-2-yl group, 5-methoxypyridin-2-yl group, 5-difluoromethoxypyridin-2-yl group, pyridin-3-yl group, 6-fluoropyridin-3-yl group, 6-chloropyridin-3-yl group, 6-methylpyridin-3-yl group, 6-ethylpyridin-3-yl group, 6-trifluoromethylpyridin-3-yl group, 6-methoxypyridin-3-yl group, 6-difluoromethoxypyridin-3-yl group, pyridin-4-yl group or pyrimidin-2-yl group,

(15) the medical composition described in the above-mentioned (1), wherein $R^1$ represents a hydrogen atom, methyl group, ethyl group, propyl group, isopropyl group, tert-butyl group or hexyl group, $R^2$ and $R^3$ each independently represent a hydrogen atom or methyl group, Y represents a benzofuran-2-yl group, 6-fluorobenzofuran-2-yl group, 6-chlorobenzofuran-2-yl group, 6-methoxybenzofuran-2-yl group, benzo[b]thiophen-2-yl group, 6-fluorobenzo[b]thiophen-2-yl group, 6-chlorobenzo[b]thiophen-2-yl group, 6-methoxybenzo[b]thiophen-2-yl group, biphenyl-4-yl group, 2'-fluorobiphenyl-4-yl group, 3'-fluorobiphenyl-4-yl group, 4'-fluorobiphenyl-4-yl group, 2'-chlorobiphenyl-4-yl group, 3'-chlorobiphenyl-4-yl group, 4'-chlorobiphenyl-4-yl group, 3'-methylbiphenyl-4-yl group, 3'-trifluoromethylbiphenyl-4-yl group, 4-(thiophen-2-yl)phenyl group, 4-(thiophen-3-yl)phenyl group, 4-(pyrazol-1-yl)phenyl group, 4-(oxazol-2-yl)phenyl group, 4-(oxazol-4-yl)phenyl group, 4-(thiazol-2-yl)phenyl group, 4-(4-fluorothiazol-2-yl)phenyl group, 4-(4-chlorothiazol-2-yl)phenyl group, 4-(5-chlorothiazol-2-yl)phenyl group, 4-(5-methylthiazol-2-yl)phenyl group, 4-(4,5-dimethylthiazol-2-yl)phenyl group, 4-(4-trifluoromethylthiazol-2-yl)phenyl group, 4-(thiazol-4-yl)phenyl group, 4-(2-fluorothiazol-4-yl)

phenyl group, 4-(2-chlorothiazol-4-yl)phenyl group, 4-(thiazol-5-yl)phenyl group, 4-(1,2,4-triazol-1-yl)phenyl group, 4-(pyridin-2-yl)phenyl group, 4-(pyridazin-3-yl)phenyl group, 4-(pyridazin-4-yl)phenyl group, 4-(pyrimidin-2-yl)phenyl group, 4-(pyrimidin-4-yl)phenyl group, 4-(pyrimidin-5-yl)phenyl group, 4-(4,5-dihydrothiazol-2-yl)phenyl group or 6-phenylpyridazin-3-yl group, and Z represents a phenyl group, 2-fluorophenyl group, 3-fluorophenyl group, 4-fluorophenyl group, 3,4-difluorophenyl group, 3,5-difluorophenyl group, 2-chlorophenyl group, 3-chlorophenyl group, 4-chlorophenyl group, 2,6-dichlorophenyl group, 4-chloro-3-fluorophenyl group, 4-methylphenyl group, 3-fluoro-4-methylphenyl group, 4-ethylphenyl group, 4-ethyl-3-fluorophenyl group, 4-trifluoromethylphenyl group, 3-fluoro-4-trifluoromethylphenyl group, 4-methoxyphenyl group, 3-fluoro-4-methoxyphenyl group, 4-difluoromethoxyphenyl group, 4-difluoromethoxy-3-fluorophenyl group, thiophen-2-yl group, thiophen-3-yl group, pyridin-2-yl group, 5-fluoropyridin-2-yl group, 5-chloropyridin-2-yl group, 5-methoxypyridin-2-yl group, pyridin-3-yl group, 6-fluoropyridin-3-yl group, 6-chloropyridin-3-yl group, 6-methoxypyridin-3-yl group or pyridin-4-yl group,

(16) the medical composition described in the above-mentioned (1), wherein $R^1$ represents a hydrogen atom, methyl group, ethyl group, isopropyl group or hexyl group, $R^2$ and $R^3$ both represent hydrogen atoms, Y represents a benzofuran-2-yl group, 6-fluorobenzofuran-2-yl group, 6-chlorobenzofuran-2-yl group, 6-methoxybenzofuran-2-yl group, benzo[b]thiophen-2-yl group, 6-fluorobenzo[b]thiophen-2-yl group, 6-chlorobenzo[b]thiophen-2-yl group, 6-methoxybenzo[b]thiophen-2-yl group, biphenyl-4-yl group, 2'-fluorobiphenyl-4-yl group, 3'-fluorobiphenyl-4-yl group, 4'-fluorobiphenyl-4-yl group, 2'-chlorobiphenyl-4-yl group, 3'-chlorobiphenyl-4-yl group, 4'-chlorobiphenyl-4-yl group, 3'-methylbiphenyl-4-yl group, 3'-trifluoromethylbiphenyl-4-yl group, 4-(thiophen-2-yl)phenyl group, 4-(thiophen-3-yl)phenyl group, 4-(pyrazol-1-yl)phenyl group, 4-(oxazol-2-yl)phenyl group, 4-(oxazol-4-yl)phenyl group, 4-(thiazol-2-yl)phenyl group, 4-(4-fluorothiazol-2-yl)phenyl group, 4-(4-chlorothiazol-2-yl)phenyl group, 4-(5-chlorothiazol-2-yl)phenyl group, 4-(5-methylthiazol-2-yl)phenyl group, 4-(4,5-dimethylthiazol-2-yl)phenyl group, 4-(4-trifluoromethylthiazol-2-yl)phenyl group, 4-(thiazol-4-yl)phenyl group, 4-(2-fluorothiazol-4-yl)phenyl group, 4-(2-chlorothiazol-4-yl)phenyl group, 4-(thiazol-5-yl)phenyl group, 4-(1,2,4-triazol-1-yl)phenyl group, 4-(pyridin-2-yl)phenyl group, 4-(pyridazin-3-yl)phenyl group, 4-(pyridazin-4-yl)phenyl group, 4-(pyrimidin-2-yl)phenyl group, 4-(pyrimidin-4-yl)phenyl group, 4-(pyrimidin-5-yl)phenyl group, 4-(4,5-dihydrothiazol-2-yl)phenyl group or 6-phenylpyridazin-3-yl group, and Z represents a phenyl group, 2-fluorophenyl group, 3-fluorophenyl group, 4-fluorophenyl group, 2-chlorophenyl group, 3-chlorophenyl group, 4-chlorophenyl group, 2,6-dichlorophenyl group, 4-methoxyphenyl group, pyridin-2-yl group or pyridin-3-yl group,

(17) the medical composition described in the above-mentioned (1), wherein $R^1$ represents a hydrogen atom, methyl group, ethyl group, isopropyl group or hexyl group, $R^2$ and $R^3$ both represent hydrogen atoms, Y represents a benzofuran-2-yl group, benzo[b]thiophen-2-yl group, 6-chlorobenzo-[b]thiophen-2-yl group, 6-methoxybenzo[b]thiophen-2-yl group, biphenyl-4-yl group, 4'-fluorobiphenyl-4-yl group, 4'-chlorobiphenyl-4-yl group, 4-(pyrazol-1-yl)phenyl group, 4-(thiazol-2-yl)phenyl group, 4-(5-chlorothiazol-2-yl)phenyl group, 4-(5-methylthiazol-2-yl) phenyl group, 4-(4,5-dimethylthiazol-2-yl)phenyl group, 4-(4-trifluoromethylthiazol-2-yl)phenyl group, 4-(thiazol-4-yl)phenyl group, 4-(1,2,4-triazol-1-yl)-phenyl group, 4-(pyridin-2-yl)phenyl group, 4-(pyridazin-4-yl)phenyl group, 4-(pyrimidin-2-yl)phenyl group, 4-(4,5-dihydrothiazol-2-yl) phenyl group or 6-phenylpyridazin-3-yl group, and Z represents a phenyl group, 2-fluorophenyl group, 3-fluorophenyl group, 4-fluorophenyl group, 2-chlorophenyl group, 3-chlorophenyl group, 4-chlorophenyl group, 2,6-dichlorophenyl group, 4-methoxyphenyl group, pyridin-2-yl group or pyridin-3-yl group,

(18) the medical composition described in the above-mentioned (1), wherein the pyridylaminoacetic acid compound is {6-[(benzofuran-2-ylmethyl)(pyridin-3-ylsulfonyl)aminomethyl]pyridin-2-ylamino}-acetic acid, {6-[(benzo[b]thiophen-2-ylmethyl)(pyridin-3-ylsulfonyl)aminomethyl]pyridin-2-ylamino}acetic acid, {6-[(6-chlorobenzo[b]thiophen-2-ylmethyl)(pyridin-3-ylsulfonyl)aminomethyl]pyridin-2-ylamino}acetic acid, {6-[(6-methoxybenzo[b]thiophen-2-ylmethyl)(pyridin-3-ylsulfonyl)aminomethyl]-pyridin-2-ylamino}acetic acid, {6-[biphenyl-4-ylmethyl)(pyridin-2-ylsulfonyl)aminomethyl]pyridin-2-ylamino}acetic acid, {6-[biphenyl-4-ylmethyl)(pyridin-3-ylsulfonyl)aminomethyl]pyridin-2-ylamino}acetic acid, {6-[(4'-fluorobiphenyl-4-ylmethyl)(pyridin-3-ylsulfonyl)aminomethyl]pyridin-2-ylamino}acetic acid, {6-[(4'-chlorobiphenyl-4-ylmethyl)(pyridin-3-ylsulfonyl)aminomethyl]pyridin-2-ylamino}acetic acid, (6-{(4-fluorobenzenesulfonyl)[4-(pyrazol-1-yl)benzyl]aminomethyl}pyridin-2-ylamino)acetic acid, (6-{[4-(pyrazol-1-yl)benzyl](pyridin-2-ylsulfonyl)aminomethyl}pyridin-2-ylamino)-acetic acid, (6-{[4-(pyrazol-1-yl)benzyl](pyridin-3-ylsulfonyl)aminomethyl}pyridin-2-ylamino)-acetic acid, isopropyl(6-{(pyridin-2-ylsulfonyl)[4-(thiazol-2-yl)benzyl]aminomethyl}pyridin-2-ylamino)acetate, ethyl(6-{(pyridin-2-ylsulfonyl)[4-(thiazol-2-yl)benzyl]aminomethyl}pyridin-2-ylamino)acetate, (6-{(4-fluorobenzenesulfonyl)[4-(thiazol-2-yl)benzyl]aminomethyl}pyridin-2-ylamino)acetic acid, (6-{(pyridin-2-ylsulfonyl)[4-(thiazol-2-yl)benzyl]aminomethyl}pyridin-2-ylamino)-acetic acid, (6-{(pyridin-3-ylsulfonyl)[4-(thiazol-2-yl)benzyl]aminomethyl}pyridin-2-ylamino)-acetic acid, (6-{(pyridin-2-ylsulfonyl)[4-(4-trifluoromethylthiazol-2-yl)benzyl]aminomethyl}-pyridin-2-ylamino)acetic acid, (6-{(pyridin-2-ylsulfonyl)[4-(thiazol-4-yl)benzyl]aminomethyl}pyridin-2-ylamino)-acetic acid, (6-{[4-(pyridin-2-yl)benzyl](pyridin-3-ylsulfonyl)aminomethyl}pyridin-2-ylamino)-acetic acid, (6-{[4-(pyridazin-4-yl)benzyl](pyridin-3-ylsulfonyl)aminomethyl}pyridin-2-ylamino)-acetic acid, (6-{(pyridin-2-ylsulfonyl)[4-(pyrimidin-2-yl)benzyl]aminomethyl}pyridin-2-ylamino)-acetic acid, (6-{[4-(4,5-dihydrothiazol-2-yl)benzyl](4-fluorobenzenesulfonyl)aminomethyl}pyridin-2-ylamino)acetic acid, {6-[(6-phenylpyridazin-3-ylmethyl)(pyridin-3-ylsulfonyl)aminomethyl]pyridin-2-ylamino}acetic acid, hexyl(6-{(pyridin-2-ylsulfonyl)[4-(thiazol-2-yl)benzyl]aminomethyl}pyridin-2-ylamino)acetate, (6-{[4-(5-chlorothiazol-2-yl)benzyl](pyridin-2-ylsulfonyl)aminomethyl}pyridin-2-ylamino)acetic acid, (6-{[4-(5-methylthiazol-2-yl)benzyl](pyridin-2-ylsulfonyl)aminomethyl}pyridin-2-ylamino)acetic acid, (6-{[4-(4,5-dimethylthiazol-2-yl)benzyl](pyridin-2-ylsulfonyl)aminomethyl}pyridin-2-ylamino)acetic acid, (6-{(pyridin-3-ylsulfonyl)[4-(1,2,4-triazol-1-yl)benzyl]
aminomethyl}pyridin-2-ylamino)acetic acid,
(6-{[4-(pyrazol-1-yl)benzyl](pyridin-3-ylsulfonyl)
aminomethyl}pyridin-2-ylamino)-ethyl acetate or
(6-{[4-(pyrazol-1-yl)benzyl](pyridin-3-ylsulfonyl)
aminomethyl}pyridin-2-ylamino)-isopropyl acetate.

Effects of the Invention

The pyridylaminoacetic acid compound represented by the formula (1) or a pharmaceutically acceptable salt thereof which is an effective ingredient of a medical composition of the present invention has ocular hypotensive effect by high EP2 receptor selectivity and potent EP2 agonistic action, and also has excellent properties in terms of tissue distribution, fast-acting pharmacological effect, sustained pharmacological effect, toxicity, etc., so that it is effective for glaucoma. Accordingly, a medical composition containing the pyridylaminoacetic acid compound represented by the formula (1) or a pharmaceutically acceptable salt thereof according to the present invention as an effective ingredient is also useful as a medicine for the treatment and/or prophylaxis of glaucoma.

BEST MODE TO CARRY OUT THE INVENTION

In the compound represented by the above-mentioned formula (I), the "$C_1$-$C_6$ alkyl group" represented by $R^1$ means, for example, a linear or branched $C_1$-$C_6$ alkyl group such as a methyl group, ethyl group, propyl group, isopropyl group, butyl group, isobutyl group, sec-butyl group, tert-butyl group, pentyl group, isopentyl group, neopentyl group, tert-pentyl group, 1-methylbutyl group, 2-methylbutyl group, 1-ethylpropyl group, 1,2-dimethylpropyl group, hexyl group, 1-methylpentyl group, 2-methylpentyl group, 3-methylpentyl group, 4-methylpentyl group, 1-ethylbutyl group, 2-ethylbutyl group, 1,1-dimethylbutyl group, 1,2-dimethylbutyl group, 1,3-dimethylbutyl group, 2,2-dimethylbutyl group, 2,3-dimethylbutyl group, 3,3-dimethylbutyl group, 1-ethyl-1-methylpropyl group, 1-ethyl-2-methylpropyl group, 1,1,2-trimethylpropyl group or 1,2,2-trimethylpropyl group, etc. It is preferably a methyl group, ethyl group, propyl group, isopropyl group, butyl group, isobutyl group, sec-butyl group, tert-butyl group, pentyl group or hexyl group, more preferably a methyl group, ethyl group, propyl group, isopropyl group, tert-butyl group or hexyl group, particularly preferably a methyl group, ethyl group, isopropyl group or hexyl group.

As $R^1$, it is preferably a hydrogen atom, methyl group, ethyl group, propyl group, isopropyl group, butyl group, isobutyl group, sec-butyl group, tert-butyl group, pentyl group or hexyl group, more preferably a hydrogen atom, methyl group, ethyl group, propyl group, isopropyl group, tert-butyl group or hexyl group, particularly preferably a hydrogen atom, methyl group, ethyl group, isopropyl group or hexyl group.

In the compound represented by the above-mentioned formula (I), as the "$C_1$-$C_6$ alkyl group" of $R^2$; "$C_1$-$C_6$ alkyl group" of $R^3$; "$C_1$-$C_6$ alkyl group" as a substituent of the bicyclic heteroaromatic ring group, "$C_1$-$C_6$ alkyl group portion" of the halogeno $C_1$-$C_6$ alkyl group, "$C_1$-$C_6$ alkyl group portion" of the $C_1$-$C_6$ alkylthio group of Y; in the group $-Q^1$-$Q^2$ of Y, "$C_1$-$C_6$ alkyl group" as a substituent for the aromatic group or 5- to 6-membered ring heterocyclic group of $Q^2$, "$C_1$-$C_6$ alkyl group portion" of the halogeno $C_1$-$C_6$ alkyl group; "$C_1$-$C_6$ alkyl group" as a substituent for the aromatic group or 5- to 6-membered ring heteroaromatic ring group of Z, and "$C_1$-$C_6$ alkyl group portion" of the halogeno $C_1$-$C_6$ alkyl group each has the same meaning and examples as the "$C_1$-$C_6$ alkyl group" of the above-mentioned $R^1$. It is preferably a $C_1$-$C_4$ alkyl group, more preferably a methyl group, ethyl group, propyl group, isopropyl group or tert-butyl group, particularly preferably a methyl group or ethyl group.

$R^2$ is preferably a hydrogen atom, methyl group, ethyl group, propyl group or isopropyl group, more preferably a hydrogen atom or methyl group, and particularly preferably a hydrogen atom.

$R^3$ is preferably a hydrogen atom, methyl group, ethyl group, propyl group or isopropyl group, more preferably a hydrogen atom or methyl group, and particularly preferably a hydrogen atom.

In the compound represented by the above-mentioned formula (I), "the halogen atom" means a fluorine atom, chlorine atom, bromine atom or iodine atom, preferably a fluorine atom, chlorine atom or bromine atom, particularly preferably a fluorine atom or chlorine atom. Each of the "halogen atom" as a substituent for the bicyclic heteroaromatic ring group, the "halogeno portion" of the halogeno $C_1$-$C_6$ alkyl group and the "halogen portion" of the halogeno $C_1$-$C_6$ alkoxyl group shown by Y; the "halogen atom" as a substituent for the aromatic group or 5- to 6-membered ring heterocyclic group, the "halogen portion" of the halogeno $C_1$-$C_6$ alkyl group and the "halogeno portion" of the halogeno $C_1$-$C_6$ alkoxyl group shown by $Q^2$ in the group $-Q^1$-$Q^2$ of Y; and the "halogen atom" as a substituent for the aromatic group or 5- to 6-membered heteroaromatic ring group, the "halogeno portion" of the halogeno $C_1$-$C_6$ alkyl group and the "halogeno portion" of the halogeno $C_1$-$C_6$ alkoxyl group shown by Z has the same meanings and examples as those of the above-mentioned "halogen atom".

In the compound represented by the above-mentioned formula (I), the "halogeno $C_1$-$C_6$ alkyl group" means the above-mentioned "$C_1$-$C_6$ alkyl group" substituted by at least one of the same or different above-mentioned "halogen atom". Each of the "halogeno $C_1$-$C_6$ alkyl group" as a substituent for the bicyclic heteroaromatic ring group; the halogen $C_1$-$C_6$ alkyl group" as a substituent for the aromatic group or 5- to 6-membered ring heterocyclic group shown by $Q^2$ in the group $-Q^1$-$Q^2$ of Y; and the "halogeno $C_1$-$C_6$ alkyl group" as a substituent for the aromatic group or 5- to 6-membered heteroaromatic ring group shown by Z has the same meanings as those of the above-mentioned "halogeno $C_1$-$C_6$ alkyl group". Such a "halogen $C_1$-$C_6$ alkyl group" may be mentioned a linear or branched halogeno $C_1$-$C_6$ alkyl group, for example, a trifluoromethyl group, difluoromethyl group, fluoromethyl group, trichloromethyl group, dichloromethyl group, chloromethyl group, pentafluoroethyl group, 2,2,2-trifluoroethyl group, 2-fluoroethyl group, 2,2,2-trichloroethyl group, 2-chloroethyl group, 2-bromoethyl group, heptafluoropropyl group, 3,3,3-trifluoropropyl group, 3-fluoropropyl group, 3-chloropropyl group, 1,2,2,2-tetra fluoro-1-trifluoromethyl-ethyl group, 2,2,2-trifluoro-1-methylethyl group, 2-fluoro-1-methyl ethyl group, 2-chloro-1-methyl ethyl group, perfluorobutyl group, 4,4,4-trifluorobutyl group, 4-fluorobutyl group, 4-chlorobutyl group, perfluoro-tert-butyl group, 2,2,2-trifluoro-1,1-dimethylethyl group, 2-fluoro-1,1-dimethylethyl group, 2-chloro-1,1-dimethylethyl group, perfluoropentyl group or perfluorohexyl group, etc., preferably a fluoro $C_1$-$C_4$ alkyl group or chloro $C_1$-$C_4$ alkyl group, more preferably a trifluoromethyl group, difluoromethyl group, trichloromethyl group, dichloromethyl group, 2,2,2-trifluoroethyl group or 2,2,2-trichloroethyl group, and particularly preferably a trifluoromethyl group.

In the compound represented by the above-mentioned formula (I), the "$C_1$-$C_6$ alkoxyl group" means the above-mentioned "$C_1$-$C_6$ alkyl group" bonded through oxygen (that is, —O—($C_1$-$C_6$ alkyl) group). Each of the "$C_1$-$C_6$ alkoxyl group" as a substituent for the bicyclic heteroaromatic ring group and the "$C_1$-$C_6$ alkoxyl group portion" of the halogeno $C_1$-$C_6$ alkoxyl group shown by Y; the "$C_1$-$C_6$ alkoxyl group" as a substituent for the aromatic group or 5- to 6-membered ring heterocyclic group and the "$C_1$-$C_6$ alkoxyl group portion" of the halogeno $C_1$-$C_6$ alkoxyl group shown by $Q^2$ in the group -$Q^1$-$Q^2$ of Y; the "$C_1$-$C_6$ alkoxyl group" as a substituent for the aromatic group or 5- to 6-membered heteroaromatic ring group and the "$C_1$-$C_6$ alkoxyl group portion" of the halogen $C_1$-$C_6$ alkoxyl group aromatic group or 5- to 6-membered heteroaromatic ring group shown by Z has the same meanings as those of the above-mentioned "$C_1$-$C_6$ alkoxyl group". Such a "$C_1$-$C_6$ alkoxyl group" may be mentioned a linear or branched $C_1$-$C_6$ alkoxyl group, for example, a methoxy group, ethoxy group, propoxy group, isopropoxy group, butoxy group, isobutoxy group, sec-butoxy group, tert-butoxy group, pentyloxy group, isopentyloxy group, neopentyloxy group, tert-pentyloxy group, 1-methylbutoxy group, 2-methylbutoxy group, 1-ethylpropoxy group, 1,2-dimethylpropoxy group, hexyloxy group, 1-methylpentyloxy group, 2-methylpentyloxy group, 3-methylpentyloxy group, 4-methylpentyloxy group, 1-ethylbutoxy group, 2-ethylbutoxy group, 1,1-dimethylbutoxy group, 1,2-dimethylbutoxy group, 1,3-dimethylbutoxy group, 2,2-dimethylbutoxy group, 2,3-dimethylbutoxy group, 3,3-dimethylbutoxy group, 1-ethyl-1-methylpropoxy group, 1-ethyl-2-methylpropoxy group, 1,1,2-trimethylpropoxy group or 1,2,2-trimethylpropoxy group, etc., preferably a $C_1$-$C_4$ alkoxyl group, more preferably a methoxy group, ethoxy group, propoxy group, isopropoxy group or tert-butoxy group, particularly preferably a methoxy group.

In the compound represented by the above-mentioned formula (I), the "halogeno $C_1$-$C_6$ alkoxyl group" means the above-mentioned "$C_1$-$C_6$ alkoxyl group" substituted by at least one of the above-mentioned same or different "halogen atom". Each of the "halogen $C_1$-$C_6$ alkoxyl group" as a substituent for the bicyclic heteroaromatic ring group shown by Y; the "halogeno $C_1$-$C_6$ alkoxyl group" as a substituent for the aromatic group or 5- to 6-membered ring heterocyclic group shown by $Q^2$ in the group -$Q^1$-$Q^2$ of Y; and the "halogeno $C_1$-$C_6$ alkoxyl group" as a substituent for the aromatic group or 5- to 6-membered heteroaromatic ring group shown by Z has the same meanings as those of the above-mentioned "halogen $C_1$-$C_6$ alkoxyl group". Such a "halogeno $C_1$-$C_6$ alkoxyl group" may be mentioned a linear or branched halogeno $C_1$-$C_6$ alkoxyl group, for example, a trifluoromethoxy group, difluoromethoxy group, trichloromethoxy group, dichloromethoxy group, pentafluoroethoxy group, 2,2,2-trifluoroethoxy group, 2-fluoroethoxy group, 2,2,2-trichloroethoxy group, 2-chloroethoxy group, 2-bromoethoxy group, heptafluoropropoxy group, 3,3,3-trifluoropropoxy group, 3-fluoropropoxy group, 3-chloropropoxy group, 1,2,2,2-tetrafluoro-1-trifluoromethylethoxy group, 2,2,2-trifluoro-1-methylethoxy group, 2-fluoro-1-methylethoxy group, 2-chloro-1-methylethoxy group, perfluorobutoxy group, 4,4,4-trifluorobutoxy group, 4-fluorobutoxy group, 4-chlorobutoxy group, perfluoro-tert-butoxy group, 2,2,2-trifluoro-1,1-dimethylethoxy group, 2-fluoro-1,1-dimethylethoxy group, 2-chloro-1,1-dimethylethoxy group, perfluoro pentyloxy group or perfluoro hexyloxy group, etc., preferably a fluoro $C_1$-$C_4$ alkoxyl group or chloro $C_1$-$C_4$ alkoxyl group, more preferably a trifluoromethoxy group, difluoromethoxy group, trichloromethoxy group or dichloromethoxy group, and particularly preferably a difluoromethoxy group.

In the compound represented by the above-mentioned formula (I), the "$C_1$-$C_6$ alkylthio group" means as a substituent for the bicyclic heteroaromatic ring group of Y means the above-mentioned "$C_1$-$C_6$ alkyl group" bonded through sulfur (that is, —S—($C_1$-$C_6$ alkyl) group), and may be mentioned a linear or branched $C_1$-$C_6$ alkylthio group, for example, a methylthio group, ethylthio group, propylthio group, isopropylthio group, butylthio group, isobutylthio group, sec-butylthio group, tert-butylthio group, pentylthio group, isopentylthio group, neopentylthio group, tert-pentylthio group, 1-methylbutylthio group, 2-methylbutylthio group, 1-ethylpropylthio group, 1,2-dimethylpropylthio group, hexylthio group, 1-methylpentylthio group, 2-methylpentylthio group, 3-methylpentylthio group, 4-methylpentylthio group, 1-ethylbutylthio group, 2-ethylbutylthio group, 1,1-dimethylbutylthio group, 1,2-dimethylbutylthio group, 1,3-dimethylbutylthio group, 2,2-dimethylbutylthio group, 2,3-dimethylbutylthio group, 3,3-dimethylbutylthio group, 1-ethyl-1-methylpropylthio group, 1-ethyl-2-methylpropylthio group, 1,1,2-trimethylpropylthio group or 1,2,2-trimethylpropylthio group, etc., preferably a $C_1$-$C_4$ alkylthio group, more preferably a methylthio group, ethylthio group, propylthio group, isopropylthio group or tert-butylthio group, and particularly preferably a methylthio group.

The substituent of the bicyclic heteroaromatic ring group shown by Y may be preferably mentioned a halogen atom, $C_1$-$C_4$ alkyl group, halogen $C_1$-$C_4$ alkyl group, $C_1$-$C_4$ alkoxyl group, halogeno $C_1$-$C_4$ alkoxyl group or $C_1$-$C_4$ alkylthio group, for example, fluorine atom, chlorine atom, bromine atom, methyl group, ethyl group, propyl group, isopropyl group, tert-butyl group, trifluoromethyl group, difluoromethyl group, trichloromethyl group, dichloromethyl group, 2,2,2-trifluoroethyl group, 2,2,2-trichloroethyl group, methoxy group, ethoxy group, propoxy group, isopropoxy group, tert-butoxy group, trifluoromethoxy group, difluoromethoxy group, trichloromethoxy group, dichloromethoxy group, methylthio group, ethylthio group, propylthio group, isopropylthio group or tert-butylthio group, and particularly a fluorine atom, chlorine atom, methyl group, ethyl group, trifluoromethyl group, methoxy group, difluoromethoxy group or methylthio group. It is particularly preferably a halogen atom or $C_1$-$C_4$ alkoxyl group, for example, fluorine atom, chlorine atom or methoxy group.

A number of the substituent(s) on the bicyclic heteroaromatic ring group of Y is, for example, 1 to 5, preferably 1 to 3, particularly preferably 1 to 2, and when it is a plural number of substituents, they may be the same or different from each other.

The "bicyclic heteroaromatic ring group" of Y means a completely unsaturated 9 to 10-membered bicyclic group containing 1 to 4 hetero atoms (in case of a plural number, each independently represents) selected from the group consisting of an oxygen atom, nitrogen atom and sulfur atom as a constitutional element(s) of the ring, and there may be mentioned, for example, a benzofuryl group, benzothienyl group, benzoxazolyl group, benzothiazolyl group, isoindolyl group, indolyl group, indazolyl group, benzoimidazolyl group, isoquinolyl group or quinolyl group, etc., preferably a benzofuryl group, benzothienyl group, benzoxazolyl group or benzothiazolyl group, particularly preferably a benzofuryl group or benzothienyl group.

The "bicyclic heteroaromatic ring group which may be substituted by a group(s) selected from the group consisting of a halogen atom, $C_1$-$C_6$ alkyl group, halogeno $C_1$-$C_6$ alkyl group, $C_1$-$C_6$ alkoxyl group, halogeno $C_1$-$C_6$ alkoxyl group and $C_1$-$C_6$ alkylthio group" of Y may be mentioned, for example, a benzofuran-2-yl group, 5-fluorobenzofuran-2-yl group, 6-fluorobenzofuran-2-yl group, 7-fluorobenzofuran-2-yl group, 5,6-difluorobenzofuran-2-yl group, 5-chlorobenzofuran-2-yl group, 6-chlorobenzofuran-2-yl group, 7-chlorobenzofuran-2-yl group, 6-chloro-5-fluorobenzofuran-2-yl group, 6-bromobenzofuran-2-yl group, 5-methylbenzofuran-2-yl group, 6-methylbenzofuran-2-yl group, 5-fluoro-6-methylbenzofuran-2-yl group, 5-ethylbenzofuran-2-yl group, 6-ethylbenzofuran-2-yl group, 6-ethyl-5-fluorobenzofuran-2-yl group, 6-propylbenzofuran-2-yl group, 6-isopropylbenzofuran-2-yl group, 6-tert-butylbenzofuran-2-yl group, 5-trifluoromethylbenzofuran-2-yl group, 6-trifluoromethylbenzofuran-2-yl group, 5-fluoro-6-trifluoromethylbenzofuran-2-yl group, 6-difluoromethylbenzofuran-2-yl group, 6-trichloromethylbenzofuran-2-yl group, 6-dichloromethylbenzofuran-2-yl group, 6-(2,2,2-trifluoroethyl)benzofuran-2-yl group, 6-(2,2,2-trichloroethyl)benzofuran-2-yl group, 5-methoxybenzofuran-2-yl group, 6-methoxybenzofuran-2-yl group, 7-methoxybenzofuran-2-yl group, 5-fluoro-6-methoxybenzofuran-2-yl group, 6-ethoxybenzofuran-2-yl group, 6-propoxybenzofuran-2-yl group, 6-isopropoxybenzofuran-2-yl group, 6-tert-butoxybenzofuran-2-yl group, 6-trifluoromethoxybenzofuran-2-yl group, 5-difluoromethoxybenzofuran-2-yl group, 6-difluoromethoxybenzofuran-2-yl group, 6-difluoromethoxy-5-fluorobenzofuran-2-yl group, 6-trichloromethoxybenzofuran-2-yl group, 6-dichloromethoxybenzofuran-2-yl group, 5-methylthiobenzofuran-2-yl group, 6-methylthiobenzofuran-2-yl group, 5-fluoro-6-methylthiobenzofuran-2-yl group, 6-ethylthiobenzofuran-2-yl group, 6-propylthiobenzofuran-2-yl group, 6-isopropylthiobenzofuran-2-yl group, 6-tert-butylthiobenzofuran-2-yl group, benzo[b]thiophen-2-yl group, 5-fluorobenzo[b]thiophen-2-yl group, 6-fluorobenzo[b]thiophen-2-yl group, 7-fluorobenzo[b]thiophen-2-yl group, 5,6-difluorobenzo-[b]thiophen-2-yl group, 5-chlorobenzo[b]thiophen-2-yl group, 6-chlorobenzo[b]thiophen-2-yl group, 7-chlorobenzo[b]thiophen-2-yl group, 6-chloro-5-fluorobenzo[b]-thiophen-2-yl group, 6-bromobenzo[b]thiophen-2-yl group, 5-methylbenzo[b]thiophen-2-yl group, 6-methylbenzo[b]thiophen-2-yl group, 5-fluoro-6-methylbenzo[b]thiophen-2-yl group, 5-ethylbenzo[b]thiophen-2-yl group, 6-ethylbenzo[b]thiophen-2-yl group, 6-ethyl-5-fluorobenzo[b]thiophen-2-yl group, 6-propylbenzo[b]thiophen-2-yl group, 6-isopropylbenzo[b]thiophen-2-yl group, 6-butylbenzo[b]thiophen-2-yl group, 6-isobutylbenzo[b]thiophen-2-yl group, 6-sec-butylbenzo[b]thiophen-2-yl group, 6-tert-butylbenzo[b]thiophen-2-yl group, 6-pentylbenzo[b]thiophen-2-yl group, 6-hexylbenzo[b]-thiophen-2-yl group, 5-trifluoromethylbenzo[b]thiophen-2-yl group, 6-trifluoromethylbenzo[b]thiophen-2-yl group, 5-fluoro-6-trifluoromethylbenzo[b]thiophen-2-yl group, 6-difluoromethylbenzo[b]thiophen-2-yl group, 6-trichloromethylbenzo[b]thiophen-2-yl group, 6-dichloromethylbenzo[b]thiophen-2-yl group, 6-(2,2,2-trifluoroethyl)benzo[b]-thiophen-2-yl group, 6-(2,2,2-trichloroethyl)benzo[b]thiophen-2-yl group, 5-methoxybenzo[b]thiophen-2-yl group, 6-methoxybenzo[b]thiophen-2-yl group, 7-methoxybenzo[b]thiophen-2-yl group, 5-fluoro-6-methoxybenzo[b]thiophen-2-yl group, 6-ethoxybenzo[b]thiophen-2-yl group, 6-propoxybenzo[b]thiophen-2-yl group, 6-isopropoxybenzo[b]thiophen-2-yl group, 6-butoxybenzo[b]thiophen-2-yl group, 6-isobutoxybenzo[b]thiophen-2-yl group, 6-sec-butoxybenzo[b]thiophen-2-yl group, 6-tert-butoxybenzo[b]thiophen-2-yl group, 6-pentyloxybenzo[b]thiophen-2-yl group, 6-hexyloxybenzo[b]thiophen-2-yl group, 6-trifluoromethoxybenzo[b]thiophen-2-yl group, 5-difluoromethoxybenzo[b]thiophen-2-yl group, 6-difluoromethoxybenzo[b]thiophen-2-yl group, 6-difluoromethoxy-5-fluorobenzo[b]thiophen-2-yl group, 6-trichloromethoxybenzo[b]thiophen-2-yl group, 6-dichloromethoxybenzo[b]thiophen-2-yl group, 5-methylthiobenzo[b]thiophen-2-yl group, 6-methylthiobenzo[b]thiophen-2-yl group, 5-fluoro-6-methylthiobenzo[b]thiophen-2-yl group, 6-ethylthiobenzo[b]thiophen-2-yl group, 6-propylthiobenzo[b]thiophen-2-yl group, 6-isopropylthiobenzo[b]thiophen-2-yl group, 6-tert-butylthiobenzo[b]thiophen-2-yl group, benzoxazol-2-yl group, 6-fluorobenzoxazol-2-yl group, 6-chlorobenzoxazol-2-yl group, 6-methoxybenzoxazol-2-yl group, benzothiazol-2-yl group, 6-fluorobenzothiazol-2-yl group, 6-chlorobenzothiazol-2-yl group, 6-methoxybenzothiazol-2-yl group, isoindol-2-yl group, 1H-indol-2-yl group, 6-fluoro-1H-indol-2-yl group, 6-chloro-1H-indol-2-yl group, 6-methoxy-1H-indol-2-yl group, indazol-2-yl group, 1H-benzoimidazol-2-yl group, isoquinolin-3-yl group, 7-fluoroisoquinolin-3-yl group, 7-chloroisoquinolin-3-yl group, 7-methoxyisoquinolin-3-yl group, quinolin-2-yl group, 6-fluoroquinolin-2-yl group, 6-chloroquinolin-2-yl group or 6-methoxyquinolin-2-yl group, etc.

It is preferably a benzofuran-2-yl group, 6-fluorobenzofuran-2-yl group, 5,6-difluorobenzofuran-2-yl group, 6-chlorobenzofuran-2-yl group, 6-chloro-5-fluorobenzofuran-2-yl group, 6-methylbenzofuran-2-yl group, 5-fluoro-6-methylbenzofuran-2-yl group, 6-ethylbenzofuran-2-yl group, 6-ethyl-5-fluorobenzofuran-2-yl group, 6-trifluoromethylbenzofuran-2-yl group, 5-fluoro-6-trifluoromethylbenzofuran-2-yl group, 6-methoxybenzofuran-2-yl group, 5-fluoro-6-methoxybenzofuran-2-yl group, 6-difluoromethoxybenzofuran-2-yl group, 6-difluoromethoxy-5-fluorobenzofuran-2-yl group, 6-methylthiobenzofuran-2-yl group, 5-fluoro-6-methylthiobenzofuran-2-yl group, benzo[b]thiophen-2-yl group, 6-fluorobenzo[b]thiophen-2-yl group, 5,6-difluorobenzo[b]thiophen-2-yl group, 6-chlorobenzo[b]thiophen-2-yl group, 6-chloro-5-fluorobenzo[b]thiophen-2-yl group, 6-bromobenzo[b]thiophen-2-yl group, 6-methylbenzo-[b]thiophen-2-yl group, 5-fluoro-6-methylbenzo[b]thiophen-2-yl group, 6-ethylbenzo-[b]thiophen-2-yl group, 6-ethyl-5-fluorobenzo[b]thiophen-2-yl group, 6-propylbenzo-[b]thiophen-2-yl group, 6-isopropylbenzo[b]thiophen-2-yl group, 6-tert-butylbenzo-[b]thiophen-2-yl group, 6-trifluoromethylbenzo[b]thiophen-2-yl group, 5-fluoro-6-trifluoromethylbenzo[b]thiophen-2-yl group, 6-difluoromethylbenzo[b]thiophen-2-yl group, 6-trichloromethylbenzo[b]thiophen-2-yl group, 6-dichloromethylbenzo[b]-thiophen-2-yl group, 6-(2,2,2-trifluoroethyl)benzo[b]thiophen-2-yl group, 6-(2,2,2-trichloroethyl)benzo[b]thiophen-2-yl group, 6-methoxybenzo[b]thiophen-2-yl group, 5-fluoro-6-methoxybenzo[b]thiophen-2-yl group, 6-ethoxybenzo[b]thiophen-2-yl group, 6-propoxybenzo[b]thiophen-2-yl group, 6-isopropoxybenzo[b]thiophen-2-yl group, 6-tert-butoxybenzo[b]thiophen-2-yl group, 6-trifluoromethoxybenzo[b]thiophen-2-yl group, 6-difluoromethoxybenzo[b]thiophen-2-yl group, 6-difluoromethoxy-5-fluorobenzo[b]thiophen-2-yl group, 6-trichloromethoxybenzo[b]thiophen-2-yl group, 6-dichloromethoxybenzo[b]thiophen-2-yl group, 6-methylthiobenzo[b]thiophen-2-yl group, 5-fluoro-6-methylthiobenzo[b]thiophen-2-yl group, 6-ethylthiobenzo[b]thiophen-2-yl group, 6-propylthiobenzo[b]thiophen-2-yl group, 6-isopropylthiobenzo[b]-thiophen-2-yl group, 6-tert-butylthiobenzo[b]thiophen-2-yl group, benzoxazol-2-yl group, 6-chlorobenzoxazol-2-yl group, 6-methoxybenzoxazol-2-yl group, benzothiazol-2-yl group, 6-chlorobenzothiazol-2-yl group or 6-methoxybenzothiazol-2-yl group.

It is more preferably mentioned a benzofuran-2-yl group, 6-fluorobenzofuran-2-yl group, 6-chlorobenzofuran-2-yl group, 6-methoxybenzofuran-2-yl group, benzo-[b]thiophen-2-yl group, 6-fluorobenzo[b]thiophen-2-yl group, 5,6-difluorobenzo[b]-thiophen-2-yl group, 6-chlorobenzo[b]thiophen-2-yl group, 6-chloro-5-fluorobenzo-[b]thiophen-2-yl group, 6-methylbenzo[b]thiophen-2-yl group, 5-fluoro-6-methylbenzo-[b]thiophen-2-yl group, 6-ethylbenzo[b]thiophen-2-yl group, 6-ethyl-5-fluorobenzo[b]-thiophen-2-yl group, 6-trifluoromethylbenzo[b]thiophen-2-yl group, 5-fluoro-6-trifluoromethylbenzo[b]thiophen-2-yl group, 6-methoxybenzo[b]thiophen-2-yl group, 5-fluoro-6-methoxybenzo[b]thiophen-2-yl group, 6-difluoromethoxybenzo[b]thiophen-2-yl group, 6-difluoromethoxy-5-fluorobenzo[b]thiophen-2-yl group, 6-methylthiobenzo-[b]thiophen-2-yl group or 5-fluoro-6-methylthiobenzo[b]thiophen-2-yl group, particularly preferably a benzofuran-2-yl group, benzo[b]thiophen-2-yl group, 6-chlorobenzo-[b]thiophen-2-yl group or 6-methoxybenzo[b]thiophen-2-yl group.

In the group $-Q^1-Q^2$ of Y, the "arylene group" of $Q^1$ means a divalent group of an aromatic hydrocarbon with a 6 to 10 membered ring, and there may be mentioned, for example, a phenylene group or naphthylene group, preferably a phenylene group.

In the group $-Q^1-Q^2$ of Y, the "5- to 6-membered heteroarylene group" of $Q^1$ means a completely unsaturated 5- to 6-membered ring divalent group containing 1 to 4 hetero atoms (when it is a plural number, each independently represents) selected from the group consisting of an oxygen atom, nitrogen atom and sulfur atom as a constitutional element(s) of the ring, and there may be mentioned, for example, furylene group, thienylene group, thiazolylene group, pyridylene group, pyridazinylene group or pyrimidinylene group, etc., preferably thienylene group, pyridazinylene group or pyrimidinylene group, and particularly preferably pyridazinylene group.

In Y, "$Q^1$" is preferably a phenylene group, thienylene group, pyridazinylene group or pyrimidinylene group, more preferably a phenylene group or pyridazinylene group, and particularly preferably a 1,4-phenylene group or 3,6-pyridazinylene group.

In the group $-Q^1-Q^2$ of Y, the "aromatic group" of $Q^2$; and the "aromatic group" of Z each means a 6- to 10-membered aromatic hydrocarbon group, and such an "aromatic group" may be mentioned, for example, a phenyl group or naphthyl group, preferably phenyl group.

In the group $-Q^1-Q^2$ of Y, the "5- to 6-membered ring heterocyclic group" of $Q^2$ means a completely unsaturated, partially unsaturated or completely saturated 5- to 6-membered cyclic group containing 1 to 4 hetero atoms (when it is a plural number, each independently represents) selected from the group consisting of an oxygen atom, nitrogen atom and sulfur atom as a constitutional element(s) of the ring, and the completely unsaturated 5- to 6-membered ring heterocyclic group may include, for example, a pyrrolyl group, furyl group, thienyl group, pyrazolyl group, imidazolyl group, oxazolyl group, thiazolyl group, 1,2,4-triazolyl group, pyridyl group, pyridazinyl group, pyrimidinyl group or pyrazinyl group, etc., the partially unsaturated 5- to 6-membered ring heterocyclic group may include, for example, a 4,5-dihydro-1H-imidazolyl group, 4,5-dihydroxazolyl group, 4,5-dihydrothiazolyl group, 1,4,5,6-tetrahydro pyrimidinyl group, 5,6-dihydro-4H-1,3-oxadinyl group or 5,6-dihydro-4H-1,3-thiazinyl group, etc., and the completely saturated 5- to 6-membered ring heterocyclic group may include, for example, a pyrrolidinyl group, tetrahydrofuryl group, 1,3-dioxolanyl group, piperidinyl group, tetrahydropyranyl group, piperazinyl group, morpholinyl group, thiomorpholinyl group, 1,3-dioxanyl group or 1,4-dioxanyl group, etc. The "5- to 6-membered ring heterocyclic group" of $Q^2$ is preferably a thienyl group, pyrazolyl group, oxazolyl group, thiazolyl group, 1,2,4-triazolyl group, pyridyl group, pyridazinyl group, pyrimidinyl group, 4,5-dihydrothiazolyl group, pyrrolidinyl group or piperidinyl group, more preferably a thienyl group, pyrazolyl group, oxazolyl group, thiazolyl group, 1,2,4-triazolyl group, pyridyl group, pyridazinyl group, pyrimidinyl group or 4,5-dihydrothiazolyl group, and particularly preferably a pyrazolyl group, thiazolyl group, 1,2,4-triazolyl group, pyridyl group, pyridazinyl group, pyrimidinyl group or 4,5-dihydrothiazolyl group.

In the group $-Q^1-Q^2$ of Y, the substituent for the aromatic group and 5- to 6-membered ring heterocyclic group of $Q^2$ may be preferably mentioned a halogen atom, hydroxyl group, $C_1$-$C_4$ alkyl group, halogeno $C_1$-$C_4$ alkyl group, $C_1$-$C_4$ alkoxyl group or halogeno $C_1$-$C_4$ alkoxyl group, for example, fluorine atom, chlorine atom, bromine atom, methyl group, ethyl group, propyl group, isopropyl group, tert-butyl group, trifluoromethyl group, difluoromethyl group, trichloromethyl group, dichloromethyl group, 2,2,2-trifluoroethyl group, 2,2,2-trichloroethyl group, methoxy group, ethoxy group, propoxy group, isopropoxy group, tert-butoxy group, trifluoromethoxy group, difluoromethoxy group, trichloromethoxy group or dichloromethoxy group, particularly a fluorine atom, chlorine atom, hydroxyl group, methyl group, ethyl group, trifluoromethyl group, methoxy group or difluoromethoxy group. It is particularly preferably a halogen atom, $C_1$-$C_4$ alkyl group or halogeno $C_1$-$C_4$ alkyl group, for example, fluorine atom, chlorine atom, methyl group or trifluoromethyl group.

In Y, a number of the substituents on the aromatic group and 5- to 6-membered ring heterocyclic group of $Q^2$ is, for example, 1 to 5, preferably 1 to 3, and particularly preferably 1 to 2, and when it is a plural number, the substituents may be the same or different from each other.

In the group $-Q^1-Q^2$ of Y, the "aromatic group which may be substituted by a group(s) selected from the group consisting of a halogen atom, hydroxyl group, $C_1$-$C_6$ alkyl group, halogeno $C_1$-$C_6$ alkyl group, $C_1$-$C_6$ alkoxyl group and halogeno $C_1$-$C_6$ alkoxyl group" of $Q^2$ may be mentioned, for example, phenyl group, 1-naphthyl group, 2-naphthyl group, 2-fluorophenyl group, 3-fluorophenyl group, 4-fluorophenyl group, 3-fluoro-1-naphthyl group, 4-fluoro-1-naphthyl group, 4-fluoro-2-naphthyl group, 2,3-difluorophenyl group, 2,4-difluorophenyl group, 2,5-difluorophenyl group, 2,6-difluorophenyl group, 3,4-difluorophenyl group, 3,5-difluorophenyl group, 2,3,4-trifluorophenyl group, 2,3,5-trifluorophenyl group, 2,3,6-trifluorophenyl group, 2,4,5-trifluorophenyl group, 2,4,6-trifluorophenyl group, 3,4,5-trifluorophenyl group, 2,3,4,5,6-pentafluorophenyl group, 2-chlorophenyl group, 3-chlorophenyl group, 4-chlorophenyl group, 3-chloro-1-naphthyl group, 4-chloro-1-naphthyl group, 4-chloro-2-naphthyl group, 2,3-dichlorophenyl group, 2,4-dichlorophenyl group, 2,5-dichlorophenyl group, 2,6-dichlorophenyl group, 3,4-dichlorophenyl group, 3,5-dichlorophenyl group, 3-chloro-4-fluorophenyl group, 3-chloro-5-fluorophenyl group, 4-chloro-2-fluorophenyl group, 4-chloro-3-fluorophenyl group, 3-bromophenyl group, 4-bromophenyl group, 3-iodo phenyl group, 2-hydroxyphenyl group, 3-hydroxyphenyl group, 4-hydroxyphenyl group, 2-methylphenyl group, 3-methylphenyl group, 4-methylphenyl group, 2-ethylphenyl group, 3-ethylphenyl group, 4-ethylphenyl group, 3-propylphenyl group, 4-propylphenyl group, 3-isopropylphenyl group, 4-isopropylphenyl group, 3-butylphenyl group, 3-isobutylphenyl group, 3-sec-butylphenyl group, 3-tert-butylphenyl group, 4-tert-butylphenyl group, 3-pentyl phenyl group, 3-hexylphenyl group, 2-trifluoromethylphenyl group, 3-trifluoromethylphenyl group, 4-trifluoromethylphenyl group, 3-difluoromethylphenyl group, 4-difluoromethylphenyl group, 3-trichloromethylphenyl group, 4-trichloromethylphenyl group, 3-dichloromethylphenyl group, 4-dichloromethylphenyl group, 3-(2,2,2-trifluoroethyl)phenyl group, 4-(2,2,2-trifluoroethyl)phenyl group, 3-(2,2,2-trichloroethyl)phenyl group, 4-(2,2,2-trichloroethyl)phenyl group, 2-methoxyphenyl group, 3-methoxyphenyl group, 4-methoxyphenyl group, 3-ethoxyphenyl group, 4-ethoxyphenyl group, 3-propoxyphenyl group, 4-propoxyphenyl group, 3-isopropoxyphenyl group, 4-isopropoxyphenyl group, 3-butoxyphenyl group, 3-isobutoxyphenyl group, 3-sec-butoxyphenyl group, 3-tert-butoxyphenyl group, 4-tert-butoxyphenyl group, 3-pentyloxyphenyl group, 3-hexyloxyphenyl group, 3-trifluoromethoxyphenyl group, 4-trifluoromethoxyphenyl group, 2-difluoromethoxyphenyl group, 3-difluoromethoxyphenyl group, 4-difluoromethoxyphenyl group, 3-trichloromethoxyphenyl group, 4-trichloromethoxyphenyl group, 3-dichloromethoxyphenyl group or 4-dichloromethoxyphenyl group, etc., preferably phenyl group, 2-fluorophenyl group, 3-fluorophenyl group, 4-fluorophenyl group, 2,4-difluorophenyl group, 3,4-difluorophenyl group, 2-chlorophenyl group, 3-chlorophenyl group, 4-chlorophenyl group, 2,4-dichlorophenyl group, 3,4-dichlorophenyl group, 4-chloro-2-fluorophenyl group, 4-chloro-3-fluorophenyl group, 3-bromophenyl group, 3-hydroxyphenyl group, 4-hydroxyphenyl group, 3-methylphenyl group, 3-ethylphenyl group, 3-propylphenyl group, 3-isopropylphenyl group, 3-tert-butylphenyl group, 3-trifluoromethylphenyl group, 3-difluoromethylphenyl group, 3-trichloromethylphenyl group, 3-dichloromethylphenyl group, 3-(2,2,2-trifluoroethyl)phenyl group, 3-(2,2,2-trichloroethyl)phenyl group, 3-methoxyphenyl group, 3-ethoxyphenyl group, 3-propoxyphenyl group, 3-isopropoxyphenyl group, 3-tert-butoxyphenyl group, 3-trifluoromethoxyphenyl group, 3-difluoromethoxyphenyl group, 3-trichloromethoxyphenyl group or 3-dichloromethoxyphenyl group, more preferably phenyl group, 2-fluorophenyl group, 3-fluorophenyl group, 4-fluorophenyl group, 2,4-difluorophenyl group, 3,4-difluorophenyl group, 2-chlorophenyl group, 3-chlorophenyl group, 4-chlorophenyl group, 4-chloro-2-fluorophenyl group, 4-chloro-3-fluorophenyl group, 4-hydroxyphenyl group, 3-methylphenyl group, 3-ethylphenyl group, 3-trifluoromethylphenyl group, 3-methoxyphenyl group or 3-difluoromethoxyphenyl group, and particularly preferably phenyl group, 4-fluorophenyl group or 4-chlorophenyl group.

In the group -$Q^1$-$Q^2$ of Y, the "5- to 6-membered ring heterocyclic group which may be substituted by a group(s) selected from the group consisting of a halogen atom, hydroxyl group, $C_1$-$C_6$ alkyl group, halogen $C_1$-$C_6$ alkyl group, $C_1$-$C_6$ alkoxyl group and halogeno $C_1$-$C_6$ alkoxyl group" of $Q^2$ may be mentioned, for example, pyrrol-1-yl group, furan-2-yl group, furan-3-yl group, thiophen-2-yl group, thiophen-3-yl group, pyrazol-1-yl group, 4-fluoropyrazol-1-yl group, 4-chloropyrazol-1-yl group, 1H-imidazol-2-yl group, oxazol-2-yl group, oxazol-4-yl group, thiazol-2-yl group, 4-fluorothiazol-2-yl group, 4-chlorothiazol-2-yl group, 5-chlorothiazol-2-yl group, 4-bromothiazol-2-yl group, 4-methylthiazol-2-yl group, 5-methylthiazol-2-yl group, 4,5-dimethylthiazol-2-yl group, 4-ethylthiazol-2-yl group, 4-propylthiazol-2-yl group, 4-isopropylthiazol-2-yl group, 4-tert-butylthiazol-2-yl group, 4-trifluoromethylthiazol-2-yl group, 4-difluoromethylthiazol-2-yl group, 4-trichloromethylthiazol-2-yl group, 4-dichloromethylthiazol-2-yl group, 4-(2,2,2-trifluoroethyl)thiazol-2-yl group, 4-(2,2,2-trichloroethyl)thiazol-2-yl group, 4-methoxythiazol-2-yl group, 4-ethoxythiazol-2-yl group, 4-propoxythiazol-2-yl group, 4-isopropoxythiazol-2-yl group, 4-tert-butoxythiazol-2-yl group, 4-trifluoromethoxythiazol-2-yl group, 4-difluoromethoxythiazol-2-yl group, 4-trichloromethoxythiazol-2-yl group, 4-dichloromethoxythiazol-2-yl group, thiazol-4-yl group, 2-fluorothiazol-4-yl group, 2-chlorothiazol-4-yl group, 2-bromothiazol-4-yl group, 2-methylthiazol-4-yl group, 2-ethylthiazol-4-yl group, 2-propylthiazol-4-yl group, 2-isopropylthiazol-4-yl group, 2-tert-butylthiazol-4-yl group, 2-trifluoromethylthiazol-4-yl group, 2-difluoromethylthiazol-4-yl group, 2-trichloromethylthiazol-4-yl group, 2-dichloromethylthiazol-4-yl group, 2-(2,2,2-trifluoroethyl)thiazol-4-yl group, 2-(2,2,2-trichloroethyl)thiazol-4-yl group, 2-methoxythiazol-4-yl group, 2-ethoxythiazol-4-yl group, 2-propoxythiazol-4-yl group, 2-isopropoxythiazol-4-yl group, 2-tert-butoxythiazol-4-yl group, 2-trifluoromethoxythiazol-4-yl group, 2-difluoromethoxythiazol-4-yl group, 2-trichloromethoxythiazol-4-yl group, 2-dichloromethoxythiazol-4-yl group, thiazol-5-yl group, 1,2,4-triazol-1-yl group, pyridin-2-yl group, pyridin-3-yl group, pyridin-4-yl group, pyridazin-3-yl group, pyridazin-4-yl group, pyrimidin-2-yl group, 4-fluoropyrimidin-2-yl group, 5-fluoropyrimidin-2-yl group, 4-chloropyrimidin-2-yl group, 5-chloropyrimidin-2-yl group, 5-hydroxypyrimidin-2-yl group, 4-methylpyrimidin-2-yl group, 4-ethylpyrimidin-2-yl group, 4-trifluoromethylpyrimidin-2-yl group, 4-methoxypyrimidin-2-yl group, 4-difluoromethoxypyrimidin-2-yl group, pyrimidin-4-yl group, pyrimidin-5-yl group, pyrazin-2-yl group, 4,5-dihydro-1H-imidazol-2-yl group, 4,5-dihydrooxazol-2-yl group, 4,5-dihydrothiazol-2-yl group, 1,4,5,6-tetrahydropyrimidin-2-yl group, 5,6-dihydro-4H-1,3-oxazin-2-yl group, 5,6-dihydro-4H-1,3-thiazin-2-yl group, pyrrolidin-1-yl group, tetrahydrofuran-2-yl group, 1,3-dioxolan-2-yl group, piperidin-1-yl group, tetrahydropyran-2-yl group, piperazin-1-yl group, morpholin-4-yl group, thiomorpholin-4-yl group, 1,3-dioxan-2-yl group or 1,4-dioxan-2-yl group, etc., preferably a thiophen-2-yl group, thiophen-3-yl group, pyrazol-1-yl group, 4-fluoropyrazol-1-yl group, 4-chloropyrazol-1-yl group, oxazol-2-yl group, oxazol-4-yl group, thiazol-2-yl group, 4-fluorothiazol-2-yl group, 4-chlorothiazol-2-yl group, 5-chlorothiazol-2-yl group, 4-methylthiazol-2-yl group, 5-methylthiazol-2-yl group, 4,5-dimethylthiazol-2-yl group, 4-ethylthiazol-2-yl group, 4-trifluoromethylthiazol-2-yl group, 4-methoxythiazol-2-yl group, 4-difluoromethoxythiazol-2-yl group, thiazol-4-yl group, 2-fluorothiazol-4-yl group, 2-chlorothiazol-4-yl group, 2-methylthiazol-4-yl group, 2-ethylthiazol-4-yl group, 2-trifluoromethylthiazol-4-yl group, 2-methoxythiazol-4-yl group, 2-difluoromethoxythiazol-4-yl group, thiazol-5-yl group, 1,2,4-triazol-1-yl group, pyridin-2-yl group, pyridin-3-yl group, pyridin-4-yl group, pyridazin-3-yl group, pyridazin-4-yl group, pyrimidin-2-yl group, 5-fluoropyrimidin-2-yl group, 5-chloropyrimidin-2-yl group, 5-hydroxypyrimidin-2-yl group, pyrimidin-4-yl group, pyrimidin-5-yl group, 4,5-dihydrothiazol-2-yl group, pyrrolidin-1-yl group or piperidin-1-yl group, more preferably a thiophen-2-yl group, thiophen-3-yl group, pyrazol-1-yl group, oxazol-2-yl group, oxazol-4-yl group, thiazol-2-yl group, 4-fluorothiazol-2-yl group, 4-chlorothiazol-2-yl group, 5-chlorothiazol-2-yl group, 5-methylthiazol-2-yl group, 4,5-dimethylthiazol-2-yl group, 4-trifluoromethylthiazol-2-yl group, thiazol-4-yl group, 2-fluorothiazol-4-yl group, 2-chlorothiazol-4-yl group, thiazol-5-yl group, 1,2,4-triazol-1-yl group, pyridin-2-yl group, pyridazin-3-yl group, pyridazin-4-yl group, pyrimidin-2-yl group, 5-hydroxypyrimidin-2-yl group, pyrimidin-4-yl group, pyrimidin-5-yl group or 4,5-dihydrothiazol-2-yl group, and particularly preferably a pyrazol-1-yl group, thiazol-2-yl group, 5-chlorothiazol-2-yl group, 5-methylthiazol-2-yl group, 4,5-dimethylthiazol-2-yl group, 4-trifluoromethylthiazol-2-yl group, thiazol-4-yl group, 1,2,4-triazol-1-yl group, pyridin-2-yl group, pyridazin-4-yl group, pyrimidin-2-yl group or 4,5-dihydrothiazol-2-yl group.

In the group -$Q^1$-$Q^2$ of Y, "$Q^2$" is preferably a phenyl group, thienyl group, pyrazolyl group, oxazolyl group, thiazolyl group, 1,2,4-triazolyl group, pyridyl group, pyridazinyl group, pyrimidinyl group, 4,5-dihydrothiazolyl group, pyrrolidinyl group or piperidinyl group, for example, phenyl group, 2-fluorophenyl group, 3-fluorophenyl group, 4-fluorophenyl group, 2,4-difluorophenyl group, 3,4-difluorophenyl group, 2-chlorophenyl group, 3-chlorophenyl group, 4-chlorophenyl group, 2,4-dichlorophenyl group, 3,4-dichlorophenyl group, 4-chloro-2-fluorophenyl group, 4-chloro-3-fluorophenyl group, 3-bromophenyl group, 3-hydroxyphenyl group, 4-hydroxyphenyl group, 3-methylphenyl group, 3-ethylphenyl group, 3-propylphenyl group, 3-isopropylphenyl group, 3-tert-butylphenyl group, 3-trifluoromethylphenyl group, 3-difluoromethylphenyl group, 3-trichloromethylphenyl group, 3-dichloromethylphenyl group, 3-(2,2,2-trifluoroethyl)phenyl group, 3-(2,2,2-trichloroethyl)phenyl group, 3-methoxyphenyl group, 3-ethoxyphenyl group, 3-propoxyphenyl group, 3-isopropoxyphenyl group, 3-tert-butoxyphenyl group, 3-trifluoromethoxyphenyl group, 3-difluoromethoxyphenyl group, 3-trichloromethoxyphenyl group, 3-dichloromethoxyphenyl group, thiophen-2-yl group, thiophen-3-yl group, pyrazol-1-yl group, 4-fluoropyrazol-1-yl group, 4-chloropyrazol-1-yl group, oxazol-2-yl group, oxazol-4-yl group, thiazol-2-yl group, 4-fluorothiazol-2-yl group, 4-chlorothiazol-2-yl group, 5-chlorothiazol-2-yl group, 4-methylthiazol-2-yl group, 5-methylthiazol-2-yl group, 4,5-dimethylthiazol-2-yl group, 4-ethylthiazol-2-yl group, 4-trifluoromethylthiazol-2-yl group, 4-methoxythiazol-2-yl group, 4-difluoromethoxythiazol-2-yl group, thiazol-4-yl group, 2-fluorothiazol-4-yl group, 2-chlorothiazol-4-yl group, 2-methylthiazol-4-yl group, 2-ethylthiazol-4-yl group, 2-trifluoromethylthiazol-4-yl group, 2-methoxythiazol-4-yl group, 2-difluoromethoxythiazol-4-yl group, thiazol-5-yl group, 1,2,4-triazol-1-yl group, pyridin-2-yl group, pyridin-3-yl group, pyridin-4-yl group, pyridazin-3-yl group, pyridazin-4-yl group, pyrimidin-2-yl group, 5-fluoropyrimidin-2-yl group, 5-chloropyrimidin-2-yl group, 5-hydroxypyrimidin-2-yl group, pyrimidin-4-yl group, pyrimidin-5-yl group, 4,5-dihydrothiazol-2-yl group, pyrrolidin-1-yl group or piperidin-1-yl group, each of which may be substituted by a group(s) selected from the group consisting of a halogen atom, hydroxyl group, $C_1$-$C_4$ alkyl group, halogeno $C_1$-$C_4$ alkyl group, $C_1$-$C_4$ alkoxyl group and halogeno $C_1$-$C_4$ alkoxyl group, particularly a phenyl group, 2-fluorophenyl group, 3-fluorophenyl group, 4-fluorophenyl group, 2,4-difluorophenyl group, 3,4-difluorophenyl group, 2-chlorophenyl group, 3-chlorophenyl group, 4-chlorophenyl group, 4-chloro-2-fluorophenyl group, 4-chloro-3-fluorophenyl group, 4-hydroxyphenyl group, 3-methylphenyl group, 3-ethylphenyl group, 3-trifluoromethylphenyl group, 3-methoxyphenyl group, 3-difluoromethoxyphenyl group, thiophen-2-yl group, thiophen-3-yl group, pyrazol-1-yl group, oxazol-2-yl group, oxazol-4-yl group, thiazol-2-yl group, 4-fluorothiazol-2-yl group, 4-chlorothiazol-2-yl group, 5-chlorothiazol-2-yl group, 5-methylthiazol-2-yl group, 4,5-dimethylthiazol-2-yl group, 4-trifluoromethylthiazol-2-yl group, thiazol-4-yl group, 2-fluorothiazol-4-yl group, 2-chlorothiazol-4-yl group, thiazol-5-yl group, 1,2,4-triazol-1-yl group, pyridin-2-yl group, pyridazin-3-yl group, pyridazin-4-yl group, pyrimidin-2-yl group, 5-hydroxypyrimidin-2-yl group, pyrimidin-4-yl group, pyrimidin-5-yl group or 4,5-dihydrothiazol-2-yl group. "$Q^2$" is particularly preferably a phenyl group, pyrazolyl group, thiazolyl group, 1,2,4-triazolyl group, pyridyl group, pyridazinyl group, pyrimidinyl group or 4,5-dihydrothiazolyl group, for example, phenyl group, 4-fluorophenyl group, 4-chlorophenyl group, pyrazol-1-yl group, thiazol-2-yl group, 5-chlorothiazol-2-yl group, 5-methylthiazol-2-yl group, 4,5-dimethylthiazol-2-yl group, 4-trifluoromethylthiazol-2-yl group, thiazol-4-yl group, 1,2,4-triazol-1-yl group, pyridin-2-yl group, pyridazin-4-yl group, pyrimidin-2-yl group or 4,5-dihydrothiazol-2-yl group each of which may be substituted by a group(s) selected from the group consisting of a halogen atom, $C_1$-$C_4$ alkyl group and halogeno $C_1$-$C_4$ alkyl group.

As the group -$Q^1$-$Q^2$ of Y, there may be mentioned, for example, a biphenyl-3-yl group, biphenyl-4-yl group, 4-(naphthalen-1-yl)phenyl group, 4-(naphthalen-2-yl)phenyl group, 2'-fluorobiphenyl-4-yl group, 3'-fluorobiphenyl-4-yl group, 4'-fluorobiphenyl-4-yl group, 2',3'-difluorobiphenyl-4-yl group, 2',4'-difluorobiphenyl-4-yl group, 2',5'-difluorobiphenyl-4-yl group, 2',6'-difluorobiphenyl-4-yl group, 3',4'-difluorobiphenyl-4-yl group, 3',5'-difluorobiphenyl-4-yl group, 2'-chlorobiphenyl-4-yl group, 3'-chlorobiphenyl-4-yl group, 4'-chlorobiphenyl-4-yl group, 2',3'-dichlorobiphenyl-4-yl group, 2',4'-dichlorobiphenyl-4-yl group, 2',5'-dichlorobiphenyl-4-yl group, 2',6'-dichlorobiphenyl-4-yl group, 3',4'-dichlorobiphenyl-4-yl group, 3',5'-dichlorobiphenyl-4-yl group, 3'-chloro-4'-fluorobiphenyl-4-yl group, 3'-chloro-5'-fluorobiphenyl-4-yl group, 4'-chloro-2'-fluorobiphenyl-4-yl group, 4'-chloro-3'-fluorobiphenyl-4-yl group, 3'-bromobiphenyl-4-yl group, 4'-bromobiphenyl-4-yl group, 3'-iodobiphenyl-4-yl group, 2'-hydroxybiphenyl-4-yl group, 3'-hydroxybiphenyl-4-yl group, 4'-hydroxybiphenyl-4-yl group, 2'-methylbiphenyl-4-yl group, 3'-methylbiphenyl-4-yl group, 4'-methylbiphenyl-4-yl group, 2'-ethylbiphenyl-4-yl group, 3'-ethylbiphenyl-4-yl group, 4'-ethylbiphenyl-4-yl group, 3'-propylbiphenyl-4-yl group, 4'-propylbiphenyl-4-yl group, 3'-isopropylbiphenyl-4-yl group, 4'-isopropylbiphenyl-4-yl group, 3'-tert-butylbiphenyl-4-yl group, 4'-tert-butylbiphenyl-4-yl group, 2'-trifluoromethylbiphenyl-4-yl group, 3'-trifluoromethylbiphenyl-4-yl group, 4'-trifluoromethylbiphenyl-4-yl group, 3'-difluoromethylbiphenyl-4-yl group, 4'-difluoromethylbiphenyl-4-yl group, 3'-trichloromethylbiphenyl-4-yl group, 4'-trichloromethylbiphenyl-4-yl group, 3'-dichloromethylbiphenyl-4-yl group, 4'-dichloromethylbiphenyl-4-yl group, 3'-(2,2,2-trifluoroethyl)biphenyl-4-yl group, 4'-(2,2,2-trifluoroethyl)biphenyl-4-yl group, 3'-(2,2,2-trichloroethyl)biphenyl-4-yl group, 4'-(2,2,2-trichloroethyl)biphenyl-4-yl group, 2'-methoxybiphenyl-4-yl group, 3'-methoxybiphenyl-4-yl group, 4'-methoxybiphenyl-4-yl group, 3'-ethoxybiphenyl-4-yl group, 4'-ethoxybiphenyl-4-yl group, 3'-propoxybiphenyl-4-yl group, 4'-propoxybiphenyl-4-yl group, 3'-isopropoxybiphenyl-4-yl group, 4'-isopropoxybiphenyl-4-yl group, 3'-tert-butoxybiphenyl-4-yl group, 4'-tert-butoxybiphenyl-4-yl group, 3'-trifluoromethoxybiphenyl-4-yl group, 4'-trifluoromethoxybiphenyl-4-yl group, 2'-difluoromethoxybiphenyl-4-yl group, 3'-difluoromethoxybiphenyl-4-yl group, 4'-difluoromethoxybiphenyl-4-yl group, 3'-trichloromethoxybiphenyl-4-yl group, 4'-trichloromethoxybiphenyl-4-yl group, 3'-dichloromethoxybiphenyl-4-yl group, 4'-dichloromethoxybiphenyl-4-yl group, 4-(pyrrol-1-yl)phenyl group, 4-(furan-2-yl)phenyl group, 4-(furan-3-yl)phenyl group, 4-(thiophen-2-yl)phenyl group, 4-(thiophen-3-yl)phenyl group, 4-(pyrazol-1-yl)phenyl group, 4-(4-fluoropyrazol-1-yl)phenyl group, 4-(4-chloropyrazol-1-yl)phenyl group, 4-(1H-imidazol-2-yl)phenyl group, 4-(oxazol-2-yl)phenyl group, 4-(oxazol-4-yl)phenyl group, 3-(thiazol-2-yl)phenyl group, 4-(thiazol-2-yl)phenyl group, 4-(4-fluorothiazol-2-yl)phenyl group, 4-(4-chlorothiazol-2-yl)phenyl group, 4-(5-chlorothiazol-2-yl)phenyl group, 4-(4-bromothiazol-2-yl)phenyl group, 4-(4-methylthiazol-2-yl)phenyl group, 4-(5-methylthiazol-2-yl)phenyl group, 4-(4,5-dimethylthiazol-2-yl)phenyl group, 4-(4-ethylthiazol-2-yl)phenyl group, 4-(4-propylthiazol-2-yl)phenyl group, 4-(4-isopropylthiazol-2-yl)phenyl group, 4-(4-tert-butylthiazol-2-yl)phenyl group, 4-(4-trifluoromethylthiazol-2-yl)phenyl group, 4-(4-difluoromethylthiazol-2-yl)phenyl group, 4-(4-trichloromethylthiazol-2-yl)phenyl group, 4-(4-dichloromethylthiazol-2-yl)phenyl group, 4-[4-(2,2,2-trifluoroethyl)thiazol-2-yl]phenyl group, 4-[4-(2,2,2-trichloroethyl)thiazol-2-yl]phenyl group, 4-(4-methoxythiazol-2-yl)phenyl group, 4-(4-ethoxythiazol-2-yl)phenyl group, 4-(4-propoxythiazol-2-yl)phenyl group, 4-(4-isopropoxythiazol-2-yl)phenyl group, 4-(4-tert-butoxythiazol-2-yl)phenyl group, 4-(4-trifluoromethoxythiazol-2-yl)phenyl group, 4-(4-difluoromethoxythiazol-2-yl)phenyl group, 4-(4-trichloromethoxythiazol-2-yl)phenyl group, 4-(4-dichloromethoxythiazol-2-yl)phenyl group, 3-(thiazol-4-yl)phenyl group, 4-(thiazol-4-yl)phenyl group, 4-(2-fluorothiazol-4-yl)phenyl group, 4-(2-chlorothiazol-4-yl)phenyl group, 4-(2-bromothiazol-4-yl)phenyl group, 4-(2-methylthiazol-4-yl)phenyl group, 4-(2-ethylthiazol-4-yl)phenyl group, 4-(2-propylthiazol-4-yl)phenyl group, 4-(2-isopropylthiazol-4-yl)phenyl group, 4-(2-tert-butylthiazol-4-yl)phenyl group, 4-(2-trifluoromethylthiazol-4-yl)phenyl group, 4-(2-difluoromethylthiazol-4-yl)phenyl group, 4-(2-trichloromethylthiazol-4-yl)phenyl group, 4-(2-dichloromethylthiazol-4-yl)phenyl group, 4-[2-(2,2,2-trifluoroethyl)thiazol-4-yl]phenyl group, 4-[2-(2,2,2-trichloroethyl)thiazol-4-yl]phenyl group, 4-(2-methoxythiazol-4-yl)phenyl group, 4-(2-ethoxythiazol-4-yl)phenyl group, 4-(2-propoxythiazol-4-yl)phenyl group, 4-(2-isopropoxythiazol-4-yl)phenyl group, 4-(2-tert-butoxythiazol-4-yl)phenyl group, 4-(2-trifluoromethoxythiazol-4-yl)phenyl group, 4-(2-difluoromethoxythiazol-4-yl)phenyl group, 4-(2-trichloromethoxythiazol-4-yl)phenyl group, 4-(2-dichloromethoxythiazol-4-yl)phenyl group, 4-(thiazol-5-yl)phenyl group, 4-(1,2,4-triazol-1-yl)phenyl group, 4-(pyridin-2-yl)phenyl group, 4-(pyridin-3-yl)phenyl group, 4-(pyridin-4-yl)phenyl group, 4-(pyridazin-3-yl)phenyl group, 4-(pyridazin-4-yl)phenyl group, 4-(pyrimidin-2-yl)phenyl group, 4-(4-fluoropyrimidin-2-yl)phenyl group, 4-(5-fluoropyrimidin-2-yl)phenyl group, 4-(4-chloropyrimidin-2-yl)phenyl group, 4-(5-chloropyrimidin-2-yl)phenyl group, 4-(5-hydroxypyrimidin-2-yl)phenyl group, 4-(4-methylpyrimidin-2-yl)phenyl group, 4-(4-ethylpyrimidin-2-yl)phenyl group, 4-(4-trifluoromethylpyrimidin-2-yl)phenyl group, 4-(4-methoxypyrimidin-2-yl)phenyl group, 4-(4-difluoromethoxypyrimidin-2-yl)phenyl group, 4-(pyrimidin-4-yl)phenyl group, 4-(pyrimidin-5-yl)phenyl group, 4-(pyrazin-2-yl)phenyl group, 4-(4,5-dihydro-1H-imidazol-2-yl)phenyl group, 4-(4,5-dihydroxazol-2-yl)phenyl group, 4-(4,5-dihydrothiazol-2-yl)phenyl group, 4-(1,4,5,6-tetrahydropyrimidin-2-yl)phenyl group, 4-(5,6-dihydro-4H-1,3-oxazin-2-yl)phenyl group, 4-(5,6-dihydro-4H-1,3-thiazin-2-yl)phenyl group, 4-(pyrrolidin-1-yl)phenyl group, 4-(tetrahydrofuran-2-yl)phenyl group, 4-(1,3-dioxolan-2-yl)phenyl group, 4-(piperidin-1-yl)phenyl group, 4-(tetrahydropyran-2-yl)phenyl group, 4-(piperazin-1-yl)phenyl group, 4-(morpholin-4-yl)phenyl group, 4-(thiomorpholin-4-yl)phenyl group, 4-(1,3-dioxan-2-yl)phenyl group, 4-(1,4-dioxan-2-yl)phenyl group, 4-phenyl-naphthalen-1-yl group, 5-phenylfuran-2-yl group, 5-phenylthiophen-2-yl group, 5-(thiazol-2-yl)thiophen-2-yl group, 5-(thiazol-4-yl)thiophen-2-yl group, 2-phenylthiazol-5-yl group, 5-phenylpyridin-2-yl group, 6-phenylpyridin-3-yl group, 6-phenylpyridazin-3-yl group, 6-(4-fluorophenyl)pyridazin-3-yl group, 6-(4-chlorophenyl)pyridazin-3-yl group, 6-(pyrazol-1-yl)pyridazin-3-yl group, 6-(thiazol-2-yl)pyridazin-3-yl group, 6-(thiazol-4-yl)pyridazin-3-yl group, 6-(pyrimidin-2-yl)pyridazin-3-yl group, 2-phenylpyrimidin-4-yl group, 2-(thiazol-2-yl)pyrimidin-4-yl group or 2-(thiazol-4-yl)pyrimidin-4-yl group, etc., preferably a biphenyl-3-yl group, biphenyl-4-yl group, 2'-fluorobiphenyl-4-yl group, 3'-fluorobiphenyl-4-yl group, 4'-fluorobiphenyl-4-yl group, 2',4'-difluorobiphenyl-4-yl group, 3',4'-difluorobiphenyl-4-yl group, 2'-chlorobiphenyl-4-yl group, 3'-chlorobiphenyl-4-yl group, 4'-chlorobiphenyl-4-yl group, 2',4'-dichlorobiphenyl-4-yl group, 3',4'-dichlorobiphenyl-4-yl group, 4'-chloro-2'-fluorobiphenyl-4-yl group, 4'-chloro-3'-fluorobiphenyl-4-yl group, 3'-bromobiphenyl-4-yl group, 3'-hydroxybiphenyl-4-yl group, 4'-hydroxybiphenyl-4-yl group, 3'-methylbiphenyl-4-yl group, 3'-ethylbiphenyl-4-yl group, 3'-propylbiphenyl-4-yl group, 3'-isopropylbiphenyl-4-yl group, 3'-tert-butylbiphenyl-4-yl group, 3'-trifluoromethylbiphenyl-4-yl group, 3'-difluoromethylbiphenyl-4-yl group, 3'-trichloromethylbiphenyl-4-yl group, 3'-dichloromethylbiphenyl-4-yl group, 3'-(2,2,2-trifluoroethyl)biphenyl-4-yl group, 3'-(2,2,2-trichloroethyl)biphenyl-4-yl group, 3'-methoxybiphenyl-4-yl group, 3'-ethoxybiphenyl-4-yl group, 3'-propoxybiphenyl-4-yl group, 3'-isopropoxybiphenyl-4-yl group, 3'-tert-butoxybiphenyl-4-yl group, 3'-trifluoromethoxybiphenyl-4-yl group, 3'-difluoromethoxybiphenyl-4-yl group, 3'-trichloromethoxybiphenyl-4-yl group, 3'-dichloromethoxybiphenyl-4-yl group, 4-(thiophen-2-yl)phenyl group, 4-(thiophen-3-yl)phenyl group, 4-(pyrazol-1-yl)phenyl group, 4-(4-fluoropyrazol-1-yl)phenyl group, 4-(4-chloropyrazol-1-yl)phenyl group, 4-(oxazol-2-yl)phenyl group, 4-(oxazol-4-yl)phenyl group, 4-(thiazol-2-yl)phenyl group, 4-(4-fluorothiazol-2-yl)phenyl group, 4-(4-chlorothiazol-2-yl)phenyl group, 4-(5-chlorothiazol-2-yl)phenyl group, 4-(4-methylthiazol-2-yl)phenyl group, 4-(5-methylthiazol-2-yl)phenyl group, 4-(4,5-dimethylthiazol-2-yl)phenyl group, 4-(4-ethylthiazol-2-yl)phenyl group, 4-(4-trifluoromethylthiazol-2-yl)phenyl group, 4-(4-methoxythiazol-2-yl)phenyl group, 4-(4-difluoromethoxythiazol-2-yl)phenyl group, 4-(thiazol-4-yl)phenyl group, 4-(2-fluorothiazol-4-yl)phenyl group, 4-(2-chlorothiazol-4-yl)phenyl group, 4-(2-methylthiazol-4-yl)phenyl group, 4-(2-ethylthiazol-4-yl)phenyl group, 4-(2-trifluoromethylthiazol-4-yl)phenyl group, 4-(2-methoxythiazol-4-yl)phenyl group, 4-(2-difluoromethoxythiazol-4-yl)phenyl group, 4-(thiazol-5-yl)phenyl group, 4-(1,2,4-triazol-1-yl)phenyl group, 4-(pyridin-2-yl)phenyl group, 4-(pyridin-3-yl)phenyl group, 4-(pyridin-4-yl)phenyl group, 4-(pyridazin-3-yl)phenyl group, 4-(pyridazin-4-yl)phenyl group, 4-(pyrimidin-2-yl)phenyl group, 4-(5-fluoropyrimidin-2-yl)phenyl group, 4-(5-chloropyrimidin-2-yl)phenyl group, 4-(5-hydroxypyrimidin-2-yl)phenyl group, 4-(pyrimidin-4-yl)phenyl group, 4-(pyrimidin-5-yl)phenyl group, 4-(4,5-dihydrothiazol-2-yl)phenyl group, 4-(pyrrolidin-1-yl)phenyl group, 4-(piperidin-1-yl)phenyl group, 5-phenylthiophen-2-yl group, 5-(thiazol-2-yl)thiophen-2-yl group, 5-(thiazol-4-yl)thiophen-2-yl group, 6-phenylpyridazin-3-yl group, 6-(thiazol-2-yl)pyridazin-3-yl group, 6-(thiazol-4-yl)pyridazin-3-yl group, 2-phenylpyrimidin-4-yl group, 2-(thiazol-2-yl)pyrimidin-4-yl group or 2-(thiazol-4-yl)pyrimidin-4-yl group, more preferably biphenyl-4-yl group, 2'-fluorobiphenyl-4-yl group, 3'-fluorobiphenyl-4-yl group, 4'-fluorobiphenyl-4-yl group, 2',4'-difluorobiphenyl-4-yl group, 3',4'-difluorobiphenyl-4-yl group, 2'-chlorobiphenyl-4-yl group, 3'-chlorobiphenyl-4-yl group, 4'-chlorobiphenyl-4-yl group, 4'-chloro-2'-fluorobiphenyl-4-yl group, 4'-chloro-3'-fluorobiphenyl-4-yl group, 4'-hydroxybiphenyl-4-yl group, 3'-methylbiphenyl-4-yl group, 3'-ethylbiphenyl-4-yl group, 3'-trifluoromethylbiphenyl-4-yl group, 3'-methoxybiphenyl-4-yl group, 3'-difluoromethoxybiphenyl-4-yl group, 4-(thiophen-2-yl)phenyl group, 4-(thiophen-3-yl)phenyl group, 4-(pyrazol-1-yl)phenyl group, 4-(oxazol-2-yl)phenyl group, 4-(oxazol-4-yl)phenyl group, 4-(thiazol-2-yl)phenyl group, 4-(4-fluorothiazol-2-yl)phenyl group, 4-(4-chlorothiazol-2-yl)phenyl group, 4-(5-chlorothiazol-2-yl)phenyl group, 4-(5-methylthiazol-2-yl)phenyl group, 4-(4,5-dimethylthiazol-2-yl)phenyl group, 4-(4-trifluoromethylthiazol-2-yl)phenyl group, 4-(thiazol-4-yl)phenyl group, 4-(2-fluorothiazol-4-yl)phenyl group, 4-(2-chlorothiazol-4-yl)phenyl group, 4-(thiazol-5-yl)phenyl group, 4-(1,2,4-triazol-1-yl)phenyl group, 4-(pyridin-2-yl)phenyl group, 4-(pyridazin-3-yl)phenyl group, 4-(pyridazin-4-yl)phenyl group, 4-(pyrimidin-2-yl)phenyl group, 4-(5-hydroxypyrimidin-2-yl)phenyl group, 4-(pyrimidin-4-yl)phenyl group, 4-(pyrimidin-5-yl)phenyl group, 4-(4,5-dihydrothiazol-2-yl)phenyl group, 6-phenylpyridazin-3-yl group, 6-(thiazol-2-yl)pyridazin-3-yl group or 6-(thiazol-4-yl)pyridazin-3-yl group, particularly preferably biphenyl-4-yl group, 4'-fluorobiphenyl-4-yl group, 4'-chlorobiphenyl-4-yl group, 4-(pyrazol-1-yl)phenyl group, 4-(thiazol-2-yl)phenyl group, 4-(5-chlorothiazol-2-yl)phenyl group, 4-(5-methylthiazol-2-yl)phenyl group, 4-(4,5-dimethylthiazol-2-yl)phenyl group, 4-(4-trifluoromethylthiazol-2-yl)phenyl group, 4-(thiazol-4-yl)phenyl group, 4-(1,2,4-triazol-1-yl)phenyl group, 4-(pyridin-2-yl)phenyl group, 4-(pyridazin-4-yl)phenyl group, 4-(pyrimidin-2-yl)phenyl group, 4-(4,5-dihydrothiazol-2-yl)phenyl group or 6-phenylpyridazin-3-yl group.

As Y, there may be preferably mentioned a benzofuryl group, benzothienyl group, benzoxazolyl group or benzothiazolyl group each of which may be substituted by a group(s) selected from the group consisting of a halogen atom, $C_1$-$C_4$ alkyl group, halogeno $C_1$-$C_4$ alkyl group, $C_1$-$C_4$ alkoxyl group, halogeno $C_1$-$C_4$ alkoxyl group and $C_1$-$C_4$ alkylthio group, or in the group -$Q^1$-$Q^2$ of $Q^1$ represents a phenylene group, thienylene group, pyridazinylene group or pyrimidinylene group, and $Q^2$ represents a phenyl group, thienyl group, pyrazolyl group, oxazolyl group, thiazolyl group, 1,2,4-triazolyl group, pyridyl group, pyridazinyl group, pyrimidinyl group, 4,5-dihydrothiazolyl group, pyrrolidinyl group or piperidinyl group each of which may be substituted by a group(s) selected from the group consisting of a halogen atom, hydroxyl group, $C_1$-$C_4$ alkyl group, halogeno $C_1$-$C_4$ alkyl group, $C_1$-$C_4$ alkoxyl group and halogeno $C_1$-$C_4$ alkoxyl group, more preferably a benzofuryl group, benzothienyl group, benzoxazolyl group or benzothiazolyl group each of which may be substituted by a group(s) selected from the group consisting of a fluorine atom, chlorine atom, bromine atom, methyl group, ethyl group, propyl group, isopropyl group, tert-butyl group, trifluoromethyl group, difluoromethyl group, trichloromethyl group, dichloromethyl group, 2,2,2-trifluoroethyl group, 2,2,2-trichloroethyl group, methoxy group, ethoxy group, propoxy group, isopropoxy group, tert-butoxy group, trifluoromethoxy group, difluoromethoxy group, trichloromethoxy group, dichloromethoxy group, methylthio group, ethylthio group, propylthio group, isopropylthio group and tert-butylthio group, or in the group $Q^1$-$Q^2$ of Y, $Q^1$ represents a phenylene group, thienylene group, pyridazinylene group or pyrimidinylene group, and $Q^2$ represents a phenyl group, thienyl group, pyrazolyl group, oxazolyl group, thiazolyl group, 1,2,4-triazolyl group, pyridyl group, pyridazinyl group, pyrimidinyl group, 4,5-dihydrothiazolyl group, pyrrolidinyl group or piperidinyl group each of which may be substituted by a group(s)-selected from the group consisting of a fluorine atom, chlorine atom, bromine atom, hydroxyl group, methyl group, ethyl group, propyl group, isopropyl group, tert-butyl group, trifluoromethyl group, difluoromethyl group, trichloromethyl group, dichloromethyl group, 2,2,2-trifluoroethyl group, 2,2,2-trichloroethyl group, methoxy group, ethoxy group, propoxy group, isopropoxy group, tert-butoxy group, trifluoromethoxy group, difluoromethoxy group, trichloromethoxy group and dichloromethoxy group.

Such examples may be preferably mentioned a benzofuran-2-yl group, 6-fluorobenzofuran-2-yl group, 5,6-difluorobenzofuran-2-yl group, 6-chlorobenzofuran-2-yl group, 6-chloro-5-fluorobenzofuran-2-yl group, 6-methylbenzofuran-2-yl group, 5-fluoro-6-methylbenzofuran-2-yl group, 6-ethylbenzofuran-2-yl group, 6-ethyl-5-fluorobenzofuran-2-yl group, 6-trifluoromethylbenzofuran-2-yl group, 5-fluoro-6-trifluoromethylbenzofuran-2-yl group, 6-methoxybenzofuran-2-yl group, 5-fluoro-6-methoxybenzofuran-2-yl group, 6-difluoromethoxybenzofuran-2-yl group, 6-difluoromethoxy-5-fluorobenzofuran-2-yl group, 6-methylthiobenzofuran-2-yl group, 5-fluoro-6-methylthiobenzofuran-2-yl group, benzo[b]thiophen-2-yl group, 6-fluorobenzo[b]thiophen-2-yl group, 5,6-difluorobenzo[b]thiophen-2-yl group, 6-chlorobenzo[b]thiophen-2-yl group, 6-chloro-5-fluorobenzo[b]thiophen-2-yl group, 6-bromobenzo[b]thiophen-2-yl group, 6-methylbenzo[b]thiophen-2-yl group, 5-fluoro-6-methylbenzo[b]thiophen-2-yl group, 6-ethylbenzo[b]thiophen-2-yl group, 6-ethyl-5-fluorobenzo[b]thiophen-2-yl group, 6-propylbenzo[b]thiophen-2-yl group, 6-isopropylbenzo[b]thiophen-2-yl group, 6-tert-butylbenzo[b]thiophen-2-yl group, 6-trifluoromethylbenzo[b]thiophen-2-yl group, 5-fluoro-6-trifluoromethylbenzo[b]thiophen-2-yl group, 6-difluoromethylbenzo[b]thiophen-2-yl group, 6-trichloromethylbenzo[b]thiophen-2-yl group, 6-dichloromethylbenzo[b]thiophen-2-yl group, 6-(2,2,2-trifluoroethyl)benzo[b]thiophen-2-yl group, 6-(2,2,2-trichloroethyl)benzo[b]thiophen-2-yl group, 6-methoxybenzo[b]thiophen-2-yl group, 5-fluoro-6-methoxybenzo[b]thiophen-2-yl group, 6-ethoxybenzo[b]thiophen-2-yl group, 6-propoxybenzo[b]thiophen-2-yl group, 6-isopropoxybenzo[b]thiophen-2-yl group, 6-tert-butoxybenzo[b]thiophen-2-yl group, 6-trifluoromethoxybenzo[b]thiophen-2-yl group, 6-difluoromethoxybenzo[b]thiophen-2-yl group, 6-difluoromethoxy-5-fluorobenzo[b]thiophen-2-yl group, 6-trichloromethoxybenzo[b]thiophen-2-yl group, 6-dichloromethoxybenzo[b]thiophen-2-yl group, 6-methylthiobenzo[b]thiophen-2-yl group, 5-fluoro-6-methylthiobenzo[b]thiophen-2-yl group, 6-ethylthiobenzo[b]thiophen-2-yl group, 6-propylthiobenzo[b]thiophen-2-yl group, 6-isopropylthiobenzo[b]-thiophen-2-yl group, 6-tert-butylthiobenzo[b]thiophen-2-yl group, benzoxazol-2-yl group, 6-chlorobenzoxazol-2-yl group, 6-methoxybenzoxazol-2-yl group, benzothiazol-2-yl group, 6-chlorobenzothiazol-2-yl group, 6-methoxybenzothiazol-2-yl group, biphenyl-3-yl group, biphenyl-4-yl group, 2'-fluorobiphenyl-4-yl group, 3'-fluorobiphenyl-4-yl group, 4'-fluorobiphenyl-4-yl group, 2',4'-difluorobiphenyl-4-yl group, 3',4'-difluorobiphenyl-4-yl group, 2'-chlorobiphenyl-4-yl group, 3'-chlorobiphenyl-4-yl group, 4'-chlorobiphenyl-4-yl group, 2',4'-dichlorobiphenyl-4-yl group, 3',4'-dichlorobiphenyl-4-yl group, 4'-chloro-2'-fluorobiphenyl-4-yl group, 4'-chloro-3'-fluorobiphenyl-4-yl group, 3'-bromobiphenyl-4-yl group, 3'-hydroxybiphenyl-4-yl group, 4'-hydroxybiphenyl-4-yl group, 3'-methylbiphenyl-4-yl group, 3'-ethylbiphenyl-4-yl group, 3'-propylbiphenyl-4-yl group, 3'-isopropylbiphenyl-4-yl group, 3'-tert-butylbiphenyl-4-yl group, 3'-trifluoromethylbiphenyl-4-yl group, 3'-difluoromethylbiphenyl-4-yl group, 3'-trichloromethylbiphenyl-4-yl group, 3'-dichloromethylbiphenyl-4-yl group, 3'-(2,2,2-trifluoroethyl)biphenyl-4-yl group, 3'-(2,2,2-trichloroethyl)biphenyl-4-yl group, 3'-methoxybiphenyl-4-yl group, 3'-ethoxybiphenyl-4-yl group, 3'-propoxybiphenyl-4-yl group, 3'-isopropoxybiphenyl-4-yl group, 3'-tert-butoxybiphenyl-4-yl group, 3'-trifluoromethoxybiphenyl-4-yl group, 3'-difluoromethoxybiphenyl-4-yl group, 3'-trichloromethoxybiphenyl-4-yl group, 3'-dichloromethoxybiphenyl-4-yl group, 4-(thiophen-2-yl)phenyl group, 4-(thiophen-3-yl)phenyl group, 4-(pyrazol-1-yl)phenyl group, 4-(4-fluoropyrazol-1-yl)phenyl group, 4-(4-chloropyrazol-1-yl)phenyl group, 4-(oxazol-2-yl)phenyl group, 4-(oxazol-4-yl)phenyl group, 4-(thiazol-2-yl)phenyl group, 4-(4-fluorothiazol-2-yl)phenyl group, 4-(4-chlorothiazol-2-yl)phenyl group, 4-(5-chlorothiazol-2-yl)phenyl group, 4-(4-methylthiazol-2-yl)phenyl group, 4-(5-methylthiazol-2-yl)phenyl group, 4-(4,5-dimethylthiazol-2-yl)phenyl group, 4-(4-ethylthiazol-2-yl)phenyl group, 4-(4-trifluoromethylthiazol-2-yl)phenyl group, 4-(4-methoxythiazol-2-yl)phenyl group, 4-(4-difluoromethoxythiazol-2-yl)phenyl group, 4-(thiazol-4-yl)phenyl group, 4-(2-fluorothiazol-4-yl)phenyl group, 4-(2-chlorothiazol-4-yl)phenyl group, 4-(2-methylthiazol-4-yl)phenyl group, 4-(2-ethylthiazol-4-yl)phenyl group, 4-(2-trifluoromethylthiazol-4-yl)phenyl group, 4-(2-methoxythiazol-4-yl)phenyl group, 4-(2-difluoromethoxythiazol-4-yl)phenyl group, 4-(thiazol-5-yl)phenyl group, 4-(1,2,4-triazol-1-yl)phenyl group, 4-(pyridin-2-yl)phenyl group, 4-(pyridin-3-yl)phenyl group, 4-(pyridin-4-yl)phenyl group, 4-(pyridazin-3-yl)phenyl group, 4-(pyridazin-4-yl)phenyl group, 4-(pyrimidin-2-yl)phenyl group, 4-(5-fluoropyrimidin-2-yl)phenyl group, 4-(5-chloropyrimidin-2-yl)phenyl group, 4-(5-hydroxypyrimidin-2-yl)phenyl group, 4-(pyrimidin-4-yl)phenyl group, 4-(pyrimidin-5-yl)phenyl group, 4-(4,5-dihydrothiazol-2-yl)phenyl group, 4-(pyrrolidin-1-yl)phenyl group, 4-(piperidin-1-yl)phenyl group, 5-phenylthiophen-2-yl group, 5-(thiazol-2-yl)thiophen-2-yl group, 5-(thiazol-4-yl)thiophen-2-yl group, 6-phenylpyridazin-3-yl group, 6-(thiazol-2-yl)pyridazin-3-yl group, 6-(thiazol-4-yl)pyridazin-3-yl group, 2-phenylpyrimidin-4-yl group, 2-(thiazol-2-yl)pyrimidin-4-yl group or 2-(thiazol-4-yl)pyrimidin-4-yl group.

It is more preferably a benzofuran-2-yl group, 6-fluorobenzofuran-2-yl group, 6-chlorobenzofuran-2-yl group, 6-methoxybenzofuran-2-yl group, benzo[b]thiophen-2-yl group, 6-fluorobenzo[b]thiophen-2-yl group, 5,6-difluorobenzo[b]thiophen-2-yl group, 6-chlorobenzo[b]thiophen-2-yl group, 6-chloro-5-fluorobenzo[b]thiophen-2-yl group, 6-methylbenzo[b]thiophen-2-yl group, 5-fluoro-6-methylbenzo[b]thiophen-2-yl group, 6-ethylbenzo[b]thiophen-2-yl group, 6-ethyl-5-fluorobenzo[b]thiophen-2-yl group, 6-trifluoromethylbenzo[b]thiophen-2-yl group, 5-fluoro-6-trifluoromethylbenzo-[b]thiophen-2-yl group, 6-methoxybenzo[b]thiophen-2-yl group, 5-fluoro-6-methoxybenzo[b]thiophen-2-yl group, 6-difluoromethoxybenzo[b]thiophen-2-yl group, 6-difluoromethoxy-5-fluorobenzo[b]thiophen-2-yl group, 6-methylthiobenzo[b]thiophen-2-yl group, 5-fluoro-6-methylthiobenzo[b]thiophen-2-yl group, biphenyl-4-yl group, 2'-fluorobiphenyl-4-yl group, 3'-fluorobiphenyl-4-yl group, 4'-fluorobiphenyl-4-yl group, 2',4'-difluorobiphenyl-4-yl group, 3',4'-difluorobiphenyl-4-yl group, 2'-chlorobiphenyl-4-yl group, 3'-chlorobiphenyl-4-yl group, 4'-chlorobiphenyl-4-yl group, 4'-chloro-2'-fluorobiphenyl-4-yl group, 4'-chloro-3'-fluorobiphenyl-4-yl group, 4'-hydroxybiphenyl-4-yl group, 3'-methylbiphenyl-4-yl group, 3'-ethylbiphenyl-4-yl group, 3'-trifluoromethylbiphenyl-4-yl group, 3'-methoxybiphenyl-4-yl group, 3'-difluoromethoxybiphenyl-4-yl group, 4-(thiophen-2-yl)phenyl group, 4-(thiophen-3-yl)phenyl group, 4-(pyrazol-1-yl)phenyl group, 4-(oxazol-2-yl)phenyl group, 4-(oxazol-4-yl)phenyl group, 4-(thiazol-2-yl)phenyl group, 4-(4-fluorothiazol-2-yl)phenyl group, 4-(4-chlorothiazol-2-yl)phenyl group, 4-(5-chlorothiazol-2-yl)phenyl group, 4-(5-methylthiazol-2-yl)phenyl group, 4-(4,5-dimethylthiazol-2-yl)phenyl group, 4-(4-trifluoromethylthiazol-2-yl)phenyl group, 4-(thiazol-4-yl)phenyl group, 4-(2-fluorothiazol-4-yl)phenyl group, 4-(2-chlorothiazol-4-yl)phenyl group, 4-(thiazol-5-yl)phenyl group, 4-(1,2,4-triazol-1-yl)phenyl group, 4-(pyridin-2-yl)phenyl group, 4-(pyridazin-3-yl)phenyl group, 4-(pyridazin-4-yl)phenyl group, 4-(pyrimidin-2-yl)phenyl group, 4-(5-hydroxypyrimidin-2-yl)phenyl group, 4-(pyrimidin-4-yl)phenyl group, 4-(pyrimidin-5-yl)phenyl group, 4-(4,5-dihydrothiazol-2-yl)phenyl group, 6-phenylpyridazin-3-yl group, 6-(thiazol-2-yl)pyridazin-3-yl group or 6-(thiazol-4-yl)pyridazin-3-yl group. particularly preferably Y is a benzofuryl group or benzothienyl group each of which may be substituted by a group(s) selected from the group consisting of a halogen atom and $C_1$-$C_4$ alkoxyl group, or in the group -$Q^1$-$Q^2$ of Y, $Q^1$ is a phenylene group or pyridazinylene group, and $Q^2$ is a phenyl group, pyrazolyl group, thiazolyl group, 1,2,4-triazolyl group, pyridyl group, pyridazinyl group, pyrimidinyl group or 4,5-dihydrothiazolyl group each of which may be substituted by a group(s) selected from the group consisting of a halogen atom, $C_1$-$C_4$ alkyl group and halogen $C_1$-$C_4$ alkyl group, and for example, benzofuran-2-yl group, benzo[b]thiophen-2-yl group, 6-chlorobenzo[b]-thiophen-2-yl group, 6-methoxybenzo[b]thiophen-2-yl group, biphenyl-4-yl group, 4'-fluorobiphenyl-4-yl group, 4'-chlorobiphenyl-4-yl group, 4-(pyrazol-1-yl)phenyl group, 4-(thiazol-2-yl)phenyl group, 4-(5-chlorothiazol-2-yl)phenyl group, 4-(5-methylthiazol-2-yl)phenyl group, 4-(4,5-dimethylthiazol-2-yl)phenyl group, 4-(4-trifluoromethylthiazol-2-yl)phenyl group, 4-(thiazol-4-yl)phenyl group, 4-(1,2,4-triazol-1-yl)phenyl group, 4-(pyridin-2-yl)phenyl group, 4-(pyridazin-4-yl)phenyl group, 4-(pyrimidin-2-yl)phenyl group, 4-(4,5-dihydrothiazol-2-yl)phenyl group or 6-phenylpyridazin-3-yl group.

The "5- to 6-membered heteroaromatic ring group" of Z has the same meanings and examples as those of the above-mentioned "completely unsaturated 5- to 6-membered ring heterocyclic group", preferably a thienyl group, imidazolyl group, thiazolyl group, pyridyl group or pyrimidinyl group, more preferably a thienyl group or pyridyl group, and particularly preferably a pyridyl group.

The substituent(s) for the aromatic group or 5- to 6-membered heteroaromatic ring group of Z may be preferably mentioned a halogen atom, $C_1$-$C_4$ alkyl group, halogeno $C_1$-$C_4$ alkyl group, $C_1$-$C_4$ alkoxyl group or halogeno $C_1$-$C_4$ alkoxyl group, for example, fluorine atom, chlorine atom, bromine atom, methyl group, ethyl group, propyl group, isopropyl group, tert-butyl group, trifluoromethyl group, difluoromethyl group, trichloromethyl group, dichloromethyl group, 2,2,2-trifluoroethyl group, 2,2,2-trichloroethyl group, methoxy group, ethoxy group, propoxy group, isopropoxy group, tert-butoxy group, trifluoromethoxy group, difluoromethoxy group, trichloromethoxy group or dichloromethoxy group, particularly a fluorine atom, chlorine atom, methyl group, ethyl group, trifluoromethyl group, methoxy group or difluoromethoxy group, and particularly preferably a halogen atom or $C_1$-$C_4$ alkoxyl group, for example, a fluorine atom, chlorine atom or methoxy group.

A number of the substituent(s) on the aromatic group or 5- to 6-membered heteroaromatic ring group of Z is, for example, 1 to 5, preferably 1 to 3, particularly preferably 1 to 2, and when it is a plural number of substituents, they may be the same or different from each other.

The "aromatic group which may be substituted by a group(s) selected from the group consisting of a halogen atom, $C_1$-$C_6$ alkyl group, halogeno $C_1$-$C_6$ alkyl group, $C_1$-$C_6$ alkoxyl group and halogeno $C_1$-$C_6$ alkoxyl group" of Z may be mentioned, for example, a phenyl group, 1-naphthyl group, 2-naphthyl group, 2-fluorophenyl group, 3-fluorophenyl group, 4-fluorophenyl group, 3-fluoro-1-naphthyl group, 4-fluoro-1-naphthyl group, 4-fluoro-2-naphthyl group, 2,3-difluorophenyl group, 2,4-difluorophenyl group, 2,5-difluorophenyl group, 2,6-difluorophenyl group, 3,4-difluorophenyl group, 3,5-difluorophenyl group, 2,3,4-trifluorophenyl group, 2,3,5-trifluorophenyl group, 2,3,6-trifluorophenyl group, 2,4,5-trifluorophenyl group, 2,4,6-trifluorophenyl group, 3,4,5-trifluorophenyl group, 2,3,4,5,6-pentafluorophenyl group, 2-chlorophenyl group, 3-chlorophenyl group, 4-chlorophenyl group, 3-chloro-1-naphthyl group, 4-chloro-1-naphthyl group, 4-chloro-2-naphthyl group, 2,3-dichlorophenyl group, 2,4-dichlorophenyl group, 2,5-dichlorophenyl group, 2,6-dichlorophenyl group, 3,4-dichlorophenyl group, 3,5-dichlorophenyl group, 4-chloro-2-fluorophenyl group, 4-chloro-3-fluorophenyl group, 4-chloro-2,3-difluorophenyl group, 4-chloro-2,5-difluorophenyl group, 4-chloro-2,6-difluorophenyl group, 4-chloro-3,5-difluorophenyl group, 3-bromophenyl group, 4-bromophenyl group, 4-iodo phenyl group, 2-methylphenyl group, 3-methylphenyl group, 4-methylphenyl group, 3-fluoro-4-methylphenyl group, 2-ethylphenyl group, 3-ethylphenyl group, 4-ethylphenyl group, 4-ethyl-3-fluorophenyl group, 3-propylphenyl group, 4-propylphenyl group, 3-isopropylphenyl group, 4-isopropylphenyl group, 4-butylphenyl group, 4-isobutylphenyl group, 4-sec-butylphenyl group, 3-tert-butylphenyl group, 4-tert-butylphenyl group, 4-pentyl phenyl group, 4-hexylphenyl group, 2-trifluoromethylphenyl group, 3-trifluoromethylphenyl group, 4-trifluoromethylphenyl group, 3-fluoro-4-trifluoromethylphenyl group, 3-difluoromethylphenyl group, 4-difluoromethylphenyl group, 3-trichloromethylphenyl group, 4-trichloromethylphenyl group, 3-dichloromethylphenyl group, 4-dichloromethylphenyl group, 3-(2,2,2-trifluoroethyl)phenyl group, 4-(2,2,2-trifluoroethyl)phenyl group, 3-(2,2,2-trichloroethyl)phenyl group, 4-(2,2,2-trichloroethyl)phenyl group, 2-methoxyphenyl group, 3-methoxyphenyl group, 4-methoxyphenyl group, 3-methoxy-1-naphthyl group, 4-methoxy-1-naphthyl group, 4-methoxy-2-naphthyl group, 2-fluoro-4-methoxyphenyl group, 3-fluoro-4-methoxyphenyl group, 2,3-difluoro-4-methoxyphenyl group, 2,5-difluoro-4-methoxyphenyl group, 2,6-difluoro-4-methoxyphenyl group, 3,5-difluoro-4-methoxyphenyl group, 3-ethoxyphenyl group, 4-ethoxyphenyl group, 3-propoxyphenyl group, 4-propoxyphenyl group, 3-isopropoxyphenyl group, 4-isopropoxyphenyl group, 4-butoxyphenyl group, 4-isobutoxyphenyl group, 4-sec-butoxyphenyl group, 3-tert-butoxyphenyl group, 4-tert-butoxyphenyl group, 4-pentyloxyphenyl group, 4-hexyloxyphenyl group, 3-trifluoromethoxyphenyl group, 4-trifluoromethoxyphenyl group, 2-difluoromethoxyphenyl group, 3-difluoromethoxyphenyl group, 4-difluoromethoxyphenyl group, 4-difluoromethoxy-3-fluorophenyl group, 3-trichloromethoxyphenyl group, 4-trichloromethoxyphenyl group, 3-dichloromethoxyphenyl group or 4-dichloromethoxyphenyl group, etc., preferably a phenyl group, 2-fluorophenyl group, 3-fluorophenyl group, 4-fluorophenyl group, 3,4-difluorophenyl group, 3,5-difluorophenyl group, 3,4,5-trifluorophenyl group, 2-chlorophenyl group, 3-chlorophenyl group, 4-chlorophenyl group, 2,6-dichlorophenyl group, 4-chloro-3-fluorophenyl group, 4-chloro-3,5-difluorophenyl group, 4-bromophenyl group, 4-methylphenyl group, 3-fluoro-4-methylphenyl group, 4-ethylphenyl group, 4-ethyl-3-fluorophenyl group, 4-propylphenyl group, 4-isopropylphenyl group, 4-tert-butylphenyl group, 4-trifluoromethylphenyl group, 3-fluoro-4-trifluoromethylphenyl group, 4-difluoromethylphenyl group, 4-trichloromethylphenyl group, 4-dichloromethylphenyl group, 4-(2,2,2-trifluoroethyl)phenyl group, 4-(2,2,2-trichloroethyl)phenyl group, 4-methoxyphenyl group, 3-fluoro-4-methoxyphenyl group, 4-ethoxyphenyl group, 4-propoxyphenyl group, 4-isopropoxyphenyl group, 4-tert-butoxyphenyl group, 4-trifluoromethoxyphenyl group, 4-difluoromethoxyphenyl group, 4-difluoromethoxy-3-fluorophenyl group, 4-trichloromethoxyphenyl group or 4-dichloromethoxyphenyl group, more preferably a phenyl group, 2-fluorophenyl group, 3-fluorophenyl group, 4-fluorophenyl group, 3,4-difluorophenyl group, 3,5-difluorophenyl group, 2-chlorophenyl group, 3-chlorophenyl group, 4-chlorophenyl group, 2,6-dichlorophenyl group, 4-chloro-3-fluorophenyl group, 4-methylphenyl group, 3-fluoro-4-methylphenyl group, 4-ethylphenyl group, 4-ethyl-3-fluorophenyl group, 4-trifluoromethylphenyl group, 3-fluoro-4-trifluoromethylphenyl group, 4-methoxyphenyl group, 3-fluoro-4-methoxyphenyl group, 4-difluoromethoxyphenyl group or 4-difluoromethoxy-3-fluorophenyl group, particularly preferably a phenyl group, 2-fluorophenyl group, 3-fluorophenyl group, 4-fluorophenyl group, 2-chlorophenyl group, 3-chlorophenyl group, 4-chlorophenyl group, 2,6-dichlorophenyl group or 4-methoxyphenyl group.

The "5- to 6-membered heteroaromatic ring group which may be substituted by a group(s) selected from the group consisting of a halogen atom, $C_1$-$C_6$ alkyl group, halogen $C_1$-$C_6$ alkyl group, $C_1$-$C_6$ alkoxyl group and halogen $C_1$-$C_6$ alkoxyl group" of Z may be mentioned, for example, a pyrrol-1-yl group, furan-2-yl group, furan-3-yl group, thiophen-2-yl group, thiophen-3-yl group, 5-fluorothiophen-2-yl group, 5-chlorothiophen-2-yl group, 5-methylthiophen-2-yl group, 5-ethylthiophen-2-yl group, 5-trifluoromethylthiophen-2-yl group, 5-methoxythiophen-2-yl group, 5-difluoromethoxythiophen-2-yl group, pyrazol-1-yl group, 1-methyl-1H-imidazol-4-yl group, 1-ethyl-1H-imidazol-4-yl group, oxazol-2-yl group, thiazol-2-yl group, pyridin-2-yl group, 5-fluoropyridin-2-yl group, 5-chloropyridin-2-yl group, 5-bromopyridin-2-yl group, 5-methylpyridin-2-yl group, 5-ethylpyridin-2-yl group, 5-propylpyridin-2-yl group, 5-isopropylpyridin-2-yl group, 5-butylpyridin-2-yl group, 5-isobutylpyridin-2-yl group, 5-sec-butylpyridin-2-yl group, 5-tert-butylpyridin-2-yl group, 5-pentylpyridin-2-yl group, 5-hexylpyridin-2-yl group, 5-trifluoromethylpyridin-2-yl group, 5-difluoromethylpyridin-2-yl group, 5-trichloromethylpyridin-2-yl group, 5-dichloromethylpyridin-2-yl group, 5-(2,2,2-trifluoroethyl)pyridin-2-yl group, 5-(2,2,2-trichloroethyl)pyridin-2-yl group, 5-methoxypyridin-2-yl group, 5-ethoxypyridin-2-yl group, 5-propoxypyridin-2-yl group, 5-isopropoxypyridin-2-yl group, 5-tert-butoxypyridin-2-yl group, 5-trifluoromethoxypyridin-2-yl group, 5-difluoromethoxypyridin-2-yl group, 5-trichloromethoxypyridin-2-yl group, 5-dichloromethoxypyridin-2-yl group, pyridin-3-yl group, 6-fluoropyridin-3-yl group, 6-chloropyridin-3-yl group, 6-bromopyridin-3-yl group, 6-methylpyridin-3-yl group, 6-ethylpyridin-3-yl group, 6-propylpyridin-3-yl group, 6-isopropylpyridin-3-yl group, 6-butylpyridin-3-yl group, 6-isobutylpyridin-3-yl group, 6-sec-butylpyridin-3-yl group, 6-tert-butylpyridin-3-yl group, 6-pentylpyridin-3-yl group, 6-hexylpyridin-3-yl group, 6-trifluoromethylpyridin-3-yl group, 6-difluoromethylpyridin-3-yl group, 6-trichloromethylpyridin-3-yl group, 6-dichloromethylpyridin-3-yl group, 6-(2,2,2-trifluoroethyl)pyridin-3-yl group, 6-(2,2,2-trichloroethyl)pyridin-3-yl group, 6-methoxypyridin-3-yl group, 6-ethoxypyridin-3-yl group, 6-propoxypyridin-3-yl group, 6-isopropoxypyridin-3-yl group, 6-tert-butoxypyridin-3-yl group, 6-trifluoromethoxypyridin-3-yl group, 6-difluoromethoxypyridin-3-yl group, 6-trichloromethoxypyridin-3-yl group, 6-dichloromethoxypyridin-3-yl group, pyridin-4-yl group, pyridazin-3-yl group, pyridazin-4-yl group, pyrimidin-2-yl group, pyrimidin-4-yl group, pyrimidin-5-yl group or pyrazin-2-yl group, etc., preferably a thiophen-2-yl group, thiophen-3-yl group, 5-chloro thiophen-2-yl group, 1-methyl-1H-imidazol-4-yl group, thiazol-2-yl group, pyridin-2-yl group, 5-fluoropyridin-2-yl group, 5-chloropyridin-2-yl group, 5-methylpyridin-2-yl group, 5-ethylpyridin-2-yl group, 5-trifluoromethylpyridin-2-yl group, 5-methoxypyridin-2-yl group, 5-difluoromethoxypyridin-2-yl group, pyridin-3-yl group, 6-fluoropyridin-3-yl group, 6-chloropyridin-3-yl group, 6-methylpyridin-3-yl group, 6-ethylpyridin-3-yl group, 6-trifluoromethylpyridin-3-yl group, 6-methoxypyridin-3-yl group, 6-difluoromethoxypyridin-3-yl group, pyridin-4-yl group or pyrimidin-2-yl group, more preferably a thiophen-2-yl group, thiophen-3-yl group, pyridin-2-yl group, 5-fluoropyridin-2-yl group, 5-chloropyridin-2-yl group, 5-methoxypyridin-2-yl group, pyridin-3-yl group, 6-fluoropyridin-3-yl group, 6-chloropyridin-3-yl group, 6-methoxypyridin-3-yl group or pyridin-4-yl group, and particularly preferably a pyridin-2-yl group or pyridin-3-yl group.

Z is preferably a phenyl group, thienyl group, imidazolyl group, thiazolyl group, pyridyl group or pyrimidinyl group each of which may be substituted by a group(s) selected from the group consisting of a halogen atom, $C_1$-$C_4$ alkyl group, halogeno $C_1$-$C_4$ alkyl group, $C_1$-$C_4$ alkoxyl group or halogen $C_1$-$C_4$ alkoxyl group, for example, fluorine atom, chlorine atom, bromine atom, methyl group, ethyl group, propyl group, isopropyl group, tert-butyl group, trifluoromethyl group, difluoromethyl group, trifluoromethyl group, dichloromethyl group, 2,2,2-trifluoroethyl group, 2,2,2-trichloroethyl group, methoxy group, ethoxy group, propoxy group, isopropoxy group, tert-butoxy group, trifluoromethoxy group, difluoromethoxy group, trichloromethoxy group and dichloromethoxy group, more preferably a phenyl group, 2-fluorophenyl group, 3-fluorophenyl group, 4-fluorophenyl group, 3,4-difluorophenyl group, 3,5-difluorophenyl group, 3,4,5-trifluorophenyl group, 2-chlorophenyl group, 3-chlorophenyl group, 4-chlorophenyl group, 2,6-dichlorophenyl group, 4-chloro-3-fluorophenyl group, 4-chloro-3,5-difluorophenyl group, 4-bromophenyl group, 4-methylphenyl group, 3-fluoro-4-methylphenyl group, 4-ethylphenyl group, 4-ethyl-3-fluorophenyl group, 4-propylphenyl group, 4-isopropylphenyl group, 4-tert-butylphenyl group, 4-trifluoromethylphenyl group, 3-fluoro-4-trifluoromethylphenyl group, 4-difluoromethylphenyl group, 4-trichloromethylphenyl group, 4-dichloromethylphenyl group, 4-(2,2,2-trifluoroethyl)phenyl group, 4-(2,2,2-trichloroethyl)phenyl group, 4-methoxyphenyl group, 3-fluoro-4-methoxyphenyl group, 4-ethoxyphenyl group, 4-propoxyphenyl group, 4-isopropoxyphenyl group, 4-tert-butoxyphenyl group, 4-trifluoromethoxyphenyl group, 4-difluoromethoxyphenyl group, 4-difluoromethoxy-3-fluorophenyl group, 4-trichloromethoxyphenyl group, 4-dichloromethoxyphenyl group, thiophen-2-yl group, thiophen-3-yl group, 5-chloro thiophen-2-yl group, 1-methyl-1H-imidazol-4-yl group, thiazol-2-yl group, pyridin-2-yl group, 5-fluoropyridin-2-yl group; 5-chloropyridin-2-yl group, 5-methylpyridin-2-yl group, 5-ethylpyridin-2-yl group, 5-trifluoromethylpyridin-2-yl group, 5-methoxypyridin-2-yl group, 5-difluoromethoxypyridin-2-yl group, pyridin-3-yl group, 6-fluoropyridin-3-yl group, 6-chloropyridin-3-yl group, 6-methylpyridin-3-yl group, 6-ethylpyridin-3-yl group, 6-trifluoromethylpyridin-3-yl group, 6-methoxypyridin-3-yl group, 6-difluoromethoxypyridin-3-yl group, pyridin-4-yl group or pyrimidin-2-yl group, further more preferably a phenyl group, 2-fluorophenyl group, 3-fluorophenyl group, 4-fluorophenyl group, 3,4-difluorophenyl group, 3,5-difluorophenyl group, 2-chlorophenyl group, 3-chlorophenyl group, 4-chlorophenyl group, 2,6-dichlorophenyl group, 4-chloro-3-fluorophenyl group, 4-methylphenyl group, 3-fluoro-4-methylphenyl group, 4-ethylphenyl group, 4-ethyl-3-fluorophenyl group, 4-trifluoromethylphenyl group, 3-fluoro-4-trifluoromethylphenyl group, 4-methoxyphenyl group, 3-fluoro-4-methoxyphenyl group, 4-difluoromethoxyphenyl group, 4-difluoromethoxy-3-fluorophenyl group, thiophen-2-yl group, thiophen-3-yl group, pyridin-2-yl group, 5-fluoropyridin-2-yl group, 5-chloropyridin-2-yl group, 5-methoxypyridin-2-yl group, pyridin-3-yl group, 6-fluoropyridin-3-yl group, 6-chloropyridin-3-yl group, 6-methoxypyridin-3-yl group or pyridin-4-yl group, particularly preferably a phenyl group or pyridyl group each of which may be substituted by a group(s) selected from the group consisting of a halogen atom and $C_1$-$C_4$ alkoxyl group, and, for example, a phenyl group, 2-fluorophenyl group, 3-fluorophenyl group, 4-fluorophenyl group, 2-chlorophenyl group, 3-chlorophenyl group, 4-chlorophenyl group, 2,6-dichlorophenyl group, 4-methoxyphenyl group, pyridin-2-yl group or pyridin-3-yl group.

In the substituent referred to in the present invention, respective atoms or respective rings are also contained. When optical isomers are present in the compound represented by the formula (1) which is an effective ingredient of the present invention, these isomers are also contained in the scope of the present invention, and when proton tautomers are present, these tautomeric isomers are also contained in the scope of the present invention.

The compound represented by the formula (1) which is an effective ingredient of the present invention can be easily converted into a pharmacologically acceptable salt by treating it with an acid. Examples of such a salt include, for example, inorganic acid salts such as hydrochloride, hydrobromide, hydroiodide, nitrate, sulfate or phosphate; or organic acid salts such as acetate, trifluoroacetate, benzoate, oxalate, malonate, succinate, maleate, fumarate, tartrate, citrate, methanesulfonate, ethanesulfonate, trifluoromethanesulfonate, benzenesulfonate, p-toluenesulfonate, glutamate or aspartate, preferably hydrochloride or trifluoroacetate.

The compound represented by the formula (1) which is an effective ingredient of the present invention can be easily converted into a pharmacologically acceptable salt by treating it with a base when $R^1$ is a hydrogen atom. Examples of such a salt include, for example, metal salts such as a sodium salt, a potassium salt, a calcium salt or a magnesium salt, etc.: inorganic salts such as an ammonium salt, etc.: or organic amine salts such as a triethylamine salt or a guanidine salt, etc.

Further, the compound represented by the formula (1) which is an effective ingredient of the present invention or a pharmacologically acceptable salt thereof can be present as a hydrate or solvate, and they are also included in the present invention.

In the compound represented by the formula (1) which is an effective ingredient of the present invention, it is preferably
(1) a compound wherein $R^1$ is a hydrogen atom, methyl group, ethyl group, propyl group, isopropyl group, butyl group, isobutyl group, sec-butyl group, tert-butyl group, pentyl group or hexyl group,
(2) a compound wherein $R^1$ is a hydrogen atom, methyl group, ethyl group, propyl group, isopropyl group, tert-butyl group or hexyl group,
(3) a compound wherein $R^1$ is a hydrogen atom, methyl group, ethyl group, isopropyl group or hexyl group,
(4) a compound wherein $R^2$ and $R^3$ each independently represent a hydrogen atom, methyl group, ethyl group, propyl group or isopropyl group,
(5) a compound wherein $R^2$ and $R^3$ each independently represent a hydrogen atom or methyl group,
(6) a compound wherein $R^2$ and $R^3$ are both hydrogen atoms,
(7) a compound wherein Y is a bicyclic heteroaromatic ring group which may be substituted with a group(s) selected from the group consisting of a halogen atom, $C_1$-$C_4$ alkyl group, halogeno $C_1$-$C_4$ alkyl group, $C_1$-$C_4$ alkoxyl group, halogeno $C_1$-$C_4$ alkoxyl group and $C_1$-$C_4$ alkylthio group, or a group -$Q^1$-$Q^2$ (wherein $Q^1$ represents an arylene group or 5- to 6-membered heteroarylene group, and $Q^2$ represents an aromatic group or 5- to 6-membered ring heterocyclic group each of which may be substituted by a group(s) selected from the group consisting of a halogen atom, hydroxyl group, $C_1$-$C_4$ alkyl group, halogeno $C_1$-$C_4$ alkyl group, $C_1$-$C_4$ alkoxyl group and halogen $C_1$-$C_4$ alkoxyl group),
(8) a compound wherein Y represents a benzofuryl group, benzothienyl group, benzoxazolyl group or benzothiazolyl group each of which may be substituted by a group(s) selected from the group consisting of a halogen atom, $C_1$-$C_4$ alkyl group, halogen $C_1$-$C_4$ alkyl group, $C_1$-$C_4$ alkoxyl group, halogeno $C_1$-$C_4$ alkoxyl group and $C_1$-$C_4$ alkylthio group, or a group -$Q^1$-$Q^2$
wherein $Q^1$ represents a phenylene group, thienylene group, pyridazinylene group or pyrimidinylene group, $Q^2$ represents a phenyl group, thienyl group, pyrazolyl group, oxazolyl group, thiazolyl group, 1,2,4-triazolyl group, pyridyl group, pyridazinyl group, pyrimidinyl group, 4,5-dihydrothiazolyl group, pyrrolidinyl group or piperidinyl group each of which may be substituted by a group(s) selected from the group consisting of a halogen atom, hydroxyl group, $C_1$-$C_4$ alkyl group, halogeno $C_1$-$C_4$ alkyl group, $C_1$-$C_4$ alkoxyl group and halogeno $C_1$-$C_4$ alkoxyl group,
(9) a compound wherein Y represents a benzofuryl group, benzothienyl group, benzoxazolyl group or benzothiazolyl group each of which may be substituted by a group(s) selected from the group consisting of a fluorine atom, chlorine atom, bromine atom, methyl group, ethyl group, propyl group, isopropyl group, tert-butyl group, trifluoromethyl group, difluoromethyl group, trichloromethyl group, dichloromethyl group, 2,2,2-trifluoroethyl group, 2,2,2-trichloroethyl group, methoxy group, ethoxy group, propoxy group, isopropoxy group, tert-butoxy group, trifluoromethoxy group, difluoromethoxy group, trichloromethoxy group, dichloromethoxy group, methylthio group, ethylthio group, propylthio group, isopropylthio group and tert-butylthio group, or a group -$Q^1$-$Q^2$
wherein $Q^1$ represents a phenylene group, thienylene group, pyridazinylene group or pyrimidinylene group, $Q^2$ represents a phenyl group, thienyl group, pyrazolyl group, oxazolyl group, thiazolyl group, 1,2,4-triazolyl group, pyridyl group, pyridazinyl group, pyrimidinyl group, 4,5-dihydrothiazolyl group, pyrrolidinyl group or piperidinyl group each of which may be substituted by a group(s) selected from the group consisting of a fluorine atom, chlorine atom, bromine atom, hydroxyl group, methyl group, ethyl group, propyl group, isopropyl group, tert-butyl group, trifluoromethyl group, difluoromethyl group, trichloromethyl group, dichloromethyl group, 2,2,2-trifluoroethyl group, 2,2,2-trichloroethyl group, methoxy group, ethoxy group, propoxy group, isopropoxy group, tert-butoxy group, trifluoromethoxy group, difluoromethoxy group, trichloromethoxy group and dichloromethoxy group,
(10) a compound wherein Y is a benzofuran-2-yl group, 6-fluorobenzofuran-2-yl group, 5,6-difluorobenzofuran-2-yl group, 6-chlorobenzofuran-2-yl group, 6-chloro-5-fluorobenzofuran-2-yl group, 6-methylbenzofuran-2-yl group, 5-fluoro-6-methylbenzofuran-2-yl group, 6-ethylbenzofuran-2-yl group, 6-ethyl-5-fluorobenzofuran-2-yl group, 6-trifluoromethylbenzofuran-2-yl group, 5-fluoro-6-trifluoromethylbenzofuran-2-yl group, 6-methoxybenzofuran-2-yl group, 5-fluoro-6-methoxybenzofuran-2-yl group, 6-difluoromethoxybenzofuran-2-yl group, 6-difluoromethoxy-5-fluorobenzofuran-2-yl group, 6-methylthiobenzofuran-2-yl group, 5-fluoro-6-methylthiobenzofuran-2-yl group, benzo[b]thiophen-2-yl group, 6-fluorobenzo[b]thiophen-2-yl group, 5,6-difluorobenzo[b]thiophen-2-yl group, 6-chlorobenzo[b]thiophen-2-yl group, 6-chloro-5-fluorobenzo[b]thiophen-2-yl group, 6-bromobenzo[b]thiophen-2-yl group, 6-methylbenzo[b]-thiophen-2-yl group, 5-fluoro-6-methylbenzo[b]thiophen-2-yl group, 6-ethylbenzo[b]-thiophen-2-yl group, 6-ethyl-5-fluorobenzo[b]thiophen-2-yl group, 6-propylbenzo[b]-thiophen-2-yl group, 6-isopropylbenzo[b]thiophen-2-yl group, 6-tert-butylbenzo[b]-thiophen-2-yl group, 6-trifluoromethylbenzo[b]thiophen-2-yl group, 5-fluoro-6-trifluoromethylbenzo[b]thiophen-2-yl group, 6-difluoromethylbenzo[b]thiophen-2-yl group, 6-trichloromethylbenzo[b]thiophen-2-yl group, 6-dichloromethylbenzo[b]thiophen-2-yl group, 6-(2,2,2-trifluoroethyl)benzo[b]thiophen-2-yl group, 6-(2,2,2-trichloroethyl)benzo[b]thiophen-2-yl group, 6-methoxybenzo[b]thiophen-2-yl group, 5-fluoro-6-methoxybenzo[b]thiophen-2-yl group, 6-ethoxybenzo[b]thiophen-2-yl group, 6-propoxybenzo[b]thiophen-2-yl group, 6-isopropoxybenzo[b]thiophen-2-yl group, 6-tert-butoxybenzo[b]thiophen-2-yl group, 6-trifluoromethoxybenzo[b]thiophen-2-yl group, 6-difluoromethoxybenzo[b]thiophen-2-yl group, 6-difluoromethoxy-5-fluorobenzo[b]thiophen-2-yl group, 6-trichloromethoxybenzo[b]thiophen-2-yl group, 6-dichloromethoxybenzo[b]thiophen-2-yl group, 6-methylthiobenzo[b]thiophen-2-yl group, 5-fluoro-6-methylthiobenzo[b]thiophen-2-yl group, 6-ethylthiobenzo[b]thiophen-2-yl group, 6-propylthiobenzo[b]thiophen-2-yl group, 6-isopropylthiobenzo[b]-thiophen-2-yl group, 6-tert-butylthiobenzo[b]thiophen-2-yl group, benzoxazol-2-yl group, 6-chlorobenzoxazol-2-yl group, 6-methoxybenzoxazol-2-yl group, benzothiazol-2-yl group, 6-chlorobenzothiazol-2-yl group, 6-methoxybenzothiazol-2-yl group, biphenyl-3-yl group, biphenyl-4-yl group, 2'-fluorobiphenyl-4-yl group, 3'-fluorobiphenyl-4-yl group, 4'-fluorobiphenyl-4-yl group, 2',4'-difluorobiphenyl-4-yl group, 3',4'-difluorobiphenyl-4-yl group, 2'-chlorobiphenyl-4-yl group, 3'-chlorobiphenyl-4-yl group, 4'-chlorobiphenyl-4-yl group, 2',4'-dichlorobiphenyl-4-yl group, 3',4'-dichlorobiphenyl-4-yl group, 4'-chloro-2'-fluorobiphenyl-4-yl group, 4'-chloro-3'-fluorobiphenyl-4-yl group, 3'-bromobiphenyl-4-yl group, 3'-hydroxybiphenyl-4-yl group, 4'-hydroxybiphenyl-4-yl group, 3'-methylbiphenyl-4-yl group, 3'-ethylbiphenyl-4-yl group, 3'-propylbiphenyl-4-yl group, 3'-isopropylbiphenyl-4-yl group, 3'-tert-butylbiphenyl-4-yl group, 3'-trifluoromethylbiphenyl-4-yl group, 3'-difluoromethylbiphenyl-4-yl group, 3'-trichloromethylbiphenyl-4-yl group, 3'-dichloromethylbiphenyl-4-yl group, 3'-(2,2,2-trifluoroethyl)biphenyl-4-yl group, 3'-(2,2,2-trichloroethyl)biphenyl-4-yl group, 3'-methoxybiphenyl-4-yl group, 3'-ethoxybiphenyl-4-yl group, 3'-propoxybiphenyl-4-yl group, 3'-isopropoxybiphenyl-4-yl group, 3'-tert-butoxybiphenyl-4-yl group, 3'-trifluoromethoxybiphenyl-4-yl group, 3'-difluoromethoxybiphenyl-4-yl group, 3'-trichloromethoxybiphenyl-4-yl group, 3'-dichloromethoxybiphenyl-4-yl group, 4-(thiophen-2-yl)phenyl group, 4-(thiophen-3-yl)phenyl group, 4-(pyrazol-1-yl)phenyl group, 4-(4-fluoropyrazol-1-yl)phenyl group, 4-(4-chloropyrazol-1-yl)phenyl group, 4-(oxazol-2-yl)phenyl group, 4-(oxazol-4-yl)phenyl group, 4-(thiazol-2-yl)phenyl group, 4-(4-fluorothiazol-2-yl)phenyl group, 4-(4-chlorothiazol-2-yl)phenyl group, 4-(5-chlorothiazol-2-yl)phenyl group, 4-(4-methylthiazol-2-yl)phenyl group, 4-(5-methylthiazol-2-yl)phenyl group, 4-(4,5-dimethylthiazol-2-yl)phenyl group, 4-(4-ethylthiazol-2-yl)phenyl group, 4-(4-trifluoromethylthiazol-2-yl)phenyl group, 4-(4-methoxythiazol-2-yl)phenyl group, 4-(4-difluoromethoxythiazol-2-yl)phenyl group, 4-(thiazol-4-yl)phenyl group, 4-(2-fluorothiazol-4-yl)phenyl group, 4-(2-chlorothiazol-4-yl)phenyl group, 4-(2-methylthiazol-4-yl)phenyl group, 4-(2-ethylthiazol-4-yl)phenyl group, 4-(2-trifluoromethylthiazol-4-yl)phenyl group, 4-(2-methoxythiazol-4-yl)phenyl group, 4-(2-difluoromethoxythiazol-4-yl)phenyl group, 4-(thiazol-5-yl)phenyl group, 4-(1,2,4-triazol-1-yl)phenyl group, 4-(pyridin-2-yl)phenyl group, 4-(pyridin-3-yl)phenyl group, 4-(pyridin-4-yl)phenyl group, 4-(pyridazin-3-yl)phenyl group, 4-(pyridazin-4-yl)phenyl group, 4-(pyrimidin-2-yl)phenyl group, 4-(5-fluoropyrimidin-2-yl)phenyl group, 4-(5-chloropyrimidin-2-yl)phenyl group, 4-(5-hydroxypyrimidin-2-yl)phenyl group, 4-(pyrimidin-4-yl)phenyl group, 4-(pyrimidin-5-yl)phenyl group, 4-(4,5-dihydrothiazol-2-yl)phenyl group, 4-(pyrrolidin-1-yl)phenyl group, 4-(piperidin-1-yl)phenyl group, 5-phenylthiophen-2-yl group, 5-(thiazol-2-yl)thiophen-2-yl group, 5-(thiazol-4-yl)thiophen-2-yl group, 6-phenylpyridazin-3-yl group, 6-(thiazol-2-yl)pyridazin-3-yl group, 6-(thiazol-4-yl)pyridazin-3-yl group, 2-phenylpyrimidin-4-yl group, 2-(thiazol-2-yl)pyrimidin-4-yl group or 2-(thiazol-4-yl)pyrimidin-4-yl group,

(11) a compound wherein Y is a benzofuran-2-yl group, 6-fluorobenzofuran-2-yl group, 6-chlorobenzofuran-2-yl group, 6-methoxybenzofuran-2-yl group, benzo[b]thiophen-2-yl group, 6-fluorobenzo[b]thiophen-2-yl group, 5,6-difluorobenzo[b]thiophen-2-yl group, 6-chlorobenzo[b]thiophen-2-yl group, 6-chloro-5-fluorobenzo[b]thiophen-2-yl group, 6-methylbenzo[b]thiophen-2-yl group, 5-fluoro-6-methylbenzo[b]thiophen-2-yl group, 6-ethylbenzo[b]thiophen-2-yl group, 6-ethyl-5-fluorobenzo[b]thiophen-2-yl group, 6-trifluoromethylbenzo[b]thiophen-2-yl group, 5-fluoro-6-trifluoromethylbenzo-[b]thiophen-2-yl group, 6-methoxybenzo[b]thiophen-2-yl group, 5-fluoro-6-methoxybenzo[b]thiophen-2-yl group, 6-difluoromethoxybenzo[b]thiophen-2-yl group, 6-difluoromethoxy-5-fluorobenzo[b]thiophen-2-yl group, 6-methylthiobenzo[b]thiophen-2-yl group, 5-fluoro-6-methylthiobenzo[b]thiophen-2-yl group, biphenyl-4-yl group, 2'-fluorobiphenyl-4-yl group, 3'-fluorobiphenyl-4-yl group, 4'-fluorobiphenyl-4-yl group, 2',4'-difluorobiphenyl-4-yl group, 3',4'-difluorobiphenyl-4-yl group, 2'-chlorobiphenyl-4-yl group, 3'-chlorobiphenyl-4-yl group, 4'-chlorobiphenyl-4-yl group, 4'-chloro-2'-fluorobiphenyl-4-yl group, 4'-chloro-3'-fluorobiphenyl-4-yl group, 4'-hydroxybiphenyl-4-yl group, 3'-methylbiphenyl-4-yl group, 3'-ethylbiphenyl-4-yl group, 3'-trifluoromethylbiphenyl-4-yl group, 3'-methoxybiphenyl-4-yl group, 3'-difluoromethoxybiphenyl-4-yl group, 4-(thiophen-2-yl)phenyl group, 4-(thiophen-3-yl)phenyl group, 4-(pyrazol-1-yl)phenyl group, 4-(oxazol-2-yl)phenyl group, 4-(oxazol-4-yl)phenyl group, 4-(thiazol-2-yl)phenyl group, 4-(4-fluorothiazol-2-yl)phenyl group, 4-(4-chlorothiazol-2-yl)phenyl group, 4-(5-chlorothiazol-2-yl)phenyl group, 4-(5-methylthiazol-2-yl)phenyl group, 4-(4,5-dimethylthiazol-2-yl)phenyl group, 4-(4-trifluoromethylthiazol-2-yl)phenyl group, 4-(thiazol-4-yl)phenyl group, 4-(2-fluorothiazol-4-yl)phenyl group, 4-(2-chlorothiazol-4-yl)phenyl group, 4-(thiazol-5-yl)phenyl group, 4-(1,2,4-triazol-1-yl)phenyl group, 4-(pyridin-2-yl)phenyl group, 4-(pyridazin-3-yl)phenyl group, 4-(pyridazin-4-yl)phenyl group, 4-(pyrimidin-2-yl)phenyl group, 4-(pyrimidin-4-yl)phenyl group, 4-(pyrimidin-5-yl)phenyl group, 4-(4,5-dihydrothiazol-2-yl)phenyl group, 6-phenylpyridazin-3-yl group,

(13) a compound wherein Y is a benzofuryl group or a benzothienyl group each of which may be substituted by a group(s) selected from the group consisting of a halogen atom and $C_1$-$C_4$ alkoxyl group, or a group -$Q^1$-$Q^2$
wherein $Q^1$ represents a phenylene group or pyridazinylene group, $Q^2$ represents a phenyl group, pyrazolyl group, thiazolyl group, 1,2,4-triazolyl group, pyridyl group, pyridazinyl group, pyrimidinyl group or 4,5-dihydrothiazolyl group each of which may be substituted by a group(s) selected from the group consisting of a halogen atom, $C_1$-$C_4$ alkyl group and halogeno $C_1$-$C_4$ alkyl group,

(14) a compound wherein Y is a benzofuran-2-yl group, benzo[b]thiophen-2-yl group, 6-chlorobenzo[b]thiophen-2-yl group, 6-methoxybenzo[b]thiophen-2-yl group, biphenyl-4-yl group, 4'-fluorobiphenyl-4-yl group, 4'-chlorobiphenyl-4-yl group, 4-(pyrazol-1-yl)phenyl group, 4-(thiazol-2-yl)phenyl group, 4-(5-chlorothiazol-2-yl)phenyl group, 4-(5-methylthiazol-2-yl)phenyl group, 4-(4,5-dimethylthiazol-2-yl)phenyl group, 4-(4-trifluoromethylthiazol-2-yl)phenyl group, 4-(thiazol-4-yl)phenyl group, 4-(1,2,4-triazol-1-yl)

phenyl group, 4-(pyridin-2-yl)phenyl group, 4-(pyridazin-4-yl)phenyl group, 4-(pyrimidin-2-yl)phenyl group, 4-(4,5-dihydrothiazol-2-yl)phenyl group or 6-phenylpyridazin-3-yl group,

(15) a compound wherein Z is an aromatic group or 5- to 6-membered heteroaromatic ring group each of which may be substituted by a group(s) selected from the group consisting of a halogen atom, $C_1$-$C_4$ alkyl group, halogeno $C_1$-$C_4$ alkyl group, $C_1$-$C_4$ alkoxyl group and halogeno $C_1$-$C_4$ alkoxyl group,

(16) a compound wherein Z is a phenyl group, thienyl group, imidazolyl group, thiazolyl group, pyridyl group or pyrimidinyl group each of which may be substituted by a group(s) selected from the group consisting of a halogen atom, $C_1$-$C_4$ alkyl group, halogeno $C_1$-$C_4$ alkyl group, $C_1$-$C_4$ alkoxyl group and halogeno $C_1$-$C_4$ alkoxyl group,

(17) a compound wherein Z is a phenyl group, thienyl group, imidazolyl group, thiazolyl group, pyridyl group or pyrimidinyl group each of which may be substituted by a group(s) selected from the group consisting of a fluorine atom, chlorine atom, bromine atom, methyl group, ethyl group, propyl group, isopropyl group, tert-butyl group, trifluoromethyl group, difluoromethyl group, trichloromethyl group, dichloromethyl group, 2,2,2-trifluoroethyl group, 2,2,2-trichloroethyl group, methoxy group, ethoxy group, propoxy group, isopropoxy group, tert-butoxy group, trifluoromethoxy group, difluoromethoxy group, trichloromethoxy group and dichloromethoxy group,

(18) a compound wherein Z is a phenyl group, 2-fluorophenyl group, 3-fluorophenyl group, 4-fluorophenyl group, 3,4-difluorophenyl group, 3,5-difluorophenyl group, 3,4,5-trifluorophenyl group, 2-chlorophenyl group, 3-chlorophenyl group, 4-chlorophenyl group, 2,6-dichlorophenyl group, 4-chloro-3-fluorophenyl group, 4-chloro-3,5-difluorophenyl group, 4-bromophenyl group, 4-methylphenyl group, 3-fluoro-4-methylphenyl group, 4-ethylphenyl group, 4-ethyl-3-fluorophenyl group, 4-propylphenyl group, 4-isopropylphenyl group, 4-tert-butylphenyl group, 4-trifluoromethylphenyl group, 3-fluoro-4-trifluoromethylphenyl group, 4-difluoromethylphenyl group, 4-trichloromethylphenyl group, 4-dichloromethylphenyl group, 4-(2,2,2-trifluoroethyl)phenyl group, 4-(2,2,2-trichloroethyl)phenyl group, 4-methoxyphenyl group, 3-fluoro-4-methoxyphenyl group, 4-ethoxyphenyl group, 4-propoxyphenyl group, 4-isopropoxyphenyl group, 4-tert-butoxyphenyl group, 4-trifluoromethoxyphenyl group, 4-difluoromethoxyphenyl group, 4-difluoromethoxy-3-fluorophenyl group, 4-trichloromethoxyphenyl group, 4-dichloromethoxyphenyl group, thiophen-2-yl group, thiophen-3-yl group, 5-chloro thiophen-2-yl group, 1-methyl-1H-imidazol-4-yl group, thiazol-2-yl group, pyridin-2-yl group, 5-fluoropyridin-2-yl group, 5-chloropyridin-2-yl group, 5-methylpyridin-2-yl group, 5-ethylpyridin-2-yl group, 5-trifluoromethylpyridin-2-yl group, 5-methoxypyridin-2-yl group, 5-difluoromethoxypyridin-2-yl group, pyridin-3-yl group, 6-fluoropyridin-3-yl group, 6-chloropyridin-3-yl group, 6-methylpyridin-3-yl group, 6-ethylpyridin-3-yl group, 6-trifluoromethylpyridin-3-yl group, 6-methoxypyridin-3-yl group, 6-difluoromethoxypyridin-3-yl group, pyridin-4-yl group or pyrimidin-2-yl group,

(19) a compound wherein Z is a phenyl group, 2-fluorophenyl group, 3-fluorophenyl group, 4-fluorophenyl group, 3,4-difluorophenyl group, 3,5-difluorophenyl group, 2-chlorophenyl group, 3-chlorophenyl group, 4-chlorophenyl group, 2,6-dichlorophenyl group, 4-chloro-3-fluorophenyl group, 4-methylphenyl group, 3-fluoro-4-methylphenyl group, 4-ethylphenyl group, 4-ethyl-3-fluorophenyl group, 4-trifluoromethylphenyl group, 3-fluoro-4-trifluoromethylphenyl group, 4-methoxyphenyl group, 3-fluoro-4-methoxyphenyl group, 4-difluoromethoxyphenyl group, 4-difluoromethoxy-3-fluorophenyl group, thiophen-2-yl group, thiophen-3-yl group, pyridin-2-yl group, 5-fluoropyridin-2-yl group, 5-chloropyridin-2-yl group, 5-methoxypyridin-2-yl group, pyridin-3-yl group, 6-fluoropyridin-3-yl group, 6-chloropyridin-3-yl group, 6-methoxypyridin-3-yl group or pyridin-4-yl group,

(20) a compound wherein Z is a phenyl group or pyridyl group each of which may be substituted by a group(s) selected from the group consisting of a halogen atom and $C_1$-$C_4$ alkoxyl group,

(21) a compound wherein Z is a phenyl group, 2-fluorophenyl group, 3-fluorophenyl group, 4-fluorophenyl group, 2-chlorophenyl group, 3-chlorophenyl group, 4-chlorophenyl group, 2,6-dichlorophenyl group, 4-methoxyphenyl group, pyridin-2-yl group or pyridin-3-yl group.

Further, in the above-mentioned groups of (1)-(3), (4)-(6), (7)-(14) and (15)-(21), as the number becomes larger, a more preferred compound is indicated, and a compound obtained by optionally selecting $R^1$ from the groups (1)-(3), $R^2$ and $R^3$ from the groups (4)-(6), Y from the groups (7)-(14), and Z from the group (15)-(21), or by optionally combining them is also a preferred compound.

Such a compound may be mentioned

(22) a compound wherein $R^1$ is a hydrogen atom, methyl group, ethyl group, propyl group, isopropyl group, butyl group, isobutyl group, sec-butyl group, tert-butyl group, pentyl group or hexyl group, $R^2$ and $R^3$ each independently represent a hydrogen atom, methyl group, ethyl group, propyl group or isopropyl group, Y represents a benzofuryl group, benzothienyl group, benzoxazolyl group or benzothiazolyl group each of which may be substituted by a group(s) selected from the group consisting of a fluorine atom, chlorine atom, bromine atom, methyl group, ethyl group, propyl group, isopropyl group, tert-butyl group, trifluoromethyl group, difluoromethyl group, trichloromethyl group, dichloromethyl group, 2,2,2-trifluoroethyl group, 2,2,2-trichloroethyl group, methoxy group, ethoxy group, propoxy group, isopropoxy group, tert-butoxy group, trifluoromethoxy group, difluoromethoxy group, trichloromethoxy group, dichloromethoxy group, methylthio group, ethylthio group, propylthio group, isopropylthio group and tert-butylthio group, or in the group -$Q^1$-$Q^2$ of Y, $Q^1$ is a phenylene group, thienylene group, pyridazinylene group or pyrimidinylene group, and $Q^2$ is a phenyl group, thienyl group, pyrazolyl group, oxazolyl group, thiazolyl group, 1,2,4-triazolyl group, pyridyl group, pyridazinyl group, pyrimidinyl group, 4,5-dihydrothiazolyl group, pyrrolidinyl group or piperidinyl group each of which may be substituted by a group(s) selected from the group consisting of a fluorine atom, chlorine atom, bromine atom, hydroxyl group, methyl group, ethyl group, propyl group, isopropyl group, tert-butyl group, trifluoromethyl group, difluoromethyl group, trichloromethyl group, dichloromethyl group, 2,2,2-trifluoroethyl group, 2,2,2-trichloroethyl group, methoxy group, ethoxy group, propoxy group, isopropoxy group, tert-butoxy group, trifluoromethoxy group, difluoromethoxy group, trichloromethoxy group and dichloromethoxy group, Z is a phenyl group, thienyl group, imidazolyl group, thiazolyl group, pyridyl group or pyrimidinyl group each of which may be substituted by a group(s) selected from the group consisting of a fluorine atom, chlorine atom, bromine atom, methyl group, ethyl group, propyl group, isopropyl group, tert-butyl group, trifluoromethyl group, difluoromethyl group, trichloromethyl group, dichloromethyl group, 2,2,2-trifluoroethyl group, 2,2,2-trichloroethyl group, methoxy group, ethoxy group, propoxy group, isopropoxy group, tert-butoxy group, trifluoromethoxy group, difluoromethoxy group, trichloromethoxy group and dichloromethoxy group,
(23) a compound wherein $R^1$ is a hydrogen atom, methyl group, ethyl group, propyl group, isopropyl group, butyl group, isobutyl group, sec-butyl group, tert-butyl group, pentyl group or hexyl group, $R^2$ and $R^3$ each independently represent a hydrogen atom or methyl group, Y is a benzofuran-2-yl group, 6-fluorobenzofuran-2-yl group, 6-chlorobenzofuran-2-yl group, 6-methoxybenzofuran-2-yl group, benzo[b]thiophen-2-yl group, 6-fluorobenzo[b]thiophen-2-yl group, 5,6-difluorobenzo[b]thiophen-2-yl group, 6-chlorobenzo[b]thiophen-2-yl group, 6-chloro-5-fluorobenzo[b]thiophen-2-yl group, 6-methylbenzo[b]thiophen-2-yl group, 5-fluoro-6-methylbenzo[b]thiophen-2-yl group, 6-ethylbenzo[b]thiophen-2-yl group, 6-ethyl-5-fluorobenzo[b]thiophen-2-yl group, 6-trifluoromethylbenzo[b]thiophen-2-yl group, 5-fluoro-6-trifluoromethylbenzo[b]thiophen-2-yl group, 6-methoxybenzo[b]thiophen-2-yl group, 5-fluoro-6-methoxybenzo[b]thiophen-2-yl group, 6-difluoromethoxybenzo[b]thiophen-2-yl group, 6-difluoromethoxy-5-fluorobenzo[b]thiophen-2-yl group, 6-methylthiobenzo[b]thiophen-2-yl group, 5-fluoro-6-methylthiobenzo[b]thiophen-2-yl group, biphenyl-4-yl group, 2'-fluorobiphenyl-4-yl group, 3'-fluorobiphenyl-4-yl group, 4'-fluorobiphenyl-4-yl group, 2',4'-difluorobiphenyl-4-yl group, 3',4'-difluorobiphenyl-4-yl group, 2'-chlorobiphenyl-4-yl group, 3'-chlorobiphenyl-4-yl group, 4'-chlorobiphenyl-4-yl group, 4'-chloro-2'-fluorobiphenyl-4-yl group, 4'-chloro-3'-fluorobiphenyl-4-yl group, 4'-hydroxybiphenyl-4-yl group, 3'-methylbiphenyl-4-yl group, 3'-ethylbiphenyl-4-yl group, 3'-trifluoromethylbiphenyl-4-yl group, 3'-methoxybiphenyl-4-yl group, 3'-difluoromethoxybiphenyl-4-yl group, 4-(thiophen-2-yl)phenyl group, 4-(thiophen-3-yl)phenyl group, 4-(pyrazol-1-yl)phenyl group, 4-(oxazol-2-yl)phenyl group, 4-(oxazol-4-yl)phenyl group, 4-(thiazol-2-yl)phenyl group, 4-(4-fluorothiazol-2-yl)phenyl group, 4-(4-chlorothiazol-2-yl)phenyl group, 4-(5-chlorothiazol-2-yl)phenyl group, 4-(5-methylthiazol-2-yl)phenyl group, 4-(4,5-dimethylthiazol-2-yl)phenyl group, 4-(4-trifluoromethylthiazol-2-yl)phenyl group, 4-(thiazol-4-yl)phenyl group, 4-(2-fluorothiazol-4-yl)phenyl group, 4-(2-chlorothiazol-4-yl)phenyl group, 4-(thiazol-5-yl)phenyl group, 4-(1,2,4-triazol-1-yl)phenyl group, 4-(pyridin-2-yl)phenyl group, 4-(pyridazin-3-yl)phenyl group, 4-(pyridazin-4-yl)phenyl group, 4-(pyrimidin-2-yl)phenyl group, 4-(5-hydroxypyrimidin-2-yl)phenyl group, 4-(pyrimidin-4-yl)phenyl group, 4-(pyrimidin-5-yl)phenyl group, 4-(4,5-dihydrothiazol-2-yl)phenyl group, 6-phenylpyridazin-3-yl group, 6-(thiazol-2-yl)pyridazin-3-yl group or 6-(thiazol-4-yl)pyridazin-3-yl group, Z is a phenyl group, 2-fluorophenyl group, 3-fluorophenyl group, 4-fluorophenyl group, 3,4-difluorophenyl group, 3,5-difluorophenyl group, 3,4,5-trifluorophenyl group, 2-chlorophenyl group, 3-chlorophenyl group, 4-chlorophenyl group, 2,6-dichlorophenyl group, 4-chloro-3-fluorophenyl group, 4-chloro-3,5-difluorophenyl group, 4-bromophenyl group, 4-methylphenyl group, 3-fluoro-4-methylphenyl group, 4-ethylphenyl group, 4-ethyl-3-fluorophenyl group, 4-propylphenyl group, 4-isopropylphenyl group, 4-tert-butylphenyl group, 4-trifluoromethylphenyl group, 3-fluoro-4-trifluoromethylphenyl group, 4-difluoromethylphenyl group, 4-trichloromethylphenyl group, 4-dichloromethylphenyl group, 4-(2,2,2-trifluoroethyl)phenyl group, 4-(2,2,2-trichloroethyl)phenyl group, 4-methoxyphenyl group, 3-fluoro-4-methoxyphenyl group, 4-ethoxyphenyl group, 4-propoxyphenyl group, 4-isopropoxyphenyl group, 4-tert-butoxyphenyl group, 4-trifluoromethoxyphenyl group, 4-difluoromethoxyphenyl group, 4-difluoromethoxy-3-fluorophenyl group, 4-trichloromethoxyphenyl group, 4-dichloromethoxyphenyl group, thiophen-2-yl group, thiophen-3-yl group, 5-chloro thiophen-2-yl group, 1-methyl-1H-imidazol-4-yl group, thiazol-2-yl group, pyridin-2-yl group, 5-fluoropyridin-2-yl group, 5-chloropyridin-2-yl group, 5-methylpyridin-2-yl group, 5-ethylpyridin-2-yl group, 5-trifluoromethylpyridin-2-yl group, 5-methoxypyridin-2-yl group, 5-difluoromethoxypyridin-2-yl group, pyridin-3-yl group, 6-fluoropyridin-3-yl group, 6-chloropyridin-3-yl group, 6-methylpyridin-3-yl group, 6-ethylpyridin-3-yl group, 6-trifluoromethylpyridin-3-yl group, 6-methoxypyridin-3-yl group, 6-difluoromethoxypyridin-3-yl group, pyridin-4-yl group or pyrimidin-2-yl group,

(24) a compound wherein $R^1$ is a hydrogen atom, methyl group, ethyl group, propyl group, isopropyl group, tert-butyl group or hexyl group, $R^2$ and $R^3$ each independently represent a hydrogen atom or methyl group, Y is a benzofuran-2-yl group, 6-fluorobenzofuran-2-yl group, 6-chlorobenzofuran-2-yl group, 6-methoxybenzofuran-2-yl group, benzo[b]thiophen-2-yl group, 6-fluorobenzo[b]thiophen-2-yl group, 6-chlorobenzo[b]thiophen-2-yl group, 6-methoxybenzo[b]thiophen-2-yl group, biphenyl-4-yl group, 2'-fluorobiphenyl-4-yl group, 3'-fluorobiphenyl-4-yl group, 4'-fluorobiphenyl-4-yl group, 2'-chlorobiphenyl-4-yl group, 3'-chlorobiphenyl-4-yl group, 4'-chlorobiphenyl-4-yl group, 3'-methylbiphenyl-4-yl group, 3'-trifluoromethylbiphenyl-4-yl group, 4-(thiophen-2-yl)phenyl group, 4-(thiophen-3-yl)phenyl group, 4-(pyrazol-1-yl)phenyl group, 4-(oxazol-2-yl)phenyl group, 4-(oxazol-4-yl)phenyl group, 4-(thiazol-2-yl)phenyl group, 4-(4-fluorothiazol-2-yl)phenyl group, 4-(4-chlorothiazol-2-yl)phenyl group, 4-(5-chlorothiazol-2-yl)phenyl group, 4-(5-methylthiazol-2-yl)phenyl group, 4-(4,5-dimethylthiazol-2-yl)phenyl group, 4-(4-trifluoromethylthiazol-2-yl)phenyl group, 4-(thiazol-4-yl)phenyl group, 4-(2-fluorothiazol-4-yl)phenyl group, 4-(2-chlorothiazol-4-yl)phenyl group, 4-(thiazol-5-yl)phenyl group, 4-(1,2,4-triazol-1-yl)phenyl group, 4-(pyridin-2-yl)phenyl group, 4-(pyridazin-3-yl)phenyl group, 4-(pyridazin-4-yl)phenyl group, 4-(pyrimidin-2-yl)phenyl group, 4-(pyrimidin-4-yl)phenyl group, 4-(pyrimidin-5-yl)phenyl group, 4-(4,5-dihydrothiazol-2-yl)phenyl group, 6-phenylpyridazin-3-yl group, Z is a phenyl group, 2-fluorophenyl group, 3-fluorophenyl group, 4-fluorophenyl group, 3,4-difluorophenyl group, 3,5-difluorophenyl group, 2-chlorophenyl group, 3-chlorophenyl group, 4-chlorophenyl group, 2,6-dichlorophenyl group, 4-chloro-3-fluorophenyl group, 4-methylphenyl group, 3-fluoro-4-methylphenyl group, 4-ethylphenyl group, 4-ethyl-3-fluorophenyl group, 4-trifluoromethylphenyl group, 3-fluoro-4-trifluoromethylphenyl group, 4-methoxyphenyl group, 3-fluoro-4-methoxyphenyl group, 4-difluoromethoxyphenyl group, 4-difluoromethoxy-3-fluorophenyl group, thiophen-2-yl group, thiophen-3-yl group, pyridin-2-yl group, 5-fluoropyridin-2-yl group, 5-chloropyridin-2-yl group, 5-methoxypyridin-2-yl group, pyridin-3-yl group, 6-fluoropyridin-3-yl group, 6-chloropyridin-3-yl group, 6-methoxypyridin-3-yl group or pyridin-4-yl group,

(25) a compound wherein $R^1$ is a hydrogen atom, methyl group, ethyl group, isopropyl group or hexyl group, $R^2$ and $R^3$ are both hydrogen atoms, Y is a benzofuran-2-yl group, 6-fluorobenzofuran-2-yl group, 6-chlorobenzofuran-2-yl group, 6-methoxybenzofuran-2-yl group, benzo[b]thiophen-2-yl group, 6-fluorobenzo[b]thiophen-2-yl group, 6-chlorobenzo[b]thiophen-2-yl group, 6-methoxybenzo[b]thiophen-2-yl group, biphenyl-4-yl group, 2'-fluorobiphenyl-4-yl group, 3'-fluorobiphenyl-4-yl group, 4'-fluorobiphenyl-4-yl group, 2'-chlorobiphenyl-4-yl group, 3'-chlorobiphenyl-4-yl group, 4'-chlorobiphenyl-4-yl group, 3'-methylbiphenyl-4-yl group, 3'-trifluoromethylbiphenyl-4-yl group, 4-(thiophen-2-yl)phenyl group, 4-(thiophen-3-yl)phenyl group, 4-(pyrazol-1-yl)phenyl group, 4-(oxazol-2-yl)phenyl group, 4-(oxazol-4-yl)phenyl group, 4-(thiazol-2-yl)phenyl group, 4-(4-fluorothiazol-2-yl)phenyl group, 4-(4-chlorothiazol-2-yl)phenyl group, 4-(5-chlorothiazol-2-yl)phenyl group, 4-(5-methylthiazol-2-yl)phenyl group, 4-(4,5-dimethylthiazol-2-yl)phenyl group, 4-(4-trifluoromethylthiazol-2-yl)phenyl group, 4-(thiazol-4-yl)phenyl group, 4-(2-fluorothiazol-4-yl)phenyl group, 4-(2-chlorothiazol-4-yl)phenyl group, 4-(thiazol-5-yl)phenyl group, 4-(1,2,4-triazol-1-yl)phenyl group, 4-(pyridin-2-yl)phenyl group, 4-(pyridazin-3-yl)phenyl group, 4-(pyridazin-4-yl)phenyl group, 4-(pyrimidin-2-yl)phenyl group, 4-(pyrimidin-4-yl)phenyl group, 4-(pyrimidin-5-yl)phenyl group, 4-(4,5-dihydrothiazol-2-yl)phenyl group, 6-phenylpyridazin-3-yl group, Z is a phenyl group, 2-fluorophenyl group, 3-fluorophenyl group, 4-fluorophenyl group, 2-chlorophenyl group, 3-chlorophenyl group, 4-chlorophenyl group, 2,6-dichlorophenyl group, 4-methoxyphenyl group, pyridin-2-yl group or pyridin-3-yl group, or

(26) a compound wherein $R^1$ is a hydrogen atom, methyl group, ethyl group, isopropyl group or hexyl group, $R^2$ and $R^3$ are both hydrogen atoms, Y is a benzofuran-2-yl group, benzo[b]thiophen-2-yl group, 6-chlorobenzo-[b]thiophen-2-yl group, 6-methoxybenzo[b]thiophen-2-yl group, biphenyl-4-yl group, 4'-fluorobiphenyl-4-yl group, 4'-chlorobiphenyl-4-yl group, 4-(pyrazol-1-yl)phenyl group, 4-(thiazol-2-yl)phenyl group, 4-(5-chlorothiazol-2-yl)phenyl group, 4-(5-methylthiazol-2-yl)phenyl group, 4-(4,5-dimethylthiazol-2-yl)phenyl group, 4-(4-trifluoromethylthiazol-2-yl)phenyl group, 4-(thiazol-4-yl)phenyl group, 4-(1,2,4-triazol-1-yl)phenyl group, 4-(pyridin-2-yl)phenyl group, 4-(pyridazin-4-yl)phenyl group, 4-(pyrimidin-2-yl)phenyl group, 4-(4,5-dihydrothiazol-2-yl)phenyl group or 6-phenylpyridazin-3-yl group, Z is a phenyl group, 2-fluorophenyl group, 3-fluorophenyl group, 4-fluorophenyl group, 2-chlorophenyl group, 3-chlorophenyl group, 4-chlorophenyl group, 2,6-dichlorophenyl group, 4-methoxyphenyl group, pyridin-2-yl group or pyridin-3-yl group.

(27) The pyridylaminoacetic acid compound is
{6-[(benzofuran-2-ylmethyl)(pyridin-3-ylsulfonyl)aminomethyl]pyridin-2-ylamino}-acetic acid,
{6-[(benzo[b]thiophen-2-ylmethyl)(pyridin-3-ylsulfonyl)aminomethyl]pyridin-2-ylamino}acetic acid,
{6-[(6-chlorobenzo[b]thiophen-2-ylmethyl)(pyridin-3-ylsulfonyl)aminomethyl]pyridin-2-ylamino}acetic acid,
{6-[(6-methoxybenzo[b]thiophen-2-ylmethyl)(pyridin-3-ylsulfonyl)aminomethyl]-pyridin-2-ylamino}acetic acid,
{6-[(biphenyl-4-ylmethyl)(pyridin-2-ylsulfonyl)aminomethyl]pyridin-2-ylamino}acetic acid,
{6-[(biphenyl-4-ylmethyl)(pyridin-3-ylsulfonyl)aminomethyl]pyridin-2-ylamino}acetic acid,
{6-[(4'-fluorobiphenyl-4-ylmethyl)(pyridin-3-ylsulfonyl)aminomethyl]pyridin-2-ylamino}acetic acid,
{6-[(4'-chlorobiphenyl-4-ylmethyl)(pyridin-3-ylsulfonyl)aminomethyl]pyridin-2-ylamino}acetic acid,
(6-{(4-fluorobenzenesulfonyl)[4-(pyrazol-1-yl)benzyl]aminomethyl}pyridin-2-ylamino)acetic acid,
(6-{[4-(pyrazol-1-yl)benzyl](pyridin-2-ylsulfonyl)aminomethyl}pyridin-2-ylamino)acetic acid,
(6-{[4-(pyrazol-1-yl)benzyl](pyridin-3-ylsulfonyl)aminomethyl}pyridin-2-ylamino)acetic acid,
isopropyl(6-{(pyridin-2-ylsulfonyl)[4-(thiazol-2-yl)benzyl]aminomethyl}pyridin-2-ylamino)acetate,
ethyl(6-{(pyridin-2-ylsulfonyl)[4-(thiazol-2-yl)benzyl]aminomethyl}pyridin-2-ylamino)acetate,
(6-{(4-fluorobenzenesulfonyl)[4-(thiazol-2-yl)benzyl]aminomethyl}pyridin-2-ylamino)acetic acid,
(6-{(pyridin-2-ylsulfonyl)[4-(thiazol-2-yl)benzyl]aminomethyl}pyridin-2-ylamino)acetic acid,
(6-{(pyridin-3-ylsulfonyl)[4-(thiazol-2-yl)benzyl]aminomethyl}pyridin-2-ylamino)acetic acid,
(6-{(pyridin-2-ylsulfonyl)[4-(4-trifluoromethylthiazol-2-yl)benzyl]aminomethyl}-pyridin-2-ylamino)acetic acid,
(6-{(pyridin-2-ylsulfonyl)[4-(thiazol-4-yl)benzyl]aminomethyl}pyridin-2-ylamino)acetic acid,
(6-{[4-(pyridin-2-yl)benzyl](pyridin-3-ylsulfonyl)aminomethyl}pyridin-2-ylamino)acetic acid,
(6-{[4-(pyridazin-4-yl)benzyl](pyridin-3-ylsulfonyl)aminomethyl}pyridin-2-ylamino)acetic acid,
(6-{(pyridin-2-ylsulfonyl)[4-(pyrimidin-2-yl)benzyl]aminomethyl}pyridin-2-ylamino)acetic acid,
(6-{[4-(4,5-dihydrothiazol-2-yl)benzyl](4-fluorobenzenesulfonyl)aminomethyl}pyridin-2-ylamino)acetic acid,
{6-[(6-phenylpyridazin-3-ylmethyl)(pyridin-3-ylsulfonyl)aminomethyl]pyridin-2-ylamino}acetic acid,
hexyl(6-{(pyridin-2-ylsulfonyl)[4-(thiazol-2-yl)benzyl]aminomethyl}pyridin-2-ylamino)acetate,
(6-{[4-(5-chlorothiazol-2-yl)benzyl](pyridin-2-ylsulfonyl)aminomethyl}pyridin-2-ylamino)acetic acid,
(6-{[4-(5-methylthiazol-2-yl)benzyl](pyridin-2-ylsulfonyl)aminomethyl}pyridin-2-ylamino)acetic acid,
(6-{[4-(4,5-dimethylthiazol-2-yl)benzyl](pyridin-2-ylsulfonyl)aminomethyl}pyridin-2-ylamino)acetic acid,
(6-{(pyridin-3-ylsulfonyl)[4-(1,2,4-triazol-1-yl)benzyl]aminomethyl}pyridin-2-ylamino)acetic acid,
(6-{[4-(pyrazol-1-yl)benzyl](pyridin-3-ylsulfonyl)aminomethyl}pyridin-2-ylamino)ethyl acetate or
(6-{[4-(pyrazol-1-yl)benzyl](pyridin-3-ylsulfonyl)aminomethyl}pyridin-2-ylamino)isopropyl acetate, etc.

As the preferred compound having the formula (1) which is an effective ingredient of the medical composition of the present invention, the compounds shown in Table 1 can be specifically exemplified.

[Chemical formula 2]

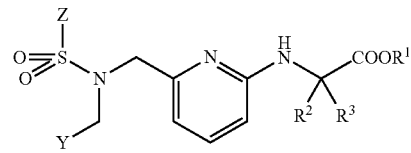

(1)

TABLE 1

| Compound No. | $R^1$ | $R^2$ | $R^3$ | Y | Z |
|---|---|---|---|---|---|
| 1 | H | H | H | Bfu-2-yl | Ph |
| 2 | H | H | H | Bfu-2-yl | 2-F—Ph |
| 3 | H | H | H | Bfu-2-yl | 3-F—Ph |

TABLE 1-continued

| Compound No. | R¹ | R² | R³ | Y | Z |
|---|---|---|---|---|---|
| 4 | H | H | H | Bfu-2-yl | 4-F—Ph |
| 5 | H | H | H | Bfu-2-yl | 3,4-diF—Ph |
| 6 | H | H | H | Bfu-2-yl | 3,5-diF—Ph |
| 7 | H | H | H | Bfu-2-yl | 2-Cl—Ph |
| 8 | H | H | H | Bfu-2-yl | 3-Cl—Ph |
| 9 | H | H | H | Bfu-2-yl | 4-Cl—Ph |
| 10 | H | H | H | Bfu-2-yl | 2,6-diCl—Ph |
| 11 | H | H | H | Bfu-2-yl | 4-Cl-3-F—Ph |
| 12 | H | H | H | Bfu-2-yl | 4-Me—Ph |
| 13 | H | H | H | Bfu-2-yl | 3-F-4-Me—Ph |
| 14 | H | H | H | Bfu-2-yl | 4-Et—Ph |
| 15 | H | H | H | Bfu-2-yl | 4-Et-3-F—Ph |
| 16 | H | H | H | Bfu-2-yl | 4-CF₃—Ph |
| 17 | H | H | H | Bfu-2-yl | 3-F-4-CF₃—Ph |
| 18 | H | H | H | Bfu-2-yl | 4-OMe—Ph |
| 19 | H | H | H | Bfu-2-yl | 3-F-4-OMe—Ph |
| 20 | H | H | H | Bfu-2-yl | 4-OCHF₂—Ph |
| 21 | H | H | H | Bfu-2-yl | 4-OCHF₂-3-F—Ph |
| 22 | H | H | H | Bfu-2-yl | Th-2-yl |
| 23 | H | H | H | Bfu-2-yl | Th-3-yl |
| 24 | H | H | H | Bfu-2-yl | Py-2-yl |
| 25 | H | H | H | Bfu-2-yl | 5-F—Py-2-yl |
| 26 | H | H | H | Bfu-2-yl | 5-Cl—Py-2-yl |
| 27 | H | H | H | Bfu-2-yl | 5-OMe—Py-2-yl |
| 28 | H | H | H | Bfu-2-yl | Py-3-yl |
| 29 | H | H | H | Bfu-2-yl | 6-F—Py-3-yl |
| 30 | H | H | H | Bfu-2-yl | 6-Cl—Py-3-yl |
| 31 | H | H | H | Bfu-2-yl | 6-OMe—Py-3-yl |
| 32 | H | H | H | Bfu-2-yl | Py-4-yl |
| 33 | H | H | H | 6-F-Bfu-2-yl | Ph |
| 34 | H | H | H | 6-F-Bfu-2-yl | 2-F—Ph |
| 35 | H | H | H | 6-F-Bfu-2-yl | 3-F—Ph |
| 36 | H | H | H | 6-F-Bfu-2-yl | 4-F—Ph |
| 37 | H | H | H | 6-F-Bfu-2-yl | 2-Cl—Ph |
| 38 | H | H | H | 6-F-Bfu-2-yl | 3-Cl—Ph |
| 39 | H | H | H | 6-F-Bfu-2-yl | 4-Cl—Ph |
| 40 | H | H | H | 6-F-Bfu-2-yl | 2,6-diCl—Ph |
| 41 | H | H | H | 6-F-Bfu-2-yl | 4-OMe—Ph |
| 42 | H | H | H | 6-F-Bfu-2-yl | Py-2-yl |
| 43 | H | H | H | 6-F-Bfu-2-yl | Py-3-yl |
| 44 | H | H | H | 5,6-diF-Bfu-2-yl | 4-F—Ph |
| 45 | H | H | H | 5,6-diF-Bfu-2-yl | Py-2-yl |
| 46 | H | H | H | 5,6-diF-Bfu-2-yl | Py-3-yl |
| 47 | H | H | H | 6-Cl-Bfu-2-yl | Ph |
| 48 | H | H | H | 6-Cl-Bfu-2-yl | 2-F—Ph |
| 49 | H | H | H | 6-Cl-Bfu-2-yl | 3-F—Ph |
| 50 | H | H | H | 6-Cl-Bfu-2-yl | 4-F—Ph |
| 51 | H | H | H | 6-Cl-Bfu-2-yl | 2-Cl—Ph |
| 52 | H | H | H | 6-Cl-Bfu-2-yl | 3-Cl—Ph |
| 53 | H | H | H | 6-Cl-Bfu-2-yl | 4-Cl—Ph |
| 54 | H | H | H | 6-Cl-Bfu-2-yl | 2,6-diCl—Ph |
| 55 | H | H | H | 6-Cl-Bfu-2-yl | 4-OMe—Ph |
| 56 | H | H | H | 6-Cl-Bfu-2-yl | Py-2-yl |
| 57 | H | H | H | 6-Cl-Bfu-2-yl | Py-3-yl |
| 58 | H | H | H | 6-Cl-5-F-Bfu-2-yl | 4-F—Ph |
| 59 | H | H | H | 6-Cl-5-F-Bfu-2-yl | Py-2-yl |
| 60 | H | H | H | 6-Cl-5-F-Bfu-2-yl | Py-3-yl |
| 61 | H | H | H | 6-Me-Bfu-2-yl | 4-F—Ph |
| 62 | H | H | H | 6-Me-Bfu-2-yl | Py-2-yl |
| 63 | H | H | H | 6-Me-Bfu-2-yl | Py-3-yl |
| 64 | H | H | H | 5-F-6-Me-Bfu-2-yl | 4-F—Ph |
| 65 | H | H | H | 5-F-6-Me-Bfu-2-yl | Py-2-yl |
| 66 | H | H | H | 5-F-6-Me-Bfu-2-yl | Py-3-yl |
| 67 | H | H | H | 6-Et-Bfu-2-yl | 4-F—Ph |
| 68 | H | H | H | 6-Et-Bfu-2-yl | Py-2-yl |
| 69 | H | H | H | 6-Et-Bfu-2-yl | Py-3-yl |
| 70 | H | H | H | 6-Et-5-F-Bfu-2-yl | 4-F—Ph |
| 71 | H | H | H | 6-Et-5-F-Bfu-2-yl | Py-2-yl |
| 72 | H | H | H | 6-Et-5-F-Bfu-2-yl | Py-3-yl |
| 73 | H | H | H | 6-CF₃-Bfu-2-yl | 4-F—Ph |
| 74 | H | H | H | 6-CF₃-Bfu-2-yl | Py-2-yl |
| 75 | H | H | H | 6-CF₃-Bfu-2-yl | Py-3-yl |
| 76 | H | H | H | 5-F-6-CF₃-Bfu-2-yl | 4-F—Ph |
| 77 | H | H | H | 5-F-6-CF₃-Bfu-2-yl | Py-2-yl |
| 78 | H | H | H | 5-F-6-CF₃-Bfu-2-yl | Py-3-yl |
| 79 | H | H | H | 6-OMe-Bfu-2-yl | Ph |
| 80 | H | H | H | 6-OMe-Bfu-2-yl | 2-F—Ph |
| 81 | H | H | H | 6-OMe-Bfu-2-yl | 3-F—Ph |
| 82 | H | H | H | 6-OMe-Bfu-2-yl | 4-F—Ph |
| 83 | H | H | H | 6-OMe-Bfu-2-yl | 2-Cl—Ph |
| 84 | H | H | H | 6-OMe-Bfu-2-yl | 3-Cl—Ph |
| 85 | H | H | H | 6-OMe-Bfu-2-yl | 4-Cl—Ph |
| 86 | H | H | H | 6-OMe-Bfu-2-yl | 2,6-diCl—Ph |
| 87 | H | H | H | 6-OMe-Bfu-2-yl | 4-OMe—Ph |
| 88 | H | H | H | 6-OMe-Bfu-2-yl | Py-2-yl |
| 89 | H | H | H | 6-OMe-Bfu-2-yl | Py-3-yl |
| 90 | H | H | H | 5-F-6-OMe-Bfu-2-yl | 4-F—Ph |
| 91 | H | H | H | 5-F-6-OMe-Bfu-2-yl | Py-2-yl |
| 92 | H | H | H | 5-F-6-OMe-Bfu-2-yl | Py-3-yl |
| 93 | H | H | H | 6-OCHF₂-Bfu-2-yl | 4-F—Ph |
| 94 | H | H | H | 6-OCHF₂-Bfu-2-yl | Py-2-yl |
| 95 | H | H | H | 6-OCHF₂-Bfu-2-yl | Py-3-yl |
| 96 | H | H | H | 6-OCHF₂-5-F-Bfu-2-yl | 4-F—Ph |
| 97 | H | H | H | 6-OCHF₂-5-F-Bfu-2-yl | Py-2-yl |
| 98 | H | H | H | 6-OCHF₂-5-F-Bfu-2-yl | Py-3-yl |
| 99 | H | H | H | 6-SMe-Bfu-2-yl | 4-F—Ph |
| 100 | H | H | H | 6-SMe-Bfu-2-yl | Py-2-yl |
| 101 | H | H | H | 6-SMe-Bfu-2-yl | Py-3-yl |
| 102 | H | H | H | 5-F-6-SMe-Bfu-2-yl | 4-F—Ph |
| 103 | H | H | H | 5-F-6-SMe-Bfu-2-yl | Py-2-yl |
| 104 | H | H | H | 5-F-6-SMe-Bfu-2-yl | Py-3-yl |
| 105 | H | H | H | Bth-2-yl | Ph |
| 106 | H | H | H | Bth-2-yl | 2-F—Ph |
| 107 | H | H | H | Bth-2-yl | 3-F—Ph |
| 108 | H | H | H | Bth-2-yl | 4-F—Ph |
| 109 | H | H | H | Bth-2-yl | 3,4-diF—Ph |
| 110 | H | H | H | Bth-2-yl | 3,5-diF—Ph |
| 111 | H | H | H | Bth-2-yl | 2-Cl—Ph |
| 112 | H | H | H | Bth-2-yl | 3-Cl—Ph |
| 113 | H | H | H | Bth-2-yl | 4-Cl—Ph |
| 114 | H | H | H | Bth-2-yl | 2,6-diCl—Ph |
| 115 | H | H | H | Bth-2-yl | 4-Cl-3-F—Ph |
| 116 | H | H | H | Bth-2-yl | 4-Me—Ph |
| 117 | H | H | H | Bth-2-yl | 3-F-4-Me—Ph |
| 118 | H | H | H | Bth-2-yl | 4-Et—Ph |
| 119 | H | H | H | Bth-2-yl | 4-Et-3-F—Ph |
| 120 | H | H | H | Bth-2-yl | 4-CF₃—Ph |
| 121 | H | H | H | Bth-2-yl | 3-F-4-CF₃—Ph |
| 122 | H | H | H | Bth-2-yl | 4-OMe—Ph |
| 123 | H | H | H | Bth-2-yl | 3-F-4-OMe—Ph |
| 124 | H | H | H | Bth-2-yl | 4-OCHF₂—Ph |
| 125 | H | H | H | Bth-2-yl | 4-OCHF₂-3-F—Ph |
| 126 | H | H | H | Bth-2-yl | Th-2-yl |
| 127 | H | H | H | Bth-2-yl | Th-3-yl |
| 128 | H | H | H | Bth-2-yl | Py-2-yl |
| 129 | H | H | H | Bth-2-yl | 5-F—Py-2-yl |
| 130 | H | H | H | Bth-2-yl | 5-Cl—Py-2-yl |
| 131 | H | H | H | Bth-2-yl | 5-OMe—Py-2-yl |
| 132 | H | H | H | Bth-2-yl | Py-3-yl |
| 133 | H | H | H | Bth-2-yl | 6-F—Py-3-yl |
| 134 | H | H | H | Bth-2-yl | 6-Cl—Py-3-yl |
| 135 | H | H | H | Bth-2-yl | 6-OMe—Py-3-yl |
| 136 | H | H | H | Bth-2-yl | Py-4-yl |
| 137 | H | H | H | 6-F-Bth-2-yl | Ph |
| 138 | H | H | H | 6-F-Bth-2-yl | 2-F—Ph |
| 139 | H | H | H | 6-F-Bth-2-yl | 3-F—Ph |
| 140 | H | H | H | 6-F-Bth-2-yl | 4-F—Ph |
| 141 | H | H | H | 6-F-Bth-2-yl | 2-Cl—Ph |
| 142 | H | H | H | 6-F-Bth-2-yl | 3-Cl—Ph |
| 143 | H | H | H | 6-F-Bth-2-yl | 4-Cl—Ph |
| 144 | H | H | H | 6-F-Bth-2-yl | 2,6-diCl—Ph |
| 145 | H | H | H | 6-F-Bth-2-yl | 4-OMe—Ph |
| 146 | H | H | H | 6-F-Bth-2-yl | Py-2-yl |
| 147 | H | H | H | 6-F-Bth-2-yl | Py-3-yl |
| 148 | H | H | H | 5,6-diF-Bth-2-yl | Ph |
| 149 | H | H | H | 5,6-diF-Bth-2-yl | 2-F—Ph |
| 150 | H | H | H | 5,6-diF-Bth-2-yl | 3-F—Ph |
| 151 | H | H | H | 5,6-diF-Bth-2-yl | 4-F—Ph |
| 152 | H | H | H | 5,6-diF-Bth-2-yl | 2-Cl—Ph |
| 153 | H | H | H | 5,6-diF-Bth-2-yl | 3-Cl—Ph |
| 154 | H | H | H | 5,6-diF-Bth-2-yl | 4-Cl—Ph |
| 155 | H | H | H | 5,6-diF-Bth-2-yl | 2,6-diCl—Ph |

TABLE 1-continued

| Compound No. | R¹ | R² | R³ | Y | Z |
|---|---|---|---|---|---|
| 156 | H | H | H | 5,6-diF-Bth-2-yl | 4-OMe—Ph |
| 157 | H | H | H | 5,6-diF-Bth-2-yl | Py-2-yl |
| 158 | H | H | H | 5,6-diF-Bth-2-yl | Py-3-yl |
| 159 | H | H | H | 6-Cl-Bth-2-yl | Ph |
| 160 | H | H | H | 6-Cl-Bth-2-yl | 2-F—Ph |
| 161 | H | H | H | 6-Cl-Bth-2-yl | 3-F—Ph |
| 162 | H | H | H | 6-Cl-Bth-2-yl | 4-F—Ph |
| 163 | H | H | H | 6-Cl-Bth-2-yl | 3,4-diF—Ph |
| 164 | H | H | H | 6-Cl-Bth-2-yl | 3,5-diF—Ph |
| 165 | H | H | H | 6-Cl-Bth-2-yl | 2-Cl—Ph |
| 166 | H | H | H | 6-Cl-Bth-2-yl | 3-Cl—Ph |
| 167 | H | H | H | 6-Cl-Bth-2-yl | 4-Cl—Ph |
| 168 | H | H | H | 6-Cl-Bth-2-yl | 2,6-diCl—Ph |
| 169 | H | H | H | 6-Cl-Bth-2-yl | 4-Cl-3-F—Ph |
| 170 | H | H | H | 6-Cl-Bth-2-yl | 4-Me—Ph |
| 171 | H | H | H | 6-Cl-Bth-2-yl | 3-F-4-Me—Ph |
| 172 | H | H | H | 6-Cl-Bth-2-yl | 4-Et—Ph |
| 173 | H | H | H | 6-Cl-Bth-2-yl | 4-Et-3-F—Ph |
| 174 | H | H | H | 6-Cl-Bth-2-yl | 4-CF₃—Ph |
| 175 | H | H | H | 6-Cl-Bth-2-yl | 3-F-4-CF₃—Ph |
| 176 | H | H | H | 6-Cl-Bth-2-yl | 4-OMe—Ph |
| 177 | H | H | H | 6-Cl-Bth-2-yl | 3-F-4-OMe—Ph |
| 178 | H | H | H | 6-Cl-Bth-2-yl | 4-OCHF₂—Ph |
| 179 | H | H | H | 6-Cl-Bth-2-yl | 4-OCHF₂-3-F—Ph |
| 180 | H | H | H | 6-Cl-Bth-2-yl | Th-2-yl |
| 181 | H | H | H | 6-Cl-Bth-2-yl | Th-3-yl |
| 182 | H | H | H | 6-Cl-Bth-2-yl | Py-2-yl |
| 183 | H | H | H | 6-Cl-Bth-2-yl | 5-F—Py-2-yl |
| 184 | H | H | H | 6-Cl-Bth-2-yl | 5-Cl—Py-2-yl |
| 185 | H | H | H | 6-Cl-Bth-2-yl | 5-OMe—Py-2-yl |
| 186 | H | H | H | 6-Cl-Bth-2-yl | Py-3-yl |
| 187 | H | H | H | 6-Cl-Bth-2-yl | 6-F—Py-3-yl |
| 188 | H | H | H | 6-Cl-Bth-2-yl | 6-Cl—Py-3-yl |
| 189 | H | H | H | 6-Cl-Bth-2-yl | 6-OMe—Py-3-yl |
| 190 | H | H | H | 6-Cl-Bth-2-yl | Py-4-yl |
| 191 | H | H | H | 6-Cl-5-F-Bth-2-yl | Ph |
| 192 | H | H | H | 6-Cl-5-F-Bth-2-yl | 2-F—Ph |
| 193 | H | H | H | 6-Cl-5-F-Bth-2-yl | 3-F—Ph |
| 194 | H | H | H | 6-Cl-5-F-Bth-2-yl | 4-F—Ph |
| 195 | H | H | H | 6-Cl-5-F-Bth-2-yl | 2-Cl—Ph |
| 196 | H | H | H | 6-Cl-5-F-Bth-2-yl | 3-Cl—Ph |
| 197 | H | H | H | 6-Cl-5-F-Bth-2-yl | 4-Cl—Ph |
| 198 | H | H | H | 6-Cl-5-F-Bth-2-yl | 2,6-diCl—Ph |
| 199 | H | H | H | 6-Cl-5-F-Bth-2-yl | 4-OMe—Ph |
| 200 | H | H | H | 6-Cl-5-F-Bth-2-yl | Py-2-yl |
| 201 | H | H | H | 6-Cl-5-F-Bth-2-yl | Py-3-yl |
| 202 | H | H | H | 6-Br-Bth-2-yl | 4-F—Ph |
| 203 | H | H | H | 6-Br-Bth-2-yl | Py-2-yl |
| 204 | H | H | H | 6-Br-Bth-2-yl | Py-3-yl |
| 205 | H | H | H | 6-Me-Bth-2-yl | Ph |
| 206 | H | H | H | 6-Me-Bth-2-yl | 2-F—Ph |
| 207 | H | H | H | 6-Me-Bth-2-yl | 3-F—Ph |
| 208 | H | H | H | 6-Me-Bth-2-yl | 4-F—Ph |
| 209 | H | H | H | 6-Me-Bth-2-yl | 2-Cl—Ph |
| 210 | H | H | H | 6-Me-Bth-2-yl | 3-Cl—Ph |
| 211 | H | H | H | 6-Me-Bth-2-yl | 4-Cl—Ph |
| 212 | H | H | H | 6-Me-Bth-2-yl | 2,6-diCl—Ph |
| 213 | H | H | H | 6-Me-Bth-2-yl | 4-OMe—Ph |
| 214 | H | H | H | 6-Me-Bth-2-yl | Py-2-yl |
| 215 | H | H | H | 6-Me-Bth-2-yl | Py-3-yl |
| 216 | H | H | H | 5-F-6-Me-Bth-2-yl | Ph |
| 217 | H | H | H | 5-F-6-Me-Bth-2-yl | 2-F—Ph |
| 218 | H | H | H | 5-F-6-Me-Bth-2-yl | 3-F—Ph |
| 219 | H | H | H | 5-F-6-Me-Bth-2-yl | 4-F—Ph |
| 220 | H | H | H | 5-F-6-Me-Bth-2-yl | 2-Cl—Ph |
| 221 | H | H | H | 5-F-6-Me-Bth-2-yl | 3-Cl—Ph |
| 222 | H | H | H | 5-F-6-Me-Bth-2-yl | 4-Cl—Ph |
| 223 | H | H | H | 5-F-6-Me-Bth-2-yl | 2,6-diCl—Ph |
| 224 | H | H | H | 5-F-6-Me-Bth-2-yl | 4-OMe—Ph |
| 225 | H | H | H | 5-F-6-Me-Bth-2-yl | Py-2-yl |
| 226 | H | H | H | 5-F-6-Me-Bth-2-yl | Py-3-yl |
| 227 | H | H | H | 6-Et-Bth-2-yl | Ph |
| 228 | H | H | H | 6-Et-Bth-2-yl | 2-F—Ph |
| 229 | H | H | H | 6-Et-Bth-2-yl | 3-F—Ph |
| 230 | H | H | H | 6-Et-Bth-2-yl | 4-F—Ph |
| 231 | H | H | H | 6-Et-Bth-2-yl | 2-Cl—Ph |
| 232 | H | H | H | 6-Et-Bth-2-yl | 3-Cl—Ph |
| 233 | H | H | H | 6-Et-Bth-2-yl | 4-Cl—Ph |
| 234 | H | H | H | 6-Et-Bth-2-yl | 2,6-diCl—Ph |
| 235 | H | H | H | 6-Et-Bth-2-yl | 4-OMe—Ph |
| 236 | H | H | H | 6-Et-Bth-2-yl | Py-2-yl |
| 237 | H | H | H | 6-Et-Bth-2-yl | Py-3-yl |
| 238 | H | H | H | 6-Et-5-F-Bth-2-yl | Ph |
| 239 | H | H | H | 6-Et-5-F-Bth-2-yl | 2-F—Ph |
| 240 | H | H | H | 6-Et-5-F-Bth-2-yl | 3-F—Ph |
| 241 | H | H | H | 6-Et-5-F-Bth-2-yl | 4-F—Ph |
| 242 | H | H | H | 6-Et-5-F-Bth-2-yl | 2-Cl—Ph |
| 243 | H | H | H | 6-Et-5-F-Bth-2-yl | 3-Cl—Ph |
| 244 | H | H | H | 6-Et-5-F-Bth-2-yl | 4-Cl—Ph |
| 245 | H | H | H | 6-Et-5-F-Bth-2-yl | 2,6-diCl—Ph |
| 246 | H | H | H | 6-Et-5-F-Bth-2-yl | 4-OMe—Ph |
| 247 | H | H | H | 6-Et-5-F-Bth-2-yl | Py-2-yl |
| 248 | H | H | H | 6-Et-5-F-Bth-2-yl | Py-3-yl |
| 249 | H | H | H | 6-Pr-Bth-2-yl | 4-F—Ph |
| 250 | H | H | H | 6-Pr-Bth-2-yl | Py-2-yl |
| 251 | H | H | H | 6-Pr-Bth-2-yl | Py-3-yl |
| 252 | H | H | H | 6-iPr-Bth-2-yl | 4-F—Ph |
| 253 | H | H | H | 6-iPr-Bth-2-yl | Py-2-yl |
| 254 | H | H | H | 6-iPr-Bth-2-yl | Py-3-yl |
| 255 | H | H | H | 6-tBu-Bth-2-yl | 4-F—Ph |
| 256 | H | H | H | 6-tBu-Bth-2-yl | Py-2-yl |
| 257 | H | H | H | 6-tBu-Bth-2-yl | Py-3-yl |
| 258 | H | H | H | 6-CF₃-Bth-2-yl | Ph |
| 259 | H | H | H | 6-CF₃-Bth-2-yl | 2-F—Ph |
| 260 | H | H | H | 6-CF₃-Bth-2-yl | 3-F—Ph |
| 261 | H | H | H | 6-CF₃-Bth-2-yl | 4-F—Ph |
| 262 | H | H | H | 6-CF₃-Bth-2-yl | 2-Cl—Ph |
| 263 | H | H | H | 6-CF₃-Bth-2-yl | 3-Cl—Ph |
| 264 | H | H | H | 6-CF₃-Bth-2-yl | 4-Cl—Ph |
| 265 | H | H | H | 6-CF₃-Bth-2-yl | 2,6-diCl—Ph |
| 266 | H | H | H | 6-CF₃-Bth-2-yl | 4-OMe—Ph |
| 267 | H | H | H | 6-CF₃-Bth-2-yl | Py-2-yl |
| 268 | H | H | H | 6-CF₃-Bth-2-yl | Py-3-yl |
| 269 | H | H | H | 5-F-6-CF₃-Bth-2-yl | Ph |
| 270 | H | H | H | 5-F-6-CF₃-Bth-2-yl | 2-F—Ph |
| 271 | H | H | H | 5-F-6-CF₃-Bth-2-yl | 3-F—Ph |
| 272 | H | H | H | 5-F-6-CF₃-Bth-2-yl | 4-F—Ph |
| 273 | H | H | H | 5-F-6-CF₃-Bth-2-yl | 2-Cl—Ph |
| 274 | H | H | H | 5-F-6-CF₃-Bth-2-yl | 3-Cl—Ph |
| 275 | H | H | H | 5-F-6-CF₃-Bth-2-yl | 4-Cl—Ph |
| 276 | H | H | H | 5-F-6-CF₃-Bth-2-yl | 2,6-diCl—Ph |
| 277 | H | H | H | 5-F-6-CF₃-Bth-2-yl | 4-OMe—Ph |
| 278 | H | H | H | 5-F-6-CF₃-Bth-2-yl | Py-2-yl |
| 279 | H | H | H | 5-F-6-CF₃-Bth-2-yl | Py-3-yl |
| 280 | H | H | H | 6-CHF₂-Bth-2-yl | 4-F—Ph |
| 281 | H | H | H | 6-CHF₂-Bth-2-yl | Py-2-yl |
| 282 | H | H | H | 6-CHF₂-Bth-2-yl | Py-3-yl |
| 283 | H | H | H | 6-CCl₃-Bth-2-yl | 4-F—Ph |
| 284 | H | H | H | 6-CCl₃-Bth-2-yl | Py-2-yl |
| 285 | H | H | H | 6-CCl₃-Bth-2-yl | Py-3-yl |
| 286 | H | H | H | 6-CHCl₂-Bth-2-yl | 4-F—Ph |
| 287 | H | H | H | 6-CHCl₂-Bth-2-yl | Py-2-yl |
| 288 | H | H | H | 6-CHCl₂-Bth-2-yl | Py-3-yl |
| 289 | H | H | H | 6-CH₂CF₃-Bth-2-yl | 4-F—Ph |
| 290 | H | H | H | 6-CH₂CF₃-Bth-2-yl | Py-2-yl |
| 291 | H | H | H | 6-CH₂CF₃-Bth-2-yl | Py-3-yl |
| 292 | H | H | H | 6-CH₂CCl₃-Bth-2-yl | 4-F—Ph |
| 293 | H | H | H | 6-CH₂CCl₃-Bth-2-yl | Py-2-yl |
| 294 | H | H | H | 6-CH₂CCl₃-Bth-2-yl | Py-3-yl |
| 295 | Me | H | H | 6-OMe-Bth-2-yl | 4-F—Ph |
| 296 | Me | H | H | 6-OMe-Bth-2-yl | Py-2-yl |
| 297 | Me | H | H | 6-OMe-Bth-2-yl | Py-3-yl |
| 298 | Et | H | H | 6-OMe-Bth-2-yl | 4-F—Ph |
| 299 | Et | H | H | 6-OMe-Bth-2-yl | Py-2-yl |
| 300 | Et | H | H | 6-OMe-Bth-2-yl | Py-3-yl |
| 301 | Me | Me | Me | 6-OMe-Bth-2-yl | Py-2-yl |
| 302 | Et | Me | Me | 6-OMe-Bth-2-yl | Py-2-yl |
| 303 | H | Me | Me | 6-OMe-Bth-2-yl | 4-F—Ph |
| 304 | H | Me | Me | 6-OMe-Bth-2-yl | Py-2-yl |
| 305 | H | Me | Me | 6-OMe-Bth-2-yl | Py-3-yl |
| 306 | H | Me | H | 6-OMe-Bth-2-yl | 4-F—Ph |
| 307 | H | Me | H | 6-OMe-Bth-2-yl | Py-2-yl |

TABLE 1-continued

| Compound No. | R¹ | R² | R³ | Y | Z |
|---|---|---|---|---|---|
| 308 | H | Me | H | 6-OMe-Bth-2-yl | Py-3-yl |
| 309 | H | H | H | 6-OMe-Bth-2-yl | Ph |
| 310 | H | H | H | 6-OMe-Bth-2-yl | 2-F—Ph |
| 311 | H | H | H | 6-OMe-Bth-2-yl | 3-F—Ph |
| 312 | H | H | H | 6-OMe-Bth-2-yl | 4-F—Ph |
| 313 | H | H | H | 6-OMe-Bth-2-yl | 3,4-diF—Ph |
| 314 | H | H | H | 6-OMe-Bth-2-yl | 3,5-diF—Ph |
| 315 | H | H | H | 6-OMe-Bth-2-yl | 3,4,5-triF—Ph |
| 316 | H | H | H | 6-OMe-Bth-2-yl | 2-Cl—Ph |
| 317 | H | H | H | 6-OMe-Bth-2-yl | 3-Cl—Ph |
| 318 | H | H | H | 6-OMe-Bth-2-yl | 4-Cl—Ph |
| 319 | H | H | H | 6-OMe-Bth-2-yl | 2,6-diCl—Ph |
| 320 | H | H | H | 6-OMe-Bth-2-yl | 4-Cl-3-F—Ph |
| 321 | H | H | H | 6-OMe-Bth-2-yl | 4-Cl-3,5-diF—Ph |
| 322 | H | H | H | 6-OMe-Bth-2-yl | 4-Br—Ph |
| 323 | H | H | H | 6-OMe-Bth-2-yl | 4-Me—Ph |
| 324 | H | H | H | 6-OMe-Bth-2-yl | 3-F-4-Me—Ph |
| 325 | H | H | H | 6-OMe-Bth-2-yl | 4-Et—Ph |
| 326 | H | H | H | 6-OMe-Bth-2-yl | 4-Et-3-F—Ph |
| 327 | H | H | H | 6-OMe-Bth-2-yl | 4-Pr—Ph |
| 328 | H | H | H | 6-OMe-Bth-2-yl | 4-iPr—Ph |
| 329 | H | H | H | 6-OMe-Bth-2-yl | 4-tBu—Ph |
| 330 | H | H | H | 6-OMe-Bth-2-yl | 4-$CF_3$—Ph |
| 331 | H | H | H | 6-OMe-Bth-2-yl | 3-F-4-$CF_3$—Ph |
| 332 | H | H | H | 6-OMe-Bth-2-yl | 4-$CHF_2$—Ph |
| 333 | H | H | H | 6-OMe-Bth-2-yl | 4-$CCl_3$—Ph |
| 334 | H | H | H | 6-OMe-Bth-2-yl | 4-$CHCl_2$—Ph |
| 335 | H | H | H | 6-OMe-Bth-2-yl | 4-$CH_2CF_3$—Ph |
| 336 | H | H | H | 6-OMe-Bth-2-yl | 4-$CH_2CCl_3$—Ph |
| 337 | H | H | H | 6-OMe-Bth-2-yl | 4-OMe—Ph |
| 338 | H | H | H | 6-OMe-Bth-2-yl | 3-F-4-OMe—Ph |
| 339 | H | H | H | 6-OMe-Bth-2-yl | 4-OEt—Ph |
| 340 | H | H | H | 6-OMe-Bth-2-yl | 4-OPr—Ph |
| 341 | H | H | H | 6-OMe-Bth-2-yl | 4-OiPr—Ph |
| 342 | H | H | H | 6-OMe-Bth-2-yl | 4-OtBu—Ph |
| 343 | H | H | H | 6-OMe-Bth-2-yl | 4-$OCF_3$—Ph |
| 344 | H | H | H | 6-OMe-Bth-2-yl | 4-$OCHF_2$—Ph |
| 345 | H | H | H | 6-OMe-Bth-2-yl | 4-$OCHF_2$-3-F—Ph |
| 346 | H | H | H | 6-OMe-Bth-2-yl | 4-$OCCl_3$—Ph |
| 347 | H | H | H | 6-OMe-Bth-2-yl | 4-$OCHCl_2$—Ph |
| 348 | H | H | H | 6-OMe-Bth-2-yl | Th-2-yl |
| 349 | H | H | H | 6-OMe-Bth-2-yl | Th-3-yl |
| 350 | H | H | H | 6-OMe-Bth-2-yl | 5-Cl—Th-2-yl |
| 351 | H | H | H | 6-OMe-Bth-2-yl | 1-Me-1H-Imz-4-yl |
| 352 | H | H | H | 6-OMe-Bth-2-yl | Thz-2-yl |
| 353 | H | H | H | 6-OMe-Bth-2-yl | Py-2-yl |
| 354 | H | H | H | 6-OMe-Bth-2-yl | 5-F—Py-2-yl |
| 355 | H | H | H | 6-OMe-Bth-2-yl | 5-Cl—Py-2-yl |
| 356 | H | H | H | 6-OMe-Bth-2-yl | 5-Me—Py-2-yl |
| 357 | H | H | H | 6-OMe-Bth-2-yl | 5-Et—Py-2-yl |
| 358 | H | H | H | 6-OMe-Bth-2-yl | 5-$CF_3$—Py-2-yl |
| 359 | H | H | H | 6-OMe-Bth-2-yl | 5-OMe—Py-2-yl |
| 360 | H | H | H | 6-OMe-Bth-2-yl | 5-$OCHF_2$—Py-2-yl |
| 361 | H | H | H | 6-OMe-Bth-2-yl | Py-3-yl |
| 362 | H | H | H | 6-OMe-Bth-2-yl | 6-F—Py-3-yl |
| 363 | H | H | H | 6-OMe-Bth-2-yl | 6-Cl—Py-3-yl |
| 364 | H | H | H | 6-OMe-Bth-2-yl | 6-Me—Py-3-yl |
| 365 | H | H | H | 6-OMe-Bth-2-yl | 6-Et—Py-3-yl |
| 366 | H | H | H | 6-OMe-Bth-2-yl | 6-$CF_3$—Py-3-yl |
| 367 | H | H | H | 6-OMe-Bth-2-yl | 6-OMe—Py-3-yl |
| 368 | H | H | H | 6-OMe-Bth-2-yl | 6-$OCHF_2$—Py-3-yl |
| 369 | H | H | H | 6-OMe-Bth-2-yl | Py-4-yl |
| 370 | H | H | H | 6-OMe-Bth-2-yl | Pym-2-yl |
| 371 | H | H | H | 5-F-6-OMe-Bth-2-yl | Ph |
| 372 | H | H | H | 5-F-6-OMe-Bth-2-yl | 2-F—Ph |
| 373 | H | H | H | 5-F-6-OMe-Bth-2-yl | 3-F—Ph |
| 374 | H | H | H | 5-F-6-OMe-Bth-2-yl | 4-F—Ph |
| 375 | H | H | H | 5-F-6-OMe-Bth-2-yl | 2-Cl—Ph |
| 376 | H | H | H | 5-F-6-OMe-Bth-2-yl | 3-Cl—Ph |
| 377 | H | H | H | 5-F-6-OMe-Bth-2-yl | 4-Cl—Ph |
| 378 | H | H | H | 5-F-6-OMe-Bth-2-yl | 2,6-diCl—Ph |
| 379 | H | H | H | 5-F-6-OMe-Bth-2-yl | 4-OMe—Ph |
| 380 | H | H | H | 5-F-6-OMe-Bth-2-yl | Py-2-yl |
| 381 | H | H | H | 5-F-6-OMe-Bth-2-yl | Py-3-yl |
| 382 | H | H | H | 6-OEt-Bth-2-yl | 4-F—Ph |
| 383 | H | H | H | 6-OEt-Bth-2-yl | Py-2-yl |
| 384 | H | H | H | 6-OEt-Bth-2-yl | Py-3-yl |
| 385 | H | H | H | 6-OPr-Bth-2-yl | 4-F—Ph |
| 386 | H | H | H | 6-OPr-Bth-2-yl | Py-2-yl |
| 387 | H | H | H | 6-OPr-Bth-2-yl | Py-3-yl |
| 388 | H | H | H | 6-OiPr-Bth-2-yl | 4-F—Ph |
| 389 | H | H | H | 6-OiPr-Bth-2-yl | Py-2-yl |
| 390 | H | H | H | 6-OiPr-Bth-2-yl | Py-3-yl |
| 391 | H | H | H | 6-OtBu-Bth-2-yl | 4-F—Ph |
| 392 | H | H | H | 6-OtBu-Bth-2-yl | Py-2-yl |
| 393 | H | H | H | 6-OtBu-Bth-2-yl | Py-3-yl |
| 394 | H | H | H | 6-$OCF_3$-Bth-2-yl | 4-F—Ph |
| 395 | H | H | H | 6-$OCF_3$-Bth-2-yl | Py-2-yl |
| 396 | H | H | H | 6-$OCF_3$-Bth-2-yl | Py-3-yl |
| 397 | H | H | H | 6-$OCHF_2$-Bth-2-yl | Ph |
| 398 | H | H | H | 6-$OCHF_2$-Bth-2-yl | 2-F—Ph |
| 399 | H | H | H | 6-$OCHF_2$-Bth-2-yl | 3-F—Ph |
| 400 | H | H | H | 6-$OCHF_2$-Bth-2-yl | 4-F—Ph |
| 401 | H | H | H | 6-$OCHF_2$-Bth-2-yl | 2-Cl—Ph |
| 402 | H | H | H | 6-$OCHF_2$-Bth-2-yl | 3-Cl—Ph |
| 403 | H | H | H | 6-$OCHF_2$-Bth-2-yl | 4-Cl—Ph |
| 404 | H | H | H | 6-$OCHF_2$-Bth-2-yl | 2,6-diCl—Ph |
| 405 | H | H | H | 6-$OCHF_2$-Bth-2-yl | 4-OMe—Ph |
| 406 | H | H | H | 6-$OCHF_2$-Bth-2-yl | Py-2-yl |
| 407 | H | H | H | 6-$OCHF_2$-Bth-2-yl | Py-3-yl |
| 408 | H | H | H | 6-$OCHF_2$-5-F-Bth-2-yl | Ph |
| 409 | H | H | H | 6-$OCHF_2$-5-F-Bth-2-yl | 2-F—Ph |
| 410 | H | H | H | 6-$OCHF_2$-5-F-Bth-2-yl | 3-F—Ph |
| 411 | H | H | H | 6-$OCHF_2$-5-F-Bth-2-yl | 4-F—Ph |
| 412 | H | H | H | 6-$OCHF_2$-5-F-Bth-2-yl | 2-Cl—Ph |
| 413 | H | H | H | 6-$OCHF_2$-5-F-Bth-2-yl | 3-Cl—Ph |
| 414 | H | H | H | 6-$OCHF_2$-5-F-Bth-2-yl | 4-Cl—Ph |
| 415 | H | H | H | 6-$OCHF_2$-5-F-Bth-2-yl | 2,6-diCl—Ph |
| 416 | H | H | H | 6-$OCHF_2$-5-F-Bth-2-yl | 4-OMe—Ph |
| 417 | H | H | H | 6-$OCHF_2$-5-F-Bth-2-yl | Py-2-yl |
| 418 | H | H | H | 6-$OCHF_2$-5-F-Bth-2-yl | Py-3-yl |
| 419 | H | H | H | 6-$OCCl_3$-Bth-2-yl | 4-F—Ph |
| 420 | H | H | H | 6-$OCCl_3$-Bth-2-yl | Py-2-yl |
| 421 | H | H | H | 6-$OCCl_3$-Bth-2-yl | Py-3-yl |
| 422 | H | H | H | 6-$OCHCl_2$-Bth-2-yl | 4-F—Ph |
| 423 | H | H | H | 6-$OCHCl_2$-Bth-2-yl | Py-2-yl |
| 424 | H | H | H | 6-$OCHCl_2$-Bth-2-yl | Py-3-yl |
| 425 | H | H | H | 6-SMe-Bth-2-yl | Ph |
| 426 | H | H | H | 6-SMe-Bth-2-yl | 2-F—Ph |
| 427 | H | H | H | 6-SMe-Bth-2-yl | 3-F—Ph |
| 428 | H | H | H | 6-SMe-Bth-2-yl | 4-F—Ph |
| 429 | H | H | H | 6-SMe-Bth-2-yl | 2-Cl—Ph |
| 430 | H | H | H | 6-SMe-Bth-2-yl | 3-Cl—Ph |
| 431 | H | H | H | 6-SMe-Bth-2-yl | 4-Cl—Ph |
| 432 | H | H | H | 6-SMe-Bth-2-yl | 2,6-diCl—Ph |
| 433 | H | H | H | 6-SMe-Bth-2-yl | 4-OMe—Ph |
| 434 | H | H | H | 6-SMe-Bth-2-yl | Py-2-yl |
| 435 | H | H | H | 6-SMe-Bth-2-yl | Py-3-yl |
| 436 | H | H | H | 5-F-6-SMe-Bth-2-yl | Ph |
| 437 | H | H | H | 5-F-6-SMe-Bth-2-yl | 2-F—Ph |
| 438 | H | H | H | 5-F-6-SMe-Bth-2-yl | 3-F—Ph |
| 439 | H | H | H | 5-F-6-SMe-Bth-2-yl | 4-F—Ph |
| 440 | H | H | H | 5-F-6-SMe-Bth-2-yl | 2-Cl—Ph |
| 441 | H | H | H | 5-F-6-SMe-Bth-2-yl | 3-Cl—Ph |
| 442 | H | H | H | 5-F-6-SMe-Bth-2-yl | 4-Cl—Ph |
| 443 | H | H | H | 5-F-6-SMe-Bth-2-yl | 2,6-diCl—Ph |
| 444 | H | H | H | 5-F-6-SMe-Bth-2-yl | 4-OMe—Ph |
| 445 | H | H | H | 5-F-6-SMe-Bth-2-yl | Py-2-yl |
| 446 | H | H | H | 5-F-6-SMe-Bth-2-yl | Py-3-yl |
| 447 | H | H | H | 6-SEt-Bth-2-yl | 4-F—Ph |
| 448 | H | H | H | 6-SEt-Bth-2-yl | Py-2-yl |
| 449 | H | H | H | 6-SEt-Bth-2-yl | Py-3-yl |
| 450 | H | H | H | 6-SPr-Bth-2-yl | 4-F—Ph |
| 451 | H | H | H | 6-SPr-Bth-2-yl | Py-2-yl |
| 452 | H | H | H | 6-SPr-Bth-2-yl | Py-3-yl |
| 453 | H | H | H | 6-SiPr-Bth-2-yl | 4-F—Ph |
| 454 | H | H | H | 6-SiPr-Bth-2-yl | Py-2-yl |
| 455 | H | H | H | 6-SiPr-Bth-2-yl | Py-3-yl |
| 456 | H | H | H | 6-StBu-Bth-2-yl | 4-F—Ph |
| 457 | H | H | H | 6-StBu-Bth-2-yl | Py-2-yl |
| 458 | H | H | H | 6-StBu-Bth-2-yl | Py-3-yl |
| 459 | H | H | H | Boxz-2-yl | 4-F—Ph |

TABLE 1-continued

| Compound No. | R¹ | R² | R³ | Y | Z |
|---|---|---|---|---|---|
| 460 | H | H | H | Boxz-2-yl | Py-2-yl |
| 461 | H | H | H | Boxz-2-yl | Py-3-yl |
| 462 | H | H | H | 6-Cl-Boxz-2-yl | 4-F—Ph |
| 463 | H | H | H | 6-Cl-Boxz-2-yl | Py-2-yl |
| 464 | H | H | H | 6-Cl-Boxz-2-yl | Py-3-yl |
| 465 | H | H | H | 6-OMe-Boxz-2-yl | 4-F—Ph |
| 466 | H | H | H | 6-OMe-Boxz-2-yl | Py-2-yl |
| 467 | H | H | H | 6-OMe-Boxz-2-yl | Py-3-yl |
| 468 | H | H | H | Bthz-2-yl | 4-F—Ph |
| 469 | H | H | H | Bthz-2-yl | Py-2-yl |
| 470 | H | H | H | Bthz-2-yl | Py-3-yl |
| 471 | H | H | H | 6-Cl-Bthz-2-yl | 4-F—Ph |
| 472 | H | H | H | 6-Cl-Bthz-2-yl | Py-2-yl |
| 473 | H | H | H | 6-Cl-Bthz-2-yl | Py-3-yl |
| 474 | H | H | H | 6-OMe-Bthz-2-yl | 4-F—Ph |
| 475 | H | H | H | 6-OMe-Bthz-2-yl | Py-2-yl |
| 476 | H | H | H | 6-OMe-Bthz-2-yl | Py-3-yl |
| 477 | H | H | H | biPh-3-yl | 4-F—Ph |
| 478 | H | H | H | biPh-3-yl | Py-2-yl |
| 479 | H | H | H | biPh-3-yl | Py-3-yl |
| 480 | Me | H | H | biPh-4-yl | 4-F—Ph |
| 481 | Me | H | H | biPh-4-yl | Py-2-yl |
| 482 | Me | H | H | biPh-4-yl | Py-3-yl |
| 483 | Et | H | H | biPh-4-yl | 4-F—Ph |
| 484 | Et | H | H | biPh-4-yl | Py-2-yl |
| 485 | Et | H | H | biPh-4-yl | Py-3-yl |
| 486 | Me | Me | Me | biPh-4-yl | Py-2-yl |
| 487 | Et | Me | Me | biPh-4-yl | Py-2-yl |
| 488 | H | Me | Me | biPh-4-yl | 4-F—Ph |
| 489 | H | Me | Me | biPh-4-yl | Py-2-yl |
| 490 | H | Me | Me | biPh-4-yl | Py-3-yl |
| 491 | H | Me | H | biPh-4-yl | 4-F—Ph |
| 492 | H | Me | H | biPh-4-yl | Py-2-yl |
| 493 | H | Me | H | biPh-4-yl | Py-3-yl |
| 494 | H | H | H | biPh-4-yl | Ph |
| 495 | H | H | H | biPh-4-yl | 2-F—Ph |
| 496 | H | H | H | biPh-4-yl | 3-F—Ph |
| 497 | H | H | H | biPh-4-yl | 4-F—Ph |
| 498 | H | H | H | biPh-4-yl | 3,4-diF—Ph |
| 499 | H | H | H | biPh-4-yl | 3,5-diF—Ph |
| 500 | H | H | H | biPh-4-yl | 3,4,5-triF—Ph |
| 501 | H | H | H | biPh-4-yl | 2-Cl—Ph |
| 502 | H | H | H | biPh-4-yl | 3-Cl—Ph |
| 503 | H | H | H | biPh-4-yl | 4-Cl—Ph |
| 504 | H | H | H | biPh-4-yl | 2,6-diCl—Ph |
| 505 | H | H | H | biPh-4-yl | 4-Cl-3-F—Ph |
| 506 | H | H | H | biPh-4-yl | 4-Cl-3,5-diF—Ph |
| 507 | H | H | H | biPh-4-yl | 4-Br—Ph |
| 508 | H | H | H | biPh-4-yl | 4-Me—Ph |
| 509 | H | H | H | biPh-4-yl | 3-F-4-Me—Ph |
| 510 | H | H | H | biPh-4-yl | 4-Et—Ph |
| 511 | H | H | H | biPh-4-yl | 4-Et-3-F—Ph |
| 512 | H | H | H | biPh-4-yl | 4-Pr—Ph |
| 513 | H | H | H | biPh-4-yl | 4-iPr—Ph |
| 514 | H | H | H | biPh-4-yl | 4-tBu—Ph |
| 515 | H | H | H | biPh-4-yl | 4-$CF_3$—Ph |
| 516 | H | H | H | biPh-4-yl | 3-F-4-$CF_3$—Ph |
| 517 | H | H | H | biPh-4-yl | 4-$CHF_2$—Ph |
| 518 | H | H | H | biPh-4-yl | 4-$CCl_3$—Ph |
| 519 | H | H | H | biPh-4-yl | 4-$CHCl_2$—Ph |
| 520 | H | H | H | biPh-4-yl | 4-$CH_2CF_3$—Ph |
| 521 | H | H | H | biPh-4-yl | 4-$CH_2CCl_3$—Ph |
| 522 | H | H | H | biPh-4-yl | 4-OMe—Ph |
| 523 | H | H | H | biPh-4-yl | 3-F-4-OMe—Ph |
| 524 | H | H | H | biPh-4-yl | 4-OEt—Ph |
| 525 | H | H | H | biPh-4-yl | 4-OPr—Ph |
| 526 | H | H | H | biPh-4-yl | 4-OiPr—Ph |
| 527 | H | H | H | biPh-4-yl | 4-OtBu—Ph |
| 528 | H | H | H | biPh-4-yl | 4-$OCF_3$—Ph |
| 529 | H | H | H | biPh-4-yl | 4-$OCHF_2$—Ph |
| 530 | H | H | H | biPh-4-yl | 4-$OCHF_2$-3-F—Ph |
| 531 | H | H | H | biPh-4-yl | 4-$OCCl_3$—Ph |
| 532 | H | H | H | biPh-4-yl | 4-$OCHCl_2$—Ph |
| 533 | H | H | H | biPh-4-yl | Th-2-yl |
| 534 | H | H | H | biPh-4-yl | Th-3-yl |
| 535 | H | H | H | biPh-4-yl | 5-Cl—Th-2-yl |
| 536 | H | H | H | biPh-4-yl | 1-Me—1H-Imz-4-yl |
| 537 | H | H | H | biPh-4-yl | Thz-2-yl |
| 538 | H | H | H | biPh-4-yl | Py-2-yl |
| 539 | H | H | H | biPh-4-yl | 5-F—Py-2-yl |
| 540 | H | H | H | biPh-4-yl | 5-Cl—Py-2-yl |
| 541 | H | H | H | biPh-4-yl | 5-Me—Py-2-yl |
| 542 | H | H | H | biPh-4-yl | 5-Et—Py-2-yl |
| 543 | H | H | H | biPh-4-yl | 5-$CF_3$—Py-2-yl |
| 544 | H | H | H | biPh-4-yl | 5-OMe—Py-2-yl |
| 545 | H | H | H | biPh-4-yl | 5-$OCHF_2$—Py-2-yl |
| 546 | H | H | H | biPh-4-yl | Py-3-yl |
| 547 | H | H | H | biPh-4-yl | 6-F—Py-3-yl |
| 548 | H | H | H | biPh-4-yl | 6-Cl—Py-3-yl |
| 549 | H | H | H | biPh-4-yl | 6-Me—Py-3-yl |
| 550 | H | H | H | biPh-4-yl | 6-Et—Py-3-yl |
| 551 | H | H | H | biPh-4-yl | 6-$CF_3$—Py-3-yl |
| 552 | H | H | H | biPh-4-yl | 6-OMe—Py-3-yl |
| 553 | H | H | H | biPh-4-yl | 6-$OCHF_2$—Py-3-yl |
| 554 | H | H | H | biPh-4-yl | Py-4-yl |
| 555 | H | H | H | biPh-4-yl | Pym-2-yl |
| 556 | H | H | H | 2'-F-biPh-4-yl | Ph |
| 557 | H | H | H | 2'-F-biPh-4-yl | 2-F—Ph |
| 558 | H | H | H | 2'-F-biPh-4-yl | 3-F—Ph |
| 559 | H | H | H | 2'-F-biPh-4-yl | 4-F—Ph |
| 560 | H | H | H | 2'-F-biPh-4-yl | 2-Cl—Ph |
| 561 | H | H | H | 2'-F-biPh-4-yl | 3-Cl—Ph |
| 562 | H | H | H | 2'-F-biPh-4-yl | 4-Cl—Ph |
| 563 | H | H | H | 2'-F-biPh-4-yl | 2,6-diCl—Ph |
| 564 | H | H | H | 2'-F-biPh-4-yl | 4-OMe—Ph |
| 565 | H | H | H | 2'-F-biPh-4-yl | Py-2-yl |
| 566 | H | H | H | 2'-F-biPh-4-yl | Py-3-yl |
| 567 | H | H | H | 3'-F-biPh-4-yl | Ph |
| 568 | H | H | H | 3'-F-biPh-4-yl | 2-F—Ph |
| 569 | H | H | H | 3'-F-biPh-4-yl | 3-F—Ph |
| 570 | H | H | H | 3'-F-biPh-4-yl | 4-F—Ph |
| 571 | H | H | H | 3'-F-biPh-4-yl | 2-Cl—Ph |
| 572 | H | H | H | 3'-F-biPh-4-yl | 3-Cl—Ph |
| 573 | H | H | H | 3'-F-biPh-4-yl | 4-Cl—Ph |
| 574 | H | H | H | 3'-F-biPh-4-yl | 2,6-diCl—Ph |
| 575 | H | H | H | 3'-F-biPh-4-yl | 4-OMe—Ph |
| 576 | H | H | H | 3'-F-biPh-4-yl | Py-2-yl |
| 577 | H | H | H | 3'-F-biPh-4-yl | Py-3-yl |
| 578 | H | H | H | 4'-F-biPh-4-yl | Ph |
| 579 | H | H | H | 4'-F-biPh-4-yl | 2-F—Ph |
| 580 | H | H | H | 4'-F-biPh-4-yl | 3-F—Ph |
| 581 | H | H | H | 4'-F-biPh-4-yl | 4-F—Ph |
| 582 | H | H | H | 4'-F-biPh-4-yl | 3,4-diF—Ph |
| 583 | H | H | H | 4'-F-biPh-4-yl | 3,5-diF—Ph |
| 584 | H | H | H | 4'-F-biPh-4-yl | 2-Cl—Ph |
| 585 | H | H | H | 4'-F-biPh-4-yl | 3-Cl—Ph |
| 586 | H | H | H | 4'-F-biPh-4-yl | 4-Cl—Ph |
| 587 | H | H | H | 4'-F-biPh-4-yl | 2,6-diCl—Ph |
| 588 | H | H | H | 4'-F-biPh-4-yl | 4-Cl-3-F—Ph |
| 589 | H | H | H | 4'-F-biPh-4-yl | 4-Me—Ph |
| 590 | H | H | H | 4'-F-biPh-4-yl | 3-F-4-Me—Ph |
| 591 | H | H | H | 4'-F-biPh-4-yl | 4-Et—Ph |
| 592 | H | H | H | 4'-F-biPh-4-yl | 4-Et-3-F—Ph |
| 593 | H | H | H | 4'-F-biPh-4-yl | 4-$CF_3$—Ph |
| 594 | H | H | H | 4'-F-biPh-4-yl | 3-F-4-$CF_3$—Ph |
| 595 | H | H | H | 4'-F-biPh-4-yl | 4-OMe—Ph |
| 596 | H | H | H | 4'-F-biPh-4-yl | 3-F-4-OMe—Ph |
| 597 | H | H | H | 4'-F-biPh-4-yl | 4-$OCHF_2$—Ph |
| 598 | H | H | H | 4'-F-biPh-4-yl | 4-$OCHF_2$-3-F—Ph |
| 599 | H | H | H | 4'-F-biPh-4-yl | Th-2-yl |
| 600 | H | H | H | 4'-F-biPh-4-yl | Th-3-yl |
| 601 | H | H | H | 4'-F-biPh-4-yl | Py-2-yl |
| 602 | H | H | H | 4'-F-biPh-4-yl | 5-F—Py-2-yl |
| 603 | H | H | H | 4'-F-biPh-4-yl | 5-Cl—Py-2-yl |
| 604 | H | H | H | 4'-F-biPh-4-yl | 5-OMe—Py-2-yl |
| 605 | H | H | H | 4'-F-biPh-4-yl | Py-3-yl |
| 606 | H | H | H | 4'-F-biPh-4-yl | 6-F—Py-3-yl |
| 607 | H | H | H | 4'-F-biPh-4-yl | 6-Cl—Py-3-yl |
| 608 | H | H | H | 4'-F-biPh-4-yl | 6-OMe—Py-3-yl |
| 609 | H | H | H | 4'-F-biPh-4-yl | Py-4-yl |
| 610 | H | H | H | 2',4'-diF-biPh-4-yl | Ph |
| 611 | H | H | H | 2',4'-diF-biPh-4-yl | 2-F—Ph |

TABLE 1-continued

| Compound No. | R¹ | R² | R³ | Y | Z |
|---|---|---|---|---|---|
| 612 | H | H | H | 2',4'-diF-biPh-4-yl | 3-F—Ph |
| 613 | H | H | H | 2',4'-diF-biPh-4-yl | 4-F—Ph |
| 614 | H | H | H | 2',4'-diF-biPh-4-yl | 2-Cl—Ph |
| 615 | H | H | H | 2',4'-diF-biPh-4-yl | 3-Cl—Ph |
| 616 | H | H | H | 2',4'-diF-biPh-4-yl | 4-Cl—Ph |
| 617 | H | H | H | 2',4'-diF-biPh-4-yl | 2,6-diCl—Ph |
| 618 | H | H | H | 2',4'-diF-biPh-4-yl | 4-OMe—Ph |
| 619 | H | H | H | 2',4'-diF-biPh-4-yl | Py-2-yl |
| 620 | H | H | H | 2',4'-diF-biPh-4-yl | Py-3-yl |
| 621 | H | H | H | 3',4'-diF-biPh-4-yl | Ph |
| 622 | H | H | H | 3',4'-diF-biPh-4-yl | 2-F—Ph |
| 623 | H | H | H | 3',4'-diF-biPh-4-yl | 3-F—Ph |
| 624 | H | H | H | 3',4'-diF-biPh-4-yl | 4-F—Ph |
| 625 | H | H | H | 3',4'-diF-biPh-4-yl | 2-Cl—Ph |
| 626 | H | H | H | 3',4'-diF-biPh-4-yl | 3-Cl—Ph |
| 627 | H | H | H | 3',4'-diF-biPh-4-yl | 4-Cl—Ph |
| 628 | H | H | H | 3',4'-diF-biPh-4-yl | 2,6-diCl—Ph |
| 629 | H | H | H | 3',4'-diF-biPh-4-yl | 4-OMe—Ph |
| 630 | H | H | H | 3',4'-diF-biPh-4-yl | Py-2-yl |
| 631 | H | H | H | 3',4'-diF-biPh-4-yl | Py-3-yl |
| 632 | H | H | H | 2'-Cl-biPh-4-yl | Ph |
| 633 | H | H | H | 2'-Cl-biPh-4-yl | 2-F—Ph |
| 634 | H | H | H | 2'-Cl-biPh-4-yl | 3-F—Ph |
| 635 | H | H | H | 2'-Cl-biPh-4-yl | 4-F—Ph |
| 636 | H | H | H | 2'-Cl-biPh-4-yl | 2-Cl—Ph |
| 637 | H | H | H | 2'-Cl-biPh-4-yl | 3-Cl—Ph |
| 638 | H | H | H | 2'-Cl-biPh-4-yl | 4-Cl—Ph |
| 639 | H | H | H | 2'-Cl-biPh-4-yl | 2,6-diCl—Ph |
| 640 | H | H | H | 2'-Cl-biPh-4-yl | 4-OMe—Ph |
| 641 | H | H | H | 2'-Cl-biPh-4-yl | Py-2-yl |
| 642 | H | H | H | 2'-Cl-biPh-4-yl | Py-3-yl |
| 643 | H | H | H | 3'-Cl-biPh-4-yl | Ph |
| 644 | H | H | H | 3'-Cl-biPh-4-yl | 2-F—Ph |
| 645 | H | H | H | 3'-Cl-biPh-4-yl | 3-F—Ph |
| 646 | H | H | H | 3'-Cl-biPh-4-yl | 4-F—Ph |
| 647 | H | H | H | 3'-Cl-biPh-4-yl | 2-Cl—Ph |
| 648 | H | H | H | 3'-Cl-biPh-4-yl | 3-Cl—Ph |
| 649 | H | H | H | 3'-Cl-biPh-4-yl | 4-Cl—Ph |
| 650 | H | H | H | 3'-Cl-biPh-4-yl | 2,6-diCl—Ph |
| 651 | H | H | H | 3'-Cl-biPh-4-yl | 4-OMe—Ph |
| 652 | H | H | H | 3'-Cl-biPh-4-yl | Py-2-yl |
| 653 | H | H | H | 3'-Cl-biPh-4-yl | Py-3-yl |
| 654 | H | H | H | 4'-Cl-biPh-4-yl | Ph |
| 655 | H | H | H | 4'-Cl-biPh-4-yl | 2-F—Ph |
| 656 | H | H | H | 4'-Cl-biPh-4-yl | 3-F—Ph |
| 657 | H | H | H | 4'-Cl-biPh-4-yl | 4-F—Ph |
| 658 | H | H | H | 4'-Cl-biPh-4-yl | 3,4-diF—Ph |
| 659 | H | H | H | 4'-Cl-biPh-4-yl | 3,5-diF—Ph |
| 660 | H | H | H | 4'-Cl-biPh-4-yl | 2-Cl—Ph |
| 661 | H | H | H | 4'-Cl-biPh-4-yl | 3-Cl—Ph |
| 662 | H | H | H | 4'-Cl-biPh-4-yl | 4-Cl—Ph |
| 663 | H | H | H | 4'-Cl-biPh-4-yl | 2,6-diCl—Ph |
| 664 | H | H | H | 4'-Cl-biPh-4-yl | 4-Cl-3-F—Ph |
| 665 | H | H | H | 4'-Cl-biPh-4-yl | 4-Me—Ph |
| 666 | H | H | H | 4'-Cl-biPh-4-yl | 3-F-4-Me—Ph |
| 667 | H | H | H | 4'-Cl-biPh-4-yl | 4-Et—Ph |
| 668 | H | H | H | 4'-Cl-biPh-4-yl | 4-Et-3-F—Ph |
| 669 | H | H | H | 4'-Cl-biPh-4-yl | 4-CF₃—Ph |
| 670 | H | H | H | 4'-Cl-biPh-4-yl | 3-F-4-CF₃—Ph |
| 671 | H | H | H | 4'-Cl-biPh-4-yl | 4-OMe—Ph |
| 672 | H | H | H | 4'-Cl-biPh-4-yl | 3-F-4-OMe—Ph |
| 673 | H | H | H | 4'-Cl-biPh-4-yl | 4-OCHF₂—Ph |
| 674 | H | H | H | 4'-Cl-biPh-4-yl | 4-OCHF₂-3-F—Ph |
| 675 | H | H | H | 4'-Cl-biPh-4-yl | Th-2-yl |
| 676 | H | H | H | 4'-Cl-biPh-4-yl | Th-3-yl |
| 677 | H | H | H | 4'-Cl-biPh-4-yl | Py-2-yl |
| 678 | H | H | H | 4'-Cl-biPh-4-yl | 5-F—Py-2-yl |
| 679 | H | H | H | 4'-Cl-biPh-4-yl | 5-Cl—Py-2-yl |
| 680 | H | H | H | 4'-Cl-biPh-4-yl | 5-OMe—Py-2-yl |
| 681 | H | H | H | 4'-Cl-biPh-4-yl | Py-3-yl |
| 682 | H | H | H | 4'-Cl-biPh-4-yl | 6-F—Py-3-yl |
| 683 | H | H | H | 4'-Cl-biPh-4-yl | 6-Cl—Py-3-yl |
| 684 | H | H | H | 4'-Cl-biPh-4-yl | 6-OMe—Py-3-yl |
| 685 | H | H | H | 4'-Cl-biPh-4-yl | Py-4-yl |
| 686 | H | H | H | 2',4'-diCl-biPh-4-yl | 4-F—Ph |
| 687 | H | H | H | 2',4'-diCl-biPh-4-yl | Py-2-yl |
| 688 | H | H | H | 2',4'-diCl-biPh-4-yl | Py-3-yl |
| 689 | H | H | H | 3',4'-diCl-biPh-4-yl | 4-F—Ph |
| 690 | H | H | H | 3',4'-diCl-biPh-4-yl | Py-2-yl |
| 691 | H | H | H | 3',4'-diCl-biPh-4-yl | Py-3-yl |
| 692 | H | H | H | 4'-Cl-2'-F-biPh-4-yl | Ph |
| 693 | H | H | H | 4'-Cl-2'-F-biPh-4-yl | 2-F—Ph |
| 694 | H | H | H | 4'-Cl-2'-F-biPh-4-yl | 3-F—Ph |
| 695 | H | H | H | 4'-Cl-2'-F-biPh-4-yl | 4-F—Ph |
| 696 | H | H | H | 4'-Cl-2'-F-biPh-4-yl | 2-Cl—Ph |
| 697 | H | H | H | 4'-Cl-2'-F-biPh-4-yl | 3-Cl—Ph |
| 698 | H | H | H | 4'-Cl-2'-F-biPh-4-yl | 4-Cl—Ph |
| 699 | H | H | H | 4'-Cl-2'-F-biPh-4-yl | 2,6-diCl—Ph |
| 700 | H | H | H | 4'-Cl-2'-F-biPh-4-yl | 4-OMe—Ph |
| 701 | H | H | H | 4'-Cl-2'-F-biPh-4-yl | Py-2-yl |
| 702 | H | H | H | 4'-Cl-2'-F-biPh-4-yl | Py-3-yl |
| 703 | H | H | H | 4'-Cl-3'-F-biPh-4-yl | Ph |
| 704 | H | H | H | 4'-Cl-3'-F-biPh-4-yl | 2-F—Ph |
| 705 | H | H | H | 4'-Cl-3'-F-biPh-4-yl | 3-F—Ph |
| 706 | H | H | H | 4'-Cl-3'-F-biPh-4-yl | 4-F—Ph |
| 707 | H | H | H | 4'-Cl-3'-F-biPh-4-yl | 2-Cl—Ph |
| 708 | H | H | H | 4'-Cl-3'-F-biPh-4-yl | 3-Cl—Ph |
| 709 | H | H | H | 4'-Cl-3'-F-biPh-4-yl | 4-Cl—Ph |
| 710 | H | H | H | 4'-Cl-3'-F-biPh-4-yl | 2,6-diCl—Ph |
| 711 | H | H | H | 4'-Cl-3'-F-biPh-4-yl | 4-OMe—Ph |
| 712 | H | H | H | 4'-Cl-3'-F-biPh-4-yl | Py-2-yl |
| 713 | H | H | H | 4'-Cl-3'-F-biPh-4-yl | Py-3-yl |
| 714 | H | H | H | 3'-Br-biPh-4-yl | 4-F—Ph |
| 715 | H | H | H | 3'-Br-biPh-4-yl | Py-2-yl |
| 716 | H | H | H | 3'-Br-biPh-4-yl | Py-3-yl |
| 717 | H | H | H | 3'-OH-biPh-4-yl | 4-F—Ph |
| 718 | H | H | H | 3'-OH-biPh-4-yl | Py-2-yl |
| 719 | H | H | H | 3'-OH-biPh-4-yl | Py-3-yl |
| 720 | H | H | H | 4'-OH-biPh-4-yl | Ph |
| 721 | H | H | H | 4'-OH-biPh-4-yl | 2-F—Ph |
| 722 | H | H | H | 4'-OH-biPh-4-yl | 3-F—Ph |
| 723 | H | H | H | 4'-OH-biPh-4-yl | 4-F—Ph |
| 724 | H | H | H | 4'-OH-biPh-4-yl | 2-Cl—Ph |
| 725 | H | H | H | 4'-OH-biPh-4-yl | 3-Cl—Ph |
| 726 | H | H | H | 4'-OH-biPh-4-yl | 4-Cl—Ph |
| 727 | H | H | H | 4'-OH-biPh-4-yl | 2,6-diCl—Ph |
| 728 | H | H | H | 4'-OH-biPh-4-yl | 4-OMe—Ph |
| 729 | H | H | H | 4'-OH-biPh-4-yl | Py-2-yl |
| 730 | H | H | H | 4'-OH-biPh-4-yl | Py-3-yl |
| 731 | H | H | H | 3'-Me-biPh-4-yl | Ph |
| 732 | H | H | H | 3'-Me-biPh-4-yl | 2-F—Ph |
| 733 | H | H | H | 3'-Me-biPh-4-yl | 3-F—Ph |
| 734 | H | H | H | 3'-Me-biPh-4-yl | 4-F—Ph |
| 735 | H | H | H | 3'-Me-biPh-4-yl | 2-Cl—Ph |
| 736 | H | H | H | 3'-Me-biPh-4-yl | 3-Cl—Ph |
| 737 | H | H | H | 3'-Me-biPh-4-yl | 4-Cl—Ph |
| 738 | H | H | H | 3'-Me-biPh-4-yl | 2,6-diCl—Ph |
| 739 | H | H | H | 3'-Me-biPh-4-yl | 4-OMe—Ph |
| 740 | H | H | H | 3'-Me-biPh-4-yl | Py-2-yl |
| 741 | H | H | H | 3'-Me-biPh-4-yl | Py-3-yl |
| 742 | H | H | H | 3'-Et-biPh-4-yl | Ph |
| 743 | H | H | H | 3'-Et-biPh-4-yl | 2-F—Ph |
| 744 | H | H | H | 3'-Et-biPh-4-yl | 3-F—Ph |
| 745 | H | H | H | 3'-Et-biPh-4-yl | 4-F—Ph |
| 746 | H | H | H | 3'-Et-biPh-4-yl | 2-Cl—Ph |
| 747 | H | H | H | 3'-Et-biPh-4-yl | 3-Cl—Ph |
| 748 | H | H | H | 3'-Et-biPh-4-yl | 4-Cl—Ph |
| 749 | H | H | H | 3'-Et-biPh-4-yl | 2,6-diCl—Ph |
| 750 | H | H | H | 3'-Et-biPh-4-yl | 4-OMe—Ph |
| 751 | H | H | H | 3'-Et-biPh-4-yl | Py-2-yl |
| 752 | H | H | H | 3'-Et-biPh-4-yl | Py-3-yl |
| 753 | H | H | H | 3'-Pr-biPh-4-yl | 4-F—Ph |
| 754 | H | H | H | 3'-Pr-biPh-4-yl | Py-2-yl |
| 755 | H | H | H | 3'-Pr-biPh-4-yl | Py-3-yl |
| 756 | H | H | H | 3'-iPr-biPh-4-yl | 4-F—Ph |
| 757 | H | H | H | 3'-iPr-biPh-4-yl | Py-2-yl |
| 758 | H | H | H | 3'-iPr-biPh-4-yl | Py-3-yl |
| 759 | H | H | H | 3'-tBu-biPh-4-yl | 4-F—Ph |
| 760 | H | H | H | 3'-tBu-biPh-4-yl | Py-2-yl |
| 761 | H | H | H | 3'-tBu-biPh-4-yl | Py-3-yl |
| 762 | H | H | H | 3'-CF₃-biPh-4-yl | Ph |
| 763 | H | H | H | 3'-CF₃-biPh-4-yl | 2-F—Ph |

TABLE 1-continued

| Compound No. | R¹ | R² | R³ | Y | Z |
|---|---|---|---|---|---|
| 764 | H | H | H | 3'-CF$_3$-biPh-4-yl | 3-F—Ph |
| 765 | H | H | H | 3'-CF$_3$-biPh-4-yl | 4-F—Ph |
| 766 | H | H | H | 3'-CF$_3$-biPh-4-yl | 2-Cl—Ph |
| 767 | H | H | H | 3'-CF$_3$-biPh-4-yl | 3-Cl—Ph |
| 768 | H | H | H | 3'-CF$_3$-biPh-4-yl | 4-Cl—Ph |
| 769 | H | H | H | 3'-CF$_3$-biPh-4-yl | 2,6-diCl—Ph |
| 770 | H | H | H | 3'-CF$_3$-biPh-4-yl | 4-OMe—Ph |
| 771 | H | H | H | 3'-CF$_3$-biPh-4-yl | Py-2-yl |
| 772 | H | H | H | 3'-CF$_3$-biPh-4-yl | Py-3-yl |
| 773 | H | H | H | 3'-CHF$_2$-biPh-4-yl | 4-F—Ph |
| 774 | H | H | H | 3'-CHF$_2$-biPh-4-yl | Py-2-yl |
| 775 | H | H | H | 3'-CHF$_2$-biPh-4-yl | Py-3-yl |
| 776 | H | H | H | 3'-CCl$_3$-biPh-4-yl | 4-F—Ph |
| 777 | H | H | H | 3'-CCl$_3$-biPh-4-yl | Py-2-yl |
| 778 | H | H | H | 3'-CCl$_3$-biPh-4-yl | Py-3-yl |
| 779 | H | H | H | 3'-CHCl$_2$-biPh-4-yl | 4-F—Ph |
| 780 | H | H | H | 3'-CHCl$_2$-biPh-4-yl | Py-2-yl |
| 781 | H | H | H | 3'-CHCl$_2$-biPh-4-yl | Py-3-yl |
| 782 | H | H | H | 3'-CH$_2$CF$_3$-biPh-4-yl | 4-F—Ph |
| 783 | H | H | H | 3'-CH$_2$CF$_3$-biPh-4-yl | Py-2-yl |
| 784 | H | H | H | 3'-CH$_2$CF$_3$-biPh-4-yl | Py-3-yl |
| 785 | H | H | H | 3'-CH$_2$CCl$_3$-biPh-4-yl | 4-F—Ph |
| 786 | H | H | H | 3'-CH$_2$CCl$_3$-biPh-4-yl | Py-2-yl |
| 787 | H | H | H | 3'-CH$_2$CCl$_3$-biPh-4-yl | Py-3-yl |
| 788 | H | H | H | 3'-OMe-biPh-4-yl | Ph |
| 789 | H | H | H | 3'-OMe-biPh-4-yl | 2-F—Ph |
| 790 | H | H | H | 3'-OMe-biPh-4-yl | 3-F—Ph |
| 791 | H | H | H | 3'-OMe-biPh-4-yl | 4-F—Ph |
| 792 | H | H | H | 3'-OMe-biPh-4-yl | 2-Cl—Ph |
| 793 | H | H | H | 3'-OMe-biPh-4-yl | 3-Cl—Ph |
| 794 | H | H | H | 3'-OMe-biPh-4-yl | 4-Cl—Ph |
| 795 | H | H | H | 3'-OMe-biPh-4-yl | 2,6-diCl—Ph |
| 796 | H | H | H | 3'-OMe-biPh-4-yl | 4-OMe—Ph |
| 797 | H | H | H | 3'-OMe-biPh-4-yl | Py-2-yl |
| 798 | H | H | H | 3'-OMe-biPh-4-yl | Py-3-yl |
| 799 | H | H | H | 3'-OEt-biPh-4-yl | 4-F—Ph |
| 800 | H | H | H | 3'-OEt-biPh-4-yl | Py-2-yl |
| 801 | H | H | H | 3'-OEt-biPh-4-yl | Py-3-yl |
| 802 | H | H | H | 3'-OPr-biPh-4-yl | 4-F—Ph |
| 803 | H | H | H | 3'-OPr-biPh-4-yl | Py-2-yl |
| 804 | H | H | H | 3'-OPr-biPh-4-yl | Py-3-yl |
| 805 | H | H | H | 3'-OiPr-biPh-4-yl | 4-F—Ph |
| 806 | H | H | H | 3'-OiPr-biPh-4-yl | Py-2-yl |
| 807 | H | H | H | 3'-OiPr-biPh-4-yl | Py-3-yl |
| 808 | H | H | H | 3'-OtBu-biPh-4-yl | 4-F—Ph |
| 809 | H | H | H | 3'-OtBu-biPh-4-yl | Py-2-yl |
| 810 | H | H | H | 3'-OtBu-biPh-4-yl | Py-3-yl |
| 811 | H | H | H | 3'-OCF$_3$-biPh-4-yl | 4-F—Ph |
| 812 | H | H | H | 3'-OCF$_3$-biPh-4-yl | Py-2-yl |
| 813 | H | H | H | 3'-OCF$_3$-biPh-4-yl | Py-3-yl |
| 814 | H | H | H | 3'-OCHF$_2$-biPh-4-yl | Ph |
| 815 | H | H | H | 3'-OCHF$_2$-biPh-4-yl | 2-F—Ph |
| 816 | H | H | H | 3'-OCHF$_2$-biPh-4-yl | 3-F—Ph |
| 817 | H | H | H | 3'-OCHF$_2$-biPh-4-yl | 4-F—Ph |
| 818 | H | H | H | 3'-OCHF$_2$-biPh-4-yl | 2-Cl—Ph |
| 819 | H | H | H | 3'-OCHF$_2$-biPh-4-yl | 3-Cl—Ph |
| 820 | H | H | H | 3'-OCHF$_2$-biPh-4-yl | 4-Cl—Ph |
| 821 | H | H | H | 3'-OCHF$_2$-biPh-4-yl | 2,6-diCl—Ph |
| 822 | H | H | H | 3'-OCHF$_2$-biPh-4-yl | 4-OMe—Ph |
| 823 | H | H | H | 3'-OCHF$_2$-biPh-4-yl | Py-2-yl |
| 824 | H | H | H | 3'-OCHF$_2$-biPh-4-yl | Py-3-yl |
| 825 | H | H | H | 3'-OCCl$_3$-biPh-4-yl | 4-F—Ph |
| 826 | H | H | H | 3'-OCCl$_3$-biPh-4-yl | Py-2-yl |
| 827 | H | H | H | 3'-OCCl$_3$-biPh-4-yl | Py-3-yl |
| 828 | H | H | H | 3'-OCHCl$_2$-biPh-4-yl | 4-F—Ph |
| 829 | H | H | H | 3'-OCHCl$_2$-biPh-4-yl | Py-2-yl |
| 830 | H | H | H | 3'-OCHCl$_2$-biPh-4-yl | Py-3-yl |
| 831 | H | H | H | 4-(Th-2-yl)Ph | Ph |
| 832 | H | H | H | 4-(Th-2-yl)Ph | 2-F—Ph |
| 833 | H | H | H | 4-(Th-2-yl)Ph | 3-F—Ph |
| 834 | H | H | H | 4-(Th-2-yl)Ph | 4-F—Ph |
| 835 | H | H | H | 4-(Th-2-yl)Ph | 2-Cl—Ph |
| 836 | H | H | H | 4-(Th-2-yl)Ph | 3-Cl—Ph |
| 837 | H | H | H | 4-(Th-2-yl)Ph | 4-Cl—Ph |
| 838 | H | H | H | 4-(Th-2-yl)Ph | 2,6-diCl—Ph |
| 839 | H | H | H | 4-(Th-2-yl)Ph | 4-OMe—Ph |
| 840 | H | H | H | 4-(Th-2-yl)Ph | Py-2-yl |
| 841 | H | H | H | 4-(Th-2-yl)Ph | Py-3-yl |
| 842 | H | H | H | 4-(Th-3-yl)Ph | Ph |
| 843 | H | H | H | 4-(Th-3-yl)Ph | 2-F—Ph |
| 844 | H | H | H | 4-(Th-3-yl)Ph | 3-F—Ph |
| 845 | H | H | H | 4-(Th-3-yl)Ph | 4-F—Ph |
| 846 | H | H | H | 4-(Th-3-yl)Ph | 2-Cl—Ph |
| 847 | H | H | H | 4-(Th-3-yl)Ph | 3-Cl—Ph |
| 848 | H | H | H | 4-(Th-3-yl)Ph | 4-Cl—Ph |
| 849 | H | H | H | 4-(Th-3-yl)Ph | 2,6-diCl—Ph |
| 850 | H | H | H | 4-(Th-3-yl)Ph | 4-OMe—Ph |
| 851 | H | H | H | 4-(Th-3-yl)Ph | Py-2-yl |
| 852 | H | H | H | 4-(Th-3-yl)Ph | Py-3-yl |
| 853 | H | H | H | 4-(Pyz-1-yl)Ph | Ph |
| 854 | H | H | H | 4-(Pyz-1-yl)Ph | 2-F—Ph |
| 855 | H | H | H | 4-(Pyz-1-yl)Ph | 3-F—Ph |
| 856 | H | H | H | 4-(Pyz-1-yl)Ph | 4-F—Ph |
| 857 | H | H | H | 4-(Pyz-1-yl)Ph | 3,4-diF—Ph |
| 858 | H | H | H | 4-(Pyz-1-yl)Ph | 3,5-diF—Ph |
| 859 | H | H | H | 4-(Pyz-1-yl)Ph | 2-Cl—Ph |
| 860 | H | H | H | 4-(Pyz-1-yl)Ph | 3-Cl—Ph |
| 861 | H | H | H | 4-(Pyz-1-yl)Ph | 4-Cl—Ph |
| 862 | H | H | H | 4-(Pyz-1-yl)Ph | 2,6-diCl—Ph |
| 863 | H | H | H | 4-(Pyz-1-yl)Ph | 4-Cl-3-F—Ph |
| 864 | H | H | H | 4-(Pyz-1-yl)Ph | 4-Me—Ph |
| 865 | H | H | H | 4-(Pyz-1-yl)Ph | 3-F-4-Me—Ph |
| 866 | H | H | H | 4-(Pyz-1-yl)Ph | 4-Et—Ph |
| 867 | H | H | H | 4-(Pyz-1-yl)Ph | 4-Et-3-F—Ph |
| 868 | H | H | H | 4-(Pyz-1-yl)Ph | 4-CF$_3$—Ph |
| 869 | H | H | H | 4-(Pyz-1-yl)Ph | 3-F-4-CF$_3$—Ph |
| 870 | H | H | H | 4-(Pyz-1-yl)Ph | 4-OMe—Ph |
| 871 | H | H | H | 4-(Pyz-1-yl)Ph | 3-F-4-OMe—Ph |
| 872 | H | H | H | 4-(Pyz-1-yl)Ph | 4-OCHF$_2$—Ph |
| 873 | H | H | H | 4-(Pyz-1-yl)Ph | 4-OCHF$_2$-3-F—Ph |
| 874 | H | H | H | 4-(Pyz-1-yl)Ph | Th-2-yl |
| 875 | H | H | H | 4-(Pyz-1-yl)Ph | Th-3-yl |
| 876 | H | H | H | 4-(Pyz-1-yl)Ph | Py-2-yl |
| 877 | H | H | H | 4-(Pyz-1-yl)Ph | 5-F—Py-2-yl |
| 878 | H | H | H | 4-(Pyz-1-yl)Ph | 5-Cl—Py-2-yl |
| 879 | H | H | H | 4-(Pyz-1-yl)Ph | 5-OMe—Py-2-yl |
| 880 | H | H | H | 4-(Pyz-1-yl)Ph | Py-3-yl |
| 881 | H | H | H | 4-(Pyz-1-yl)Ph | 6-F—Py-3-yl |
| 882 | H | H | H | 4-(Pyz-1-yl)Ph | 6-Cl—Py-3-yl |
| 883 | H | H | H | 4-(Pyz-1-yl)Ph | 6-OMe—Py-3-yl |
| 884 | H | H | H | 4-(Pyz-1-yl)Ph | Py-4-yl |
| 885 | H | H | H | 4-(4-F-Pyz-1-yl)Ph | 4-F—Ph |
| 886 | H | H | H | 4-(4-F-Pyz-1-yl)Ph | Py-2-yl |
| 887 | H | H | H | 4-(4-F-Pyz-1-yl)Ph | Py-3-yl |
| 888 | H | H | H | 4-(4-Cl-Pyz-1-yl)Ph | 4-F—Ph |
| 889 | H | H | H | 4-(4-Cl-Pyz-1-yl)Ph | Py-2-yl |
| 890 | H | H | H | 4-(4-Cl-Pyz-1-yl)Ph | Py-3-yl |
| 891 | H | H | H | 4-(Oxz-2-yl)Ph | Ph |
| 892 | H | H | H | 4-(Oxz-2-yl)Ph | 2-F—Ph |
| 893 | H | H | H | 4-(Oxz-2-yl)Ph | 3-F—Ph |
| 894 | H | H | H | 4-(Oxz-2-yl)Ph | 4-F—Ph |
| 895 | H | H | H | 4-(Oxz-2-yl)Ph | 2-Cl—Ph |
| 896 | H | H | H | 4-(Oxz-2-yl)Ph | 3-Cl—Ph |
| 897 | H | H | H | 4-(Oxz-2-yl)Ph | 4-Cl—Ph |
| 898 | H | H | H | 4-(Oxz-2-yl)Ph | 2,6-diCl—Ph |
| 899 | H | H | H | 4-(Oxz-2-yl)Ph | 4-OMe—Ph |
| 900 | H | H | H | 4-(Oxz-2-yl)Ph | Py-2-yl |
| 901 | H | H | H | 4-(Oxz-2-yl)Ph | Py-3-yl |
| 902 | H | H | H | 4-(Oxz-4-yl)Ph | Ph |
| 903 | H | H | H | 4-(Oxz-4-yl)Ph | 2-F—Ph |
| 904 | H | H | H | 4-(Oxz-4-yl)Ph | 3-F—Ph |
| 905 | H | H | H | 4-(Oxz-4-yl)Ph | 4-F—Ph |
| 906 | H | H | H | 4-(Oxz-4-yl)Ph | 2-Cl—Ph |
| 907 | H | H | H | 4-(Oxz-4-yl)Ph | 3-Cl—Ph |
| 908 | H | H | H | 4-(Oxz-4-yl)Ph | 4-Cl—Ph |
| 909 | H | H | H | 4-(Oxz-4-yl)Ph | 2,6-diCl—Ph |
| 910 | H | H | H | 4-(Oxz-4-yl)Ph | 4-OMe—Ph |
| 911 | H | H | H | 4-(Oxz-4-yl)Ph | Py-2-yl |
| 912 | H | H | H | 4-(Oxz-4-yl)Ph | Py-3-yl |
| 913 | Pr | H | H | 4-(Thz-2-yl)Ph | Py-2-yl |
| 914 | iPr | H | H | 4-(Thz-2-yl)Ph | Py-2-yl |
| 915 | tBu | H | H | 4-(Thz-2-yl)Ph | Py-2-yl |

TABLE 1-continued

| Compound No. | R¹ | R² | R³ | Y | Z |
|---|---|---|---|---|---|
| 916 | Me | H | H | 4-(Thz-2-yl)Ph | 4-F—Ph |
| 917 | Me | H | H | 4-(Thz-2-yl)Ph | Py-2-yl |
| 918 | Me | H | H | 4-(Thz-2-yl)Ph | Py-3-yl |
| 919 | Et | H | H | 4-(Thz-2-yl)Ph | 4-F—Ph |
| 920 | Et | H | H | 4-(Thz-2-yl)Ph | Py-2-yl |
| 921 | Et | H | H | 4-(Thz-2-yl)Ph | Py-3-yl |
| 922 | Me | Me | Me | 4-(Thz-2-yl)Ph | Py-2-yl |
| 923 | Et | Me | Me | 4-(Thz-2-yl)Ph | Py-2-yl |
| 924 | H | Et | Et | 4-(Thz-2-yl)Ph | Py-2-yl |
| 925 | H | Pr | Pr | 4-(Thz-2-yl)Ph | Py-2-yl |
| 926 | H | iPr | iPr | 4-(Thz-2-yl)Ph | Py-2-yl |
| 927 | H | Me | Me | 4-(Thz-2-yl)Ph | 4-F—Ph |
| 928 | H | Me | Me | 4-(Thz-2-yl)Ph | Py-2-yl |
| 929 | H | Me | Me | 4-(Thz-2-yl)Ph | Py-3-yl |
| 930 | H | Me | H | 4-(Thz-2-yl)Ph | 4-F—Ph |
| 931 | H | Me | H | 4-(Thz-2-yl)Ph | Py-2-yl |
| 932 | H | Me | H | 4-(Thz-2-yl)Ph | Py-3-yl |
| 933 | H | H | H | 4-(Thz-2-yl)Ph | Ph |
| 934 | H | H | H | 4-(Thz-2-yl)Ph | 2-F—Ph |
| 935 | H | H | H | 4-(Thz-2-yl)Ph | 3-F—Ph |
| 936 | H | H | H | 4-(Thz-2-yl)Ph | 4-F—Ph |
| 937 | H | H | H | 4-(Thz-2-yl)Ph | 3,4-diF—Ph |
| 938 | H | H | H | 4-(Thz-2-yl)Ph | 3,5-diF—Ph |
| 939 | H | H | H | 4-(Thz-2-yl)Ph | 3,4,5-triF—Ph |
| 940 | H | H | H | 4-(Thz-2-yl)Ph | 2-Cl—Ph |
| 941 | H | H | H | 4-(Thz-2-yl)Ph | 3-Cl—Ph |
| 942 | H | H | H | 4-(Thz-2-yl)Ph | 4-Cl—Ph |
| 943 | H | H | H | 4-(Thz-2-yl)Ph | 2,6-diCl—Ph |
| 944 | H | H | H | 4-(Thz-2-yl)Ph | 4-Cl-3-F—Ph |
| 945 | H | H | H | 4-(Thz-2-yl)Ph | 4-Cl-3,5-diF—Ph |
| 946 | H | H | H | 4-(Thz-2-yl)Ph | 4-Br—Ph |
| 947 | H | H | H | 4-(Thz-2-yl)Ph | 4-Me—Ph |
| 948 | H | H | H | 4-(Thz-2-yl)Ph | 3-F-4-Me—Ph |
| 949 | H | H | H | 4-(Thz-2-yl)Ph | 4-Et—Ph |
| 950 | H | H | H | 4-(Thz-2-yl)Ph | 4-Et-3-F—Ph |
| 951 | H | H | H | 4-(Thz-2-yl)Ph | 4-Pr—Ph |
| 952 | H | H | H | 4-(Thz-2-yl)Ph | 4-iPr—Ph |
| 953 | H | H | H | 4-(Thz-2-yl)Ph | 4-tBu—Ph |
| 954 | H | H | H | 4-(Thz-2-yl)Ph | 4-CF₃—Ph |
| 955 | H | H | H | 4-(Thz-2-yl)Ph | 3-F-4-CF₃—Ph |
| 956 | H | H | H | 4-(Thz-2-yl)Ph | 4-CHF₂—Ph |
| 957 | H | H | H | 4-(Thz-2-yl)Ph | 4-CCl₃—Ph |
| 958 | H | H | H | 4-(Thz-2-yl)Ph | 4-CHCl₂—Ph |
| 959 | H | H | H | 4-(Thz-2-yl)Ph | 4-CH₂CF₃—Ph |
| 960 | H | H | H | 4-(Thz-2-yl)Ph | 4-CH₂CCl₃—Ph |
| 961 | H | H | H | 4-(Thz-2-yl)Ph | 4-OMe—Ph |
| 962 | H | H | H | 4-(Thz-2-yl)Ph | 3-F-4-OMe—Ph |
| 963 | H | H | H | 4-(Thz-2-yl)Ph | 4-OEt—Ph |
| 964 | H | H | H | 4-(Thz-2-yl)Ph | 4-OPr—Ph |
| 965 | H | H | H | 4-(Thz-2-yl)Ph | 4-OiPr—Ph |
| 966 | H | H | H | 4-(Thz-2-yl)Ph | 4-OtBu—Ph |
| 967 | H | H | H | 4-(Thz-2-yl)Ph | 4-OCF₃—Ph |
| 968 | H | H | H | 4-(Thz-2-yl)Ph | 4-OCHF₂—Ph |
| 969 | H | H | H | 4-(Thz-2-yl)Ph | 4-OCHF₂-3-F—Ph |
| 970 | H | H | H | 4-(Thz-2-yl)Ph | 4-OCCl₃—Ph |
| 971 | H | H | H | 4-(Thz-2-yl)Ph | 4-OCHCl₂—Ph |
| 972 | H | H | H | 4-(Thz-2-yl)Ph | Th-2-yl |
| 973 | H | H | H | 4-(Thz-2-yl)Ph | Th-3-yl |
| 974 | H | H | H | 4-(Thz-2-yl)Ph | 5-Cl—Th-2-yl |
| 975 | H | H | H | 4-(Thz-2-yl)Ph | 1-Me-1H-Imz-4-yl |
| 976 | H | H | H | 4-(Thz-2-yl)Ph | Thz-2-yl |
| 977 | H | H | H | 4-(Thz-2-yl)Ph | Py-2-yl |
| 978 | H | H | H | 4-(Thz-2-yl)Ph | 5-F—Py-2-yl |
| 979 | H | H | H | 4-(Thz-2-yl)Ph | 5-Cl—Py-2-yl |
| 980 | H | H | H | 4-(Thz-2-yl)Ph | 5-Me—Py-2-yl |
| 981 | H | H | H | 4-(Thz-2-yl)Ph | 5-Et—Py-2-yl |
| 982 | H | H | H | 4-(Thz-2-yl)Ph | 5-CF₃—Py-2-yl |
| 983 | H | H | H | 4-(Thz-2-yl)Ph | 5-OMe—Py-2-yl |
| 984 | H | H | H | 4-(Thz-2-yl)Ph | 5-OCHF₂—Py-2-yl |
| 985 | H | H | H | 4-(Thz-2-yl)Ph | Py-3-yl |
| 986 | H | H | H | 4-(Thz-2-yl)Ph | 6-F—Py-3-yl |
| 987 | H | H | H | 4-(Thz-2-yl)Ph | 6-Cl—Py-3-yl |
| 988 | H | H | H | 4-(Thz-2-yl)Ph | 6-Me—Py-3-yl |
| 989 | H | H | H | 4-(Thz-2-yl)Ph | 6-Et—Py-3-yl |
| 990 | H | H | H | 4-(Thz-2-yl)Ph | 6-CF₃—Py-3-yl |
| 991 | H | H | H | 4-(Thz-2-yl)Ph | 6-OMe—Py-3-yl |
| 992 | H | H | H | 4-(Thz-2-yl)Ph | 6-OCHF₂—Py-3-yl |
| 993 | H | H | H | 4-(Thz-2-yl)Ph | Py-4-yl |
| 994 | H | H | H | 4-(Thz-2-yl)Ph | Pym-2-yl |
| 995 | H | H | H | 4-(4-F-Thz-2-yl)Ph | Ph |
| 996 | H | H | H | 4-(4-F-Thz-2-yl)Ph | 2-F—Ph |
| 997 | H | H | H | 4-(4-F-Thz-2-yl)Ph | 3-F—Ph |
| 998 | H | H | H | 4-(4-F-Thz-2-yl)Ph | 4-F—Ph |
| 999 | H | H | H | 4-(4-F-Thz-2-yl)Ph | 2-Cl—Ph |
| 1000 | H | H | H | 4-(4-F-Thz-2-yl)Ph | 3-Cl—Ph |
| 1001 | H | H | H | 4-(4-F-Thz-2-yl)Ph | 4-Cl—Ph |
| 1002 | H | H | H | 4-(4-F-Thz-2-yl)Ph | 2,6-diCl—Ph |
| 1003 | H | H | H | 4-(4-F-Thz-2-yl)Ph | 4-OMe—Ph |
| 1004 | H | H | H | 4-(4-F-Thz-2-yl)Ph | Py-2-yl |
| 1005 | H | H | H | 4-(4-F-Thz-2-yl)Ph | Py-3-yl |
| 1006 | H | H | H | 4-(4-Cl-Thz-2-yl)Ph | Ph |
| 1007 | H | H | H | 4-(4-Cl-Thz-2-yl)Ph | 2-F—Ph |
| 1008 | H | H | H | 4-(4-Cl-Thz-2-yl)Ph | 3-F—Ph |
| 1009 | H | H | H | 4-(4-Cl-Thz-2-yl)Ph | 4-F—Ph |
| 1010 | H | H | H | 4-(4-Cl-Thz-2-yl)Ph | 2-Cl—Ph |
| 1011 | H | H | H | 4-(4-Cl-Thz-2-yl)Ph | 3-Cl—Ph |
| 1012 | H | H | H | 4-(4-Cl-Thz-2-yl)Ph | 4-Cl—Ph |
| 1013 | H | H | H | 4-(4-Cl-Thz-2-yl)Ph | 2,6-diCl—Ph |
| 1014 | H | H | H | 4-(4-Cl-Thz-2-yl)Ph | 4-OMe—Ph |
| 1015 | H | H | H | 4-(4-Cl-Thz-2-yl)Ph | Py-2-yl |
| 1016 | H | H | H | 4-(4-Cl-Thz-2-yl)Ph | Py-3-yl |
| 1017 | H | H | H | 4-(4-Me-Thz-2-yl)Ph | 4-F—Ph |
| 1018 | H | H | H | 4-(4-Me-Thz-2-yl)Ph | Py-2-yl |
| 1019 | H | H | H | 4-(4-Me-Thz-2-yl)Ph | Py-3-yl |
| 1020 | H | H | H | 4-(4-Et-Thz-2-yl)Ph | 4-F—Ph |
| 1021 | H | H | H | 4-(4-Et-Thz-2-yl)Ph | Py-2-yl |
| 1022 | H | H | H | 4-(4-Et-Thz-2-yl)Ph | Py-3-yl |
| 1023 | H | H | H | 4-(4-CF₃-Thz-2-yl)Ph | 4-F—Ph |
| 1024 | H | H | H | 4-(4-CF₃-Thz-2-yl)Ph | Py-2-yl |
| 1025 | H | H | H | 4-(4-CF₃-Thz-2-yl)Ph | Py-3-yl |
| 1026 | H | H | H | 4-(4-OMe-Thz-2-yl)Ph | 4-F—Ph |
| 1027 | H | H | H | 4-(4-OMe-Thz-2-yl)Ph | Py-2-yl |
| 1028 | H | H | H | 4-(4-OMe-Thz-2-yl)Ph | Py-3-yl |
| 1029 | H | H | H | 4-(4-OCHF₂-Thz-2-yl)Ph | 4-F—Ph |
| 1030 | H | H | H | 4-(4-OCHF₂-Thz-2-yl)Ph | Py-2-yl |
| 1031 | H | H | H | 4-(4-OCHF₂-Thz-2-yl)Ph | Py-3-yl |
| 1032 | Me | H | H | 4-(Thz-4-yl)Ph | 4-F—Ph |
| 1033 | Me | H | H | 4-(Thz-4-yl)Ph | Py-2-yl |
| 1034 | Me | H | H | 4-(Thz-4-yl)Ph | Py-3-yl |
| 1035 | Et | H | H | 4-(Thz-4-yl)Ph | 4-F—Ph |
| 1036 | Et | H | H | 4-(Thz-4-yl)Ph | Py-2-yl |
| 1037 | Et | H | H | 4-(Thz-4-yl)Ph | Py-3-yl |
| 1038 | Me | Me | Me | 4-(Thz-4-yl)Ph | Py-2-yl |
| 1039 | Et | Me | Me | 4-(Thz-4-yl)Ph | Py-2-yl |
| 1040 | H | Me | Me | 4-(Thz-4-yl)Ph | 4-F—Ph |
| 1041 | H | Me | Me | 4-(Thz-4-yl)Ph | Py-2-yl |
| 1042 | H | Me | Me | 4-(Thz-4-yl)Ph | Py-3-yl |
| 1043 | H | Me | H | 4-(Thz-4-yl)Ph | 4-F—Ph |
| 1044 | H | Me | H | 4-(Thz-4-yl)Ph | Py-2-yl |
| 1045 | H | Me | H | 4-(Thz-4-yl)Ph | Py-3-yl |
| 1046 | H | H | H | 4-(Thz-4-yl)Ph | Ph |
| 1047 | H | H | H | 4-(Thz-4-yl)Ph | 2-F—Ph |
| 1048 | H | H | H | 4-(Thz-4-yl)Ph | 3-F—Ph |
| 1049 | H | H | H | 4-(Thz-4-yl)Ph | 4-F—Ph |
| 1050 | H | H | H | 4-(Thz-4-yl)Ph | 3,4-diF—Ph |
| 1051 | H | H | H | 4-(Thz-4-yl)Ph | 3,5-diF—Ph |
| 1052 | H | H | H | 4-(Thz-4-yl)Ph | 3,4,5-triF—Ph |
| 1053 | H | H | H | 4-(Thz-4-yl)Ph | 2-Cl—Ph |
| 1054 | H | H | H | 4-(Thz-4-yl)Ph | 3-Cl—Ph |
| 1055 | H | H | H | 4-(Thz-4-yl)Ph | 4-Cl—Ph |
| 1056 | H | H | H | 4-(Thz-4-yl)Ph | 2,6-diCl—Ph |
| 1057 | H | H | H | 4-(Thz-4-yl)Ph | 4-Cl-3-F—Ph |
| 1058 | H | H | H | 4-(Thz-4-yl)Ph | 4-Cl-3,5-diF—Ph |
| 1059 | H | H | H | 4-(Thz-4-yl)Ph | 4-Br—Ph |
| 1060 | H | H | H | 4-(Thz-4-yl)Ph | 4-Me—Ph |
| 1061 | H | H | H | 4-(Thz-4-yl)Ph | 3-F-4-Me—Ph |
| 1062 | H | H | H | 4-(Thz-4-yl)Ph | 4-Et—Ph |
| 1063 | H | H | H | 4-(Thz-4-yl)Ph | 4-Et-3-F—Ph |
| 1064 | H | H | H | 4-(Thz-4-yl)Ph | 4-Pr—Ph |
| 1065 | H | H | H | 4-(Thz-4-yl)Ph | 4-iPr—Ph |
| 1066 | H | H | H | 4-(Thz-4-yl)Ph | 4-tBu—Ph |
| 1067 | H | H | H | 4-(Thz-4-yl)Ph | 4-CF₃—Ph |

TABLE 1-continued

| Compound No. | R¹ | R² | R³ | Y | Z |
|---|---|---|---|---|---|
| 1068 | H | H | H | 4-(Thz-4-yl)Ph | 3-F-4-CF3—Ph |
| 1069 | H | H | H | 4-(Thz-4-yl)Ph | 4-CHF$_2$—Ph |
| 1070 | H | H | H | 4-(Thz-4-yl)Ph | 4-CCl$_3$—Ph |
| 1071 | H | H | H | 4-(Thz-4-yl)Ph | 4-CHCl$_2$—Ph |
| 1072 | H | H | H | 4-(Thz-4-yl)Ph | 4-CH$_2$CF$_3$—Ph |
| 1073 | H | H | H | 4-(Thz-4-yl)Ph | 4-CH$_2$CCl$_3$—Ph |
| 1074 | H | H | H | 4-(Thz-4-yl)Ph | 4-OMe—Ph |
| 1075 | H | H | H | 4-(Thz-4-yl)Ph | 3-F-4-OMe—Ph |
| 1076 | H | H | H | 4-(Thz-4-yl)Ph | 4-OEt—Ph |
| 1077 | H | H | H | 4-(Thz-4-yl)Ph | 4-OPr—Ph |
| 1078 | H | H | H | 4-(Thz-4-yl)Ph | 4-OiPr—Ph |
| 1079 | H | H | H | 4-(Thz-4-yl)Ph | 4-OtBu—Ph |
| 1080 | H | H | H | 4-(Thz-4-yl)Ph | 4-OCF$_3$—Ph |
| 1081 | H | H | H | 4-(Thz-4-yl)Ph | 4-OCHF$_2$—Ph |
| 1082 | H | H | H | 4-(Thz-4-yl)Ph | 4-OCHF$_2$-3-F—Ph |
| 1083 | H | H | H | 4-(Thz-4-yl)Ph | 4-OCCl$_3$—Ph |
| 1084 | H | H | H | 4-(Thz-4-yl)Ph | 4-OCHCl$_2$—Ph |
| 1085 | H | H | H | 4-(Thz-4-yl)Ph | Th-2-yl |
| 1086 | H | H | H | 4-(Thz-4-yl)Ph | Th-3-yl |
| 1087 | H | H | H | 4-(Thz-4-yl)Ph | 5-Cl—Th-2-yl |
| 1088 | H | H | H | 4-(Thz-4-yl)Ph | 1-Me—1H-Imz-4-yl |
| 1089 | H | H | H | 4-(Thz-4-yl)Ph | Thz-2-yl |
| 1090 | H | H | H | 4-(Thz-4-yl)Ph | Py-2-yl |
| 1091 | H | H | H | 4-(Thz-4-yl)Ph | 5-F—Py-2-yl |
| 1092 | H | H | H | 4-(Thz-4-yl)Ph | 5-Cl—Py-2-yl |
| 1093 | H | H | H | 4-(Thz-4-yl)Ph | 5-Me—Py-2-yl |
| 1094 | H | H | H | 4-(Thz-4-yl)Ph | 5-Et—Py-2-yl |
| 1095 | H | H | H | 4-(Thz-4-yl)Ph | 5-CF3—Py-2-yl |
| 1096 | H | H | H | 4-(Thz-4-yl)Ph | 5-OMe—Py-2-yl |
| 1097 | H | H | H | 4-(Thz-4-yl)Ph | 5-OCHF$_2$—Py-2-yl |
| 1098 | H | H | H | 4-(Thz-4-yl)Ph | Py-3-yl |
| 1099 | H | H | H | 4-(Thz-4-yl)Ph | 6-F—Py-3-yl |
| 1100 | H | H | H | 4-(Thz-4-yl)Ph | 6-Cl—Py-3-yl |
| 1101 | H | H | H | 4-(Thz-4-yl)Ph | 6-Me—Py-3-yl |
| 1102 | H | H | H | 4-(Thz-4-yl)Ph | 6-Et—Py-3-yl |
| 1103 | H | H | H | 4-(Thz-4-yl)Ph | 6-CF$_3$—Py-3-yl |
| 1104 | H | H | H | 4-(Thz-4-yl)Ph | 6-OMe—Py-3-yl |
| 1105 | H | H | H | 4-(Thz-4-yl)Ph | 6-OCHF$_2$—Py-3-yl |
| 1106 | H | H | H | 4-(Thz-4-yl)Ph | Py-4-yl |
| 1107 | H | H | H | 4-(Thz-4-yl)Ph | Pym-2-yl |
| 1108 | H | H | H | 4-(2-F-Thz-4-yl)Ph | Ph |
| 1109 | H | H | H | 4-(2-F-Thz-4-yl)Ph | 2-F—Ph |
| 1110 | H | H | H | 4-(2-F-Thz-4-yl)Ph | 3-F—Ph |
| 1111 | H | H | H | 4-(2-F-Thz-4-yl)Ph | 4-F—Ph |
| 1112 | H | H | H | 4-(2-F-Thz-4-yl)Ph | 2-Cl—Ph |
| 1113 | H | H | H | 4-(2-F-Thz-4-yl)Ph | 3-Cl—Ph |
| 1114 | H | H | H | 4-(2-F-Thz-4-yl)Ph | 4-Cl—Ph |
| 1115 | H | H | H | 4-(2-F-Thz-4-yl)Ph | 2,6-diCl—Ph |
| 1116 | H | H | H | 4-(2-F-Thz-4-yl)Ph | 4-OMe—Ph |
| 1117 | H | H | H | 4-(2-F-Thz-4-yl)Ph | Py-2-yl |
| 1118 | H | H | H | 4-(2-F-Thz-4-yl)Ph | Py-3-yl |
| 1119 | H | H | H | 4-(2-Cl-Thz-4-yl)Ph | Ph |
| 1120 | H | H | H | 4-(2-Cl-Thz-4-yl)Ph | 2-F—Ph |
| 1121 | H | H | H | 4-(2-Cl-Thz-4-yl)Ph | 3-F—Ph |
| 1122 | H | H | H | 4-(2-Cl-Thz-4-yl)Ph | 4-F—Ph |
| 1123 | H | H | H | 4-(2-Cl-Thz-4-yl)Ph | 2-Cl—Ph |
| 1124 | H | H | H | 4-(2-Cl-Thz-4-yl)Ph | 3-Cl—Ph |
| 1125 | H | H | H | 4-(2-Cl-Thz-4-yl)Ph | 4-Cl—Ph |
| 1126 | H | H | H | 4-(2-Cl-Thz-4-yl)Ph | 2,6-diCl—Ph |
| 1127 | H | H | H | 4-(2-Cl-Thz-4-yl)Ph | 4-OMe—Ph |
| 1128 | H | H | H | 4-(2-Cl-Thz-4-yl)Ph | Py-2-yl |
| 1129 | H | H | H | 4-(2-Cl-Thz-4-yl)Ph | Py-3-yl |
| 1130 | H | H | H | 4-(2-Me-Thz-4-yl)Ph | 4-F—Ph |
| 1131 | H | H | H | 4-(2-Me-Thz-4-yl)Ph | Py-2-yl |
| 1132 | H | H | H | 4-(2-Me-Thz-4-yl)Ph | Py-3-yl |
| 1133 | H | H | H | 4-(2-Et-Thz-4-yl)Ph | 4-F—Ph |
| 1134 | H | H | H | 4-(2-Et-Thz-4-yl)Ph | Py-2-yl |
| 1135 | H | H | H | 4-(2-Et-Thz-4-yl)Ph | Py-3-yl |
| 1136 | H | H | H | 4-(2-CF$_3$-Thz-4-yl)Ph | 4-F—Ph |
| 1137 | H | H | H | 4-(2-CF$_3$-Thz-4-yl)Ph | Py-2-yl |
| 1138 | H | H | H | 4-(2-CF$_3$-Thz-4-yl)Ph | Py-3-yl |
| 1139 | H | H | H | 4-(2-OMe-Thz-4-yl)Ph | 4-F—Ph |
| 1140 | H | H | H | 4-(2-OMe-Thz-4-yl)Ph | Py-2-yl |
| 1141 | H | H | H | 4-(2-OMe-Thz-4-yl)Ph | Py-3-yl |
| 1142 | H | H | H | 4-(2-OCHF$_2$-Thz-4-yl)Ph | 4-F—Ph |
| 1143 | H | H | H | 4-(2-OCHF$_2$-Thz-4-yl)Ph | Py-2-yl |
| 1144 | H | H | H | 4-(2-OCHF$_2$-Thz-4-yl)Ph | Py-3-yl |
| 1145 | H | H | H | 4-(Thz-5-yl)Ph | Ph |
| 1146 | H | H | H | 4-(Thz-5-yl)Ph | 2-F—Ph |
| 1147 | H | H | H | 4-(Thz-5-yl)Ph | 3-F—Ph |
| 1148 | H | H | H | 4-(Thz-5-yl)Ph | 4-F—Ph |
| 1149 | H | H | H | 4-(Thz-5-yl)Ph | 2-Cl—Ph |
| 1150 | H | H | H | 4-(Thz-5-yl)Ph | 3-Cl—Ph |
| 1151 | H | H | H | 4-(Thz-5-yl)Ph | 4-Cl—Ph |
| 1152 | H | H | H | 4-(Thz-5-yl)Ph | 2,6-diCl—Ph |
| 1153 | H | H | H | 4-(Thz-5-yl)Ph | 4-OMe—Ph |
| 1154 | H | H | H | 4-(Thz-5-yl)Ph | Py-2-yl |
| 1155 | H | H | H | 4-(Thz-5-yl)Ph | Py-3-yl |
| 1156 | H | H | H | 4-(Py-2-yl)Ph | 4-F—Ph |
| 1157 | H | H | H | 4-(Py-2-yl)Ph | Py-2-yl |
| 1158 | H | H | H | 4-(Py-2-yl)Ph | Py-3-yl |
| 1159 | H | H | H | 4-(Py-3-yl)Ph | 4-F—Ph |
| 1160 | H | H | H | 4-(Py-3-yl)Ph | Py-2-yl |
| 1161 | H | H | H | 4-(Py-3-yl)Ph | Py-3-yl |
| 1162 | H | H | H | 4-(Py-4-yl)Ph | 4-F—Ph |
| 1163 | H | H | H | 4-(Py-4-yl)Ph | Py-2-yl |
| 1164 | H | H | H | 4-(Py-4-yl)Ph | Py-3-yl |
| 1165 | H | H | H | 4-(Pyd-3-yl)Ph | Ph |
| 1166 | H | H | H | 4-(Pyd-3-yl)Ph | 2-F—Ph |
| 1167 | H | H | H | 4-(Pyd-3-yl)Ph | 3-F—Ph |
| 1168 | H | H | H | 4-(Pyd-3-yl)Ph | 4-F—Ph |
| 1169 | H | H | H | 4-(Pyd-3-yl)Ph | 2-Cl—Ph |
| 1170 | H | H | H | 4-(Pyd-3-yl)Ph | 3-Cl—Ph |
| 1171 | H | H | H | 4-(Pyd-3-yl)Ph | 4-Cl—Ph |
| 1172 | H | H | H | 4-(Pyd-3-yl)Ph | 2,6-diCl—Ph |
| 1173 | H | H | H | 4-(Pyd-3-yl)Ph | 4-OMe—Ph |
| 1174 | H | H | H | 4-(Pyd-3-yl)Ph | Py-2-yl |
| 1175 | H | H | H | 4-(Pyd-3-yl)Ph | Py-3-yl |
| 1176 | H | H | H | 4-(Pyd-4-yl)Ph | Ph |
| 1177 | H | H | H | 4-(Pyd-4-yl)Ph | 2-F—Ph |
| 1178 | H | H | H | 4-(Pyd-4-yl)Ph | 3-F—Ph |
| 1179 | H | H | H | 4-(Pyd-4-yl)Ph | 4-F—Ph |
| 1180 | H | H | H | 4-(Pyd-4-yl)Ph | 3,4-diF—Ph |
| 1181 | H | H | H | 4-(Pyd-4-yl)Ph | 3,5-diF—Ph |
| 1182 | H | H | H | 4-(Pyd-4-yl)Ph | 2-Cl—Ph |
| 1183 | H | H | H | 4-(Pyd-4-yl)Ph | 3-Cl—Ph |
| 1184 | H | H | H | 4-(Pyd-4-yl)Ph | 4-Cl—Ph |
| 1185 | H | H | H | 4-(Pyd-4-yl)Ph | 2,6-diCl—Ph |
| 1186 | H | H | H | 4-(Pyd-4-yl)Ph | 4-Cl-3-F—Ph |
| 1187 | H | H | H | 4-(Pyd-4-yl)Ph | 4-Me—Ph |
| 1188 | H | H | H | 4-(Pyd-4-yl)Ph | 3-F-4-Me—Ph |
| 1189 | H | H | H | 4-(Pyd-4-yl)Ph | 4-Et—Ph |
| 1190 | H | H | H | 4-(Pyd-4-yl)Ph | 4-Et-3-F—Ph |
| 1191 | H | H | H | 4-(Pyd-4-yl)Ph | 4-CF$_3$—Ph |
| 1192 | H | H | H | 4-(Pyd-4-yl)Ph | 3-F-4-CF$_3$—Ph |
| 1193 | H | H | H | 4-(Pyd-4-yl)Ph | 4-OMe—Ph |
| 1194 | H | H | H | 4-(Pyd-4-yl)Ph | 3-F-4-OMe—Ph |
| 1195 | H | H | H | 4-(Pyd-4-yl)Ph | 4-OCHF$_2$—Ph |
| 1196 | H | H | H | 4-(Pyd-4-yl)Ph | 4-OCHF$_2$-3-F—Ph |
| 1197 | H | H | H | 4-(Pyd-4-yl)Ph | Th-2-yl |
| 1198 | H | H | H | 4-(Pyd-4-yl)Ph | Th-3-yl |
| 1199 | H | H | H | 4-(Pyd-4-yl)Ph | Py-2-yl |
| 1200 | H | H | H | 4-(Pyd-4-yl)Ph | 5-F—Py-2-yl |
| 1201 | H | H | H | 4-(Pyd-4-yl)Ph | 5-Cl—Py-2-yl |
| 1202 | H | H | H | 4-(Pyd-4-yl)Ph | 5-OMe—Py-2-yl |
| 1203 | H | H | H | 4-(Pyd-4-yl)Ph | Py-3-yl |
| 1204 | H | H | H | 4-(Pyd-4-yl)Ph | 6-F—Py-3-yl |
| 1205 | H | H | H | 4-(Pyd-4-yl)Ph | 6-Cl—Py-3-yl |
| 1206 | H | H | H | 4-(Pyd-4-yl)Ph | 6-OMe—Py-3-yl |
| 1207 | H | H | H | 4-(Pyd-4-yl)Ph | Py-4-yl |
| 1208 | Me | H | H | 4-(Pym-2-yl)Ph | 4-F—Ph |
| 1209 | Me | H | H | 4-(Pym-2-yl)Ph | Py-2-yl |
| 1210 | Me | H | H | 4-(Pym-2-yl)Ph | Py-3-yl |
| 1211 | Et | H | H | 4-(Pym-2-yl)Ph | 4-F—Ph |
| 1212 | Et | H | H | 4-(Pym-2-yl)Ph | Py-2-yl |
| 1213 | Et | H | H | 4-(Pym-2-yl)Ph | Py-3-yl |
| 1214 | Me | Me | H | 4-(Pym-2-yl)Ph | Py-2-yl |
| 1215 | Et | Me | H | 4-(Pym-2-yl)Ph | Py-2-yl |
| 1216 | H | Me | H | 4-(Pym-2-yl)Ph | 4-F—Ph |
| 1217 | H | Me | H | 4-(Pym-2-yl)Ph | Py-2-yl |
| 1218 | H | Me | H | 4-(Pym-2-yl)Ph | Py-3-yl |
| 1219 | H | Me | H | 4-(Pym-2-yl)Ph | 4-F—Ph |

TABLE 1-continued

| Compound No. | R¹ | R² | R³ | Y | Z |
|---|---|---|---|---|---|
| 1220 | H | Me | H | 4-(Pym-2-yl)Ph | Py-2-yl |
| 1221 | H | Me | H | 4-(Pym-2-yl)Ph | Py-3-yl |
| 1222 | H | H | H | 4-(Pym-2-yl)Ph | Ph |
| 1223 | H | H | H | 4-(Pym-2-yl)Ph | 2-F—Ph |
| 1224 | H | H | H | 4-(Pym-2-yl)Ph | 3-F—Ph |
| 1225 | H | H | H | 4-(Pym-2-yl)Ph | 4-F—Ph |
| 1226 | H | H | H | 4-(Pym-2-yl)Ph | 3,4-diF—Ph |
| 1227 | H | H | H | 4-(Pym-2-yl)Ph | 3,5-diF—Ph |
| 1228 | H | H | H | 4-(Pym-2-yl)Ph | 3,4,5-triF—Ph |
| 1229 | H | H | H | 4-(Pym-2-yl)Ph | 2-Cl—Ph |
| 1230 | H | H | H | 4-(Pym-2-yl)Ph | 3-Cl—Ph |
| 1231 | H | H | H | 4-(Pym-2-yl)Ph | 4-Cl—Ph |
| 1232 | H | H | H | 4-(Pym-2-yl)Ph | 2,6-diCl—Ph |
| 1233 | H | H | H | 4-(Pym-2-yl)Ph | 4-Cl-3-F—Ph |
| 1234 | H | H | H | 4-(Pym-2-yl)Ph | 4-Cl-3,5-diF—Ph |
| 1235 | H | H | H | 4-(Pym-2-yl)Ph | 4-Br—Ph |
| 1236 | H | H | H | 4-(Pym-2-yl)Ph | 4-Me—Ph |
| 1237 | H | H | H | 4-(Pym-2-yl)Ph | 3-F-4-Me—Ph |
| 1238 | H | H | H | 4-(Pym-2-yl)Ph | 4-Et—Ph |
| 1239 | H | H | H | 4-(Pym-2-yl)Ph | 4-Et-3-F—Ph |
| 1240 | H | H | H | 4-(Pym-2-yl)Ph | 4-Pr—Ph |
| 1241 | H | H | H | 4-(Pym-2-yl)Ph | 4-iPr—Ph |
| 1242 | H | H | H | 4-(Pym-2-yl)Ph | 4-tBu—Ph |
| 1243 | H | H | H | 4-(Pym-2-yl)Ph | 4-CF₃—Ph |
| 1244 | H | H | H | 4-(Pym-2-yl)Ph | 3-F-4-CF3—Ph |
| 1245 | H | H | H | 4-(Pym-2-yl)Ph | 4-CHF₂—Ph |
| 1246 | H | H | H | 4-(Pym-2-yl)Ph | 4-CCl₃—Ph |
| 1247 | H | H | H | 4-(Pym-2-yl)Ph | 4-CHCl₂—Ph |
| 1248 | H | H | H | 4-(Pym-2-yl)Ph | 4-CH₂CF₃—Ph |
| 1249 | H | H | H | 4-(Pym-2-yl)Ph | 4-CH₂CCl₃—Ph |
| 1250 | H | H | H | 4-(Pym-2-yl)Ph | 4-OMe—Ph |
| 1251 | H | H | H | 4-(Pym-2-yl)Ph | 3-F-4-OMe—Ph |
| 1252 | H | H | H | 4-(Pym-2-yl)Ph | 4-OEt—Ph |
| 1253 | H | H | H | 4-(Pym-2-yl)Ph | 4-OPr—Ph |
| 1254 | H | H | H | 4-(Pym-2-yl)Ph | 4-OiPr—Ph |
| 1255 | H | H | H | 4-(Pym-2-yl)Ph | 4-OtBu—Ph |
| 1256 | H | H | H | 4-(Pym-2-yl)Ph | 4-OCF₃—Ph |
| 1257 | H | H | H | 4-(Pym-2-yl)Ph | 4-OCHF₂—Ph |
| 1258 | H | H | H | 4-(Pym-2-yl)Ph | 4-OCHF₂-3-F—Ph |
| 1259 | H | H | H | 4-(Pym-2-yl)Ph | 4-OCCl₃—Ph |
| 1260 | H | H | H | 4-(Pym-2-yl)Ph | 4-OCHCl₂—Ph |
| 1261 | H | H | H | 4-(Pym-2-yl)Ph | Th-2-yl |
| 1262 | H | H | H | 4-(Pym-2-yl)Ph | Th-3-yl |
| 1263 | H | H | H | 4-(Pym-2-yl)Ph | 5-Cl—Th-2-yl |
| 1264 | H | H | H | 4-(Pym-2-yl)Ph | 1-Me-1H-Imz-4-yl |
| 1265 | H | H | H | 4-(Pym-2-yl)Ph | Thz-2-yl |
| 1266 | H | H | H | 4-(Pym-2-yl)Ph | Py-2-yl |
| 1267 | H | H | H | 4-(Pym-2-yl)Ph | 5-F—Py-2-yl |
| 1268 | H | H | H | 4-(Pym-2-yl)Ph | 5-Cl—Py-2-yl |
| 1269 | H | H | H | 4-(Pym-2-yl)Ph | 5-Me—Py-2-yl |
| 1270 | H | H | H | 4-(Pym-2-yl)Ph | 5-Et—Py-2-yl |
| 1271 | H | H | H | 4-(Pym-2-yl)Ph | 5-CF₃—Py-2-yl |
| 1272 | H | H | H | 4-(Pym-2-yl)Ph | 5-OMe—Py-2-yl |
| 1273 | H | H | H | 4-(Pym-2-yl)Ph | 5-OCHF₂—Py-2-yl |
| 1274 | H | H | H | 4-(Pym-2-yl)Ph | Py-3-yl |
| 1275 | H | H | H | 4-(Pym-2-yl)Ph | 6-F—Py-3-yl |
| 1276 | H | H | H | 4-(Pym-2-yl)Ph | 6-Cl—Py-3-yl |
| 1277 | H | H | H | 4-(Pym-2-yl)Ph | 6-Me—Py-3-yl |
| 1278 | H | H | H | 4-(Pym-2-yl)Ph | 6-Et—Py-3-yl |
| 1279 | H | H | H | 4-(Pym-2-yl)Ph | 6-CF₃—Py-3-yl |
| 1280 | H | H | H | 4-(Pym-2-yl)Ph | 6-OMe—Py-3-yl |
| 1281 | H | H | H | 4-(Pym-2-yl)Ph | 6-OCHF₂—Py-3-yl |
| 1282 | H | H | H | 4-(Pym-2-yl)Ph | Py-4-yl |
| 1283 | H | H | H | 4-(Pym-2-yl)Ph | Pym-2-yl |
| 1284 | H | H | H | 4-(5-F-Pym-2-yl)Ph | 4-F—Ph |
| 1285 | H | H | H | 4-(5-F-Pym-2-yl)Ph | Py-2-yl |
| 1286 | H | H | H | 4-(5-F-Pym-2-yl)Ph | Py-3-yl |
| 1287 | H | H | H | 4-(5-Cl-Pym-2-yl)Ph | 4-F—Ph |
| 1288 | H | H | H | 4-(5-Cl-Pym-2-yl)Ph | Py-2-yl |
| 1289 | H | H | H | 4-(5-Cl-Pym-2-yl)Ph | Py-3-yl |
| 1290 | H | H | H | 4-(5-OH-Pym-2-yl)Ph | Ph |
| 1291 | H | H | H | 4-(5-OH-Pym-2-yl)Ph | 2-F—Ph |
| 1292 | H | H | H | 4-(5-OH-Pym-2-yl)Ph | 3-F—Ph |
| 1293 | H | H | H | 4-(5-OH-Pym-2-yl)Ph | 4-F—Ph |
| 1294 | H | H | H | 4-(5-OH-Pym-2-yl)Ph | 2-Cl—Ph |
| 1295 | H | H | H | 4-(5-OH-Pym-2-yl)Ph | 3-Cl—Ph |
| 1296 | H | H | H | 4-(5-OH-Pym-2-yl)Ph | 4-Cl—Ph |
| 1297 | H | H | H | 4-(5-OH-Pym-2-yl)Ph | 2,6-diCl—Ph |
| 1298 | H | H | H | 4-(5-OH-Pym-2-yl)Ph | 4-OMe—Ph |
| 1299 | H | H | H | 4-(5-OH-Pym-2-yl)Ph | Py-2-yl |
| 1300 | H | H | H | 4-(5-OH-Pym-2-yl)Ph | Py-3-yl |
| 1301 | H | H | H | 4-(Pym-4-yl)Ph | Ph |
| 1302 | H | H | H | 4-(Pym-4-yl)Ph | 2-F—Ph |
| 1303 | H | H | H | 4-(Pym-4-yl)Ph | 3-F—Ph |
| 1304 | H | H | H | 4-(Pym-4-yl)Ph | 4-F—Ph |
| 1305 | H | H | H | 4-(Pym-4-yl)Ph | 2-Cl—Ph |
| 1306 | H | H | H | 4-(Pym-4-yl)Ph | 3-Cl—Ph |
| 1307 | H | H | H | 4-(Pym-4-yl)Ph | 4-Cl—Ph |
| 1308 | H | H | H | 4-(Pym-4-yl)Ph | 2,6-diCl—Ph |
| 1309 | H | H | H | 4-(Pym-4-yl)Ph | 4-OMe—Ph |
| 1310 | H | H | H | 4-(Pym-4-yl)Ph | Py-2-yl |
| 1311 | H | H | H | 4-(Pym-4-yl)Ph | Py-3-yl |
| 1312 | H | H | H | 4-(Pym-5-yl)Ph | Ph |
| 1313 | H | H | H | 4-(Pym-5-yl)Ph | 2-F—Ph |
| 1314 | H | H | H | 4-(Pym-5-yl)Ph | 3-F—Ph |
| 1315 | H | H | H | 4-(Pym-5-yl)Ph | 4-F—Ph |
| 1316 | H | H | H | 4-(Pym-5-yl)Ph | 2-Cl—Ph |
| 1317 | H | H | H | 4-(Pym-5-yl)Ph | 3-Cl—Ph |
| 1318 | H | H | H | 4-(Pym-5-yl)Ph | 4-Cl—Ph |
| 1319 | H | H | H | 4-(Pym-5-yl)Ph | 2,6-diCl—Ph |
| 1320 | H | H | H | 4-(Pym-5-yl)Ph | 4-OMe—Ph |
| 1321 | H | H | H | 4-(Pym-5-yl)Ph | Py-2-yl |
| 1322 | H | H | H | 4-(Pym-5-yl)Ph | Py-3-yl |
| 1323 | H | H | H | 4-(4,5-diH-Thz-2-yl)Ph | Ph |
| 1324 | H | H | H | 4-(4,5-diH-Thz-2-yl)Ph | 2-F—Ph |
| 1325 | H | H | H | 4-(4,5-diH-Thz-2-yl)Ph | 3-F—Ph |
| 1326 | H | H | H | 4-(4,5-diH-Thz-2-yl)Ph | 4-F—Ph |
| 1327 | H | H | H | 4-(4,5-diH-Thz-2-yl)Ph | 3,4-diF—Ph |
| 1328 | H | H | H | 4-(4,5-diH-Thz-2-yl)Ph | 3,5-diF—Ph |
| 1329 | H | H | H | 4-(4,5-diH-Thz-2-yl)Ph | 2-Cl—Ph |
| 1330 | H | H | H | 4-(4,5-diH-Thz-2-yl)Ph | 3-Cl—Ph |
| 1331 | H | H | H | 4-(4,5-diH-Thz-2-yl)Ph | 4-Cl—Ph |
| 1332 | H | H | H | 4-(4,5-diH-Thz-2-yl)Ph | 2,6-diCl—Ph |
| 1333 | H | H | H | 4-(4,5-diH-Thz-2-yl)Ph | 4-Cl-3-F—Ph |
| 1334 | H | H | H | 4-(4,5-diH-Thz-2-yl)Ph | 4-Me—Ph |
| 1335 | H | H | H | 4-(4,5-diH-Thz-2-yl)Ph | 3-F-4-Me—Ph |
| 1336 | H | H | H | 4-(4,5-diH-Thz-2-yl)Ph | 4-Et—Ph |
| 1337 | H | H | H | 4-(4,5-diH-Thz-2-yl)Ph | 4-Et-3-F—Ph |
| 1338 | H | H | H | 4-(4,5-diH-Thz-2-yl)Ph | 4-CF₃—Ph |
| 1339 | H | H | H | 4-(4,5-diH-Thz-2-yl)Ph | 3-F-4-CF₃—Ph |
| 1340 | H | H | H | 4-(4,5-diH-Thz-2-yl)Ph | 4-OMe—Ph |
| 1341 | H | H | H | 4-(4,5-diH-Thz-2-yl)Ph | 3-F-4-OMe—Ph |
| 1342 | H | H | H | 4-(4,5-diH-Thz-2-yl)Ph | 4-OCHF₂—Ph |
| 1343 | H | H | H | 4-(4,5-diH-Thz-2-yl)Ph | 4-OCHF₂-3-F—Ph |
| 1344 | H | H | H | 4-(4,5-diH-Thz-2-yl)Ph | Th-2-yl |
| 1345 | H | H | H | 4-(4,5-diH-Thz-2-yl)Ph | Th-3-yl |
| 1346 | H | H | H | 4-(4,5-diH-Thz-2-yl)Ph | Py-2-yl |
| 1347 | H | H | H | 4-(4,5-diH-Thz-2-yl)Ph | 5-F—Py-2-yl |
| 1348 | H | H | H | 4-(4,5-diH-Thz-2-yl)Ph | 5-Cl—Py-2-yl |
| 1349 | H | H | H | 4-(4,5-diH-Thz-2-yl)Ph | 5-OMe—Py-2-yl |
| 1350 | H | H | H | 4-(4,5-diH-Thz-2-yl)Ph | Py-3-yl |
| 1351 | H | H | H | 4-(4,5-diH-Thz-2-yl)Ph | 6-F—Py-3-yl |
| 1352 | H | H | H | 4-(4,5-diH-Thz-2-yl)Ph | 6-Cl—Py-3-yl |
| 1353 | H | H | H | 4-(4,5-diH-Thz-2-yl)Ph | 6-OMe—Py-3-yl |
| 1354 | H | H | H | 4-(4,5-diH-Thz-2-yl)Ph | Py-4-yl |
| 1355 | H | H | H | 4-(Pyr-1-yl)Ph | 4-F—Ph |
| 1356 | H | H | H | 4-(Pyr-1-yl)Ph | Py-2-yl |
| 1357 | H | H | H | 4-(Pyr-1-yl)Ph | Py-3-yl |
| 1358 | H | H | H | 4-(Pip-1-yl)Ph | 4-F—Ph |
| 1359 | H | H | H | 4-(Pip-1-yl)Ph | Py-2-yl |
| 1360 | H | H | H | 4-(Pip-1-yl)Ph | Py-3-yl |
| 1361 | H | H | H | 5-Ph—Th-2-yl | 4-F—Ph |
| 1362 | H | H | H | 5-Ph—Th-2-yl | Py-2-yl |
| 1363 | H | H | H | 5-Ph—Th-2-yl | Py-3-yl |
| 1364 | H | H | H | 5-(Thz-2-yl)-Th-2-yl | 4-F—Ph |
| 1365 | H | H | H | 5-(Thz-2-yl)-Th-2-yl | Py-2-yl |
| 1366 | H | H | H | 5-(Thz-2-yl)-Th-2-yl | Py-3-yl |
| 1367 | H | H | H | 5-(Thz-4-yl)-Th-2-yl | 4-F—Ph |
| 1368 | H | H | H | 5-(Thz-4-yl)-Th-2-yl | Py-2-yl |
| 1369 | H | H | H | 5-(Thz-4-yl)-Th-2-yl | Py-3-yl |
| 1370 | H | H | H | 6-Ph-Pyd-3-yl | Ph |
| 1371 | H | H | H | 6-Ph-Pyd-3-yl | 2-F—Ph |

TABLE 1-continued

| Compound No. | R¹ | R² | R³ | Y | Z |
|---|---|---|---|---|---|
| 1372 | H | H | H | 6-Ph-Pyd-3-yl | 3-F—Ph |
| 1373 | H | H | H | 6-Ph-Pyd-3-yl | 4-F—Ph |
| 1374 | H | H | H | 6-Ph-Pyd-3-yl | 3,4-diF—Ph |
| 1375 | H | H | H | 6-Ph-Pyd-3-yl | 3,5-diF—Ph |
| 1376 | H | H | H | 6-Ph-Pyd-3-yl | 2-Cl—Ph |
| 1377 | H | H | H | 6-Ph-Pyd-3-yl | 3-Cl—Ph |
| 1378 | H | H | H | 6-Ph-Pyd-3-yl | 4-Cl—Ph |
| 1379 | H | H | H | 6-Ph-Pyd-3-yl | 2,6-diCl—Ph |
| 1380 | H | H | H | 6-Ph-Pyd-3-yl | 4-Cl-3-F—Ph |
| 1381 | H | H | H | 6-Ph-Pyd-3-yl | 4-Me—Ph |
| 1382 | H | H | H | 6-Ph-Pyd-3-yl | 3-F-4-Me—Ph |
| 1383 | H | H | H | 6-Ph-Pyd-3-yl | 4-Et—Ph |
| 1384 | H | H | H | 6-Ph-Pyd-3-yl | 4-Et-3-F—Ph |
| 1385 | H | H | H | 6-Ph-Pyd-3-yl | 4-CF₃—Ph |
| 1386 | H | H | H | 6-Ph-Pyd-3-yl | 3-F-4-CF₃—Ph |
| 1387 | H | H | H | 6-Ph-Pyd-3-yl | 4-OMe—Ph |
| 1388 | H | H | H | 6-Ph-Pyd-3-yl | 3-F-4-OMe—Ph |
| 1389 | H | H | H | 6-Ph-Pyd-3-yl | 4-OCHF₂—Ph |
| 1390 | H | H | H | 6-Ph-Pyd-3-yl | 4-OCHF₂-3-F—Ph |
| 1391 | H | H | H | 6-Ph-Pyd-3-yl | Th-2-yl |
| 1392 | H | H | H | 6-Ph-Pyd-3-yl | Th-3-yl |
| 1393 | H | H | H | 6-Ph-Pyd-3-yl | Py-2-yl |
| 1394 | H | H | H | 6-Ph-Pyd-3-yl | 5-F—Py-2-yl |
| 1395 | H | H | H | 6-Ph-Pyd-3-yl | 5-Cl—Py-2-yl |
| 1396 | H | H | H | 6-Ph-Pyd-3-yl | 5-OMe—Py-2-yl |
| 1397 | H | H | H | 6-Ph-Pyd-3-yl | Py-3-yl |
| 1398 | H | H | H | 6-Ph-Pyd-3-yl | 6-F—Py-3-yl |
| 1399 | H | H | H | 6-Ph-Pyd-3-yl | 6-Cl—Py-3-yl |
| 1400 | H | H | H | 6-Ph-Pyd-3-yl | 6-OMe—Py-3-yl |
| 1401 | H | H | H | 6-Ph-Pyd-3-yl | Py-4-yl |
| 1402 | H | H | H | 6-(Thz-2-yl)-Pyd-3-yl | Ph |
| 1403 | H | H | H | 6-(Thz-2-yl)-Pyd-3-yl | 2-F—Ph |
| 1404 | H | H | H | 6-(Thz-2-yl)-Pyd-3-yl | 3-F—Ph |
| 1405 | H | H | H | 6-(Thz-2-yl)-Pyd-3-yl | 4-F—Ph |
| 1406 | H | H | H | 6-(Thz-2-yl)-Pyd-3-yl | 2-Cl—Ph |
| 1407 | H | H | H | 6-(Thz-2-yl)-Pyd-3-yl | 3-Cl—Ph |
| 1408 | H | H | H | 6-(Thz-2-yl)-Pyd-3-yl | 4-Cl—Ph |
| 1409 | H | H | H | 6-(Thz-2-yl)-Pyd-3-yl | 2,6-diCl—Ph |
| 1410 | H | H | H | 6-(Thz-2-yl)-Pyd-3-yl | 4-OMe—Ph |
| 1411 | H | H | H | 6-(Thz-2-yl)-Pyd-3-yl | Py-2-yl |
| 1412 | H | H | H | 6-(Thz-2-yl)-Pyd-3-yl | Py-3-yl |
| 1413 | H | H | H | 6-(Thz-4-yl)-Pyd-3-yl | Ph |
| 1414 | H | H | H | 6-(Thz-4-yl)-Pyd-3-yl | 2-F—Ph |
| 1415 | H | H | H | 6-(Thz-4-yl)-Pyd-3-yl | 3-F—Ph |
| 1416 | H | H | H | 6-(Thz-4-yl)-Pyd-3-yl | 4-F—Ph |
| 1417 | H | H | H | 6-(Thz-4-yl)-Pyd-3-yl | 2-Cl—Ph |
| 1418 | H | H | H | 6-(Thz-4-yl)-Pyd-3-yl | 3-Cl—Ph |
| 1419 | H | H | H | 6-(Thz-4-yl)-Pyd-3-yl | 4-Cl—Ph |
| 1420 | H | H | H | 6-(Thz-4-yl)-Pyd-3-yl | 2,6-diCl—Ph |
| 1421 | H | H | H | 6-(Thz-4-yl)-Pyd-3-yl | 4-OMe—Ph |
| 1422 | H | H | H | 6-(Thz-4-yl)-Pyd-3-yl | Py-2-yl |
| 1423 | H | H | H | 6-(Thz-4-yl)-Pyd-3-yl | Py-3-yl |
| 1424 | H | H | H | 2-Ph-Pym-4-yl | 4-F—Ph |
| 1425 | H | H | H | 2-Ph-Pym-4-yl | Py-2-yl |
| 1426 | H | H | H | 2-Ph-Pym-4-yl | Py-3-yl |
| 1427 | H | H | H | 2-(Thz-2-yl)-Pym-4-yl | 4-F—Ph |
| 1428 | H | H | H | 2-(Thz-2-yl)-Pym-4-yl | Py-2-yl |
| 1429 | H | H | H | 2-(Thz-2-yl)-Pym-4-yl | Py-3-yl |
| 1430 | H | H | H | 2-(Thz-4-yl)-Pym-4-yl | 4-F—Ph |
| 1431 | H | H | H | 2-(Thz-4-yl)-Pym-4-yl | Py-2-yl |
| 1432 | H | H | H | 2-(Thz-4-yl)-Pym-4-yl | Py-3-yl |
| 1433 | Hx | H | H | 4-(Thz-2-yl)Ph | Py-2-yl |
| 1434 | H | H | H | 4-(5-Cl-Thz-2-yl)Ph | Ph |
| 1435 | H | H | H | 4-(5-Cl-Thz-2-yl)Ph | 3-F—Ph |
| 1436 | H | H | H | 4-(5-Cl-Thz-2-yl)Ph | 4-F—Ph |
| 1437 | H | H | H | 4-(5-Cl-Thz-2-yl)Ph | 4-Cl—Ph |
| 1438 | H | H | H | 4-(5-Cl-Thz-2-yl)Ph | 4-OMe—Ph |
| 1439 | H | H | H | 4-(5-Cl-Thz-2-yl)Ph | Py-2-yl |
| 1440 | H | H | H | 4-(5-Cl-Thz-2-yl)Ph | Py-3-yl |
| 1441 | H | H | H | 4-(5-Me-Thz-2-yl)Ph | Ph |
| 1442 | H | H | H | 4-(5-Me-Thz-2-yl)Ph | 3-F—Ph |
| 1443 | H | H | H | 4-(5-Me-Thz-2-yl)Ph | 4-F—Ph |
| 1444 | H | H | H | 4-(5-Me-Thz-2-yl)Ph | 4-Cl—Ph |
| 1445 | H | H | H | 4-(5-Me-Thz-2-yl)Ph | 4-OMe—Ph |
| 1446 | H | H | H | 4-(5-Me-Thz-2-yl)Ph | Py-2-yl |
| 1447 | H | H | H | 4-(5-Me-Thz-2-yl)Ph | Py-3-yl |
| 1448 | H | H | H | 4-(4,5-diMe-Thz-2-yl)Ph | Ph |
| 1449 | H | H | H | 4-(4,5-diMe-Thz-2-yl)Ph | 3-F—Ph |
| 1450 | H | H | H | 4-(4,5-diMe-Thz-2-yl)Ph | 4-F—Ph |
| 1451 | H | H | H | 4-(4,5-diMe-Thz-2-yl)Ph | 4-Cl—Ph |
| 1452 | H | H | H | 4-(4,5-diMe-Thz-2-yl)Ph | 4-OMe—Ph |
| 1453 | H | H | H | 4-(4,5-diMe-Thz-2-yl)Ph | Py-2-yl |
| 1454 | H | H | H | 4-(4,5-diMe-Thz-2-yl)Ph | Py-3-yl |
| 1455 | H | H | H | 4-(1,2,4-Trz-1-yl)Ph | Ph |
| 1456 | H | H | H | 4-(1,2,4-Trz-1-yl)Ph | 3-F—Ph |
| 1457 | H | H | H | 4-(1,2,4-Trz-1-yl)Ph | 4-F—Ph |
| 1458 | H | H | H | 4-(1,2,4-Trz-1-yl)Ph | 4-Cl—Ph |
| 1459 | H | H | H | 4-(1,2,4-Trz-1-yl)Ph | 4-OMe—Ph |
| 1460 | H | H | H | 4-(1,2,4-Trz-1-yl)Ph | Py-2-yl |
| 1461 | H | H | H | 4-(1,2,4-Trz-1-yl)Ph | Py-3-yl |
| 1462 | Me | H | H | 4-(Pyz-1-yl)Ph | 4-F—Ph |
| 1463 | Me | H | H | 4-(Pyz-1-yl)Ph | Py-2-yl |
| 1464 | Me | H | H | 4-(Pyz-1-yl)Ph | Py-3-yl |
| 1465 | Et | H | H | 4-(Pyz-1-yl)Ph | 4-F—Ph |
| 1466 | Et | H | H | 4-(Pyz-1-yl)Ph | Py-2-yl |
| 1467 | Et | H | H | 4-(Pyz-1-yl)Ph | Py-3-yl |
| 1468 | Pr | H | H | 4-(Pyz-1-yl)Ph | 4-F—Ph |
| 1469 | Pr | H | H | 4-(Pyz-1-yl)Ph | Py-2-yl |
| 1470 | Pr | H | H | 4-(Pyz-1-yl)Ph | Py-3-yl |
| 1471 | iPr | H | H | 4-(Pyz-1-yl)Ph | 4-F—Ph |
| 1472 | iPr | H | H | 4-(Pyz-1-yl)Ph | Py-2-yl |
| 1473 | iPr | H | H | 4-(Pyz-1-yl)Ph | Py-3-yl |
| 1474 | Bu | H | H | 4-(Pyz-1-yl)Ph | 4-F—Ph |
| 1475 | Bu | H | H | 4-(Pyz-1-yl)Ph | Py-2-yl |
| 1476 | Bu | H | H | 4-(Pyz-1-yl)Ph | Py-3-yl |
| 1477 | iBu | H | H | 4-(Pyz-1-yl)Ph | 4-F—Ph |
| 1478 | iBu | H | H | 4-(Pyz-1-yl)Ph | Py-2-yl |
| 1479 | iBu | H | H | 4-(Pyz-1-yl)Ph | Py-3-yl |
| 1480 | sBu | H | H | 4-(Pyz-1-yl)Ph | 4-F—Ph |
| 1481 | sBu | H | H | 4-(Pyz-1-yl)Ph | Py-2-yl |
| 1482 | sBu | H | H | 4-(Pyz-1-yl)Ph | Py-3-yl |
| 1483 | tBu | H | H | 4-(Pyz-1-yl)Ph | 4-F—Ph |
| 1484 | tBu | H | H | 4-(Pyz-1-yl)Ph | Py-2-yl |
| 1485 | tBu | H | H | 4-(Pyz-1-yl)Ph | Py-3-yl |
| 1486 | Pn | H | H | 4-(Pyz-1-yl)Ph | 4-F—Ph |
| 1487 | Pn | H | H | 4-(Pyz-1-yl)Ph | Py-2-yl |
| 1488 | Pn | H | H | 4-(Pyz-1-yl)Ph | Py-3-yl |
| 1489 | Hx | H | H | 4-(Pyz-1-yl)Ph | 4-F—Ph |
| 1490 | Hx | H | H | 4-(Pyz-1-yl)Ph | Py-2-yl |
| 1491 | Hx | H | H | 4-(Pyz-1-yl)Ph | Py-3-yl |

Incidentally, the abbreviation in the above-mentioned table represents the following group.

H: hydrogen atom,
Me: methyl group,
Et: ethyl group,
Pr: propyl group,
iPr: isopropyl group,
Bu: butyl group,
iBu: isobutyl group,
sBu: sec-butyl group,
tBu: tert-butyl group,
Pn: pentyl group,
Hx: hexyl group,
Bfu-2-yl: benzofuran-2-yl group,
6-F-Bfu-2-yl: 6-fluorobenzofuran-2-yl group,
5,6-diF-Bfu-2-yl: 5,6-difluorobenzofuran-2-yl group,
6-Cl-Bfu-2-yl: 6-chlorobenzofuran-2-yl group,
6-Cl-5-F-Bfu-2-yl: 6-chloro-5-fluorobenzofuran-2-yl group,
6-Me-Bfu-2-yl: 6-methylbenzofuran-2-yl group,
5-F-6-Me-Bfu-2-yl: 5-fluoro-6-methylbenzofuran-2-yl group,
6-Et-Bfu-2-yl: 6-ethylbenzofuran-2-yl group,
6-Et-5-F-Bfu-2-yl: 6-ethyl-5-fluorobenzofuran-2-yl group,
6-CF₃-Bfu-2-yl: 6-trifluoromethylbenzofuran-2-yl group,
5-F-6-CF₃-Bfu-2-yl: 5-fluoro-6-trifluoromethylbenzofuran-2-yl group, 6-OMe-Bfu-2-yl: 6-methoxybenzofuran-2-yl group,
5-F-6-OMe-Bfu-2-yl: 5-fluoro-6-methoxybenzofuran-2-yl group,
6-OCHF$_2$-Bfu-2-yl: 6-difluoromethoxybenzofuran-2-yl group,
6-OCHF$_2$-5-F-Bfu-2-yl: 6-difluoromethoxy-5-fluorobenzofuran-2-yl group,
6-SMe-Bfu-2-yl: 6-methylthiobenzofuran-2-yl group,
5-F-6-SMe-Bfu-2-yl: 5-fluoro-6-methylthiobenzofuran-2-yl group,
Bth-2-yl: benzo[b]thiophen-2-yl group,
6-F-Bth-2-yl: 6-fluorobenzo[b]thiophen-2-yl group,
5,6-diF-Bth-2-yl: 5,6-difluorobenzo[b]thiophen-2-yl group,
6-Cl-Bth-2-yl: 6-chlorobenzo[b]thiophen-2-yl group,
6-Cl-5-F-Bth-2-yl: 6-chloro-5-fluorobenzo[b]thiophen-2-yl group,
6-Br-Bth-2-yl: 6-bromobenzo[b]thiophen-2-yl group,
6-Me-Bth-2-yl: 6-methylbenzo[b]thiophen-2-yl group,
5-F-6-Me-Bth-2-yl: 5-fluoro-6-methylbenzo[b]thiophen-2-yl group,
6-Et-Bth-2-yl: 6-ethylbenzo[b]thiophen-2-yl group,
6-Et-5-F-Bth-2-yl: 6-ethyl-5-fluorobenzo[b]thiophen-2-yl group,
6-Pr-Bth-2-yl: 6-propylbenzo[b]thiophen-2-yl group,
6-iPr-Bth-2-yl: 6-isopropylbenzo[b]thiophen-2-yl group,
6-tBu-Bth-2-yl: 6-tert-butylbenzo[b]thiophen-2-yl group,
6-CF$_3$-Bth-2-yl: 6-trifluoromethylbenzo[b]thiophen-2-yl group,
5-F-6-CF$_3$-Bth-2-yl: 5-fluoro-6-trifluoromethylbenzo[b]thiophen-2-yl group,
6-CHF$_2$-Bth-2-yl: 6-difluoromethylbenzo[b]thiophen-2-yl group,
6-CCl$_3$-Bth-2-yl: 6-trichloromethylbenzo[b]thiophen-2-yl group,
6-CHCl$_2$-Bth-2-yl: 6-dichloromethylbenzo[b]thiophen-2-yl group,
6-CH$_2$CF$_3$-Bth-2-yl: 6-(2,2,2-trifluoroethyl)benzo[b]thiophen-2-yl group,
6-CH$_2$CCl$_3$-Bth-2-yl: 6-(2,2,2-trichloroethyl)benzo[b]thiophen-2-yl group,
6-OMe-Bth-2-yl: 6-methoxybenzo[b]thiophen-2-yl group,
5-F-6-OMe-Bth-2-yl: 5-fluoro-6-methoxybenzo[b]thiophen-2-yl group,
6-OEt-Bth-2-yl: 6-ethoxybenzo[b]thiophen-2-yl group,
6-OPr-Bth-2-yl: 6-propoxybenzo[b]thiophen-2-yl group,
6-OiPr-Bth-2-yl: 6-isopropoxybenzo[b]thiophen-2-yl group,
6-OtBu-Bth-2-yl: 6-tert-butoxybenzo[b]thiophen-2-yl group,
6-OCF$_3$-Bth-2-yl: 6-trifluoromethoxybenzo[b]thiophen-2-yl group,
6-OCHF$_2$-Bth-2-yl: 6-difluoromethoxybenzo[b]thiophen-2-yl group,
6-OCHF$_2$-5-F-Bth-2-yl: 6-difluoromethoxy-5-fluorobenzo[b]thiophen-2-yl group,
6-OCCl$_3$-Bth-2-yl: 6-trichloromethoxybenzo[b]thiophen-2-yl group,
6-OCHCl$_2$-Bth-2-yl: 6-dichloromethoxybenzo[b]thiophen-2-yl group,
6-SMe-Bth-2-yl: 6-methylthiobenzo[b]thiophen-2-yl group,
5-F-6-SMe-Bth-2-yl: 5-fluoro-6-methylthiobenzo[b]thiophen-2-yl group,
6-SEt-Bth-2-yl: 6-ethylthiobenzo[b]thiophen-2-yl group,
6-SPr-Bth-2-yl: 6-propylthiobenzo[b]thiophen-2-yl group,
6-SiPr-Bth-2-yl: 6-isopropylthiobenzo[b]thiophen-2-yl group,
6-StBu-Bth-2-yl: 6-tert-butylthiobenzo[b]thiophen-2-yl group,
Boxz-2-yl: benzoxazol-2-yl group,
6-Cl-Boxz-2-yl: 6-chlorobenzoxazol-2-yl group,
6-OMe-Boxz-2-yl: 6-methoxybenzoxazol-2-yl group,
Bthz-2-yl: benzothiazol-2-yl group,
6-Cl-Bthz-2-yl: 6-chlorobenzothiazol-2-yl group,
6-OMe-Bthz-2-yl: 6-methoxybenzothiazol-2-yl group,
biPh-3-yl: biphenyl-3-yl group,
biPh-4-yl: biphenyl-4-yl group,
2'-F-biPh-4-yl: 2'-fluorobiphenyl-4-yl group,
3'-F-biPh-4-yl: 3'-fluorobiphenyl-4-yl group,
4'-F-biPh-4-yl: 4'-fluorobiphenyl-4-yl group,
2',4'-diF-biPh-4-yl: 2',4'-difluorobiphenyl-4-yl group,
3',4'-diF-biPh-4-yl: 3',4'-difluorobiphenyl-4-yl group,
2'-Cl-biPh-4-yl: 2'-chlorobiphenyl-4-yl group,
3'-Cl-biPh-4-yl: 3'-chlorobiphenyl-4-yl group,
4'-Cl-biPh-4-yl: 4'-chlorobiphenyl-4-yl group,
2',4'-diCl-biPh-4-yl: 2',4'-dichlorobiphenyl-4-yl group,
3',4'-diCl-biPh-4-yl: 3',4'-dichlorobiphenyl-4-yl group,
4'-Cl-2'-F-biPh-4-yl: 4'-chloro-2'-fluorobiphenyl-4-yl group,
4'-Cl-3'-F-biPh-4-yl: 4'-chloro-3'-fluorobiphenyl-4-yl group,
3'-Br-biPh-4-yl: 3'-bromobiphenyl-4-yl group,
3'-OH-biPh-4-yl: 3'-hydroxybiphenyl-4-yl group,
4'-OH-biPh-4-yl: 4'-hydroxybiphenyl-4-yl group,
3'-Me-biPh-4-yl: 3'-methylbiphenyl-4-yl group,
3'-Et-biPh-4-yl: 3'-ethylbiphenyl-4-yl group,
3'-Pr-biPh-4-yl: 3'-propylbiphenyl-4-yl group,
3'-iPr-biPh-4-yl: 3'-isopropylbiphenyl-4-yl group,
3'-tBu-biPh-4-yl: 3'-tert-butylbiphenyl-4-yl group,
3'-CF$_3$-biPh-4-yl: 3'-trifluoromethylbiphenyl-4-yl group,
3'-CHF$_2$-biPh-4-yl: 3'-difluoromethylbiphenyl-4-yl group,
3'-CCl$_3$-biPh-4-yl: 3'-trichloromethylbiphenyl-4-yl group,
3'-CHCl$_2$-biPh-4-yl: 3'-dichloromethylbiphenyl-4-yl group,
3'-CH$_2$CF$_3$-biPh-4-yl: 3'-(2,2,2-trifluoroethyl)biphenyl-4-yl group,
3'-CH$_2$CCl$_3$-biPh-4-yl: 3'-(2,2,2-trichloroethyl)biphenyl-4-yl group,
3'-OMe-biPh-4-yl: 3'-methoxybiphenyl-4-yl group,
3'-OEt-biPh-4-yl: 3'-ethoxybiphenyl-4-yl group,
3'-OPr-biPh-4-yl: 3'-propoxybiphenyl-4-yl group,
3'-OiPr-biPh-4-yl: 3'-isopropoxybiphenyl-4-yl group,
3'-OtBu-biPh-4-yl: 3'-tert-butoxybiphenyl-4-yl group,
3'-OCF$_3$-biPh-4-yl: 3'-trifluoromethoxybiphenyl-4-yl group,
3'-OCHF$_2$-biPh-4-yl: 3'-difluoromethoxybiphenyl-4-yl group,
3'-OCCl$_3$-biPh-4-yl: 3'-trichloromethoxybiphenyl-4-yl group,
3'-OCHCl$_2$-biPh-4-yl: 3'-dichloromethoxybiphenyl-4-yl group,
4-(Th-2-yl)Ph: 4-(thiophen-2-yl)phenyl group,
4-(Th-3-yl)Ph: 4-(thiophen-3-yl)phenyl group,
4-(Pyz-1-yl)Ph: 4-(pyrazol-1-yl)phenyl group,
4-(4-F-Pyz-1-yl)Ph: 4-(4-fluoropyrazol-1-yl)phenyl group,
4-(4-Cl-Pyz-1-yl)Ph: 4-(4-chloropyrazol-1-yl)phenyl group,
4-(Oxz-2-yl)Ph: 4-(oxazol-2-yl)phenyl group,
4-(Oxz-4-yl)Ph: 4-(oxazol-4-yl)phenyl group,
4-(Thz-2-yl)Ph: 4-(thiazol-2-yl)phenyl group,
4-(4-F-Thz-2-yl)Ph: 4-(4-fluorothiazol-2-yl)phenyl group,
4-(4-Cl-Thz-2-yl)Ph: 4-(4-chlorothiazol-2-yl)phenyl group,
4-(5-Cl-Thz-2-yl)Ph: 4-(5-chlorothiazol-2-yl)phenyl group,
4-(4-Me-Thz-2-yl)Ph: 4-(4-methylthiazol-2-yl)phenyl group,
4-(5-Me-Thz-2-yl)Ph: 4-(5-methylthiazol-2-yl)phenyl group,
4-(4,5-diMe-Thz-2-yl)Ph: 4-(4,5-dimethylthiazol-2-yl)phenyl group,
4-(4-Et-Thz-2-yl)Ph: 4-(4-ethylthiazol-2-yl)phenyl group, 4-(4-CF$_3$-Thz-2-yl)Ph: 4-(4-trifluoromethylthiazol-2-yl)phenyl group,
4-(4-OMe-Thz-2-yl)Ph: 4-(4-methoxythiazol-2-yl)phenyl group,
4-(4-OCHF$_2$-Thz-2-yl)Ph: 4-(4-difluoromethoxythiazol-2-yl)phenyl group,
4-(Thz-4-yl)Ph: 4-(thiazol-4-yl)phenyl group,
4-(2-F-Thz-4-yl)Ph: 4-(2-fluorothiazol-4-yl)phenyl group,
4-(2-Cl-Thz-4-yl)Ph: 4-(2-chlorothiazol-4-yl)phenyl group,
4-(2-Me-Thz-4-yl)Ph: 4-(2-methylthiazol-4-yl)phenyl group,
4-(2-Et-Thz-4-yl)Ph: 4-(2-ethylthiazol-4-yl)phenyl group,
4-(2-CF$_3$-Thz-4-yl)Ph: 4-(2-trifluoromethylthiazol-4-yl)phenyl group,
4-(2-OMe-Thz-4-yl)Ph: 4-(2-methoxythiazol-4-yl)phenyl group,
4-(2-OCHF$_2$-Thz-4-yl)Ph: 4-(2-difluoromethoxythiazol-4-yl)phenyl group,
4-(Thz-5-yl)Ph: 4-(thiazol-5-yl)phenyl group,
4-(1,2,4-Trz-1-yl)Ph: 4-(1,2,4-triazol-1-yl)phenyl group,
4-(Py-2-yl)Ph: 4-(pyridin-2-yl)phenyl group,
4-(Py-3-yl)Ph: 4-(pyridin-3-yl)phenyl group,
4-(Py-4-yl)Ph: 4-(pyridin-4-yl)phenyl group,
4-(Pyd-3-yl)Ph: 4-(pyridazin-3-yl)phenyl group,
4-(Pyd-4-yl)Ph: 4-(pyridazin-4-yl)phenyl group,
4-(Pym-2-yl)Ph: 4-(pyrimidin-2-yl)phenyl group,
4-(5-F-Pym-2-yl)Ph: 4-(5-fluoropyrimidin-2-yl)phenyl group,
4-(5-Cl-Pym-2-yl)Ph: 4-(5-chloropyrimidin-2-yl)phenyl group,
4-(5-OH-Pym-2-yl)Ph: 4-(5-hydroxypyrimidin-2-yl)phenyl group,
4-(Pym-4-yl)Ph: 4-(pyrimidin-4-yl)phenyl group,
4-(Pym-5-yl)Ph: 4-(pyrimidin-5-yl)phenyl group,
4-(4,5-diH-Thz-2-yl)Ph: 4-(4,5-dihydrothiazol-2-yl)phenyl group,
4-(Pyr-1-yl)Ph: 4-(pyrrolidin-1-yl)phenyl group,
4-(Pip-1-yl)Ph: 4-(piperidin-1-yl)phenyl group,
5-Ph-Th-2-yl: 5-phenylthiophen-2-yl group,
5-(Thz-2-yl)-Th-2-yl: 5-(thiazol-2-yl)thiophen-2-yl group,
5-(Thz-4-yl)-Th-2-yl: 5-(thiazol-4-yl)thiophen-2-yl group,
6-Ph-Pyd-3-yl: 6-phenylpyridazin-3-yl group,
6-(Thz-2-yl)-Pyd-3-yl: 6-(thiazol-2-yl)pyridazin-3-yl group,
6-(Thz-4-yl)-Pyd-3-yl: 6-(thiazol-4-yl)pyridazin-3-yl group,
2-Ph-Pym-4-yl: 2-phenylpyrimidin-4-yl group,
2-(Thz-2-yl)-Pym-4-yl: 2-(thiazol-2-yl)pyrimidin-4-yl group,
2-(Thz-4-yl)-Pym-4-yl: 2-(thiazol-4-yl)pyrimidin-4-yl group,
Ph: phenyl group,
2-F-Ph: 2-fluorophenyl group,
3-F-Ph: 3-fluorophenyl group,
4-F-Ph: 4-fluorophenyl group,
3,4-diF-Ph: 3,4-difluorophenyl group,
3,5-diF-Ph: 3,5-difluorophenyl group,
3,4,5-triF-Ph: 3,4,5-trifluorophenyl group,
2-C$_1$-Ph: 2-chlorophenyl group,
3-Cl-Ph: 3-chlorophenyl group,
4-Cl-Ph: 4-chlorophenyl group,
2,6-diCl-Ph: 2,6-dichlorophenyl group,
4-Cl-3-F-Ph: 4-chloro-3-fluorophenyl group,
4-Cl-3,5-diF-Ph: 4-chloro-3,5-difluorophenyl group,
4-Br-Ph: 4-bromophenyl group,
4-Me-Ph: 4-methylphenyl group,
3-F-4-Me-Ph: 3-fluoro-4-methylphenyl group,
4-Et-Ph: 4-ethylphenyl group,
4-Et-3-F-Ph: 4-ethyl-3-fluorophenyl group,
4-Pr-Ph: 4-propylphenyl group,
4-iPr-Ph: 4-isopropylphenyl group,
4-tBu-Ph: 4-tert-butylphenyl group,
4-CF$_3$-Ph: 4-trifluoromethylphenyl group,
3-F-4-CF$_3$-Ph: 3-fluoro-4-trifluoromethylphenyl group,
4-CHF$_2$-Ph: 4-difluoromethylphenyl group,
4-CCl$_3$-Ph: 4-trichloromethylphenyl group,
4-CHCl$_2$-Ph: 4-dichloromethylphenyl group,
4-CH$_2$CF$_3$-Ph: 4-(2,2,2-trifluoroethyl)phenyl group,
4-CH$_2$CCl$_3$-Ph: 4-(2,2,2-trichloroethyl)phenyl group,
4-OMe-Ph: 4-methoxyphenyl group,
3-F-4-OMe-Ph: 3-fluoro-4-methoxyphenyl group,
4-OEt-Ph: 4-ethoxyphenyl group,
4-OPr-Ph: 4-propoxyphenyl group,
4-OiPr-Ph: 4-isopropoxyphenyl group,
4-OtBu-Ph: 4-tert-butoxyphenyl group,
4-OCF$_3$-Ph: 4-trifluoromethoxyphenyl group,
4-OCHF$_2$-Ph: 4-difluoromethoxyphenyl group,
4-OCHF$_2$-3-F-Ph: 4-difluoromethoxy-3-fluorophenyl group,
4-OCCl$_3$-Ph: 4-trichloromethoxyphenyl group,
4-OCHCl$_2$-Ph: 4-dichloromethoxyphenyl group,
Th-2-yl: thiophen-2-yl group,
Th-3-yl: thiophen-3-yl group,
5-Cl—Th-2-yl: 5-chloro thiophen-2-yl group,
1-Me-1H-Imz-4-yl: 1-methyl-1H-imidazol-4-yl group,
Thz-2-yl: thiazol-2-yl group,
Py-2-yl: pyridin-2-yl group,
5-F-Py-2-yl: 5-fluoropyridin-2-yl group,
5-Cl-Py-2-yl: 5-chloropyridin-2-yl group,
5-Me-Py-2-yl: 5-methylpyridin-2-yl group,
5-Et-Py-2-yl: 5-ethylpyridin-2-yl group,
5-CF$_3$-Py-2-yl: 5-trifluoromethylpyridin-2-yl group,
5-OMe-Py-2-yl: 5-methoxypyridin-2-yl group,
5-OCHF$_2$-Py-2-yl: 5-difluoromethoxypyridin-2-yl group,
Py-3-yl: pyridin-3-yl group,
6-F-Py-3-yl: 6-fluoropyridin-3-yl group,
6-Cl-Py-3-yl: 6-chloropyridin-3-yl group,
6-Me-Py-3-yl: 6-methylpyridin-3-yl group,
6-Et-Py-3-yl: 6-ethylpyridin-3-yl group,
6-CF$_3$-Py-3-yl: 6-trifluoromethylpyridin-3-yl group,
6-OMe-Py-3-yl: 6-methoxypyridin-3-yl group,
6-OCHF$_2$-Py-3-yl: 6-difluoromethoxypyridin-3-yl group,
Py-4-yl: pyridin-4-yl group or
Pym-2-yl: pyrimidin-2-yl group.

In the above-mentioned tables, more preferred are compounds of Compounds Nos 1, 2, 3, 4, 7, 8, 9, 10, 18, 24, 28, 36, 42, 43, 50, 56, 57, 82, 88, 89, 105, 106, 107, 108, 111, 112, 113, 114, 122, 128, 132, 140, 146, 147, 151, 157, 158, 159, 160, 161, 162, 165, 166, 167, 168, 176, 182, 186, 194, 200, 201, 208, 214, 215, 219, 225, 226, 230, 236, 237, 241, 247, 248, 261, 267, 268, 272, 278, 279, 309, 310, 311, 312, 313, 314, 316, 317, 318, 319, 320, 323, 324, 325, 326, 330, 331, 337, 338, 344, 345, 348, 349, 353, 354, 355, 359, 361, 362, 363, 367, 369, 374, 380, 381, 400, 406, 407, 411, 417, 418, 428, 434, 435, 439, 445, 446, 494, 495, 496, 497, 498, 499, 501, 502, 503, 504, 505, 508, 509, 510, 511, 515, 516, 522, 523, 529, 530, 533, 534, 538, 539, 540, 544, 546, 547, 548, 552, 554, 559, 565, 566, 570, 576, 577, 578, 579, 580, 581, 584, 585, 586, 587, 595, 601, 605, 613, 619, 620, 624, 630, 631, 635, 641, 642, 646, 652, 653, 654, 655, 656, 657, 660, 661, 662, 663, 671, 677, 681, 695, 701, 702, 706, 712, 713, 723, 729, 730, 734, 740, 741, 745, 751, 752, 765, 771, 772, 791, 797, 798, 817, 823, 824, 834, 840, 841, 845, 851, 852, 853, 854, 855, 856, 859, 860, 861, 862, 870, 876, 880, 894, 900, 901, 905, 911, 912, 914, 917, 920, 928, 931, 933, 934, 935, 936, 937, 938, 940, 941, 942, 943, 944, 947, 948, 949, 950, 954, 955, 961, 962, 968, 969, 972, 973, 977, 978, 979, 983, 985, 986, 987, 991, 993, 998, 1004, 1005, 1009, 1015, 1016, 1024, 1046, 1047, 1048, 1049, 1050, 1051, 1053, 1054, 1055, 1056, 1057, 1060, 1061, 1062, 1063, 1067, 1068, 1074, 1075, 1081, 1082, 1085, 1086, 1090, 1091, 1092, 1096, 1098, 1099, 1100, 1104, 1106, 1111, 1117, 1118, 1122, 1128, 1129, 1148, 1154, 1155, 1158, 1168, 1174, 1175, 1176, 1177, 1178, 1179, 1182, 1183, 1184, 1185, 1193, 1199, 1203, 1222, 1223, 1224, 1225, 1226, 1227, 1229, 1230, 1231, 1232, 1233, 1236, 1237, 1238, 1239, 1243, 1244, 1250, 1251, 1257, 1258, 1261, 1262, 1266, 1267, 1268, 1272, 1274, 1275, 1276, 1280, 1282, 1293, 1299, 1300, 1304, 1310, 1311, 1315, 1321, 1322, 1323, 1324, 1325, 1326, 1329, 1330, 1331, 1332, 1340, 1346, 1350, 1370, 1371, 1372, 1373, 1376, 1377, 1378, 1379, 1387, 1393, 1397, 1405, 1411, 1412, 1416, 1422, 1423, 1433, 1436, 1439, 1440, 1443, 1446, 1447, 1450, 1453, 1454, 1457, 1460, 1461, 1464, 1467, 1470, 1473, 1476, 1479, 1482, 1485, 1488 or 1491, further more preferred are compounds of Compounds Nos 1, 2, 3, 4, 7, 8, 9, 10, 18, 24, 28, 105, 106, 107, 108, 111, 112, 113, 114, 122, 128, 132, 159, 160, 161, 162, 165, 166, 167, 168, 176, 182, 186, 309, 310, 311, 312, 316, 317, 318, 319, 337, 353, 361, 494, 495, 496, 497, 501, 502, 503, 504, 522, 538, 546, 578, 579, 580, 581, 584, 585, 586, 587, 595, 601, 605, 654, 655, 656, 657, 660, 661, 662, 663, 671, 677, 681, 853, 854, 855, 856, 859, 860, 861, 862, 870, 876, 880, 914, 920, 933, 934, 935, 936, 940, 941, 942, 943, 961, 977, 985, 1024, 1046, 1047, 1048, 1049, 1053, 1054, 1055, 1056, 1074, 1090, 1098, 1158, 1176, 1177, 1178, 1179, 1182, 1183, 1184, 1185, 1193, 1199, 1203, 1222, 1223, 1224, 1225, 1229, 1230, 1231, 1232, 1250, 1266, 1274, 1323, 1324, 1325, 1326, 1329, 1330, 1331, 1332, 1340, 1346, 1350, 1370, 1371, 1372, 1373, 1376, 1377, 1378, 1379, 1387, 1393, 1397, 1433, 1439, 1446, 1453, 1461, 1467 or 1473, particularly preferred are compounds of Compounds Nos 4, 24, 28, 108, 128, 132, 162, 182, 186, 309, 312, 318, 353, 361, 494, 497, 503, 538, 546, 581, 601, 605, 657, 677, 681, 856, 876, 880, 914, 920, 933, 936, 942, 977, 985, 1024, 1046, 1049, 1055, 1090, 1098, 1158, 1179, 1199, 1203, 1222, 1225, 1231, 1266, 1274, 1326, 1346, 1350, 1373, 1393, 1397, 1433, 1439, 1446, 1453, 1461, 1467 or 1473, most preferred are compounds of Compound No. 28: {6-[(benzofuran-2-ylmethyl)(pyridin-3-ylsulfonyl)aminomethyl]-pyridin-2-ylamino}acetic acid, Compound No. 132: {6-[(benzo[b]thiophen-2-ylmethyl)(pyridin-3-ylsulfonyl)aminomethyl]pyridin-2-ylamino}acetic acid, Compound No. 186: {6-[(6-chlorobenzo[b]thiophen-2-ylmethyl)(pyridin-3-ylsulfonyl)aminomethyl]pyridin-2-ylamino}acetic acid, Compound No. 361: {6-[(6-methoxybenzo[b]thiophen-2-ylmethyl)(pyridin-3-ylsulfonyl)aminomethyl]pyridin-2-ylamino}acetic acid, Compound No. 538: {6-[(biphenyl-4-ylmethyl)(pyridin-2-ylsulfonyl)aminomethyl]-pyridin-2-ylamino}acetic acid, Compound No. 546: {6-[(biphenyl-4-ylmethyl)(pyridin-3-ylsulfonyl)aminomethyl]-pyridin-2-ylamino}acetic acid, Compound No. 605: {6-[(4'-fluorobiphenyl-4-ylmethyl)(pyridin-3-ylsulfonyl)aminomethyl]pyridin-2-ylamino}acetic acid, Compound No. 681: {6-[(4'-chlorobiphenyl-4-ylmethyl)(pyridin-3-ylsulfonyl)aminomethyl]pyridin-2-ylamino}acetic acid, Compound No. 856: (6-{(4-fluorobenzenesulfonyl)[4-(pyrazol-1-yl)benzyl]aminomethyl}pyridin-2-ylamino)acetic acid, Compound No. 876: (6-{[4-(pyrazol-1-yl)benzyl](pyridin-2-ylsulfonyl)aminomethyl}-pyridin-2-ylamino)acetic acid, Compound No. 880: (6-{[4-(pyrazol-1-yl)benzyl](pyridin-3-ylsulfonyl)aminomethyl}-pyridin-2-ylamino)acetic acid, Compound No. 914: isopropyl(6-{(pyridin-2-ylsulfonyl)[4-(thiazol-2-yl)benzyl]aminomethyl}pyridin-2-ylamino)acetate, Compound No. 920: ethyl(6-{(pyridin-2-ylsulfonyl)[4-(thiazol-2-yl)benzyl]aminomethyl}pyridin-2-ylamino)acetate, Compound No. 936: (6-{(4-fluorobenzenesulfonyl)[4-(thiazol-2-yl)benzyl]aminomethyl}pyridin-2-ylamino)acetic acid, Compound No. 977: (6-{(pyridin-2-ylsulfonyl)[4-(thiazol-2-yl)benzyl]aminomethyl}-pyridin-2-ylamino)acetic acid, Compound No. 985: (6-{(pyridin-3-ylsulfonyl)[4-(thiazol-2-yl)benzyl]aminomethyl}-pyridin-2-ylamino)acetic acid, Compound No. 1024: (6-{(pyridin-2-ylsulfonyl)[4-(4-trifluoromethylthiazol-2-yl)benzyl]aminomethyl}pyridin-2-ylamino)acetic acid, Compound No. 1090: (6-{(pyridin-2-ylsulfonyl)[4-(thiazol-4-yl)benzyl]aminomethyl}-pyridin-2-ylamino)acetic acid, Compound No. 1158: (6-{[4-(pyridin-2-yl)benzyl](pyridin-3-ylsulfonyl)aminomethyl}-pyridin-2-ylamino)acetic acid, Compound No. 1203: (6-{[4-(pyridazin-4-yl)benzyl](pyridin-3-ylsulfonyl)aminomethyl}pyridin-2-ylamino)acetic acid, Compound No. 1266: (6-{(pyridin-2-ylsulfonyl)[4-(pyrimidin-2-yl)benzyl]aminomethyl}pyridin-2-ylamino)acetic acid, Compound No. 1326: (6-{[4-(4,5-dihydrothiazol-2-yl)benzyl](4-fluorobenzenesulfonyl)aminomethyl}pyridin-2-ylamino)acetic acid, Compound No. 1397: {6-[(6-phenylpyridazin-3-ylmethyl)(pyridin-3-ylsulfonyl)aminomethyl]pyridin-2-ylamino}acetic acid, Compound No. 1433: hexyl(6-{(pyridin-2-ylsulfonyl)[4-(thiazol-2-yl)benzyl]aminomethyl}pyridin-2-ylamino)acetate, Compound No. 1439: (6-{[4-(5-chlorothiazol-2-yl)benzyl](pyridin-2-ylsulfonyl)aminomethyl}pyridin-2-ylamino) acetic acid, Compound No. 1446: (6-{[4-(5-methylthiazol-2-yl)benzyl](pyridin-2-ylsulfonyl)aminomethyl}pyridin-2-ylamino) acetic acid, Compound No. 1453: (6-{[4-(4,5-dimethylthiazol-2-yl)benzyl](pyridin-2-ylsulfonyl)aminomethyl}pyridin-2-ylamino)acetic acid, Compound No. 1461: (6-{(pyridin-3-ylsulfonyl)[4-(1,2,4-triazol-1-yl)benzyl]aminomethyl}pyridin-2-ylamino)acetic acid, Compound No. 1467: (6-{[4-(pyrazol-1-yl)benzyl](pyridin-3-ylsulfonyl)aminomethyl}-pyridin-2-ylamino)ethyl acetate or Compound No. 1473: (6-{[4-(pyrazol-1-yl)benzyl](pyridin-3-ylsulfonyl)aminomethyl}-pyridin-2-ylamino)isopropyl acetate.

The compound represented by the formula (1) of the present invention can be prepared by the following methods.

[Preparation Method 1]

"Preparation Method 1" is a method for preparing Compound (1a) of the present invention wherein $R^1$ in the formula (1) is a hydrogen atom and Compound (1b) of the present invention wherein $R^1$ in the formula (1) is a $C_1$-$C_6$ alkyl group.

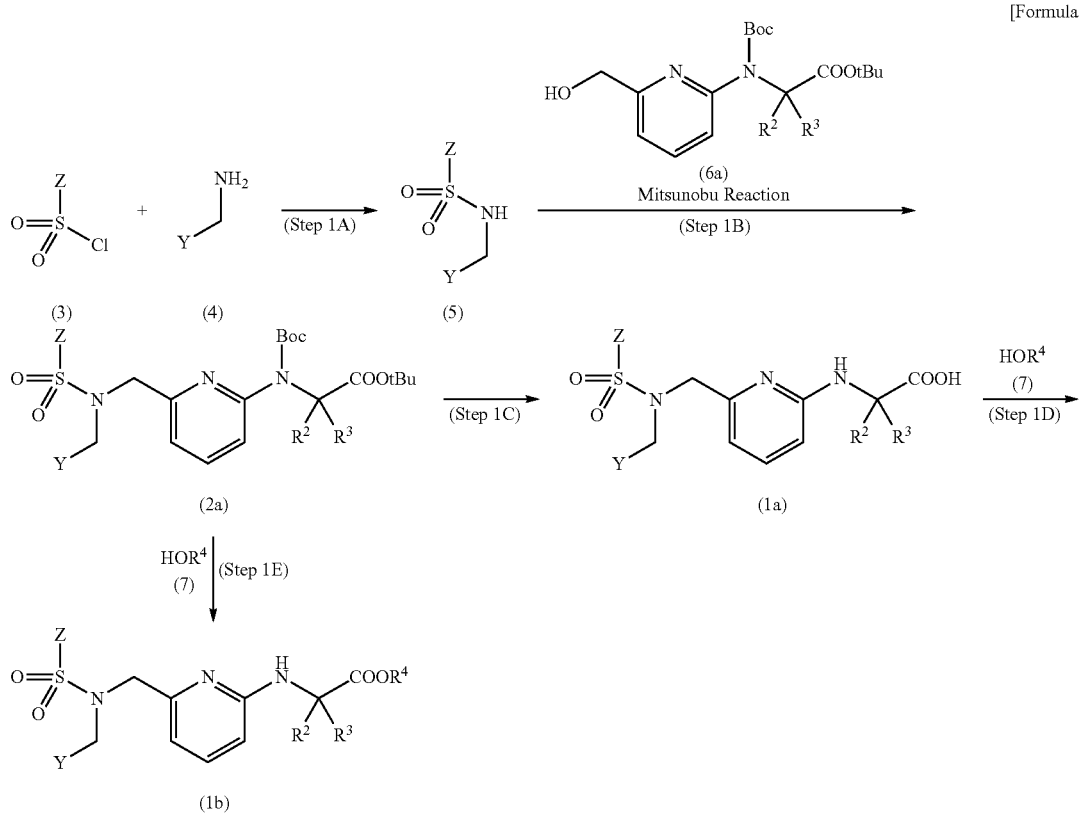

[Formula 3]

wherein $R^2$, $R^3$, Y and Z have the same meanings as defined above, $R^4$ represents a $C_1$-$C_6$ alkyl group having the same meaning as mentioned above, Boc represents a tert-butoxycarbonyl group, and tBu represents a tert-butyl group.

"Step 1A" is a step of preparing a sulfoneamide compound (5) by reacting a chlorosulfonyl compound (3) and an amine compound (4) in the presence or in the absence of (preferably in the presence) a base in an inert solvent.

The compound (3) and the compound (4) are known, or can be prepared according to the known method from the known compound(s).

The inert solvent to be used is not particularly limited so long as it does not inhibit the reaction and dissolves the starting materials with a certain extent, and there may be mentioned, for example, aromatic hydrocarbons such as benzene, toluene and xylene, etc.; halogenated aliphatic hydrocarbons such as methylene chloride, chloroform and 1,2-dichloroethane, etc.; ethers such as 1,4-dioxane, tetrahydrofuran, diethyl ether and 1,2-dimethoxyethane, etc.; amides such as N,N-dimethylformamide, N,N-dimethylacetamide and N-methylpyrrolidone, etc.; nitriles such as acetonitrile and propionitrile, etc.; or a mixed solvent of optional combination thereof, etc., preferably methylene chloride, 1,2-dichloroethane, N,N-dimethylformamide, acetonitrile or a mixed solvent thereof.

As the base to be used, there may be mentioned, for example, organic bases such as triethylamine and diisopropylethyl amine, etc.; or inorganic bases such as sodium hydrogen carbonate, potassium hydrogen carbonate, sodium carbonate and potassium carbonate, etc., preferably triethylamine or diisopropylethyl amine. An amount of the base to be used is generally 0.9 to 20-fold mol amount, preferably 1 to 10-fold mol amount based on 1 mol of Compound (3).

An amount of Compound (4) to be used is generally 0.7 to 5-fold mol amount, preferably 0.8 to 1.5-fold mol amount based on 1 mol of Compound (3).

The reaction temperature may vary depending on a kind or amount(s), etc., of the starting materials, solvent(s), etc., and is generally −20° C. to 100° C., preferably −5° C. to 50° C.

The reaction time may vary depending on a reaction temperature, etc., and is generally 1 minute to 36 hours, preferably 1 hour to 18 hours.

"Step 1B" is the so-called Mitsunobu reaction, and a step of preparing an intermediate compound (2a) by reacting Compound (5) and a hydroxymethylpyridine compound (6a) in the presence of a phosphine compound and an azo compound in an inert solvent.

Compound (6a) is a compound included in a hydroxymethylpyridine compound (6) prepared by the following mentioned "Preparation Method 11".

The inert solvent to be used is not particularly limited so long as it does not inhibit the reaction and dissolves the starting materials with a certain extent, and there may be mentioned, for example, aromatic hydrocarbons such as benzene, toluene and xylene, etc.; ethers such as diethyl ether, tetrahydrofuran, 1,4-dioxane or 1,2-dimethoxyethane, etc.; amides such as N,N-dimethylformamide, N,N-dimethylacetamide and N-methylpyrrolidone, etc.; nitriles such as acetonitrile and propionitrile, etc.; esters such as methyl acetate, ethyl acetate or isopropyl acetate, etc.; or a mixed solvent of optional combination thereof, etc., preferably tetrahydrofuran, N,N-dimethylformamide, acetonitrile or a mixed solvent thereof.

The phosphine compound to be used may be mentioned, for example, trimethylphosphine, triethylphosphine, tri-n- butylphosphine or triphenylphosphine, etc., preferably tri-n-butylphosphine or triphenylphosphine. An amount of the phosphine compound to be used is generally 0.9 to 10-fold mol amount, preferably 1 to 5-fold mol amount based on 1 mol of Compound (5).

The azo compound to be used may be mentioned, for example, diethylazodicarboxylate (DEAD), diisopropylazodicarboxylate (DIAD), N,N,N',N'-tetraisopropylazodicarboxamide (TIPA), 1,1'-(azodicarbonyl)dipiperidine (ADDP), N,N,N',N'-tetramethyl azodicarboxamide (TMAD) or 1,6-dimethyl-1,5,7-hexahydro-1,4,6,7-tetrazocin-2,5-dione (DHTD), etc., and preferably diethylazodicarboxylate (DEAD) or N,N,N',N'-tetramethylazodicarboxamide (TMAD). An amount of the azo compound to be used is generally 0.9 to 10-fold mol amount, preferably 1 to 5-fold mol amount based on 1 mol of Compound (5).

An amount of Compound (6a) to be used is generally 0.8 to 2-fold mol amount, preferably 0.9 to 1.5-fold mol amount based on 1 mol of Compound (5).

The reaction temperature may vary depending on a kind or amount(s), etc., of the starting materials, solvent(s), etc., and is generally −20° C. to 100° C., preferably −5° C. to 50° C.

The reaction time may vary depending on a reaction temperature, etc., and is generally 30 minutes to 48 hours, preferably 1 hour to 24 hours.

"Step 1C" is a step of preparing Compound (1a) by simultaneously removing the Boc group and tBu group of Compound (2a). This step can be carried out by referring to a published material (see T. W. Greene & P. G. M. Wuts, Protective Groups in Organic Synthesis 4th Ed., John Wiley & Sons, Inc., pp. 582 and 725), and, for example, by treating Compound (2a) with an acid in an inert solvent, but it is not limited to the above.

The inert solvent to be used is not particularly limited so long as it does not inhibit the reaction and dissolves the starting materials with a certain extent, and there may be mentioned, for example, ethers such as tetrahydrofuran, 1,4-dioxane and 1,2-dimethoxyethane, etc.; halogenated aliphatic hydrocarbons such as methylene chloride, chloroform and 1,2-dichloroethane, etc.; organic acids such as formic acid, acetic acid, propionic acid or trifluoroacetic acid, etc.; water; or a mixed solvent of optional combination thereof, etc., preferably tetrahydrofuran, 1,4-dioxane, methylene chloride, water or a mixed solvent thereof.

As the acid to be used, there may be mentioned, for example, hydrogen chloride, hydrochloric acid, hydrobromic acid, hydroiodic acid, sulfuric acid, phosphoric acid, p-toluenesulfonic acid, methanesulfonic acid or trifluoroacetic acid, etc., preferably hydrogen chloride, hydrochloric acid or trifluoroacetic acid. An amount of the acid to be used is generally 1 to 200-fold mol amount, preferably 5 to 100-fold mol amount based on 1 mol of Compound (2a), and it may be used with a far excess amount as a solvent.

To promote the reaction, anisole compounds such as anisole and thioanisole, etc., may be added. An amount of the anisole compound to be used is generally 1 to 200-fold mol amount, preferably 5 to 100-fold mol amount based on 1 mol of Compound (2a).

The reaction temperature may vary depending on a kind or amount(s), etc., of the starting materials, solvent(s), etc., and is generally 0° C. to 150° C., preferably 5° C. to 100° C.

The reaction time may vary depending on a reaction temperature, etc., and is generally 10 minutes to 48 hours, preferably 1 hour to 24 hours.

"Step 1D" is a step of preparing Compound (1b) by esterifying the carboxyl group of Compound (1a). This step can be carried out by referring to a published material (see T. W. Greene & P. G. M. Wuts, Protective Groups in Organic Synthesis 4th Ed., John Wiley & Sons, Inc., p. 538). For example, it can be carried out in the presence of an acid, or after activating the carboxyl group of Compound (1a), reacting with Compound (7), but it is not limited to the above.

Compound (7) is known, or can be prepared according to the known method from the known compound(s).

When "Step 1D" is a reaction carried out in the presence of an acid, it can be carried out by reacting with Compound (7) in an inert solvent or in the absence of a solvent, in the presence of an acid.

The inert solvent to be used is not particularly limited so long as it does not inhibit the reaction and dissolves the starting materials with a certain extent, and there may be mentioned, for example, aromatic hydrocarbons such as benzene, toluene and xylene, etc.; ethers such as tetrahydrofuran, 1,4-dioxane and 1,2-dimethoxyethane, etc.; halogenated aliphatic hydrocarbons such as methylene chloride, chloroform and 1,2-dichloroethane, etc.; or a mixed solvent of optional combination thereof, etc., preferably 1,4-dioxane, methylene chloride, 1,2-dichloroethane or a mixed solvent thereof.

As the acid to be used, there may be mentioned, for example, hydrogen chloride, sulfuric acid, methanesulfonic acid, p-toluenesulfonic acid or trifluoroacetic acid, etc., preferably hydrogen chloride, sulfuric acid or p-toluene sulfonic acid. An amount of the acid to be used is generally 1 to 200-fold mol amount, preferably 1 to 100-fold mol amount based on 1 mol of Compound (1a).

An amount of Compound (7) to be used is generally 1 to 100-fold mol amount, preferably 1 to 5-fold mol amount based on 1 mol of Compound (1a), and it may be used with a far excess amount as a solvent.

The reaction temperature may vary depending on a kind or amount(s), etc., of the starting materials, solvent(s), etc., and is generally −20° C. to 150° C., preferably −5° C. to 100° C.

The reaction time may vary depending on a reaction temperature, etc., and is generally 1 minute to 72 hours, preferably 1 hour to 48 hours.

When "Step 1D" is a reaction which is to activate the carboxyl group of Compound (1a), it is carried out by converting the carboxyl group to "an active form of a carboxy group" such as an acid chloride, mixed acid anhydride, imidazolide, etc. by using an activating agent in the absence of an inert solvent or solvent, and reacting with Compound (7) in the presence of or in the absence of (preferably in the presence of) a base. Incidentally, "the active form of a carboxy group" obtained by the reaction can be used for the reaction with Compound (7) without isolation.

The inert solvent to be used is not particularly limited so long as it does not inhibit the reaction and dissolves the starting materials with a certain extent, and there may be mentioned, for example, aromatic hydrocarbons such as benzene, toluene and xylene, etc.; halogenated aliphatic hydrocarbons such as methylene chloride, chloroform and 1,2-dichloroethane, etc.; ethers such as tetrahydrofuran, 1,2-dimethoxyethane and 1,4-dioxane, etc.; nitriles such as acetonitrile and propionitrile, etc.; amides such as N,N-dimethylformamide, N,N-dimethylacetamide and N-methylpyrrolidone, etc.; or a mixed solvent of optional combination thereof, etc., preferably methylene chloride, tetrahydrofuran or acetonitrile.

As the activating agent of the carboxyl group, there may be mentioned, for example, a chloride such as thionyl chloride, oxalyl chloride, phosphorus oxychloride and phosphorus pentachloride, etc.; 1,1'-carbonyldiimidazole; or a chloroformic acid ester such as chloromethyl formate and chloroethyl formate, etc., preferably thionyl chloride or 1,1'-carbonyldiimidazole. An amount of the activating agent to be used is generally 1 to 5-fold mol amount, preferably 1 to 1.5-fold mol amount based on 1 mol of Compound (1a).

As the base to be used, there may be mentioned, for example, organic bases such as triethylamine and diisopropylethyl amine, etc.; or inorganic bases such as sodium hydrogen carbonate, potassium hydrogen carbonate, sodium carbonate and potassium carbonate, etc., preferably triethylamine or diisopropylethyl amine. An amount of the base to be used is generally 1 to 100-fold mol amount, preferably 1 to 10-fold mol amount based on 1 mol of Compound (1a).

An amount of Compound (7) to be used is generally 1 to 100-fold mol amount, preferably 1 to 5-fold mol amount based on 1 mol of Compound (1a).

The reaction temperature may vary depending on a kind or amount(s), etc., of the starting materials, solvent(s), etc., and is generally $-20°$ C. to $150°$ C., preferably $-5°$ C. to $100°$ C.

The reaction time may vary depending on a reaction temperature, etc., and is generally 1 minute to 24 hours, preferably 1 hour to 12 hours.

"Step 1E" is a step for preparing Compound (1b) by removing the Boc group of Compound (2a) and simultaneously converting the tBu group to $R^4$. This step is carried out in compliance with the case of the reaction in the above-mentioned "Step 1D" in the presence of an acid except for using Compound (2a) in place of Compound (1a).

[Preparation Method 2]

"Preparation Method 2" is another method for preparing the above-mentioned Compound (1b).

[Formula 4]

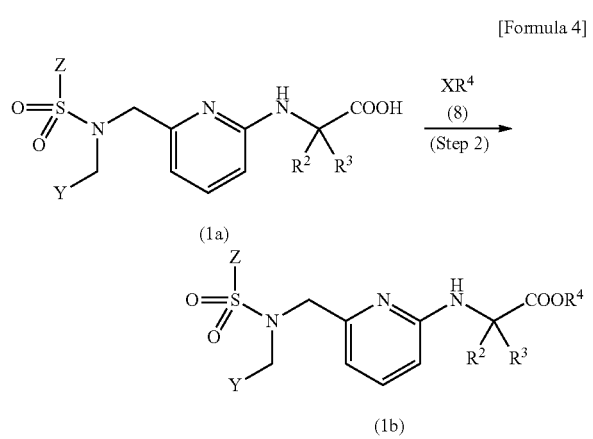

[wherein $R^2$, $R^3$, $R^4$, Y and Z have the same meanings as defined above, X represents a chlorine atom, bromine atom, iodine atom, methanesulfonyloxy group, benzenesulfonyloxy group, p-toluenesulfonyloxy group or trifluoromethanesulfonyloxy group.]

"Step 2" is carried out by reacting Compound (1a) and an alkylating agent (8) in an inert solvent in the presence of a base.

The alkylating agent (8) is known or can be prepared according to the known method from the known compound(s).

The inert solvent to be used is not particularly limited so long as it does not inhibit the reaction and dissolves the starting materials with a certain extent, and there may be mentioned, for example, aromatic hydrocarbons such as benzene, toluene and xylene, etc.; halogenated aliphatic hydrocarbons such as methylene chloride, chloroform and 1,2-dichloroethane, etc.; diethyl ether, ethers such as tetrahydrofuran, 1,4-dioxane and 1,2-dimethoxyethane, etc.; ketones such as acetone, methyl ethyl ketone, methyl isobutyl ketone and methyl tert-butyl ketone, etc.; amides such as N,N-dimethylformamide, N,N-dimethylacetamide and N-methylpyrrolidone, etc.; nitriles such as acetonitrile and propionitrile, etc.; or a mixed solvent of optional combination thereof, etc., preferably methylene chloride, 1,2-dichloroethane, acetone, N,N-dimethylformamide, acetonitrile or a mixed solvent thereof.

As the base to be used, there may be mentioned, for example, triethylamine, diisopropylethyl amine, pyridine, 4-dimethyl amino pyridine or picoline, etc., organic base; or inorganic bases such as sodium hydrogen carbonate, potassium hydrogen carbonate, sodium carbonate and potassium carbonate, etc., preferably triethylamine, diisopropylethyl amine or potassium carbonate. An amount of the base to be used is generally 1 to 100-fold mol amount, preferably 1 to 10-fold mol amount based on 1 mol of Compound (1a).

An amount of the alkylating agent (8) to be used is generally 0.9 to 10-fold mol amount, preferably 1 to 1.5-fold mol amount based on 1 mol of Compound (1a).

The reaction temperature may vary depending on a kind or amount(s), etc., of the starting materials, solvent(s), etc., and is generally $-20°$ C. to $100°$ C., and preferably $-5°$ C. to $60°$ C.

The reaction time may vary depending on a reaction temperature, etc., and is generally 1 minute to 24 hours, and preferably 1 hour to 6 hours.

[Preparation Method 3]

"Preparation Method 3" is another method to prepare Compound (1a') of the present invention which is a compound wherein Y is $Y^1$, and Z is $Z^1$ in the above-mentioned Compound (1a).

[Formula 5]

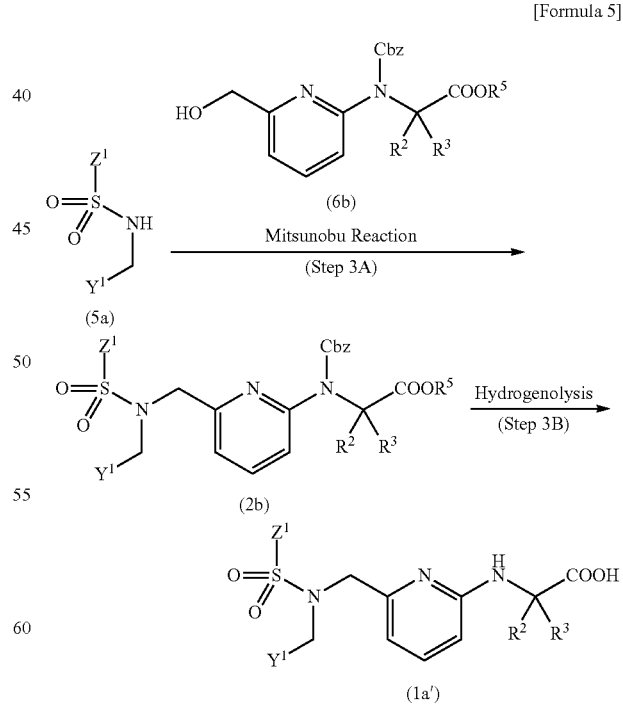

wherein $R^2$ and $R^3$ have the same meanings as defined above, $R^5$ represents a benzyl group or p-methoxy benzyl group, $Y^1$ represents a bicyclic heteroaromatic ring group or group -$Q^1$-

Q²' (wherein Q¹ has the same meaning as defined above, and Q²' represents an aromatic group or 5- to 6-membered ring heterocyclic group each of which may be substituted by a group(s) selected from the group consisting of a fluorine atom, hydroxyl group, $C_1$-$C_6$ alkyl group, fluoro $C_1$-$C_6$ alkyl group, $C_1$-$C_6$ alkoxyl group and fluoro $C_1$-$C_6$ alkoxyl group) each of which may be substituted by a group(s) selected from the group consisting of a fluorine atom, $C_1$-$C_6$ alkyl group, fluoro $C_1$-$C_6$ alkyl group, $C_1$-$C_6$ alkoxyl group, fluoro $C_1$-$C_6$ alkoxyl group and $C_1$-$C_6$ alkylthio group, $Z^1$ represents an aromatic group or 5- to 6-membered heteroaromatic ring group each of which may be substituted by a group(s) selected from the group consisting of a fluorine atom, $C_1$-$C_6$ alkyl group, fluoro $C_1$-$C_6$ alkyl group, $C_1$-$C_6$ alkoxyl group and fluoro $C_1$-$C_6$ alkoxyl group, and Cbz represents a benzyloxycarbonyl group.

"Step 3A" is a so-called Mitsunobu reaction, and is a step of preparing an intermediate compound (2b) by reacting a sulfoneamide compound (5a) and a hydroxymethylpyridine compound (6b) in an inert solvent in the presence of a phosphine compound and azo compound. The present step is carried out according to the above-mentioned "Step 1B" except for using Compound (5a) in place of Compound (5), and using Compound (6b) in place of Compound (6a), respectively.

Compound (5a) is a compound wherein Y is $Y^1$, and Z is $Z^1$ in Compound (5) which can be prepared by the above-mentioned "Step 1A". Compound (6b) is a compound included in Compound (6) which can be prepared by the below mentioned "Preparation Method 11".

"Step 3B" is a step of preparing Compound (1a') by simultaneously removing the Cbz group and $R^5$ group of Compound (2b) by a hydrogenolysis reaction. This step is carried out by reacting with hydrogen in an inert solvent and in the presence of a catalyst.

The inert solvent to be used is not particularly limited so long as it does not inhibit the reaction and dissolves the starting materials with a certain extent, and there may be mentioned, for example, alcohols such as methanol, ethanol, propanol and isopropanol, etc.; ethers such as tetrahydrofuran, 1,4-dioxane and 1,2-dimethoxyethane, etc.; halogenated aliphatic hydrocarbons such as methylene chloride, chloroform and 1,2-dichloroethane, etc.; esters such as methyl formate, ethyl formate, methyl acetate or ethyl acetate, etc.; aromatic hydrocarbons such as benzene and toluene, etc.; water; or a mixed solvent of optional combination thereof, etc., preferably methanol or ethanol.

As the catalyst to be used, there may be mentioned, for example, palladium-active carbon, platinum-active carbon, platinum black, rhodium-active carbon or Raney Nickel, etc., preferably palladium-active carbon, platinum black or Raney Nickel. An amount of the catalyst to be used is generally 0.0005 to 1-fold mol amount, preferably 0.01 to 0.3-fold mol amount based on 1 mol of Compound (2b).

A hydrogen partial pressure in the hydrogenolysis conditions is generally 1 atm to 10 atm, preferably 1 atm to 5 atm.

The reaction temperature may vary depending on a kind or amount(s), etc., of the starting materials, solvent(s), etc., and is generally 0° C. to 100° C., preferably 15° C. to 80° C.

The reaction time may vary depending on a reaction temperature, etc., and is generally 15 minutes to 72 hours, preferably 30 minutes to 48 hours.

[Preparation Method 4]

"Preparation Method 4" is another method for preparing the above-mentioned Compound (1a), Compound (1b) and Compound (1a') and Compound (1b') of the present invention wherein Y is $Y^1$ and Z is $Z^1$ in the formula (1b). The present method comprises the steps (Step 4B1-Step 4C1) for preparing Compound (1b) by removing the Boc group from an intermediate compound (2d), then, preparing Compound (1a) by hydrolysis of an ester, and the steps (Step 4B2-Step 4C2) for preparing of Compound (1b') by removing the Cbz group from an intermediate compound (2e), and then, preparing Compound (1a') by hydrolysis of an ester.

[Formula 6]

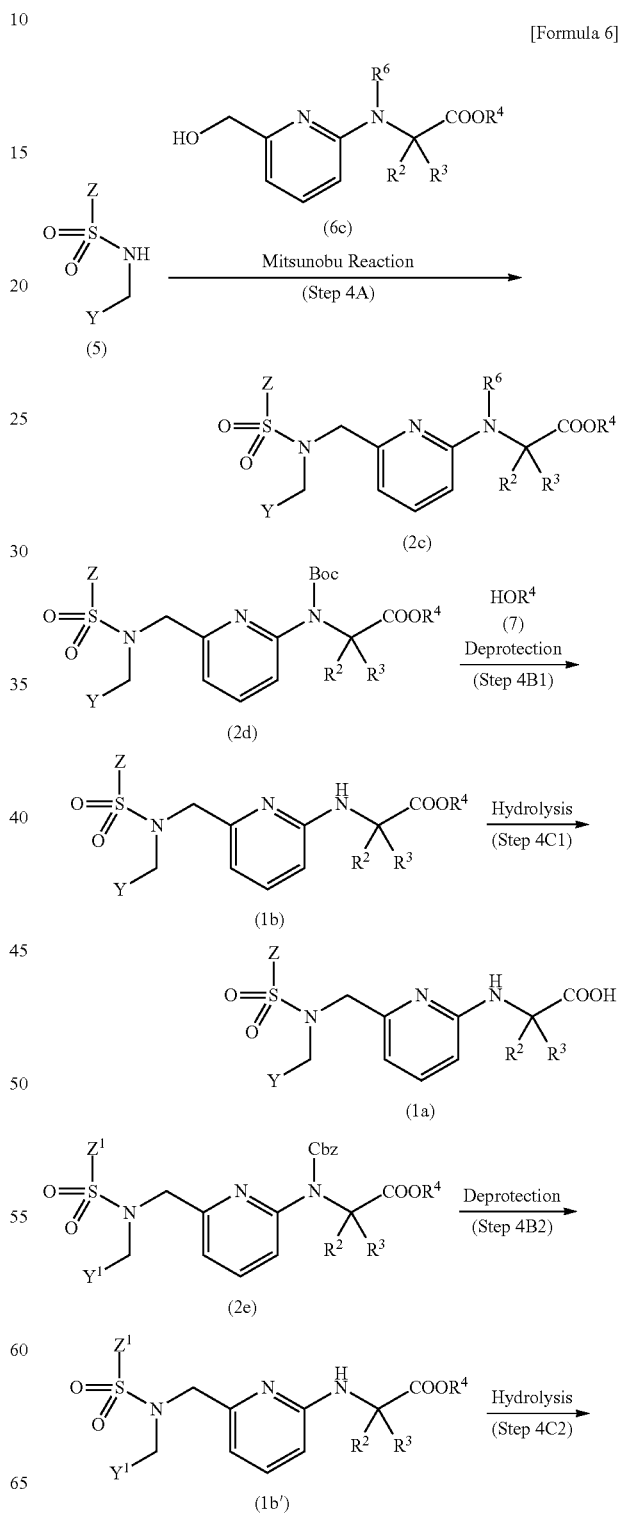

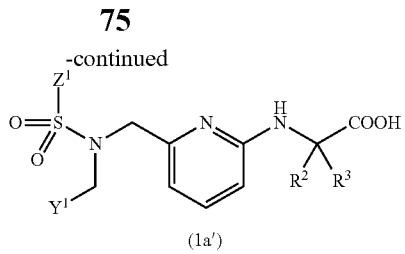

(1a')

[wherein $R^2$, $R^3$, $R^4$, Y, Z, $Y^1$ and $Z^1$ have the same meanings as defined above, and $R^6$ represents a Boc group or Cbz group.]

"Step 4A" is a so-called Mitsunobu reaction, and is a step of preparing an intermediate compound (2c) by reacting Compound (5) and a hydroxymethylpyridine compound (6c) in an inert solvent in the presence of a phosphine compound and azo compound. This step is carried out according to the above-mentioned "Step 1B" except for using Compound (6c) in place of Compound (6a).

Compound (6c) is a compound included in Compound (6) which can be prepared by the below mentioned "Preparation Method 11".

"Step 4B1" is caned out by treating Compound (2d) with an acid in the presence of Compound (7) in an inert solvent or in the absence of a solvent.

The inert solvent to be used is not particularly limited so long as it does not inhibit the reaction and dissolves the starting materials with a certain extent, and there may be mentioned, for example, aromatic hydrocarbons such as benzene, toluene and xylene, etc.; ethers such as tetrahydrofuran, 1,4-dioxane and 1,2-dimethoxyethane, etc.; halogenated aliphatic hydrocarbons such as methylene chloride, chloroform and 1,2-dichloroethane, etc.; or a mixed solvent of optional combination thereof, etc., preferably 1,4-dioxane, methylene chloride, 1,2-dichloroethane or a mixed solvent thereof.

An amount of Compound (7) to be used is generally 1 to 1000-fold mol amount, preferably 10 to 100-fold mol amount based on 1 mol of Compound (2d), and it may be used with a far excess amount as a solvent.

As the acid to be used, there may be mentioned, for example, hydrogen chloride, hydrochloric acid, sulfuric acid, methanesulfonic acid, p-toluenesulfonic acid or trifluoroacetic acid, etc., preferably hydrogen chloride, sulfuric acid, or p-toluene sulfonic acid. An amount of the acid to be used is generally 1 to 200-fold mol amount, preferably 1.5 to 100-fold mol amount based on 1 mol of Compound (2d).

The reaction temperature may vary depending on a kind or amount(s), etc., of the starting materials, solvent(s), etc., and is generally −20° C. to 150° C., preferably −5° C. to 100° C.

The reaction time may vary depending on a reaction temperature, etc., and is generally 30 minutes to 72 hours, preferably 1 hour to 48 hours.

"Step 4C1" is a step of preparing Compound (1a) by hydrolysis reaction of the ester of Compound (1b). This step is carried out under acidic conditions or under basic conditions.

When "Step 4C1" is carried out under acidic conditions, it can be carried out by treating Compound (1b) with an acid in an organic solvent in the presence of water.

The solvent to be used is not particularly limited so long as it does not inhibit the reaction and dissolves the starting materials with a certain extent, and there may be mentioned, for example, alcohols such as methanol, ethanol, propanol and isopropanol, etc.; ethers such as tetrahydrofuran, 1,4-dioxane and 1,2-dimethoxyethane, etc.; acetic acid; or a mixed solvent of optional combination thereof, etc., preferably methanol, ethanol, tetrahydrofuran, acetic acid or a mixed solvent thereof.

An amount of water to be used is generally 10 to 1000-fold mol amount based on 1 mol of Compound (1b), and it may be used with a far excess amount as a solvent.

As the acid to be used, there may be mentioned, for example, inorganic acids such as hydrochloric acid, hydrobromic acid, hydroiodic acid, sulfuric acid and phosphoric acid, etc.; or sulfonic acids such as methanesulfonic acid, benzene sulfonic acid and p-toluene sulfonic acid, etc., preferably hydrochloric acid, hydrobromic acid or sulfuric acid. An amount of the acid to be used is generally 1 to 1000-fold mol amount, preferably 10 to 100-fold mol amount based on 1 mol of Compound (1b).

The reaction temperature may vary depending on a kind or amount(s), etc., of the starting materials, solvent(s), etc., and is generally −5° C. to 150° C., preferably 0° C. to 100° C.

The reaction time may vary depending on a reaction temperature, etc., and generally 15 minutes to 72 hours, preferably 30 minutes to 48 hours.

When "Step 4C1" is carried out under basic conditions, it can be carried out by treating Compound (1b) with a base in an organic solvent in the presence of water.

The solvent to be used is not particularly limited so long as it does not inhibit the reaction and dissolves the starting materials with a certain extent, and there may be mentioned, for example, alcohols such as methanol, ethanol, propanol and isopropanol, etc.; ethers such as tetrahydrofuran, 1,4-dioxane and 1,2-dimethoxyethane, etc.; or a mixed solvent of optional combination thereof, etc., preferably methanol, ethanol, tetrahydrofuran or a mixed solvent thereof.

An amount of water to be used is generally 10 to 1000-fold mol amount based on 1 mol of Compound (1b), and it may be used with a far excess amount as a solvent.

As the base to be used, there may be mentioned, for example, lithium hydroxide, sodium hydroxide or potassium hydroxide, etc., alkali metal hydroxide; or sodium carbonate or potassium carbonate, etc., alkali metal carbonate, etc., preferably lithium hydroxide, sodium hydroxide or potassium hydroxide. An amount of the base to be used is generally 0.9 to 10-fold mol amount, preferably 1 to 5-fold mol amount based on 1 mol of Compound (1b).

The reaction temperature may vary depending on a kind or amount(s), etc., of the starting materials, solvent(s), etc., and is generally −5° C. to 150° C., preferably 0° C. to 80° C.

The reaction time may vary depending on a reaction temperature, etc., and is generally 15 minutes to 72 hours, preferably 30 minutes to 48 hours.

"Step 4B 2" is a step of preparing Compound (1b') by reacting Compound (2e) and hydrogen in an inert solvent in the presence of a catalyst. This step is carried out according to the above-mentioned "Step 3B" except for using Compound (2e) in place of Compound (2b).

"Step 4C2" is a step of preparing Compound (1a') by hydrolysis reaction of the ester of Compound (1b'), and is carried out under acidic conditions or under basic conditions. This step is carried out according to the above-mentioned "Step 4C1" except for using Compound (1b') in place of Compound (1b).

[Preparation Method 5]

"Preparation Method 5" is a general method to prepare an intermediate compound (2).

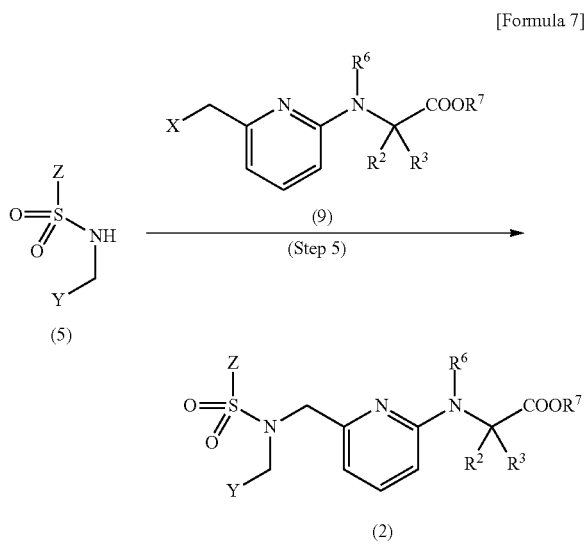

[Formula 7]

(5) + (9) → (Step 5) → (2)

[wherein $R^2$, $R^3$, $R^6$, X, Y and Z have the same meanings as defined above, $R^7$ represents a $C_1$-$C_6$ alkyl group, benzyl group or p-methoxy benzyl group which are the same meaning as defined above.]

"Step 5" is a step of preparing Compound (2) by reacting Compound (5) and Compound (9) in an inert solvent in the presence of a base.

Compound (9) can be prepared by the below mentioned "Preparation Method 15".

The inert solvent to be used is not particularly limited so long as it does not inhibit the reaction and dissolves the starting materials with a certain extent, and there may be mentioned, for example, ethers such as tetrahydrofuran, 1,4-dioxane and 1,2-dimethoxyethane, etc.; halogenated aliphatic hydrocarbons such as methylene chloride, chloroform and 1,2-dichloroethane, etc.; nitriles such as acetonitrile and propionitrile, etc.; esters such as methyl formate, ethyl formate, methyl acetate or ethyl acetate, etc.; aromatic hydrocarbons such as benzene and toluene, etc.; amides such as N,N-dimethylformamide, N,N-dimethylacetamide and N-methylpyrrolidone, etc.; sulfoxides such as dimethylsulfoxide, etc.; or a mixed solvent of optional combination thereof, etc., preferably tetrahydrofuran, N,N-dimethylformamide, methylene chloride or 1,2-dichloroethane.

As the base to be used, there may be mentioned, for example, alkali metal hydrides such as sodium hydride and potassium hydride, etc.; alkali metal amides such as lithium amide, sodium amide, lithium diisopropyl amide and lithium bistrimethylsilyl amide, etc.; alkali metal alkoxides such as sodium methoxide, sodium ethoxide, sodium tert-butoxide or potassium tert-butoxide, etc.; alkali metal carbonates such as sodium carbonate and potassium carbonate, etc.; or amines such as triethylamine, tributylamine, diisopropylethyl amine, pyridine, picoline, 2,6-lutidine or 4-dimethylaminopyridine, etc., preferably sodium hydride, potassium carbonate, triethylamine or diisopropylethyl amine. Provided that the inert solvent to be used is an ester, nitrile or halogenated aliphatic hydrocarbon, as the base, triethylamine or diisopropylethyl amine is preferred. An amount of the base to be used is generally 1 to 5-fold mol amount, preferably 1 to 2.5-fold mol amount based on 1 mol of Compound (5).

An amount of Compound (9) to be used is generally 0.5 to 3-fold mol amount, preferably 0.5 to 1.5-fold mol amount based on 1 mol of Compound (5).

The reaction temperature may vary depending on a kind or amount(s), etc., of the starting materials, solvent(s), etc., and is generally −80° C. to 100° C., preferably 0° C. to 80° C.

The reaction time may vary depending on a reaction temperature, etc., and is generally 10 minutes to 48 hours, preferably 1 hour to 24 hours.

[Preparation Method 6]

"Preparation Method 6" is another method for preparing Compound (2d) wherein $R^6$ is a Boc group and $R^7$ is $R^4$ in the above-mentioned Compound (2).

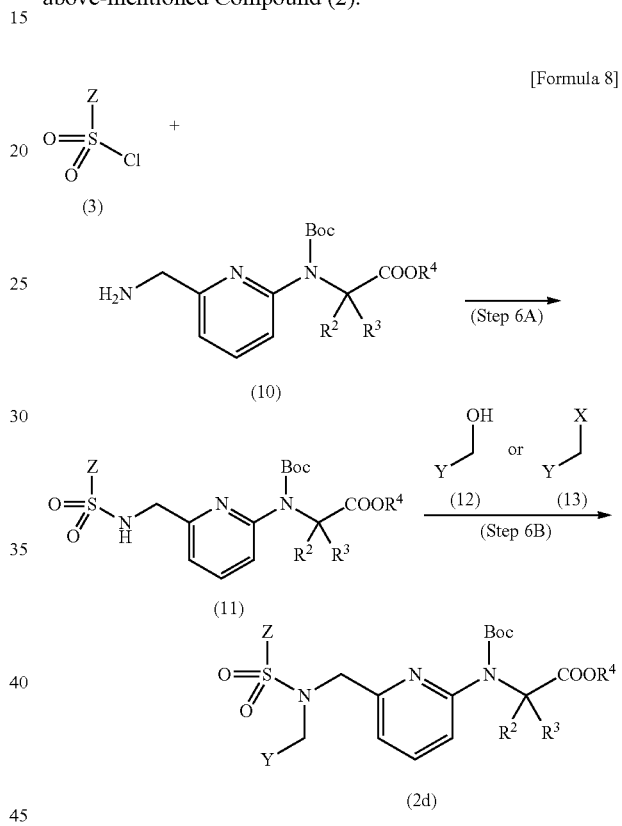

[Formula 8]

[wherein $R^2$, $R^3$, $R^4$, X, Y and Z have the same meanings as defined above.]

"Step 6A" is a step of preparing a sulfonylaminomethylpyridine compound (11) by reacting Compound (3) and an aminomethylpyridine compound (10) in an inert solvent in the presence of or in the absence of (preferably in the presence of) a base. This step is carried out according to the above-mentioned "Step 1A" except for using Compound (10) in place of Compound (4).

Compound (10) can be prepared by the below mentioned "Preparation Method 14".

"Step 6B" is a step of preparing Compound (2d) by reacting Compound (11) and a hydroxy compound (12) or Compound (13).

When Compound (12) is used in "Step 6B", it is a so-called Mitsunobu reaction, and carried out in an inert solvent in the presence of a phosphine compound and azo compound. This step is carried out according to the above-mentioned "Step 1B" except for using Compound (11) in place of Compound (5), and using Compound (12) in place of Compound (6a), respectively.

Compound (12) is known or can be prepared according to the known method from the known compound(s).

When "Step 6B" uses Compound (13), it can be carried out by reacting Compound (11) and Compound (13) in the presence of a base in an inert solvent. This step is carried out according to the above-mentioned "Step 5" except for using Compound (11) in place of Compound (5), and using Compound (13) in place of Compound (9), respectively.

Compound (13) is known or can be prepared according to the known method from the known compound(s).

[Preparation Method 7]

"Preparation Method 7" is another method to prepare an intermediate compound (2f) wherein $R^6$ is a Boc group, $R^7$ is $R^4$, Y is $Y^1$, and Z is $Z^1$ in the above-mentioned Compound (2).

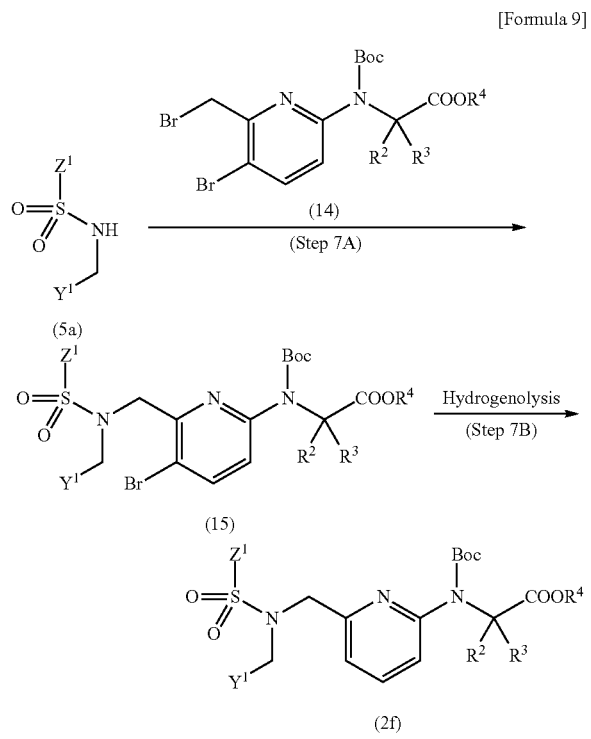

[Formula 9]

[wherein $R^2$, $R^3$, $R^4$, $Y^1$ and $Z^1$ have the same meanings as defined above.]

"Step 7A" is a step of preparing an intermediate compound (15) by reacting Compound (5a) and a bromomethylpyridine compound (14) in the presence of a base in an inert solvent. This step is carried out according to the above-mentioned "Step 5" except for using Compound (5a) in place of Compound (5), and using Compound (14) in place of Compound (9), respectively.

Compound (14) can be prepared by the below mentioned "Preparation Method 16".

"Step 7B" is a step of preparing Compound (2f) by reacting Compound (15) with hydrogen in the presence of a catalyst in an inert solvent in the presence of or in the absence of (preferably in the presence of) a base.

The inert solvent to be used is not particularly limited so long as it does not inhibit the reaction and dissolves the starting materials with a certain extent, and there may be mentioned, for example, alcohols such as methanol, ethanol, propanol and isopropanol, etc.; ethers such as tetrahydrofuran, 1,4-dioxane and 1,2-dimethoxyethane, etc.; halogenated aliphatic hydrocarbons such as methylene chloride, chloroform and 1,2-dichloroethane, etc.; esters such as methyl formate, ethyl formate, methyl acetate or ethyl acetate, etc.; aromatic hydrocarbons such as benzene and toluene, etc.; water; or a mixed solvent of optional combination thereof, etc., preferably methanol or ethanol.

As the base to be used, there may be mentioned, for example, triethylamine, diisopropylethyl amine, pyridine, 4-dimethyl amino pyridine, picoline or 2,6-lutidine etc. organic base; or inorganic bases such as sodium hydrogen carbonate, potassium hydrogen carbonate, sodium carbonate and potassium carbonate, etc., preferably triethylamine or diisopropylethyl amine. An amount of the base to be used is generally 1 to 100-fold mol amount, preferably 1 to 10-fold mol amount based on 1 mol of Compound (15).

As the catalyst to be used, there may be mentioned, for example, palladium-active carbon, platinum-active carbon, platinum black, rhodium-active carbon or Raney Nickel, etc., preferably palladium-active carbon, platinum black or Raney Nickel. An amount of the catalyst to be used is generally 0.0005 to 1-fold mol amount, preferably 0.01 to 0.3-fold mol amount based on 1 mol of Compound (15).

The hydrogen partial pressure is generally 1 atm to 10 atm, preferably 1 atm to 5 atm.

The reaction temperature may vary depending on a kind or amount(s), etc., of the starting materials, solvent(s), etc., and is generally 0° C. to 100° C., preferably 15° C. to 80° C.

The reaction time may vary depending on a reaction temperature, etc., and is generally 15 minutes to 72 hours, preferably 30 minutes to 24 hours.

[Preparation Method 8]

"Preparation Method 8" is another method to prepare the above-mentioned Compound (2).

[Formula 10]

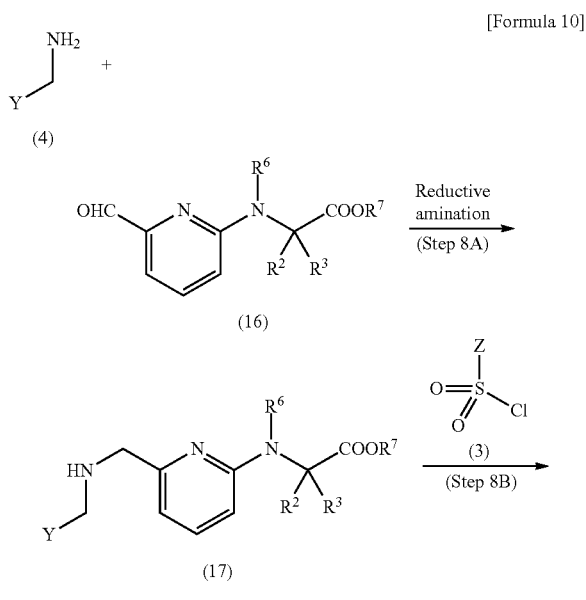

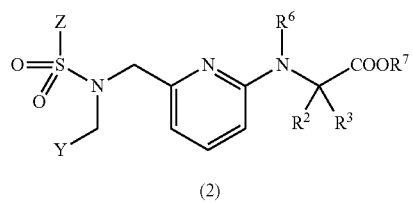

[wherein $R^2$, $R^3$, $R^6$, $R^7$, Y and Z have the same meanings as defined above.]

"Step 8A" is a step of preparing Compound (17) by reacting Compound (4) and a formylpyridine compound (16) in the presence or in the absence of a dehydrating agent in an inert solvent to prepare an imine material, and then, reducing the same by using a hydrogenated boron compound.

Compound (16) can be prepared by the below mentioned "Preparation Method 13".

The inert solvent to be used is not particularly limited so long as it does not inhibit the reaction and dissolves the starting materials with a certain extent, and there may be mentioned, for example, methylene chloride, chloroform or 1,2-dichloroethane, etc., halogenated aliphatic saturated hydrocarbon; aromatic hydrocarbons such as benzene and toluene, etc.; or methanol, ethanol or propanol, etc., alcohols, etc., preferably methylene chloride, 1,2-dichloroethane, methanol or ethanol.

As the dehydrating agent to be used, there may be mentioned, for example, molecular sieve or anhydrous magnesium sulfate, etc. An amount of the dehydrating agent to be used is generally 100 g to 2000 g, preferably 500 g to 1000 g based on 1 mol of Compound (16).

An amount of Compound (4) to be used is generally 0.4 to 10-fold mol amount, preferably 0.5 to 3-fold mol amount based on 1 mol of Compound (16). When Compound (4) is an acid addition salt (for example, hydrochloride or hydrobromide, etc.), a base may be added. In such a case, as the base to be used, there may be mentioned, for example, triethylamine or diisopropylethyl amine, etc. An amount of the base to be used is generally 1 to 10-fold mol amount, preferably 1 to 3-fold mol amount based on 1 mol of Compound (4).

The reaction temperature may vary depending on a kind or amount(s), etc., of the starting materials, solvent(s), etc., and is generally −5° C. to 100° C., preferably 0° C. to 50° C.

The reaction time may vary depending on a reaction temperature, etc., and is generally 10 minutes to 24 hours, preferably 1 hour to 12 hours.

The obtained imine material is after isolation, or without isolation, subsequently reduced by using a hydrogenated boron compound. The hydrogenated boron compound to be used may be mentioned, for example, sodium borohydride, sodium cyanoborohydride or sodium triacetoxyborohydride, etc., preferably sodium borohydride or sodium triacetoxyborohydride. An amount of the hydrogenated boron compound to be used is generally 1 to 10-fold mol amount, preferably 1 to 3-fold mol amount based on 1 mol of Compound (16).

When the obtained imine material was isolated, the inert solvent to be used in the reducing reaction is not particularly limited so long as it does not inhibit the reaction and dissolves the starting materials with a certain extent, and there may be mentioned, for example, halogenated aliphatic hydrocarbons such as methylene chloride, chloroform and 1,2-dichloroethane, etc.; aromatic hydrocarbons such as benzene and toluene, etc.; or alcohols such as methanol, ethanol and propanol, etc., preferably methylene chloride, 1,2-dichloroethane, methanol or ethanol.

The reaction temperature may vary depending on a kind or amount(s), etc., of the starting materials, solvent(s), etc., and is generally −5° C. to 100° C., preferably 0° C. to 50° C.

The reaction time may vary depending on a reaction temperature, etc., and is generally 10 minutes to 12 hours, preferably 1 hour to 6 hours.

"Step 8B" is a step of preparing Compound (2) by reacting Compound (3) and Compound (17) in the presence of a base. This step is carried out according to the above-mentioned "Step 1A" except for using Compound (17) in place of Compound (4).

[Preparation Method 9]

"Preparation Method 9" is another method to prepare a substituted aminomethylpyridine compound (17a) wherein $R^6$ is a Boc group and $R^7$ is $R^4$ in the above-mentioned Compound (17).

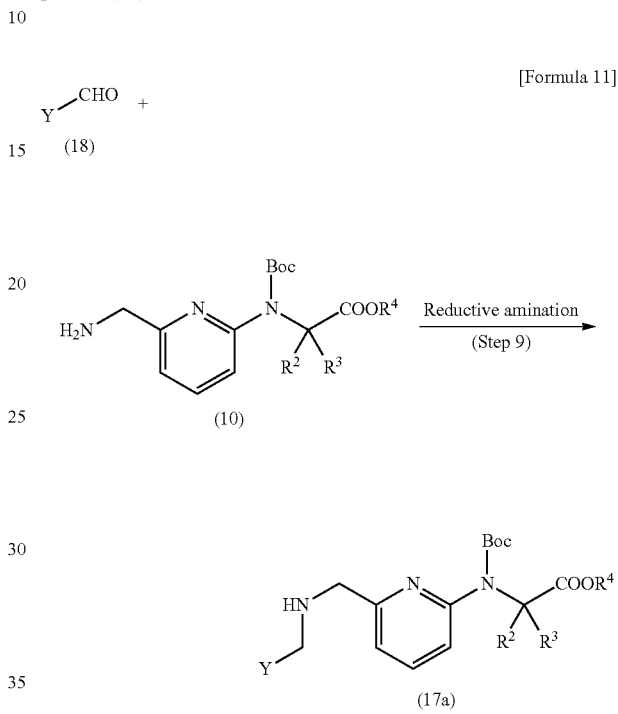

[Formula 11]

[wherein $R^2$, $R^3$, $R^4$ and Y have the same meanings as defined above.]

"Step 9" is a step of preparing Compound (17a) by reacting Compound (10) and a formyl compound (18) in the presence or in the absence of a dehydrating agent in an inert solvent to prepare an imine material, and then, reducing the same by using a hydrogenated boron compound. This step is carried out according to the above-mentioned "Step 8A" except for using Compound (10) in place of Compound (4), and using Compound (18) in place of Compound (16), respectively.

Compound (18) is known or can be prepared according to the known method from the known compound(s).

[Preparation Method 10]

"Preparation Method 10" is another method to prepare an intermediate compound (2g) wherein Z is $Z^2$ and Y is a group $-Q^1-Q^2$ in the above-mentioned Compound (2).

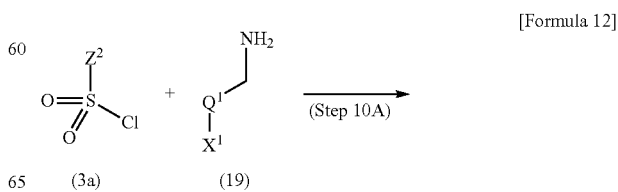

[Formula 12]

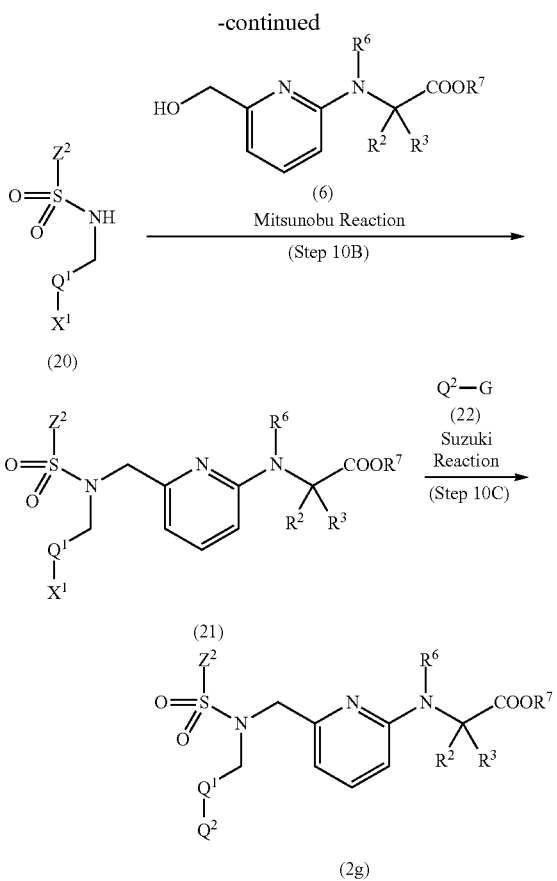

[wherein R², R³, R⁶, R⁷, Q¹ and Q² have the same meanings as defined above. G represents a boronic acid derivative group such as a dihydroxyborylboryl group and 4,4,5,5-tetramethyl [1,3,2]dioxaborolanyl group, etc., X¹ represents a chlorine atom, bromine atom or iodine atom, Z² represents an aromatic group or 5- to 6-membered heteroaromatic ring group each of which may be substituted by a group(s) selected from the group consisting of a fluorine atom, chlorine atom, $C_1$-$C_6$ alkyl group, halogeno $C_1$-$C_6$ alkyl group, $C_1$-$C_6$ alkoxyl group and halogeno $C_1$-$C_6$ alkoxyl group.]

"Step 10A" is a step of preparing a sulfonamide Compound (20) by reacting a chlorosulfonyl compound (3a) and an amine compound (19) in the presence of or in the absence of (preferably in the presence of) a base in an inert solvent. This step is carried out according to the above-mentioned "Step 1A" except for using Compound (3a) in place of Compound (3), and using Compound (19) in place of Compound (4), respectively.

Compound (3a) is a compound wherein Z is Z² in Compound (3). Compound (19) is known or can be prepared according to the known method from the known compound(s).

"Step 10B" is a so-called Mitsunobu reaction, and a step of preparing an intermediate compound (21) by reacting Compound (20) and Compound (6) in the presence of a phosphine compound and azo compound in an inert solvent. This step is carried out according to the above-mentioned "Step 1B" except for using Compound (20) in place of Compound (5), and using Compound (6) in place of Compound (6a), respectively.

Compound (6) can be prepared by the below mentioned "Preparation Method 11".

"Step 10C" is a so-called Suzuki reaction, and is a step of preparing Compound (2g) by reacting Compound (21) and a boric acid compound (22) in the presence of either a base or fluoride and a palladium a catalyst under inert gas atmosphere in an inert solvent.

Compound (22) is known or can be prepared according to the known method from the known compound(s).

The inert solvent to be used is not particularly limited so long as it does not inhibit the reaction and dissolves the starting materials, catalyst and base (or fluoride) with a certain extent, and there may be mentioned, for example, aromatic hydrocarbons such as benzene and toluene, etc.; ethers such as tetrahydrofuran, 1,2-dimethoxyethane and 1,4-dioxane, etc.; alcohols such as methanol, ethanol, propanol and isopropanol, etc.; esters such as methyl acetate and ethyl acetate, etc.; amides such as N,N-dimethylformamide, N,N-dimethylacetamide and N-methylpyrrolidone, etc.; sulfoxides such as dimethylsulfoxide, etc.; nitriles such as acetonitrile, etc.; water; or a mixed solvent of optional combination thereof, etc., preferably toluene, toluene-ethanol-water mixed solvent or toluene-water mixed solvent.

As the inert gas to be used, there may be mentioned, for example, nitrogen, helium or argon, etc.

As the palladium catalyst to be used, there may be mentioned, for example, metal palladium such as palladium-active carbon and palladium black, etc.; organic palladium complexes such as tetrakis(triphenylphosphine) palladium, bis (triphenylphosphine) palladium chloride, 1,1'-bis (diphenylphosphino)ferrocene palladium chloride and tris (dibenzylideneacetone)dipalladium, etc.; or palladium salts such as palladium chloride and palladium acetate, etc., preferably tetrakis(triphenylphosphine) palladium or palladium acetate. An amount of the palladium to be used as a catalyst is generally 0.0001 to 1-fold mol amount, preferably 0.005 to 0.3-fold mol amount based on 1 mol of Compound (21).

When tris(dibenzylideneacetone)dipalladium, palladium chloride or palladium acetate is used as a catalyst, an organic phosphine compound is preferably co-existed. As the organic phosphine compound to be used, there may be mentioned, for example, tri-n-butyl phosphine, tri-tert-butyl phosphine, tri cyclohexyl phosphine, butyl di-1-adamantylphosphine, triphenylphosphine, tri(o-tolyl)phosphine, 2-dicyclohexylphosphino-2',6'-dimethoxy biphenyl, 1,1'-bis(diphenylphosphino)ferrocene or 1,2,3,4,5-penta phenyl-1'-(di-tert-butylphosphino)ferrocene, etc., preferably tri cyclohexyl phosphine, butyl di-1-adamantylphosphine, triphenylphosphine or 2-dicyclohexyl phosphino-2',6'-dimethoxy biphenyl. An amount of the organic phosphine compound to be used is generally 1 to 5-fold mol amount, preferably 1.5 to 2.5-fold mol amount based on 1 mol of palladium.

As the base or fluoride to be used, there may be mentioned, for example, an alkali metal acetate such as sodium acetate and potassium acetate, etc.; an alkali metal carbonate such as sodium carbonate, potassium carbonate and cecium carbonate etc.; an alkali metal phosphate such as trisodium phosphate and tripotassium phosphate, etc.; an alkali metal hydroxide such as lithium hydroxide, sodium hydroxide and potassium hydroxide, etc.; a quaternary ammonium hydroxide such as tetramethyl ammonium hydroxide, tetraethyl ammonium hydroxide or tetrabutyl ammonium hydroxide etc.; or a fluoride such as cesium fluoride, tetramethyl ammonium fluoride, tetraethyl ammonium fluoride and tetrabutyl ammonium fluoride etc., preferably sodium carbonate or tripotassium phosphate. An amount of the base or fluoride to be used is generally 1 to 10-fold mol amount, preferably 1.5 to 5-fold mol amount based on 1 mol of Compound (21).

An amount of Compound (22) to be used is generally 1 to 3-fold mol amount, preferably 1 to 2-fold mol amount based on 1 mol of Compound (21).

The reaction temperature may vary depending on a kind or amount(s), etc., of the starting materials, solvent(s), etc., and is generally 0° C. to 200° C., preferably 50° C. to 150° C.

The reaction time may vary depending on a reaction temperature, etc., and is generally 10 minutes to 120 hours, preferably 1 hour to 48 hours.

[Preparation Method 11]

"Preparation Method 11" is a general method to prepare Compound (6).

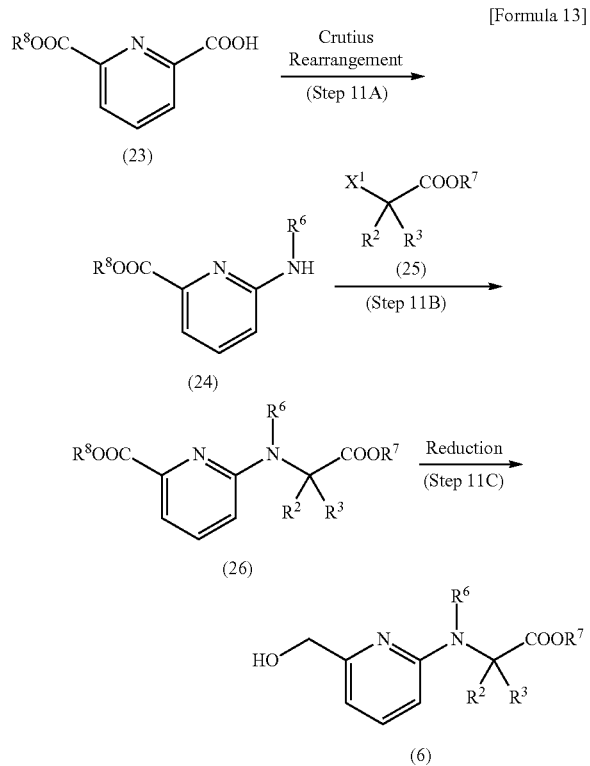

wherein $R^2$, $R^3$, $R^6$, $R^7$ and $X^1$ have the same meanings as defined above, and $R^8$ represents a methyl group or ethyl group.

"Step 11A" is a step of preparing an aminopyridyl ester compound (24) from a half ester compound (23) by the so-called Crutius rearrangement reaction, and when $R^6$ is a Boc group, it is carried out by the same method as described in WO 2006/074884A, and when $R^6$ is a Cbz group, it is carried out according to the method described in the above-mentioned publication except for using benzyl alcohol in place of tert-butanol.

Compound (23) is known or can be prepared according to the known method from the known compound(s).

"Step 11B" is a step of preparing a pyridine ester compound (26) by reacting Compound (24) and a halogenoacetic acid compound (25) in the presence of a base in an inert solvent. This step is carried out according to the above-mentioned "Step 5" except for using Compound (24) in place of Compound (5), and using Compound (25) in place of Compound (9), respectively.

Compound (25) is known or can be prepared according to the known method from the known compound(s).

"Step 11C" is a step of preparing Compound (6) by reducing Compound (26) using sodium borohydride in the presence of or in the absence of (preferably in the presence of) calcium chloride in an inert solvent.

The inert solvent to be used is not particularly limited so long as it does not inhibit the reaction and dissolves the starting materials with a certain extent, and there may be mentioned, for example, alcohols such as methanol, ethanol, propanol, isopropanol, butanol, isobutanol, sec-butanol and tert-butanol, etc.; ethers such as tetrahydrofuran, 1,4-dioxane, 1,2-dimethoxyethane, diethyleneglycol dimethyl ether, triethyleneglycol dimethyl ether or tetraethyleneglycol dimethyl ether, etc.; nitriles such as acetonitrile and propionitrile, etc.; amides such as N,N-dimethylformamide, N,N-dimethylacetamide and N-methylpyrrolidone, etc.; sulfoxides such as dimethylsulfoxide, etc.; or a mixed solvent of optional combination thereof, etc., preferably methanol, ethanol, tetrahydrofuran, tri ethylene glycol dimethyl ether, tetra ethylene glycol dimethyl ether or a mixed solvent thereof.

An amount of calcium chloride to be used is generally 0.5 to 10-fold mol amount, preferably 1 to 3-fold mol amount based on 1 mol of Compound (26).

An amount of sodium borohydride to be used is generally 0.5 to 10-fold mol amount, preferably 1 to 3-fold mol amount based on 1 mol of Compound (26).

The reaction temperature may vary depending on a kind or amount(s), etc., of the starting materials, solvent(s), etc., and is generally −10° C. to 100° C., preferably 0° C. to 50° C.

The reaction time may vary depending on a reaction temperature, etc., and is generally 10 minutes to 12 hours, preferably 15 minutes to 6 hours.

[Preparation Method 12]

"Preparation Method 12" is another method to prepare a hydroxymethylpyridine compound (6d) wherein $R^7$ is a tBu group in the above-mentioned Compound (6).

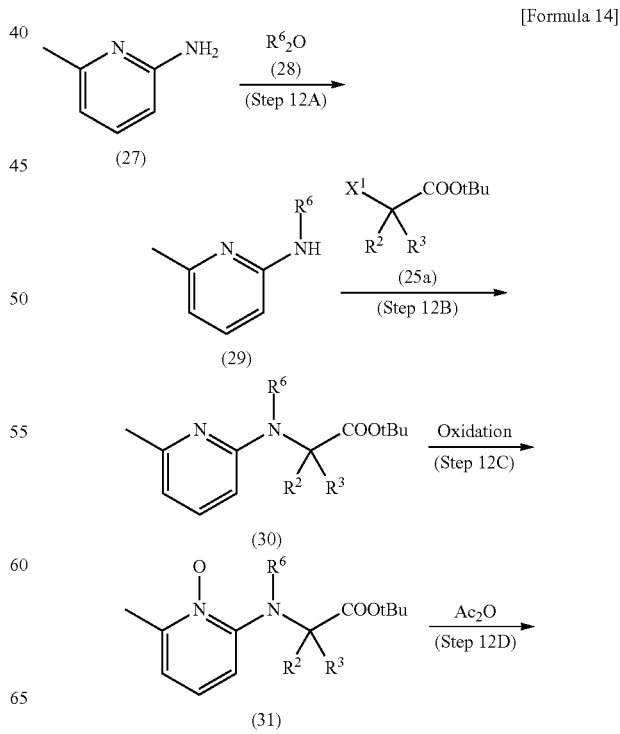

-continued

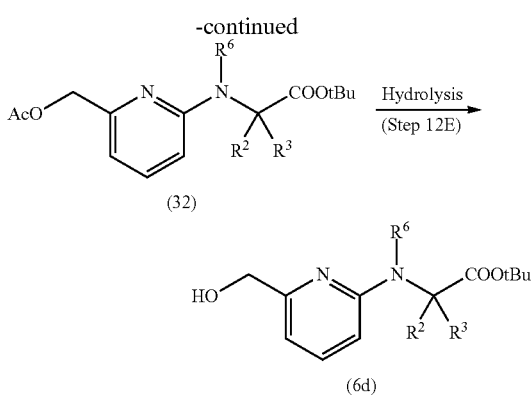

wherein $R^2$, $R^3$, $R^6$ and $X^1$ have the same meanings as defined above, and Ac represents an acetyl group.

"Step 12A" is a step of preparing a picoline compound (29) by reacting a known compound (28) and a known compound (27) in the presence of a base in an inert solvent.

The inert solvent to be used is not particularly limited so long as it does not inhibit the reaction and dissolves the starting materials with a certain extent, and there may be mentioned, for example, alcohols such as methanol, ethanol, propanol, isopropanol, butanol, isobutanol, sec-butanol, tert-butanol and benzyl alcohol, etc.; ethers such as tetrahydrofuran, 1,4-dioxane and 1,2-dimethoxyethane, etc.; nitriles such as acetonitrile and propionitrile, etc.; amides such as N,N-dimethylformamide, N,N-dimethylacetamide and N-methylpyrrolidone, etc.; sulfoxides such as dimethylsulfoxide, etc.; or a mixed solvent of optional combination thereof, etc., preferably tert-butanol or benzyl alcohol.

As the base to be used, there may be mentioned, for example, organic bases such as triethylamine, diisopropylethylamine, pyridine, 4-dimethylaminopyridine, picoline and 2,6-lutidine, etc., preferably 4-dimethylaminopyridine. An amount of the base to be used is generally 0.01 to 10-fold mol amount, preferably 0.05 to 1-fold mol amount based on 1 mol of Compound (27).

An amount of Compound (28) to be used is generally 0.9 to 5-fold mol amount, preferably 1 to 3-fold mol amount based on 1 mol of Compound (27).

The reaction temperature may vary depending on a kind or amount(s), etc., of the starting materials, solvent(s), etc., and is generally −10° C. to 100° C., preferably 0° C. to 50° C.

The reaction time may vary depending on a reaction temperature, etc., and is generally 10 minutes to 24 hours, preferably 1 hour to 12 hours.

"Step 12B" is a step of preparing a substituted amino picoline compound (30) by reacting Compound (29) and a halogenoacetic acid compound (25a) in the presence of a base in an inert solvent. This step is carried out according to the above-mentioned "Step 11B" except for using Compound (29) in place of Compound (24), and using Compound (25a) in place of Compound (25), respectively.

Compound (25a) is a compound wherein $R^7$ is a tBu group in the above-mentioned Compound (25).

"Step 12C" is a step of preparing an N-oxide Compound (31) by oxidating Compound (30) using an oxidizing agent in an inert solvent.

The inert solvent to be used is not particularly limited so long as it does not inhibit the reaction and dissolves the starting materials with a certain extent, and there may be mentioned, for example, halogenated aliphatic hydrocarbons such as methylene chloride, chloroform and 1,2-dichloroethane, etc., preferably methylene chloride.

The oxidizing agent to be used may be mentioned, for example, an oxidizing agent such as m-chloroperbenzoic acid and hydrogen peroxide, etc., preferably m-chloroperbenzoic acid. An amount of the oxidizing agent to be used is generally 1 to 10-fold mol amount, preferably 1 to 3-fold mol amount based on 1 mol of Compound (30).

The reaction temperature may vary depending on a kind or amount(s), etc., of the starting materials, solvent(s), etc., and is generally 0° C. to 100° C., preferably 10° C. to 50° C.

The reaction time may vary depending on a reaction temperature, etc., and is generally 30 minutes to 24 hours, preferably 1 hour to 6 hours.

"Step 12D" is a step of preparing an acetoxymethylpyridine compound (32) by rearrangement reaction from Compound (31) in acetic anhydride.

An amount of the acetic anhydride to be used is generally 1 to 100-fold mol amount, preferably 5 to 30-fold mol amount based on 1 mol of Compound (31), and it may be used with a far excess amount as a solvent.

The reaction temperature may vary depending on a kind or amount(s), etc., of the starting materials, solvent(s), etc., and is generally 0° C. to 150° C., preferably 50° C. to 120° C.

The reaction time may vary depending on a reaction temperature, etc., and is generally 30 minutes to 24 hours, preferably 1 hour to 12 hours.

"Step 12E" is a step of preparing Compound (6d) by treating Compound (32) with a base in the presence of water in an organic solvent. This step is carried out under basic conditions according to the above-mentioned "Step 4C1" except for using Compound (32) in place of Compound (1b), and using 0.9 to 1.1 mol amount of the base based on 1 mol of Compound (32).

[Preparation Method 13]

"Preparation Method 13" is a general method to prepare the above-mentioned Compound (16).

[Formula 15]

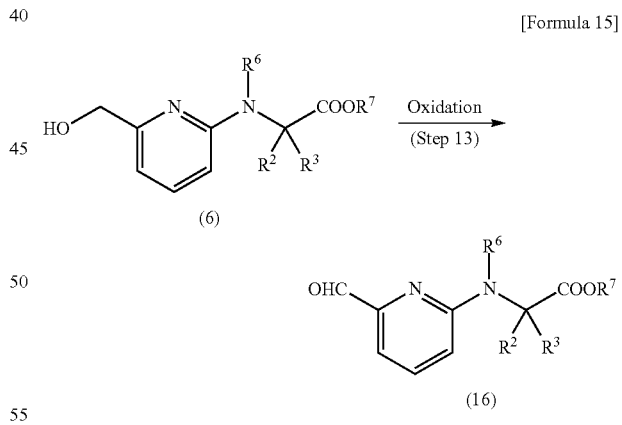

wherein $R^2$, $R^3$, $R^6$ and $R^7$ have the same meanings as defined above.

"Step 13" is a step of preparing Compound (16) by oxidizing Compound (6) using an oxidizing agent in an inert solvent. As the oxidizing agent in this step, there may be mentioned, for example, manganese dioxide, pyridinium chlorochromate (PCC), pyridinium dichromate (PDC) or 1,1,1-tris(acetoxy)-1,1-dihydro-1,2-benziodoxol-3(1H)-one (hereinafter abbreviated to as Dess-Martin reagent), or the so-called TEMPO oxidizing agent in which sodium hypochlorite and 2,2,6,6-tetramethylpiperidin 1-oxyl (hereinafter abbreviated to as TEMPO) are used in combination, etc., and it is necessary to select reaction conditions depending on the kind of the oxidizing agent to be used.

When manganese dioxide, pyridinium chlorochromate (PCC), pyridinium dichromate (PDC) or Dess-Martin reagent is used as the oxidizing agent, the reaction is carried out in an inert solvent.

The inert solvent to be used is not particularly limited so long as it does not inhibit the reaction and dissolves the starting materials with a certain extent, and there may be mentioned, for example, halogenated aliphatic hydrocarbons such as methylene chloride, chloroform and 1,2-dichloroethane, etc.; nitriles such as acetonitrile, etc.; or esters such as methyl acetate, ethyl acetate and isopropyl acetate, etc., preferably methylene chloride.

An amount of the oxidizing agent to be used may vary depending on a kind of the oxidizing agent, and is generally 0.9 to 100-fold mol amount, preferably 1 to 20-fold mol amount based on 1 mol of Compound (6).

The reaction temperature may vary depending on a kind or amount(s), etc., of the starting materials, solvent(s), etc., and is generally 0° C. to 150° C., preferably 0° C. to 100° C.

The reaction time may vary depending on a reaction temperature, etc., and is generally 30 minutes to 24 hours, preferably 1 hour to 12 hours.

When sodium hypochlorite and TEMPO are used as the oxidizing agent, and the so-called TEMPO oxidation si carried out, the reaction is carried out in the presence of potassium bromide in an inert solvent.

The inert solvent to be used is not particularly limited so long as it does not inhibit the reaction and dissolves the starting materials with a certain extent, and there may be mentioned, for example, halogenated aliphatic hydrocarbons such as methylene chloride, chloroform and 1,2-dichloroethane, etc.; water; or a mixed solvent of optional combination thereof, etc., preferably a mixed solvent of methylene chloride and water.

An amount of the sodium hypochlorite to be used is generally 0.8 to 3-fold mol amount, preferably 0.9 to 1.5-fold mol amount based on 1 mol of Compound (6). Incidentally, sodium hypochlorite may be added as an aqueous solution in which a pH of which is adjusted to 8 to 10 by sodium hydrogen carbonate.

An amount of the TEMPO to be used is generally 0.001 to 0.1-fold mol amount, preferably 0.005 to 0.05-fold mol amount based on 1 mol of Compound (6).

An amount of the potassium bromide to be used is generally 0.01 to 1-fold mol amount, preferably 0.05 to 0.2-fold mol amount based on 1 mol of Compound (6).

The reaction temperature may vary depending on a kind or amount(s), etc., of the starting materials, solvent(s), etc., and is generally −30° C. to 30° C., preferably −15° C. to 15° C.

The reaction time may vary depending on a reaction temperature, etc., and is generally 10 minutes to 12 hours, preferably 30 minutes to 6 hours.

[Preparation Method 14]

"Preparation Method 14" is a general method to prepare the above-mentioned Compound (10).

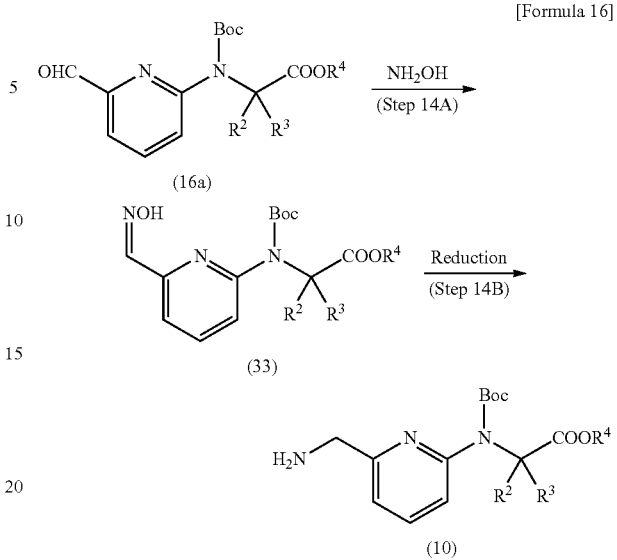

[Formula 16]

wherein $R^2$, $R^3$, and $R^4$ have the same meanings as defined above.

"Step 14A" is a step of preparing an oxime compound (33) by reacting a hydroxylamine and a formylpyridine compound (16a) in an inert solvent.

Compound (16a) is a compound wherein $R^6$ is a Boc group, and $R^7$ is $R^4$ in the above-mentioned Compound (16).

The inert solvent to be used is not particularly limited so long as it does not inhibit the reaction and dissolves the starting materials with a certain extent, and there may be mentioned, for example, alcohols such as methanol, ethanol and isopropanol, etc.; halogenated aliphatic hydrocarbons such as methylene chloride, chloroform and 1,2-dichloroethane, etc.; nitriles such as acetonitrile, etc.; or esters such as methyl acetate, ethyl acetate and isopropyl acetate, etc., preferably methanol.

An amount of the hydroxylamine to be used is generally 1 to 5-fold mol amount, preferably 1 to 2-fold mol amount.

To promote the reaction, a base, for example, triethylamine, diisopropylethyl amine or pyridine, etc., may be added. An amount of the base to be used is generally 0.5 to 20-fold mol amount, preferably 1 to 10-fold mol amount based on 1 mol of Compound (16a).

The reaction temperature may vary depending on a kind or amount(s), etc., of the starting materials, solvent(s), etc., and is generally 0° C. to 100° C., preferably 0° C. to 60° C.

The reaction time may vary depending on a reaction temperature, etc., and is generally 30 minutes to 24 hours, preferably 1 hour to 12 hours.

"Step 14B" is a step of preparing Compound (10) by reacting Compound (33) with hydrogen in the presence of a catalyst in an inert solvent. This step is carried out according to the above-mentioned "Step 3B" except for using Compound (33) in place of Compound (2b).

[Preparation Method 15]

"Preparation Method 15" is a general method to prepare the above-mentioned Compound (9).

[Formula 17]

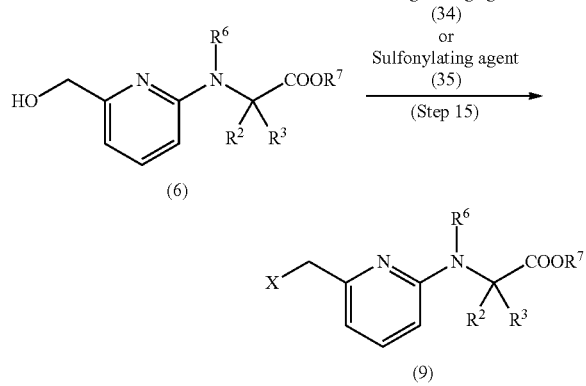

wherein $R^2$, $R^3$, $R^6$, $R^7$ and X have the same meanings as defined above.

"Step 15" is a step of preparing Compound (9) by reacting Compound (6) with a halogenating agent (34) or a sulfonylating agent (35). In this step, when the halogenating agent (34) is used, a compound wherein X is a chlorine atom, bromine atom or iodine atom in the formula (9) can be prepared, and when the sulfonylating agent (35) is used, a compound wherein X is methanesulfonyloxy group, benzenesulfonyloxy group, p-toluenesulfonyloxy group or trifluoromethane sulfonyloxy group in the formula (9) can be prepared.

In "Step 15", when a halogenating agent (34) is used, it is necessary to select reaction conditions depending on the kind of the halogenating agent (34).

The halogenating agent (34) to be used may be mentioned, for example, thionyl chloride, oxalyl chloride, phosphorus oxychloride, phosphorus pentachloride, thionyl bromide, N-chlorosuccinimide (hereinafter abbreviated to as NCS), N-bromosuccinimide (hereinafter abbreviated to as NBS), carbon tetrachloride, carbon tetrabromide or iodine, etc.

When thionyl chloride, oxalyl chloride, phosphorus oxychloride, phosphorus pentachloride or thionyl bromide is used as a halogenating agent (34), the reaction is carried out in an inert solvent.

The inert solvent to be used is not particularly limited so long as it does not inhibit the reaction and dissolves the starting materials with a certain extent, and there may be mentioned, for example, aromatic hydrocarbons such as benzene, toluene and xylene, etc.; halogenated aliphatic hydrocarbons such as methylene chloride, chloroform and 1,2-dichloroethane, etc.; ethers such as tetrahydrofuran, 1,2-dimethoxyethane and 1,4-dioxane, etc.; nitriles such as acetonitrile and propionitrile, etc.; amides such as N,N-dimethylformamide, N,N-dimethylacetamide and N-methylpyrrolidone, etc.; or a mixed solvent of optional combination thereof, etc., preferably toluene, methylene chloride, tetrahydrofuran or acetonitrile.

An amount of the halogenating agent (34) is generally 0.9 to 10-fold mol amount, preferably 1 to 1.5-fold mol amount based on 1 mol of Compound (6).

To promote the reaction, a base, for example, triethylamine, diisopropylethyl amine, imidazole, pyridine or 4-dimethyl amino pyridine, etc., may be added. An amount of the base to be used is generally 1 to 10-fold mol amount, preferably 1 to 1.5-fold mol amount based on 1 mol of Compound (6).

The reaction temperature may vary depending on a kind or amount(s), etc., of the starting materials, solvent(s), etc., and is generally −20° C. to 150° C., preferably 0° C. to 50° C.

The reaction time may vary depending on a reaction temperature, etc., and is generally 1 minute to 24 hours, and preferably 1 hour to 12 hours.

When NCS, NBS, carbon tetrachloride, carbon tetrabromide or iodine is used as a halogenating agent (34), the reaction is carried out in the presence of a phosphine compound in an inert solvent.

The inert solvent to be used is not particularly limited so long as it does not inhibit the reaction and dissolves the starting materials with a certain extent, and there may be mentioned, for example, ethers such as tetrahydrofuran, 1,2-dimethoxyethane and 1,4-dioxane, etc.; nitriles such as acetonitrile and propionitrile, etc.; amides such as N,N-dimethylformamide, N,N-dimethylacetamide and N-methylpyrrolidone, etc.; or a mixed solvent of optional combination thereof, etc., preferably tetrahydrofuran or acetonitrile.

The phosphine compound to be used may be mentioned, for example, trimethyl phosphine, triethyl phosphine, tri-n-butyl phosphine or triphenylphosphine, etc., preferably triphenylphosphine. An amount of the phosphine compound to be used is generally 0.9 to 10-fold mol amount, preferably 1 to 2-fold mol amount based on 1 mol of Compound (6).

An amount of the halogenating agent (34) is generally 0.9 to 10-fold mol amount, preferably 1 to 2-fold mol amount based on 1 mol of Compound (6). When iodine is used as a halogenating agent, to promote the reaction, a base, for example, imidazole, etc., may be added. An amount of the base to be used is generally 1 to 10-fold mol amount, preferably 1 to 2-fold mol amount based on 1 mol of Compound (6).

The reaction temperature may vary depending on a kind or amount(s), etc., of the starting materials, solvent(s), etc., and is generally 0° C. to 100° C., and preferably 0° C. to 50° C.

The reaction time may vary depending on a reaction temperature, etc., and is generally 1 minute to 24 hours, and preferably 1 hour to 12 hours.

In "Step 15", when a sulfonylating agent (35) is used, the reaction is carried out in the presence of a base in an inert solvent.

The inert solvent to be used is not particularly limited so long as it does not inhibit the reaction and dissolves the starting materials with a certain extent, and there may be mentioned, for example, aromatic hydrocarbons such as benzene, toluene and xylene, etc.; halogenated aliphatic hydrocarbons such as methylene chloride, chloroform and 1,2-dichloroethane, etc.; ethers such as tetrahydrofuran, 1,2-dimethoxyethane and 1,4-dioxane, etc.; nitriles such as acetonitrile and propionitrile, etc.; amides such as N,N-dimethylformamide, N,N-dimethylacetamide and N-methylpyrrolidone, etc.; or a mixed solvent of optional combination thereof, etc., preferably toluene, methylene chloride, tetrahydrofuran or acetonitrile.

As the base to be used, there may be mentioned, for example, organic bases such as triethylamine, diisopropylethyl amine, pyridine and 4-dimethyl amino pyridine, etc., preferably triethylamine, diisopropylethyl amine or pyridine. An amount of the base to be used is generally 0.9 to 10-fold mol amount, preferably 1 to 1.5-fold mol amount based on 1 mol of Compound (6).

The sulfonylating agent (35) to be used may be mentioned methanesulfonyl chloride, benzenesulfonyl chloride, p-toluenesulfonyl chloride or trifluoromethanesulfonic acid anhydride. An amount of the sulfonylating agent (35) to be used is generally 0.9 to 10-fold mol amount, preferably 1 to 1.5-fold mol amount based on 1 mol of Compound (6).

The reaction temperature may vary depending on a kind or amount(s), etc., of the starting materials, solvent(s), etc., and is generally −20° C. to 130° C., preferably −5° C. to 30° C.

The reaction time may vary depending on a reaction temperature, etc., and is generally 1 minute to 24 hours, preferably 1 hour to 12 hours.

[Preparation Method 16]

"Preparation Method 16" is a general method to prepare the above-mentioned Compound (14).

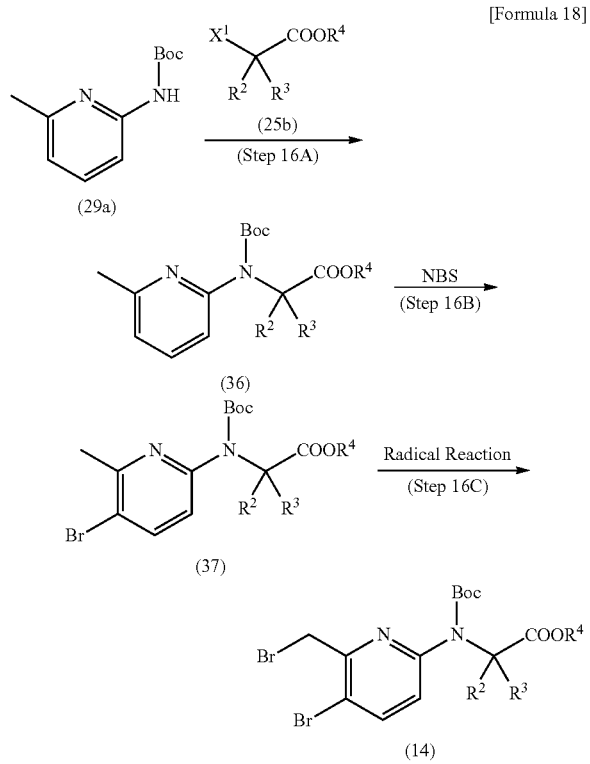

[Formula 18]

wherein $R^2$, $R^3$, $R^4$ and $X^1$ have the same meanings as defined above.

"Step 16A" is a step of preparing a substituted aminopicoline compound (36) by reacting a picoline compound (29a) and a halogenoacetic acid compound (25b) in the presence of a base in an inert solvent. This step is carried out according to the above-mentioned "Step 12B" except for using Compound (29a) in place of Compound (29), and using Compound (25b) in place of Compound (25a), respectively.

Compound (25b) is a compound wherein $R^7$ is $R^4$ in the above-mentioned Compound (25). Compound (29a) is a compound wherein $R^6$ is a Boc group in Compound (29) which can be prepared by the above-mentioned "Step 12A".

"Step 16B" is a step of preparing a bromopyridine compound (37) by treating Compound (36) with NBS in an inert solvent.

The inert solvent to be used is not particularly limited so long as it does not inhibit the reaction and dissolves the starting materials with a certain extent, and there may be mentioned, for example, aromatic hydrocarbons such as benzene and chloro benzene, etc.; halogenated aliphatic hydrocarbons such as methylene chloride, chloroform and 1,2-dichloroethane, etc.; ethers such as tetrahydrofuran, 1,2-dimethoxyethane and 1,4-dioxane, etc.; nitriles such as acetonitrile and propionitrile, etc.; amides such as N,N-dimethylformamide, N,N-dimethylacetamide and N-methylpyrrolidone, etc.; or a mixed solvent of optional combination thereof, etc., preferably acetonitrile.

An amount of the NBS to be used is generally 0.9 to 5-fold mol amount, preferably 1 to 2-fold mol amount based on 1 mol of Compound (36).

The reaction temperature may vary depending on a kind or amount(s), etc., of the starting materials, solvent(s), etc., and is generally −20° C. to 100° C., preferably 0° C. to 60° C.

The reaction time may vary depending on a reaction temperature, etc., and is generally 1 minute to 24 hours, preferably 1 hour to 12 hours.

"Step 16C" is a step of preparing Compound (14) by treating Compound (37) with NBS in the presence of a radical initiator or under photoirradiation in an inert solvent.

The inert solvent to be used is not particularly limited so long as it does not inhibit the reaction and dissolves the starting materials with a certain extent, and there may be mentioned, for example, halogenated aliphatic hydrocarbons such as methylene chloride, chloroform and 1,2-dichloroethane, etc.; or aromatic hydrocarbons such as benzene, chlorobenzene and dichlorobenzene, etc.; preferably 1,2-dichloroethane or chlorobenzene.

An amount of the NBS to be used is generally 0.9 to 5-fold mol amount, preferably 1 to 3-fold mol amount based on 1 mol of Compound (37).

As the radical initiator to be used, there may be mentioned, for example, azobisisobutyronitrile, 2,2'-azobis(2,4-dimethylvaleronitrile), 2,2'-azobis(2-methylbutyronitrile) or benzoyl peroxide, etc. An amount of the radical initiator to be used is generally 0.001 to 1-fold mol amount, preferably 0.01 to 0.5-fold mol amount based on 1 mol of Compound (37).

The reaction temperature may vary depending on a kind or amount(s), etc., of the starting materials, solvent(s), etc., and is generally 0° C. to 150° C., preferably 30° C. to 100° C.

The reaction time may vary depending on a reaction temperature, etc., and is generally 10 minutes to 12 hours, preferably 15 minutes to 6 hours.

When the reaction is carried out by generating a radical under photoirradiation, it can be carried out in accordance with the case using the radical initiator except for using a mercury lamp as a light source in place of the radical initiator.

[Preparation Method 17]

"Preparation Method 17" is another method for preparing a sulfoneamide compound (5b) wherein $Q^2$ in the group $-Q^1-Q^2$ shown by Y in the above-mentioned compound (5) is a 5,6-dihydro-4H-1,3-thiazin-2-yl group or 4,5-dihydrothiazol-2-yl group.

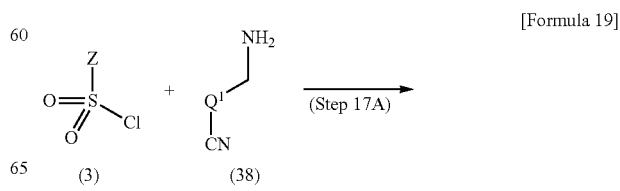

[Formula 19]

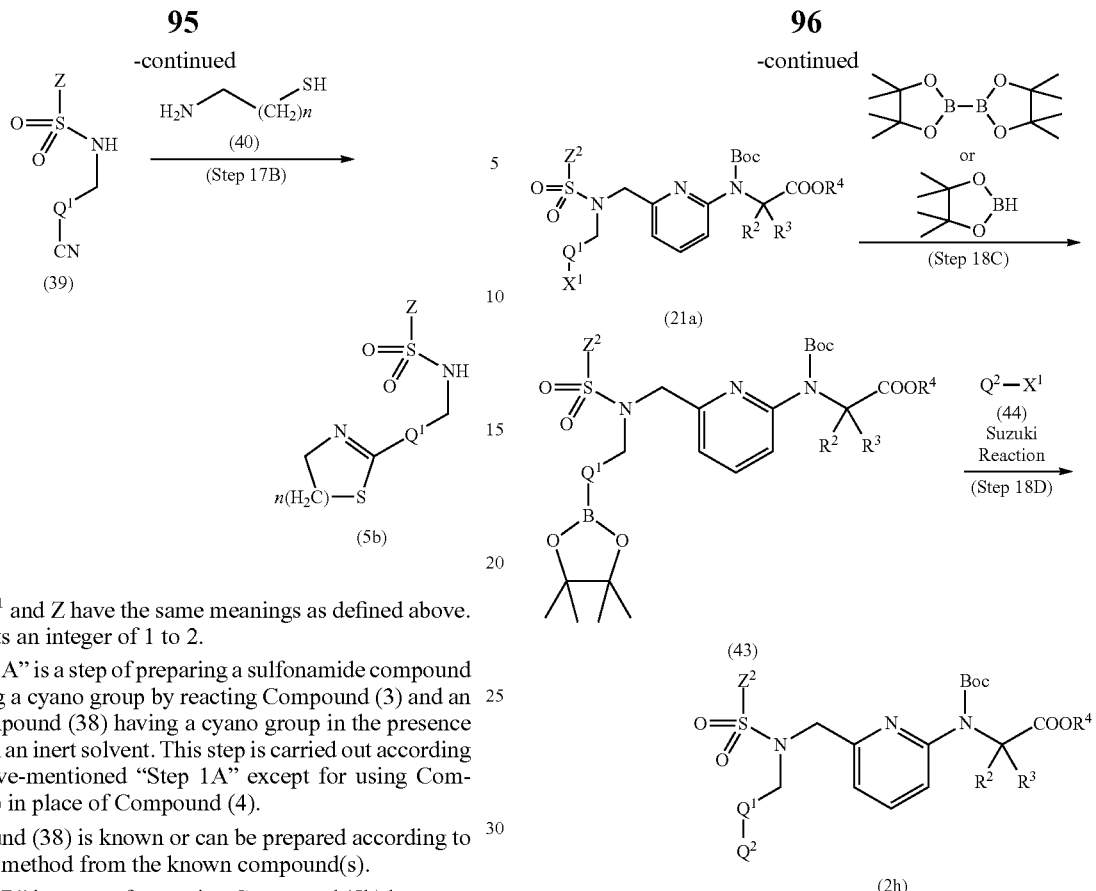

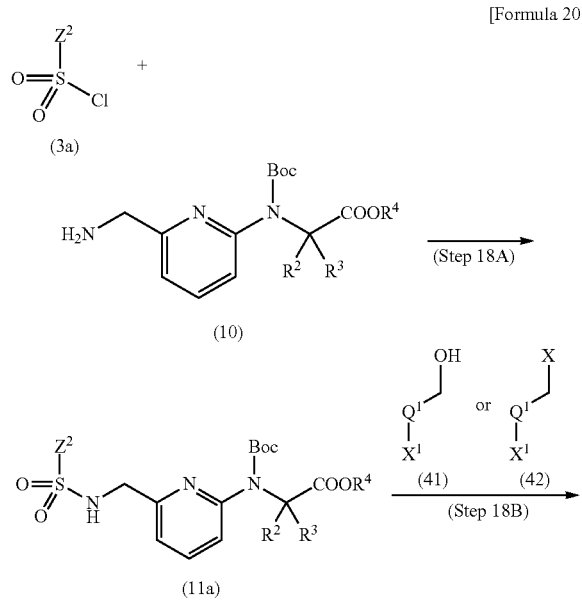

wherein $Q^1$ and Z have the same meanings as defined above. n represents an integer of 1 to 2.

"Step 17A" is a step of preparing a sulfonamide compound (39) having a cyano group by reacting Compound (3) and an amine compound (38) having a cyano group in the presence of a base in an inert solvent. This step is carried out according to the above-mentioned "Step 1A" except for using Compound (38) in place of Compound (4).

Compound (38) is known or can be prepared according to the known method from the known compound(s).

"Step 17B" is a step of preparing Compound (5b) by reacting Compound (39) and a known compound (40). This step is carried out in accordance with the known method (for example, European Journal of Medicinal Chemistry, 20, 16 (1985)).

[Preparation Method 18]

"Preparation Method 18" is another method for preparing an intermediate compound (2h) wherein $R^6$ is a Boc group and $R^7$ is $R^4$ in e above-mentioned Compound (2g).

wherein $R^2$, $R^3$, $R^4$, $Q^1$, $Q^2$, X, $X^1$ and $Z^2$ have the same meanings as defined above.

"Step 18A" is a step of preparing Compound (11a) wherein Z is $Z^2$ in the above-mentioned Compound (11) by reacting Compound (3a) and Compound (10) in the presence of or in the absence of (preferably in the presence of) a base in an inert solvent. This step is carried out according to the above-mentioned "Step 6A" except for using Compound (3a) in place of Compound (3).

"Step 18B" is a step of preparing Compound (21a) wherein $R^6$ is a Boc group and $R^7$ is $R^4$ in the above-mentioned Compound (21) by reacting Compound (11a) with Compound (41) or Compound (42).

Compound (41) and Compound (42) are known or can be prepared according to the known method from the known compound(s).

When "Step 18B" uses Compound (41), it is a so-called Mitsunobu reaction, and carried out in the presence of a phosphine compound and an azo compound in an inert solvent. This step is carried out according to the above-mentioned "Step 6B" except for using Compound (11a) in place of Compound (11), and using Compound (41) in place of Compound (12), respectively.

When "Step 18B" uses Compound (42), it is carried out in the presence of a base in an inert solvent. This step is carried out according to the above-mentioned "Step 6B" except for using Compound (11a) in place of Compound (11), and using Compound (42) in place of Compound (13), respectively.

"Step 18C" is carried out by reacting Compound (21a) and 4,4,5,5,4',4',5',5'-octamethyl-[2,2']bi([1,3,2]dioxaborolanyl) (hereinafter referred to as bis(pinacolato)diboron) or 4,4,5,5-tetramethyl-[1,3,2]dioxaborolane (hereinafter referred to as pinacolborane) in the presence of a base and a palladium catalyst in an inert gas atmosphere in an inert solvent. This step is carried out with reference to, for example, The Journal of Organic Chemistry, 60, 7508 (1995) or The Journal of Organic Chemistry, 65, 164 (2000).

The inert solvent to be used is not particularly limited so long as it does not inhibit the reaction and dissolves the starting materials, base and catalyst with a certain extent, and there may be mentioned, for example, aromatic hydrocarbons such as benzene and toluene, etc.; ethers such as tetrahydrofuran, 1,2-dimethoxyethane and 1,4-dioxane, etc.; alcohols such as methanol, ethanol, propanol and isopropanol, etc.; amides such as N,N-dimethylformamide, N,N-dimethylacetamide and N-methylpyrrolidone, etc.; sulfoxides such as dimethylsulfoxide, etc.; nitriles such as acetonitrile, etc.; water; or a mixed solvent of optional combination thereof, etc., preferably toluene, 1,4-dioxane, N,N-dimethylformamide, dimethylsulfoxide or acetonitrile.

As the inert gas to be used, there may be mentioned, for example, nitrogen, helium or argon, etc.

The palladium catalyst to be used may be mentioned, for example, an organic palladium complex such as tetrakis (triphenylphosphine) palladium, bis(triphenylphosphine) palladium chloride and 1,1'-bis(diphenylphosphino)ferrocene palladium chloride, etc., preferably 1,1'-bis (diphenylphosphino)ferrocene palladium chloride. An amount of the palladium to be used as a catalyst is generally 0.0001 to 1-fold mol amount, preferably 0.005 to 0.3-fold mol amount based on 1 mol of Compound (21a).

As the base to be used, there may be mentioned, for example, an alkali metal acetate such as sodium acetate and potassium acetate, etc.; an alkali metal carbonate such as sodium carbonate, potassium carbonate and cecium carbonate, etc.; or an organic base such as triethylamine and diisopropylethyl amine, etc., preferably sodium acetate, potassium acetate or triethylamine. An amount of the base to be used is generally 1 to 10-fold mol amount, preferably 1 to 5-fold mol amount based on 1 mol of Compound (21a).

An amount of the bis(pinacolato)diboron or pinacolborane to be used is generally 1 to 5-fold mol amount, preferably 1 to 3-fold mol amount based on 1 mol of Compound (21a).

The reaction temperature may vary depending on a kind or amount(s), etc., of the starting materials, solvent(s), etc., and is generally 0° C. to 200° C., preferably 30° C. to 150° C.

The reaction time may vary depending on a reaction temperature, etc., and is generally 10 minutes to 120 hours, preferably 1 hour to 48 hours.

"Step 18D" is a so-called Suzuki reaction, and is a step for preparing Compound (2h) by reacting Compound (43) and Compound (44) in the presence of either a base or a fluoride and a palladium catalyst under inert gas atmosphere in an inert solvent. This step is carried out according to the above-mentioned "Step 10C" except for using Compound (44) in place of Compound (21), and using Compound (43) in place of Compound (22), respectively.

Compound (44) is known or can be prepared according to the known method from the known compound(s).

The objective compound formed by the above-mentioned respective reactions can be obtained from the reaction mixture according to the conventional methods. For example, the reaction mixture is optionally neutralized, and when insoluble materials are present, after removing the same by filtration, an organic solvent which is not missible with water such as ethyl acetate, etc. is added to the mixture, the mixture is washed with water, and the organic layer containing the objective compound is separated, dried over a dryer such as anhydrous magnesium sulfate, etc., and the solvent is removed to obtain the objective compound.

The obtained objective compound can be separated and purified, if necessary, according to the conventional method, for example, by optionally combining recrystallization; reprecipitation; or a method commonly used to separate and purify an organic compound (for example, adsorption column chromatography method using a carrier such as silica gel, alumina, etc.; ion exchange chromatography method; or normal phase•reverse phase column chromatography method using silica gel or alkylated silica gel (preferably high-performance liquid chromatography)).

The compound represented by the formula (1) of the present invention can be converted into a pharmacologically acceptable salt according to the conventional method, if necessary, and it can be directly separated from the reaction mixture as a salt.

When the effective ingredient of a medical composition of the present invention is to be used as a medicine, it can be administered in the form of a tablet, capsule, powder, syrup, granule, fine particles, pill, suspension, emulsion, transdermal preparation, suppository, ointment, lotion, inhalant or injection solution, etc., orally or parenterally (intravenous administration, intramuscular administration, intraperitoneal administration, transcutaneous administration, transtracheal administration, intracutaneous administration or subcutaneous administration) prepared by mixing with an optional pharmacologically acceptable additive(s).

These preparations are prepared by commonly known methods using additives such as vehicles, lubricants, binders, disintegrators, emulsifiers, stabilizers, corrigents or diluents and the like.

The vehicles may be mentioned, for example, organic series vehicles or inorganic series vehicles. The organic series vehicles may be mentioned, for example, sugar derivatives such as lactose, sucrose, glucose, mannitol and sorbitol, etc.; starch derivatives such as corn starch, potato starch, α-starch or dextrin, etc.; cellulose derivatives such as crystalline cellulose, etc.; Gum Arabic; dextran; or pullulan, etc. The inorganic series vehicles may be mentioned, for example, light silicic anhydride; or sulfates such as calcium sulfate, etc.

The lubricant may be mentioned, for example, stearic acid; stearic acid metal salts such as calcium stearate and magnesium stearate, etc.; talc; colloidal silica; waxes such as beeswax and spermaceti, etc.; boric acid; adipic acid; sulfates such as sodium sulfate, etc.; glycol; fumaric acid; sodium benzoate; D,L-leucine; sodium lauryl sulfate; silicic acids such as silicic acid anhydride and silicic acid hydrate, etc.; or starch derivatives shown in the above-mentioned vehicles, etc.

The binder may be mentioned, for example, hydroxypropyl cellulose, hydroxypropylmethyl cellulose, polyvinylpyrrolidone, Macrogol or the compounds shown in the above-mentioned vehicles, etc.

The disintegrator may be mentioned, for example, cellulose derivatives such as low substitution degree hydroxypropyl cellulose, carboxylmethyl cellulose, calcium carboxylmethyl cellulose and internally crosslinked calcium carboxylmethyl cellulose, etc.; cross-linked polyvinyl pyrrolidone; or chemically modified starch or cellulose derivatives such as carboxylmethyl starch and sodium carboxylmethyl starch, etc.

The emulsifiers may be mentioned, for example, colloidal clays such as bentonite and bee gum; anionic surfactants such as sodium lauryl sulfate, etc.; cationic surfactants such as benzalkonium chloride, etc.; or nonionic surfactants such as polyoxyethylene alkyl ether, polyoxyethylene sorbitan fatty acid ester and sucrose fatty acid ester, etc.

The stabilizer may be mentioned, for example, para-hydroxybenzoic acid esters such as methylparaben and propylparaben, etc.; alcohols such as chlorobutanol, benzyl alcohol and phenylethyl alcohol, etc.; benzalkonium chloride; phenols such as phenol and cresol, etc; thimerosal; acetic anhydride; or sorbic acid.

The corrigent may be mentioned, for example, sweeteners such as sodium saccharin and aspartame, etc.; sour flavorings such as citric acid, malic acid and tartaric acid, etc.; or aromatics such as menthol, lemon extract and orange extract, etc.

The diluent is a compound which is usually used as a diluent, and there may be mentioned, for example, lactose, mannitol, glucose, sucrose, calcium sulfate, hydroxypropyl cellulose, microcrystalline cellulose, water, ethanol, polyethylene glycol, propylene glycol, glycerol, starch, polyvinyl pyrrolidone or mixtures thereof, etc.

When the effective ingredient of a medical composition of the present invention is used as a medicine, in addition to the above-mentioned administration forms, ophthalmic solutions can be mentioned, and it is particularly preferred for glaucoma treatment. The ophthalmic solution can be prepared by the method known to the art, and as additives, etc., an isotonic agent, buffer, pH adjuster, solubilizing agent, thickening agent, stabilizer, preservative (antiseptic), etc., may be optionally formulated. Also, by adding a pH adjuster, thickening agent, dispersant, etc., the medical component is dispersed, whereby stable ophthalmic solutions can be obtained.

As the isotonic agent, there may be mentioned, for example, glycerin, propylene glycol, sodium chloride, potassium chloride, sorbitol, mannitol, etc.

As the buffer, there may be mentioned, for example, phosphoric acid, phosphate, citric acid, acetic acid, ε-aminocaproic acid, caproic acid, etc.

As the pH adjuster, there may be mentioned, for example, hydrochloric acid, citric acid, phosphoric acid, acetic acid, sodium hydroxide, potassium hydroxide, boric acid, borax, sodium carbonate, sodium hydrogen carbonate, etc.

As the solubilizing agent, there may be mentioned, for example, Polysorbate 80, polyoxyethylene hardened castor oil 60, Macrogol 4000, etc.

As the thickening agent and dispersant, there may be mentioned, for example, cellulose series polymers such as hydroxypropylmethyl cellulose, hydroxypropyl cellulose, etc., polyvinyl alcohol, polyvinyl pyrrolidone, etc., and as the stabilizer, there may be mentioned, for example, edetic acid, disodium edetate, etc.

As the preservative (antiseptic), there may be mentioned, for example, general purpose sorbic acid, potassium sorbate, benzalkonium chloride, benzetonium chloride, methyl paraoxybenzoate, propyl paraoxybenzoate, chlorobutanol, etc., and these preservatives may be used in combination.

Ophthalmic solutions containing the effective ingredient of the medical composition according to the present invention is desirably set a pH to 4.0 to 8.5.

A dosage of the effective ingredient in a medical composition of the present invention may vary depending on a symptom, age, administration method, etc., and, for example, in the case of oral administration, it can be administered with a lower limit of 0.001 mg/Kg (preferably 0.01 mg/Kg) and an upper limit of 100 mg/Kg (preferably 10 mg/Kg) per each administration, and in the case of parenteral administration, it can be administered with a lower limit of 0.0001 mg/Kg (preferably 0.0005 mg/Kg) and an upper limit of 10 mg/Kg (preferably 5 mg/Kg) per each administration, with 1 to 6 times per day to an adult person depending on the symptoms. In the case of ophthalmic solutions, it may be eye-dropped with a concentration of preferably 0.000001 to 1% (w/v), more preferably 0.00001 to 0.1% (w/v) with one to several drops per each time once to several times (for example, 1 to 8 times) per day.

However, the administration dose may vary depending on the various conditions, so that there is a case where a less dosage than the above-mentioned administration dose may be sufficient in some cases, and there is a case where it is necessary to administer with a larger amount than the above range.

EXAMPLES

In the following, the present invention will be explained in more detail by referring to Examples and Reference examples for synthesizing the compound represented by the formula (1) which is an effective ingredient of a medical composition of the present invention and a pharmaceutically acceptable salt thereof, Test examples to show the effects of the compounds of the present invention, and Preparation examples, but the scope of the present invention is not limited by these.

Example 1

{6-[(6-Phenylpyridazin-3-ylmethyl)(pyridin-3-ylsulfonyl)aminomethyl]pyridin-2-ylamino}acetic Acid Hydrochloride (Exemplified Compound No. 1397)

1-(a) tert-Butyl({5-bromo-6-[(6-phenylpyridazin-3-ylmethyl)(pyridin-3-ylsulfonyl)aminomethyl]pyridin-2-yl}tert-butoxycarbonylamino)acetate To a solution of N-(6-phenylpyridazin-3-ylmethyl)pyridin-3-ylsulfonamide (114 mg, 0.349 mmol) obtained in Reference Example 2-(d) in N,N-dimethylformamide (1.75 ml) were added tert-butyl[(5-bromo-6-bromomethylpyridin-2-yl)tert-butoxycarbonylamino]acetate (233 mg, containing 0.35 mmol of a pure content) obtained in Reference Example 1-(c) and potassium carbonate (98.0 mg, 0.709 mmol), followed by stirring at room temperature for 20 hours. After completion of the reaction, water (5.3 ml) was added to the reaction solution, followed by extraction with ethyl acetate. The separated organic layer was washed with a saturated aqueous sodium chloride solution, dried over anhydrous sodium sulfate, and then concentrated under reduced pressure. The resulting residue was subjected to silica gel column chromatography (eluent; hexane:ethyl acetate=3:1→1:5 (V/V)), and fractions containing the desired compound were concentrated under reduced pressure to afford the title compound (242 mg) as a slightly yellow foam. (Yield: 96%)

Mass spectrum (FAB, m/z): 725 ($M^+$+1).

$^1$H-NMR spectrum (CDCl$_3$, δ ppm): 9.04 (dd, J=2.3, 0.8 Hz, 1H), 8.74 (dd, J=4.8, 1.7 Hz, 1H), 8.06-8.00 (m, 3H), 7.81 (d, J=8.8 Hz, 1H), 7.72 (d, J=8.8 Hz, 1H), 7.64-7.49 (m, 5H), 7.37 (ddd, J=8.1, 4.8, 0.8 Hz, 1H), 4.95 (s, 2H), 4.75 (s, 2H), 4.41 (s, 2H), 1.53 (s, 9H), 1.47 (s, 9H).

1-(b) tert-Butyl(tert-butoxycarbonyl{6-[(6-phenylpyridazin-3-ylmethyl)(pyridin-3-ylsulfonyl)aminomethyl]pyridin-2-yl}amino)acetate To a solution of tert-butyl({5-bromo-6-[(6-phenylpyridazin-3-ylmethyl)(pyridin-3-ylsulfonyl)aminomethyl]pyridin-2-yl}tert-butoxycarbonylamino)acetate (239 mg, 0.329 mmol) obtained in Example 1-(a) in ethanol (3.3 ml) were added triethylamine (322 μl, 2.31 mmol) and 10% palladium-active carbon (55% hydrate) (48 mg), followed by stirring at room temperature for 6 hours under hydrogen atmosphere at 1 atm. After completion of the reaction, insolubles were filtered off, and the filtrate was concentrated under reduced pressure. The resulting residue was subjected to silica gel column chromatography (eluent; hexane:ethyl acetate=1:1→1:10 (V/V)) and then to reversed phase column chromatography (column; Megabond Elut™ C18 (manufactured by Varian, Inc.), eluent; acetonitrile:water=0:1→1:0 (V/V)), and fractions containing the desired compound were concentrated under reduced pressure to afford the title compound (153 mg) as a white foam. (Yield: 72%)

Mass spectrum (FAB, m/z): 647 ($M^+$+1).

$^1$H-NMR spectrum (CDCl$_3$, δ ppm): 9.01 (dd, J=2.4, 0.8 Hz, 1H), 8.74 (dd, J=4.8, 1.7 Hz, 1H), 8.06-8.03 (m, 2H), 7.99 (ddd, J=8.1, 2.4, 1.7 Hz, 1H), 7.79 (d, J=8.8 Hz, 1H), 7.69 (d, J=8.4 Hz, 1H), 7.69 (d, J=8.8 Hz, 1H), 7.55-7.49 (m, 3H), 7.48 (dd, J=8.4, 7.3 Hz, 1H), 7.37 (ddd, J=8.1, 4.8, 0.8 Hz, 1H), 6.89 (dd, J=7.3, 0.4 Hz, 1H), 4.91 (s, 2H), 4.55 (s, 2H), 4.43 (s, 2H), 1.51 (s, 9H), 1.44 (s, 9H).

1-(c) {6-[(6-Phenylpyridazin-3-ylmethyl)(pyridin-3-ylsulfonyl)aminomethyl]pyridin-2-ylamino}acetic Acid Hydrochloride To a solution of tert-butyl(tert-butoxycarbonyl{6-[(6-phenylpyridazin-3-ylmethyl)(pyridin-3-ylsulfonyl)aminomethyl]pyridin-2-yl}amino)acetate (150 mg, 0.232 mmol) obtained in Example 1-(b) in methylene chloride (9.2 ml) was added a 4N hydrogen chloride/1,4-dioxane solution (2.3 ml), and the mixture was left at room temperature for 23 hours. After completion of the reaction, the reaction solution was concentrated under reduced pressure to afford the title compound (144 mg) substantially quantitatively as a white solid.

Rf value: 0.52 (n-butanol:acetic acid:water=3:1:1).

Mass spectrum (FAB, m/z): 491 ($M^+$+1).

$^1$H-NMR spectrum (CD$_3$OD, δ ppm): 9.28 (dd, J=2.3, 0.7 Hz, 1H), 9.01 (dd, J=5.3, 1.5 Hz, 1H), 8.70 (ddd, J=8.2, 2.3, 1.5 Hz, 1H), 8.43 (d, J=8.8 Hz, 1H), 8.11-8.06 (m, 3H), 7.98 (ddd, J=8.2, 5.3, 0.7 Hz, 1H), 7.93 (dd, J=8.8, 7.5 Hz, 1H), 7.64-7.59 (m, 3H), 7.05 (d, J=8.8 Hz, 1H), 7.01 (dd, J=7.5, 0.7 Hz, 1H), 5.13 (s, 2H), 4.83 (s, 2H), 4.41 (s, 2H).

Example 2

(6-{(Pyridin-3-ylsulfonyl)[4-(thiazol-2-yl)benzyl]aminomethyl}pyridin-2-ylamino)acetic Acid (Exemplified Compound No. 985)

2-(a) tert-Butyl[tert-butoxycarbonyl(6-{(pyridin-3-ylsulfonyl)[4-(thiazol-2-yl)benzyl]aminomethyl}pyridin-2-yl)amino]acetate To a solution of N-[4-(thiazol-2-yl)benzyl]pyridin-3-ylsulfonamide (686 mg, 2.07 mmol) obtained in Reference Example 4-(e) in tetrahydrofuran (20 ml) were added tert-butyl[tert-butoxycarbonyl(6-hydroxymethylpyridin-2-yl)amino]acetate (743 mg, 2.20 mmol) obtained in Reference Example 3-(b), tri-n-butylphosphine (980 μl, 3.92 mmol) and N,N,N',N'-tetramethylazodicarboxamide (562 mg, 3.26 mmol), followed by stirring at room temperature for 11 hours. After completion of the reaction, a saturated aqueous sodium chloride solution was added to the reaction solution, followed by extraction with ethyl acetate. The separated organic layer was washed with a saturated aqueous sodium chloride solution, dried over anhydrous magnesium sulfate, and then concentrated under reduced pressure. The resulting residue was subjected to silica gel column chromatography (eluent; hexane:ethyl acetate=95:5→50:50 (V/V)), and fractions containing the desired compound were concentrated under reduced pressure to afford the title compound (1.28 g) as a white foam. (Yield: 95%)

$^1$H-NMR spectrum (CDCl$_3$, δ ppm): 8.95 (dd, J=2.4, 0.9 Hz, 1H), 8.71 (dd, J=4.9, 1.6 Hz, 1H), 7.90-7.85 (m, 3H), 7.87 (d, J=3.2 Hz, 1H), 7.71 (d, J=8.4 Hz, 1H), 7.51 (dd, J=8.4, 7.4 Hz, 1H), 7.34-7.30 (m, 3H), 7.34 (d, J=3.2 Hz, 1H), 6.85 (d, J=7.4 Hz, 1H), 4.63 (s, 2H), 4.40 (s, 2H), 4.35 (s, 2H), 1.52 (s, 9H), 1.42 (s, 9H).

2-(b) (6-{(Pyridin-3-ylsulfonyl)[4-(thiazol-2-yl)benzyl]aminomethyl}pyridin-2-ylamino)acetic Acid Hydrochloride To a solution of tert-butyl[tert-butoxycarbonyl(6-{(pyridin-3-ylsulfonyl)[4-(thiazol-2-yl)benzyl]aminomethyl}pyridin-2-yl)amino]acetate (1.28 g, 1.96 mmol) obtained in Example 2-(a) in 1,4-dioxane (30 ml) was added a 4N hydrogen chloride/-1,4-dioxane solution (20 ml), followed by stirring at room temperature for 14 hours. After completion of the reaction, the reaction solution was concentrated under reduced pressure, and methylene chloride was added to the resulting residue, followed by sonication. A precipitated solid was collected by filtration, and the resulting solid was washed with methylene chloride, followed by drying under reduced pressure at 60° C. to afford a crude product (1.66 g) containing the title compound substantially quantitatively as a white solid.

$^1$H-NMR spectrum (CD$_3$OD, δ ppm): 9.31 (d, J=2.0 Hz, 1H), 9.03 (dd, J=5.3, 1.5 Hz, 1H), 8.75 (ddd, J=8.2, 2.0, 1.5 Hz, 1H), 8.04 (d, J=3.5 Hz, 1H), 8.04-8.00 (m, 1H), 7.85-7.82 (m, 2H), 7.83 (d, J=3.5 Hz, 1H), 7.73 (dd, J=9.0, 7.4 Hz, 1H), 7.48-7.44 (m, 2H), 6.82 (d, J=9.0 Hz, 1H), 6.78 (d, J=7.4 Hz, 1H), 4.69 (s, 2H), 4.64 (s, 2H), 4.08 (s, 2H).

2-(c) (6-{(Pyridin-3-ylsulfonyl)[4-(thiazol-2-yl)benzyl]aminomethyl}pyridin-2-ylamino)acetic Acid A solution of (6-{(pyridin-3-ylsulfonyl)[4-(thiazol-2-yl)benzyl]aminomethyl}-pyridin-2-ylamino)acetic acid hydrochloride (1.61 g) (containing 1.90 mmol of the title compound of a pure content) obtained in Example 2-(b) in tetrahydrofuran (10 ml) was homogeneously dissolved with a 1N aqueous sodium hydroxide solution (12 ml). Water (40 ml) was then added, followed by adjustment to pH 6.4 with 1N hydrochloric acid, and a precipitated solid was collected by filtration. The resulting solid was washed with water, and then dried under reduced pressure at 60° C. to afford the title compound (854 mg) as a white solid. (Yield: 91%)

Rf value: 0.55 (n-butanol:acetic acid:water=3:1:1).

Mass spectrum (FAB, m/z): 496 ($M^+$+1).

$^1$H-NMR spectrum (DMSO-d$_6$, δ ppm): 12.42 (brs, 0.6H), 8.84 (dd, J=2.4, 0.6 Hz, 1H), 8.72 (dd, J=4.8, 1.6 Hz, 1H), 8.04 (ddd, J=8.1, 2.4, 1.6 Hz, 1H), 7.93 (d, J=3.2 Hz, 1H), 7.93-7.89 (m, 2H), 7.79 (d, J=3.2 Hz, 1H), 7.48 (ddd, J=8.1, 4.8, 0.6 Hz, 1H), 7.43-7.39 (m, 2H), 7.23 (dd, J=8.3, 7.2 Hz, 1H), 6.76 (t, J=5.6 Hz, 0.9H), 6.36 (d, J=8.3 Hz, 1H), 6.33 (d, J=7.2 Hz, 1H), 4.71 (s, 2H), 4.21 (s, 2H), 3.71 (d, J=5.6 Hz, 2H).

Example 3

6-{(Pyridin-2-ylsulfonyl)[4-(thiazol-2-yl)benzyl]aminomethyl}pyridin-2-ylamino)acetic Acid (Exemplified Compound No. 977)

3-(a) tert-Butyl[tert-butoxycarbonyl(6-{(pyridin-2-ylsulfonyl)[4-(thiazol-2-yl)benzyl]aminomethyl}pyridin-2-yl)amino]acetate Reaction and post-treatment were carried out in the same manner as in Example 2-(a) except for using tert-butyl[tertbutoxycarbonyl(6-hydroxymethylpyridin-2-yl)amino]acetate (279 mg, 0.824 mmol) obtained in Reference Example 3-(b), and using N-[4-(thiazol-2-yl)benzyl]pyridin-2-ylsulfonamide (275 mg, 0.830 mmol) obtained in Reference Example 5 in place of N-[4-(thiazol-2-yl)benzyl]pyridin-3-ylsulfonamide to afford the title compound (496 mg) as a white foam. (Yield: 92%) Mass spectrum (FAB, m/z): 652 ($M^+$+1).

$^1$H-NMR spectrum (CDCl$_3$, δ ppm): 8.60 (ddd, J=4.7, 1.7, 0.9 Hz, 1H), 7.85 (d, J=3.1 Hz, 1H), 7.85-7.81 (m, 3H), 7.77 (ddd, J=7.7, 7.6, 1.7 Hz, 1H), 7.65 (d, J=8.3 Hz, 1H), 7.45 (dd, J=8.3, 7.3 Hz, 1H), 7.39 (ddd, J=7.6, 4.7, 1.3 Hz, 1H), 7.34-7.30 (m, 2H), 7.32 (d, J=3.1 Hz, 1H), 6.91 (dd, J=7.3, 0.4 Hz, 1H), 4.75 (s, 2H), 4.49 (s, 2H), 4.45 (s, 2H), 1.52 (s, 9H), 1.42 (s, 9H).

3-(b) (6-{(Pyridin-2-ylsulfonyl)[4-(thiazol-2-yl)benzyl]aminomethyl}pyridin-2-ylamino)acetic Acid Reaction was carried out in the same manner as in Example 1-(c) except for using tert-butyl[tert-butoxycarbonyl(6-{(pyridin-2-ylsulfonyl)[4-(thiazol-2-yl)benzyl]aminomethyl}pyridin-2-yl)amino]acetate (490 mg, 0.752 mmol) obtained in Example 3-(a) in place of tert-butyl(tert-butoxycarbonyl{6-[(6-phenylpyridazin-3-ylmethyl)(pyridin-3-ylsulfonyl)aminomethyl]pyridin-2-yl}amino)acetate. After completion of the reaction, the reaction solution was concentrated under reduced pressure, and tetrahydrofuran (10 ml), water (20 ml) and a 1N aqueous sodium hydroxide solution were added to the residue to adjust a pH to 12.0, and subsequently insolubles were filtered off. 1N Hydrochloric acid was added to the filtrate to adjust the pH to 4.5, and a precipitated solid was collected by filtration. The resulting solid was washed with water, and dried under reduced pressure at 50° C. to afford the title compound (147 mg) as a white solid. (Yield: 39%)

Rf value: 0.53 (n-butanol:acetic acid:water=3:1:1).
Mass spectrum (FAB, m/z): 496 ($M^+$+1).
$^1$H-NMR spectrum (DMSO-d$_6$, δ ppm): 12.40 (brs, 0.7H), 8.65 (ddd, J=4.6, 1.7, 0.9 Hz, 1H), 7.96 (ddd, J=7.8, 7.7, 1.7 Hz, 1H), 7.92 (d, J=3.2 Hz, 1H), 7.88-7.84 (m, 2H), 7.81 (ddd, J=7.8, 1.0, 0.9 Hz, 1H), 7.78 (d, J=3.2 Hz, 1H), 7.58 (ddd, J=7.7, 4.6, 1.0 Hz, 1H), 7.39-7.36 (m, 2H), 7.19 (dd, J=8.2, 7.1 Hz, 1H), 6.75 (t, J=5.6 Hz, 0.9H), 6.34 (d, J=8.2 Hz, 1H), 6.29 (d, J=7.1 Hz, 1H), 4.75 (s, 2H), 4.25 (s, 2H), 3.82 (d, J=5.6 Hz, 2H).

Example 4

(6-{(4-Fluorobenzenesulfonyl)[4-(thiazol-2-yl)benzyl]aminomethyl}pyridin-2-ylamino)acetic Acid (Exemplified Compound No. 936)

4-(a) tert-Butyl[tert-butoxycarbonyl(6-{(4-fluorobenzenesulfonyl)[4-(thiazol-2-yl)benzyl]aminomethyl}pyridin-2-yl)amino]acetate Reaction and post-treatment were carried out in the same manner as in Example 2-(a) except for using tert-butyl([tert-butoxycarbonyl(6-hydroxymethylpyridin-2-yl)amino]acetate (101 mg, 0.298 mmol) obtained in Reference Example 3-(b), and using 4-fluoro-N-[4-(thiazol-2-yl)benzyl]benzenesulfonamide (105 mg, 0.301 mmol) obtained in Reference Example 6 in place of N-[4-(thiazol-2-yl)benzyl]pyridin-3-ylsulfonamide to afford the title compound (181 mg) as a white foam. (Yield: 91%) Mass spectrum (FAB, m/z): 669 ($M^+$+1).

$^1$H-NMR spectrum (CDCl$_3$, δ ppm): 7.88-7.85 (m, 3H), 7.73-7.68 (m, 3H), 7.50 (dd, J=8.3, 7.4 Hz, 1H), 7.33 (d, J=3.3 Hz, 1H), 7.31-7.27 (m, 2H), 7.12-7.07 (m, 2H), 6.85 (d, J=7.4 Hz, 1H), 4.56 (s, 2H), 4.38 (s, 2H), 4.36 (s, 2H), 1.52 (s, 9H), 1.41 (s, 9H).

4-(b) (6-{(4-Fluorobenzenesulfonyl)[4-(thiazol-2-yl)benzyl]aminomethyl}pyridin-2-ylamino)acetic Acid Hydrochloride Reaction and post-treatment were carried out in the same manner as in Example 1-(c) except for using tert-butyl[tert-butoxycarbonyl(6-{(4-fluorobenzenesulfonyl)[4-(thiazol-2-yl)benzyl]aminomethyl}pyridin-2-yl)amino]acetate (175 mg, 0.261 mmol) obtained in Example 4-(a) in place of tert-butyl(tert-butoxycarbonyl{6-[(6-phenylpyridazin-3-ylmethyl)(pyridin-3-ylsulfonyl)aminomethyl]pyridin-2-yl}-amino)acetate to afford the title compound (151 mg) substantially quantitatively as a white solid.

$^1$H-NMR spectrum (CD$_3$OD, δ ppm): 8.07-8.02 (m, 2H), 7.95 (d, J=3.5 Hz, 1H), 7.81-7.77 (m, 2H), 7.72 (d, J=3.5 Hz, 1H), 7.69 (dd, J=8.9, 7.4 Hz, 1H), 7.45-7.40 (m, 2H), 7.40-7.36 (m, 2H), 6.79 (d, J=8.9 Hz, 1H), 6.69 (d, J=7.4 Hz, 1H), 4.51 (s, 2H), 4.48 (s, 2H), 4.04 (s, 2H).

4-(c) (6-{(4-Fluorobenzenesulfonyl)[4-(thiazol-2-yl)benzyl]aminomethyl}pyridin-2-ylamino)acetic Acid Reaction and post-treatment were carried out in the same manner as in Example 2-(c) except for using (6-{(4-fluorobenzenesulfonyl)[4-(thiazol-2-yl)benzyl]-aminomethyl}pyridin-2-ylamino)acetic acid hydrochloride (148 mg, 0.248 mmol) obtained in Example 4-(b) in place of (6-{(pyridin-3-ylsulfonyl)[4-(thiazol-2-yl)benzyl]aminomethyl}pyridin-2-ylamino)acetic acid hydrochloride to afford the title compound (122 mg) as a pale brown solid. (Yield: 95%)

Rf value: 0.66 (n-butanol:acetic acid:water=3:1:1).
Mass spectrum (FAB, m/z): 513 ($M^+$+1).
$^1$H-NMR spectrum (DMSO-d$_6$, δ ppm): 7.92 (d, J=3.3 Hz, 1H), 7.91-7.88 (m, 2H), 7.79-7.74 (m, 2H), 7.79 (d, J=3.3 Hz, 1H), 7.40-7.37 (m, 2H), 7.32-7.26 (m, 2H), 7.23 (dd, J=8.3, 7.2 Hz, 1H), 6.77 (t, J=5.5 Hz, 0.9H), 6.37 (d, J=8.3 Hz, 1H), 6.30 (d, J=7.2 Hz, 1H), 4.64 (s, 2H), 4.16 (s, 2H), 3.75 (d, J=5.5 Hz, 2H).

Example 5

(6-{[4-(4,5-Dihydrothiazol-2-yl)benzyl](4-fluorobenzenesulfonyl)aminomethyl}-pyridin-2-ylamino)acetic Acid (Exemplified Compound No. 1326)

5-(a) tert-Butyl[tert-butoxycarbonyl(6-{[4-(4,5-dihydrothiazol-2-yl)benzyl](4-fluorobenzenesulfonyl)aminomethyl}pyridin-2-yl)amino]acetate Reaction and post-treatment were carried out in the same manner as in Example 2-(a) except for using tert-butyl[tert-butoxycarbonyl(6-hydroxymethylpyridin-2-yl)amino]acetate (217 mg, 0.641 mmol) obtained in Reference Example 3-(b), and using N-[4-(4,5-dihydrothiazol-2-yl)benzyl]-4-fluorobenzenesulfonamide (225 mg, 0.641 mmol) obtained in Reference Example 7-(b) in place of N-[4-(thiazol-2-yl)benzyl]pyridin-3-ylsulfonamide to afford the title compound (404 mg) as a colorless oil. (Yield: 94%)

Mass spectrum (FAB, m/z): 671 (M$^+$+1).

$^1$H-NMR spectrum (CDCl$_3$, δ ppm): 7.75-7.66 (m, 5H), 7.50 (dd, J=8.3, 7.4 Hz, 1H), 7.27-7.23 (m, 2H), 7.12-7.06 (m, 2H), 6.83 (d, J=7.4 Hz, 1H), 4.55 (s, 2H), 4.45 (t, J=8.3 Hz, 2H), 4.37 (s, 2H), 4.33 (s, 2H), 3.42 (t, J=8.3 Hz, 2H), 1.52 (s, 9H), 1.41 (s, 9H).

5-(b) (6-{[4-(4,5-Dihydrothiazol-2-yl)benzyl](4-fluorobenzenesulfonyl)aminomethyl}-pyridin-2-ylamino)acetic Acid Reaction and post-treatment were carried out in the same manner as in with Example 3-(b) except for using tert-butyl [tert-butoxycarbonyl(6-{[4-(4,5-dihydrothiazol-2-yl)benzyl](4-fluorobenzenesulfonyl)aminomethyl}pyridin-2-yl) amino]acetate (202 mg, 0.301 mmol) obtained in Example 5-(a) in place of tert-butyl(tert-butoxycarbonyl{6-[(pyridin-2-ylsulfonyl)(4-thiazol-2-yl)benzyl]aminomethyl}pyridin-2-ylamino)acetate to afford the title compound (138 mg) as a white solid. (Yield: 89%)

Rf value: 0.54 (n-butanol:acetic acid:water=3:1:1).

Mass spectrum (FAB, m/z): 515 (M$^+$+1).

$^1$H-NMR spectrum (DMSO-d$_6$, δ ppm): 12.41 (brs, 0.4H), 7.78-7.73 (m, 2H), 7.73-7.70 (m, 2H), 7.37-7.34 (m, 2H), 7.31-7.26 (m, 2H), 7.22 (dd, J=8.4, 7.1 Hz, 1H), 6.78 (t, J=5.8 Hz, 0.9H), 6.37 (dd, J=8.4, 0.6 Hz, 1H), 6.29 (dd, J=7.1, 0.6 Hz, 1H), 4.64 (s, 2H), 4.39 (t, J=8.3 Hz, 2H), 4.14 (s, 2H), 3.75 (d, J=5.8 Hz, 2H), 3.44 (t, J=8.3 Hz, 2H).

Example 6

{6-[(Biphenyl-4-ylmethyl)(pyridin-3-ylsulfonyl) aminomethyl]pyridin-2-ylamino}acetic Acid Hydrochloride (Exemplified Compound No. 546)

6-(a) tert-Butyl({6-[(biphenyl-4-ylmethyl)(pyridin-3-ylsulfonyl)aminomethyl]pyridin-2-yl}tert-butoxycarbonylamino)acetate Reaction and post-treatment were carried out in the same manner as in Example 2-(a) except for using tert-butyl[tert-butoxycarbonyl(6-hydroxymethylpyridin-2-yl)amino]acetate (523 mg, 1.55 mmol) obtained in Reference Example 3-(b), and using N-(biphenyl-4-ylmethyl)pyridin-3-ylsulfonamide (501 mg, 1.54 mmol) obtained in Reference Example 8 in place of N-[4-(thiazol-2-yl)benzyl]pyridin-3-ylsulfonamide to afford the title compound (934 mg) as a white foam. (Yield: 94%) Mass spectrum (FAB, m/z): 645 (M$^+$+1).

$^1$H-NMR spectrum (CDCl$_3$, δ ppm): 8.96 (dd, J=2.3, 0.7 Hz, 1H), 8.71 (dd, J=4.9, 1.7 Hz, 1H), 7.87 (ddd, J=8.0, 2.3, 1.7 Hz, 1H), 7.71 (d, J=8.4 Hz, 1H), 7.57-7.54 (m, 2H), 7.52 (dd, J=8.4, 7.4 Hz, 1H), 7.51-7.48 (m, 2H), 7.46-7.41 (m, 2H), 7.37-7.33 (m, 1H), 7.33-7.28 (m, 3H), 6.87 (d, J=7.4 Hz, 1H), 4.62 (s, 2H), 4.42 (s, 2H), 4.38 (s, 2H), 1.52 (s, 9H), 1.42 (s, 9H).

6-(b) {6-[(Biphenyl-4-ylmethyl)(pyridin-3-ylsulfonyl)aminomethyl]pyridin-2-ylamino}Acetic Acid Hydrochloride To a solution of tert-butyl({6-[(biphenyl-4-ylmethyl)(pyridin-3-ylsulfonyl)aminomethyl]pyridin-2-yl}tert-butoxycarbonylamino)acetate (931 mg, 1.44 mmol) obtained in Example 6-(a) in methylene chloride (14.4 ml) was added a 4N hydrogen chloride/1,4-dioxane solution (7.2 ml), and the mixture was left at room temperature for 16 hours. Further, it was stirred at 50° C. for 2 hours. After completion of the reaction, the reaction solution was concentrated under reduced pressure, followed by addition of methylene chloride to the residue, and a precipitated solid was collected by filtration. The resulting solid was dried under reduced pressure at room temperature to afford the title compound (760 mg) as a white solid. (Yield: 94%)

Rf value: 0.62 (n-butanol:acetic acid:water=3:1:1).

Mass spectrum (FAB, m/z): 489 (M$^+$+1).

$^1$H-NMR spectrum (CD$_3$OD, δ ppm): 9.26 (dd, J=2.3, 0.8 Hz, 1H), 8.99 (dd, J=5.2, 1.5 Hz, 1H), 8.65 (ddd, J=8.1, 2.3, 1.5 Hz, 1H), 7.94 (ddd, J=8.1, 5.2, 0.8 Hz, 1H), 7.72 (dd, J=8.9, 7.3 Hz, 1H), 7.54-7.51 (m, 2H), 7.48-7.40 (m, 4H), 7.36-7.29 (m, 3H), 6.80 (d, J=8.9 Hz, 1H), 6.74 (d, J=7.3 Hz, 1H), 4.63 (s, 2H), 4.56 (s, 2H), 3.99 (s, 2H).

Example 7

(6-{[4-(Pyrazol-1-yl)benzyl](pyridin-3-ylsulfonyl) aminomethyl}pyridin-2-ylamino)acetic Acid Hydrochloride (Exemplified Compound No. 880)

7-(a) tert-Butyl[tert-butoxycarbonyl(6-{[4-(pyrazol-1-yl)benzyl](pyridin-3-ylsulfonyl) aminomethyl}pyridin-2-yl)amino]acetate Reaction and post-treatment were carried out in the same manner as in Example 2-(a) except for using tert-butyl[tert-butoxycarbonyl(6-hydroxymethylpyridin-2-yl)amino]acetate (143 mg, 0.423 mmol) obtained in Reference Example 3-(b), and using N-[4-(pyrazol-1-yl)benzyl]pyridin-3-ylsulfonamide (133 mg, 0.423 mmol) obtained in Reference Example 9-(b) in place of N-[4-(thiazol-2-yl)benzyl]pyridin-3-ylsulfonamide to afford the title compound (247 mg) as a white foam. (Yield: 92%) Mass spectrum (FAB, m/z): 635 (M$^+$+1).

$^1$H-NMR spectrum (CDCl$_3$, δ ppm): 8.95 (dd, J=2.3, 0.7 Hz, 1H), 8.71 (dd, J=4.9, 1.6 Hz, 1H), 7.91 (dd, J=2.5, 0.6 Hz, 1H), 7.87 (ddd, J=8.0, 2.3, 1.6 Hz, 1H), 7.72 (d, J=1.8, 0.6 Hz, 1H), 7.71 (d, J=8.4 Hz, 1H), 7.63-7.60 (m, 2H), 7.51 (dd, J=8.4, 7.3 Hz, 1H), 7.35-7.30 (m, 3H), 6.85 (d, J=7.3 Hz, 1H), 6.47 (dd, J=2.5, 1.8 Hz, 1H), 4.61 (s, 2H), 4.39 (s, 2H), 4.35 (s, 2H), 1.53 (s, 9H), 1.42 (s, 9H).

7-(b) (6-{[4-(Pyrazol-1-yl)benzyl](pyridin-3-ylsulfonyl)aminomethyl}pyridin-2-ylamino)acetic Acid Hydrochloride Reaction and post-treatment were carried out in the same manner as in Example 2-(b) except for using tert-butyl[tert-butoxycarbonyl(6-{[4-(pyrazol-1-yl)benzyl](pyridin-3-ylsulfonyl)aminomethyl}pyridin-2-yl)amino]acetate (240 mg, 0.378 mmol) obtained in Example 7-(a) in place of tert-butyl [tert-butoxycarbonyl(6-{(pyridin-3-ylsulfonyl)[4-(thiazol-2-yl)benzyl]aminomethyl}pyridin-2-yl)amino]acetate to afford the title compound (161 mg) as a white solid. (Yield: 72%)

Rf value: 0.52 (n-butanol:acetic acid:water=3:1:1).

Mass spectrum (FAB, m/z): 479 (M$^+$+1).

$^1$H-NMR spectrum (CD$_3$OD, δ ppm): 9.29 (d, J=2.1 Hz, 1H), 9.01 (dd, J=5.3, 1.5 Hz, 1H), 8.70 (ddd, J=8.2, 2.1, 1.5 Hz, 1H), 8.17 (d, J=2.5 Hz, 1H), 7.98 (ddd, J=8.2, 5.3, 0.6 Hz, 1H), 7.75-7.70 (m, 2H), 7.61-7.57 (m, 2H), 7.39-7.36 (m, 2H), 6.80 (d, J=9.0 Hz, 1H), 6.75 (d, J=7.2 Hz, 1H), 6.52 (dd, J=2.5, 1.8 Hz, 1H), 4.65 (s, 2H), 4.57 (s, 2H), 4.03 (s, 2H).

Example 8

{6-[(Benzofuran-2-ylmethyl)(pyridin-3-ylsulfonyl) aminomethyl]pyridin-2-ylamino}-acetic Acid Hydrochloride (Exemplified Compound No. 28)

8-(a) tert-Butyl({6-[(benzofuran-2-ylmethyl)(pyridin-3-ylsulfonyl)aminomethyl]-pyridin-2-yl}tert-butoxycarbonylamino)acetate Reaction and post-treatment were carried out in the same manner as in Example 2-(a) except for using tert-butyl[tert-butoxycarbonyl(6-hydroxymethylpyridin-2-yl)amino]acetate (252 mg, 0.745 mmol) obtained in Reference Example 3-(b), and using N-(benzofuran-2-ylmethyl)pyridin-3-ylsulfonamide (215 mg, 0.747 mmol) obtained in Reference Example 10-(c) in place of N-[4-(thiazol-2-yl)benzyl]pyridin-3-ylsulfonamide to afford the title compound (397 mg) as a white foam. (Yield: 88%) Mass spectrum (FAB, m/z): 609 ($M^+$+1).
$^1$H-NMR spectrum (CDCl$_3$, δ ppm): 9.04 (d, J=2.0 Hz, 1H), 8.66 (dd, J=4.9, 1.7 Hz, 1H), 7.96 (ddd, J=8.1, 2.0, 1.7 Hz, 1H), 7.79 (d, J=8.3 Hz, 1H), 7.62 (dd, J=8.3, 7.4 Hz, 1H), 7.48-7.44 (m, 1H), 7.26-7.16 (m, 4H), 7.09 (d, J=7.4 Hz, 1H), 6.55 (s, 1H), 4.69 (s, 2H), 4.51 (s, 2H), 4.50 (s, 2H), 1.53 (s, 9H), 1.42 (s, 9H).

8-(b) {6-[(Benzofuran-2-ylmethyl)(pyridin-3-ylsulfonyl)aminomethyl]pyridin-2-ylamino}Acetic Acid Hydrochloride Reaction and post-treatment were carried out in the same manner as in Example 2-(b) except for using tert-butyl({6-[(benzofuran-2-ylmethyl)(pyridin-3-ylsulfonyl)aminomethyl]pyridin-2-yl}tert-butoxycarbonylamino)acetate (201 mg, 0.330 mmol) obtained in Example 8-(a) in place of tert-butyl[tert-butoxycarbonyl(6-{(pyridin-3-ylsulfonyl)[4-(thiazol-2-yl)benzyl]aminomethyl}pyridin-2-yl)amino]acetate to afford the title compound (134 mg) as a white solid. (Yield: 77%)
Rf value: 0.59 (n-butanol:acetic acid:water=3:1:1).
Mass spectrum (FAB, m/z): 453 ($M^+$+1).
$^1$H-NMR spectrum (CD$_3$OD, δ ppm): 9.28 (dd, J=2.3, 0.5 Hz, 1H), 8.89 (dd, J=5.3, 1.4 Hz, 1H), 8.70 (ddd, J=8.2, 2.3, 1.4 Hz, 1H), 7.90 (ddd, J=8.2, 5.3, 0.5 Hz, 1H), 7.78 (dd, J=9.0, 7.2 Hz, 1H), 7.47-7.44 (m, 1H), 7.27-7.22 (m, 2H), 7.21-7.15 (m, 1H), 6.88 (d, J=7.2 Hz, 1H), 6.82 (d, J=9.0 Hz, 1H), 6.73 (s, 1H), 4.77 (s, 2H), 4.76 (s, 2H), 4.12 (s, 2H).

Example 9

{6-[(4'-Fluorobiphenyl-4-ylmethyl)(pyridin-3-ylsulfonyl)aminomethyl]pyridin-2-ylamino}acetic Acid Hydrochloride (Exemplified Compound No. 605)

9-(a) tert-Butyl({6-[(4-bromobenzyl)(pyridin-3-ylsulfonyl)aminomethyl]pyridin-2-yl}tert-butoxycarbonylamino)acetate Reaction and post-treatment were carried out in the same manner as in Example 2-(a) except for using tert-butyl[tert-butoxycarbonyl(6-hydroxymethylpyridin-2-yl)amino]acetate (428 mg, 1.26 mmol) obtained in Reference Example 3-(b), and using N-(4-bromobenzyl)pyridin-3-ylsulfonamide (414 mg, 1.26 mmol) obtained in Reference Example 11 in place of N-[4-(thiazol-2-yl)benzyl]pyridin-3-ylsulfonamide to afford the title compound (797 mg) as a white solid. (Yield: 98%)
$^1$H-NMR spectrum (CDCl$_3$, δ ppm): 8.93 (dd, J=2.4, 0.8 Hz, 1H), 8.71 (dd, J=4.8, 1.6 Hz, 1H), 7.85 (ddd, J=8.0, 2.4, 1.6 Hz, 1H), 7.71 (d, J=8.3 Hz, 1H), 7.51 (dd, J=8.3, 7.3 Hz, 1H), 7.42-7.39 (m, 2H), 7.31 (ddd, J=8.0, 4.8, 0.8 Hz, 1H), 7.14-7.10 (m, 2H), 6.82 (dd, J=7.3, 0.4 Hz, 1H), 4.53 (s, 2H), 4.35 (s, 2H), 4.33 (s, 2H), 1.53 (s, 9H), 1.42 (s, 9H).

9-(b) tert-Butyl(tert-butoxycarbonyl{6-[(4'-fluorobiphenyl-4-ylmethyl)(pyridin-3-ylsulfonyl)aminomethyl]pyridin-2-yl}amino)acetate To a solution of tert-butyl({6-[(4-bromobenzyl)(pyridin-3-ylsulfonyl)aminomethyl]pyridin-2-yl}tert-butoxycarbonylamino)acetate (185 mg, 0.285 mmol) obtained in Example 9-(a) in toluene (2 ml) were added 4-fluorophenylboronic acid (61.3 mg, 0.438 mmol), palladium acetate (4.9 mg, 0.044 mmol), tripotassium phosphate (202 mg, 0.953 mmol) and water (0.2 ml), followed by being subjected to argon atmosphere. Then a 20% solution of tricyclohexylphosphine in toluene (130 μl, 0.088 mmol) was added to the mixture, and it was stirred at 100° C. for 2.5 hours under argon atmosphere. After completion of the reaction, a saturated aqueous sodium chloride solution was added to the reaction solution, followed by extraction with ethyl acetate. The separated organic layer was dried over anhydrous magnesium sulfate, and then concentrated under reduced pressure. The resulting residue was subjected to silica gel column chromatography (eluent; hexane:ethyl acetate=9:1→7:3 (V/V)), and fractions containing the desired compound were concentrated under reduced pressure to afford the title compound (178 mg) as a white foam. (Yield: 94%)
$^1$H-NMR spectrum (CDCl$_3$, δ ppm): 8.96 (dd, J=2.4, 0.8 Hz, 1H), 8.71 (dd, J=4.8, 1.7 Hz, 1H), 7.88 (ddd, J=8.1, 2.4, 1.7 Hz, 1H), 7.71 (d, J=8.1 Hz, 1H), 7.53-7.49 (m, 3H), 7.46-7.43 (m, 2H), 7.31 (ddd, J=8.1, 4.8, 0.8 Hz, 1H), 7.31-7.28 (m, 2H), 7.15-7.10 (m, 2H), 6.86 (dd, J=7.3, 0.6 Hz, 1H), 4.62 (s, 2H), 4.41 (s, 2H), 4.37 (s, 2H), 1.52 (s, 9H), 1.42 (s, 9H).

9-(c) {6-[(4'-Fluorobiphenyl-4-ylmethyl)(pyridin-3-ylsulfonyl)aminomethyl]pyridin-2-ylamino}acetic Acid Hydrochloride Reaction and post-treatment were carried out in the same manner as in Example 2-(b) except for using tert-butyl(tert-butoxycarbonyl{6-[(4'-fluorobiphenyl-4-ylmethyl)(pyridin-3-ylsulfonyl)aminomethyl]pyridin-2-yl}amino)acetate (173 mg, 0.261 mmol) obtained in Example 9-(b) in place of tert-butyl[tert-butoxycarbonyl(6-{(pyridin-3-ylsulfonyl)[4-(thiazol-2-yl)benzyl]aminomethyl}pyridin-2-yl)amino]acetate to afford the title compound (134 mg) as a white solid. (Yield: 89%)
Rf value: 0.62 (n-butanol:acetic acid:water=3:1:1).
Mass spectrum (FAB, m/z): 507 ($M^+$+1).
$^1$H-NMR spectrum (CD$_3$OD, δ ppm): 9.29 (dd, J=2.2, 0.7 Hz, 1H), 9.01 (dd, J=5.3, 1.5 Hz, 1H), 8.69 (ddd, J=8.2, 2.2, 1.5 Hz, 1H), 7.98 (ddd, J=8.2, 5.3, 0.7 Hz, 1H), 7.72 (dd, J=9.0, 7.3 Hz, 1H), 7.57-7.53 (m, 2H), 7.46-7.42 (m, 2H), 7.33-7.30 (m, 2H), 7.18-7.13 (m, 2H), 6.82 (d, J=9.0 Hz, 1H), 6.74 (d, J=7.3 Hz, 1H), 4.65 (s, 2H), 4.57 (s, 2H), 4.03 (s, 2H).

Example 10

{6-[(4'-Chlorobiphenyl-4-ylmethyl)(pyridin-3-ylsulfonyl)aminomethyl]pyridin-2-ylamino}acetic Acid Hydrochloride (Exemplified Compound No. 681)

10-(a) tert-Butyl(tert-butoxycarbonyl{6-[(4'-chlorobiphenyl-4-ylmethyl)(pyridin-3-ylsulfonyl)aminomethyl]pyridin-2-yl}amino)acetate Reaction and post-treatment were carried out in the same manner as in Example 9-(b) except for using tert-butyl({6-[(4-bromobenzyl)(pyridin-3-ylsulfonyl)aminomethyl]pyridin-2-yl}tert-butoxycarbonylamino)acetate (187 mg, 0.289 mmol) obtained in Example 9-(a), and using 4-chlorophenylboronic acid (70.6 mg, 0.452 mmol) in place of 4-fluorophenylboronic acid to afford the title compound (166 mg) as a colorless oil. (Yield: 84%)

$^1$H-NMR spectrum (CDCl$_3$, δ ppm): 8.96 (dd, J=2.4, 0.8 Hz, 1H), 8.71 (dd, J=4.8, 1.6 Hz, 1H), 7.88 (ddd, J=8.0, 2.4, 1.6 Hz, 1H), 7.71 (d, J=8.4 Hz, 1H), 7.51 (dd, J=8.4, 7.3 Hz, 1H), 7.50-7.44 (m, 4H), 7.42-7.39 (m, 2H), 7.32-7.28 (m, 2H), 7.31 (ddd, J=8.0, 4.8, 0.8 Hz, 1H), 6.86 (dd, J=7.3, 0.6 Hz, 1H), 4.62 (s, 2H), 4.41 (s, 2H), 4.36 (s, 2H), 1.52 (s, 9H), 1.42 (s, 9H).

10-(b) {6-[(4'-Chlorobiphenyl-4-ylmethyl)(pyridin-3-ylsulfonyl)aminomethyl]pyridin-2-ylamino}acetic Acid Hydrochloride Reaction and post-treatment were carried out in the same manner as in Example 2-(b) except for using tert-butyl(tert-butoxycarbonyl{6-[(4'-chlorobiphenyl-4-ylmethyl)(pyridin-3-ylsulfonyl)aminomethyl]pyridin-2-yl}amino)acetate (163 mg, 0.240 mmol) obtained in Example 10-(a) in place of tert-butyl[tert-butoxycarbonyl(6-{(pyridin-3-ylsulfonyl)[4-(thiazol-2-yl)benzyl]aminomethyl}pyridin-2-yl)amino]acetate to afford the title compound (133 mg) as a white solid. (Yield: 93%)

Rf value: 0.64 (n-butanol:acetic acid:water=3:1:1).
Mass spectrum (FAB, m/z): 523 (M$^+$+1).
$^1$H-NMR spectrum (CD$_3$OD, δ ppm): 9.31 (dd, J=2.2, 0.6 Hz, 1H), 9.02 (dd, J=5.3, 1.4 Hz, 1H), 8.74 (ddd, J=8.1, 2.2, 1.4 Hz, 1H), 8.02 (ddd, J=8.1, 5.3, 0.6 Hz, 1H), 7.72 (dd, J=9.0, 7.3 Hz, 1H), 7.55-7.51 (m, 2H), 7.48-7.41 (m, 4H), 7.35-7.32 (m, 2H), 6.81 (d, J=9.0 Hz, 1H), 6.74 (d, J=7.3 Hz, 1H), 4.66 (s, 2H), 4.58 (s, 2H), 4.03 (s, 2H).

Example 11

(6-{(Pyridin-3-ylsulfonyl)[4-(thiazol-2-yl)benzyl]aminomethyl}pyridin-2-ylamino)acetic Acid Trifluoroacetate (Exemplified Compound No. 985)

11-(a) tert-Butyl[tert-butoxycarbonyl(6-{(pyridin-3-ylsulfonyl)[4-(thiazol-2-yl)benzyl]-aminomethyl}pyridin-2-yl)amino]acetate Reaction and post-treatment were carried out in the same manner as in Example 2-(a) except for using tert-butyl(tert-butoxycarbonyl{6-[(pyridin-3-ylsulfonyl)aminomethyl]pyridin-2-yl}amino)acetate (126 mg, 0.263 mmol) obtained in Reference Example 12-(d) in place of N-[4-(thiazol-2-yl)benzyl]pyridin-3-ylsulfonamide, and using 4-(thiazol-2-yl) benzyl alcohol (49.7 mg, 0.260 mmol) obtained in Reference Example 4-(a) in place of tart-butyl[tert-butoxycarbonyl(6-hydroxymethylpyridin-2-yl)amino]acetate to afford the title compound (145 mg) as a white foam. (Yield: 85%)

This compound showed the same $^1$H-NMR spectrum as that of tert-butyl[tertbutoxycarbonyl(6-{(pyridin-3-ylsulfonyl)[4-(thiazol-2-yl)benzyl]aminomethyl}pyridin-2-yl) amino]acetate obtained in Example 2-(a).

11-(b) (6-{(Pyridin-3-ylsulfonyl)[4-(thiazol-2-yl) benzyl]aminomethyl}pyridin-2-ylamino)acetic Acid Trifluoroacetate To a solution of tert-butyl[tert-butoxycarbonyl(6-{(pyridin-3-ylsulfonyl)[4-(thiazol-2-yl)benzyl] aminomethyl}pyridin-2-yl)amino]acetate (135 mg, 0.207 mmol) obtained in Example 11-(a) in methylene chloride (1.23 ml) was added a 4N hydrogen chloride/1,4-dioxane solution (1.02 nil), followed by stirring at room temperature for 16 hours. After completion of the reaction, the reaction solution was concentrated under reduced pressure. The resulting residue was subjected to reversed phase column chromatography (column; Megabond Elut™ C18 (manufactured by Varian, Inc.), eluent; a 1.0% aqueous triethylamine solution→acetonitrile:a 0.5% aqueous trifluoroacetic acid solution=1:1 (V/V)), and fractions containing the desired compound were concentrated under reduced pressure to afford the title compound (35 mg) as a pale yellow solid. (Yield: 24%)

Rf value: 0.52 (n-butanol:acetic acid:water=3:1:1).
Mass spectrum (FAB, m/z): 496 (M$^+$+1).
$^1$H-NMR spectrum (CD$_3$OD, δ ppm): 9.04 (d, J=1.9 Hz, 1H), 8.83 (dd, J=4.9, 1.6 Hz, 1H), 8.30 (ddd, J=8.0, 1.9, 1.6 Hz, 1H), 7.86 (d, J=3.3 Hz, 1H), 7.82-7.77 (m, 2H), 7.66 (ddd, J=8.0, 4.9, 0.4 Hz, 1H), 7.61 (d, J=3.3 Hz, 1H), 7.60 (dd, J=8.8, 7.2 Hz, 1H), 7.39-7.35 (m, 2H), 6.68 (d, J=8.8 Hz, 1H), 6.65 (d, J=7.2 Hz, 1H), 4.59 (s, 2H), 4.51 (s, 2H), 3.95 (s, 2H).

Example 12

{6-[(6-Chlorobenzo[b]thiophen-2-ylmethyl)(pyridin-3-ylsulfonyl)aminomethyl]pyridin-2-ylamino}acetic Acid Hydrochloride (Exemplified Compound No. 186)

12-(a) tert-Butyl(tert-butoxycarbonyl{6-[(6-chlorobenzo[b]thiophen-2-ylmethyl)(pyridin-3-ylsulfonyl)aminomethyl]pyridin-2-yl}amino)acetate Reaction and post-treatment were carried out in the same manner as in Example 2-(a) except for using tert-butyl(tert-butoxycarbonyl{6-[(pyridin-3-ylsulfonyl)aminomethyl]pyridin-2-yl}amino)acetate (100 mg, 0.209 mmol) obtained in Reference Example 12-(d) in place of N-[4-(thiazol-2-yl) benzyl]pyridin-3-ylsulfonamide, and using (6-chlorobenzo [b]thiophen-2-yl)methanol (see WO 99/37304A, 41.5 mg, 0.209 mmol) in place of tert-butyl[tert-butoxycarbonyl(6-hydroxymethylpyridin-2-yl)amino]acetate to afford the title compound (144 mg) substantially quantitatively as a slightly yellow liquid.

Mass spectrum (FAB, m/z): 659 (M$^+$+1).
$^1$H-NMR spectrum (CDCl$_3$, δ ppm): 8.98 (dd, J=2.4, 0.7 Hz, 1H), 8.71 (dd, J=4.8, 1.7 Hz, 1H), 7.91 (ddd, J=8.1, 2.4, 1.7 Hz, 1H), 7.75 (d, J=8.4 Hz, 1H), 7.72-7.70 (m, 1H), 7.58 (d, J=8.8 Hz, 1H), 7.56 (dd, J=8.4, 7.4 Hz, 1H), 7.32-7.28 (m, 2H), 7.09 (d, J=0.7 Hz, 1H), 6.94 (d, J=7.4 Hz, 1H), 4.82 (s, 2H), 4.49 (s, 2H), 4.42 (s, 2H), 1.53 (s, 9H), 1.42 (s, 9H).

12-(b) {6-[(6-Chlorobenzo[b]thiophen-2-ylmethyl)(pyridin-3-ylsulfonyl)aminomethyl]-pyridin-2-ylamino}acetic Acid Hydrochloride Reaction and post-treatment were carried out in the same manner as in Example 1-(c) except for using tert-butyl(tert-butoxycarbonyl{6-[(6-chlorobenzo[b]-thiophen-2-ylmethyl)(pyridin-3-ylsulfonyl)aminomethyl]pyridin-2-yl}amino)acetate (144 mg, 0.218 mmol) obtained in Example 12-(a) in place of tert-butyl(tert-butoxycarbonyl{6-[(6-phenylpyridazin-3-ylmethyl)(pyridin-3-ylsulfonyl)aminomethyl]-pyridin-2-yl}amino)acetate to afford the title compound (110 mg) as a white solid. (Yield: 88%)

Rf value: 0.64 (n-butanol:acetic acid:water=3:1:1).

Mass spectrum (FAB, m/z): 503 ($M^+$+1).

$^1$H-NMR spectrum (CD$_3$OD, δ ppm): 9.22 (dd, J=2.2, 0.6 Hz, 1H), 8.93 (dd, J=5.2, 1.6 Hz, 1H), 8.58 (ddd, J=8.2, 2.2, 1.6 Hz, 1H), 7.85 (ddd, J=8.2, 5.2, 0.6 Hz, 1H), 7.79 (d, J=2.0 Hz, 1H), 7.73 (dd, J=9.0, 7.3 Hz, 1H), 7.63 (d, J=8.5 Hz, 1H), 7.31 (dd, J=8.5, 2.0 Hz, 1H), 7.17 (s, 1H), 6.83 (dd, J=7.3, 0.5 Hz, 1H), 6.79 (d, J=9.0 Hz, 1H), 4.85 (s, 2H), 4.69 (s, 2H), 4.05 (s, 2H).

Example 13

{6-[(Benzo[b]thiophen-2-ylmethyl)(pyridin-3-ylsulfonyl)aminomethyl]pyridin-2-ylamino}acetic Acid Hydrochloride (Exemplified Compound No. 132)

13-(a) tert-Butyl({6-[(benzo[b]thiophen-2-ylmethyl)(pyridin-3-ylsulfonyl)aminomethyl]pyridin-2-yl}tert-butoxycarbonylamino)acetate Reaction and post-treatment were carried out in the same manner as in Example 2-(a) except for using tert-butyl(tert-butoxycarbonyl{6-[(pyridin-3-ylsulfonyl)aminomethyl]pyridin-2-yl}amino)acetate (126 mg, 0.263 mmol) obtained in Reference Example 12-(d) in place of N-[4-(thiazol-2-yl)benzyl]pyridin-3-ylsulfonamide, and using benzo[b]thiophen-2-ylmethanol (43.2 mg, 0.263 mmol) in place of tert-butyl[tert-butoxycarbonyl(6-hydroxymethylpyridin-2-yl)amino]acetate to afford the title compound (153 mg) as a slightly yellow liquid. (Yield: 93%)

$^1$H-NMR spectrum (CDCl$_3$, δ ppm): 8.99 (dd, J=2.3, 0.9 Hz, 1H), 8.69 (dd, J=4.8, 1.6 Hz, 1H), 7.91 (ddd, J=8.1, 2.3, 1.6 Hz, 1H), 7.76 (d, J=8.4 Hz, 1H), 7.74-7.66 (m, 2H), 7.57 (dd, J=8.4, 7.4 Hz, 1H), 7.35-7.28 (m, 2H), 7.28 (ddd, J=8.1, 4.8, 0.9 Hz, 1H), 7.12 (d, J=0.7 Hz, 1H), 6.96 (dd, J=7.4, 0.6 Hz, 1H), 4.84 (s, 2H), 4.50 (s, 2H), 4.44 (s, 2H), 1.53 (s, 9H), 1.42 (s, 9H).

13-(b) {6-[(Benzo[b]thiophen-2-ylmethyl)(pyridin-3-ylsulfonyl)aminomethyl]pyridin-2-ylamino}acetic Acid Hydrochloride Reaction and post-treatment were carried out in the same manner as in Example 2-(b) except for using tert-butyl({6-[(benzo[b]thiophen-2-ylmethyl)(pyridin-3-ylsulfonyl)aminomethyl]pyridin-2-yl}tert-butoxycarbonylamino)acetate (150 mg, 0.240 mmol) obtained in Example 13-(a) in place of tert-butyl[tert-butoxycarbonyl(6-{(pyridin-3-ylsulfonyl)[4-(thiazol-2-yl)benzyl]aminomethyl}pyridin-2-yl)amino]acetate to afford the title compound (96.1 mg) as a white solid. (Yield: 74%)

Rf value: 0.60 (n-butanol:acetic acid:water=3:1:1).

Mass spectrum (FAB, m/z): 469 ($M^+$+1).

$^1$H-NMR spectrum (CD$_3$OD, δ ppm): 9.27 (dd, J=2.3, 0.7 Hz, 1H), 8.94 (dd, J=5.2, 1.5 Hz, 1H), 8.66 (ddd, J=8.1, 2.3, 1.5 Hz, 1H), 7.89 (ddd, J=8.1, 5.2, 0.7 Hz, 1H), 7.75-7.64 (m, 3H), 7.34-7.28 (m, 2H), 7.17 (s, 1H), 6.85 (dd, J=7.3, 0.7 Hz, 1H), 6.76 (d, J=9.0 Hz, 1H), 4.87 (s, 2H), 4.72 (s, 2H), 4.00 (s, 2H).

Example 14

(6-{[4-(Pyridazin-4-yl)benzyl](pyridin-3-ylsulfonyl)aminomethyl}pyridin-2-ylamino)acetic Acid Hydrochloride (Exemplified Compound No. 1203)

14-(a) tert-Butyl[tert-butoxycarbonyl(6-{[4-(pyridazin-4-yl)benzyl](pyridin-3-ylsulfonyl)aminomethyl}pyridin-2-yl)amino]acetate Reaction and post-treatment were carried out in the same manner as in Example 2-(a) except for using tert-butyl(tert-butoxycarbonyl{6-[(pyridin-3-ylsulfonyl)aminomethyl]pyridin-2-yl}amino)acetate (158 mg, 0.330 mmol) obtained in Reference Example 12-(d) in place of N-[4-(thiazol-2-yl)benzyl]pyridin-3-ylsulfonamide, and using 4-(pyridazin-4-yl)benzyl alcohol (60.2 mg, 0.323 mmol) obtained in Reference Example 13 in place of tert-butyl[tert-butoxycarbonyl(6-hydroxymethylpyridin-2-yl)amino]acetate to afford the title compound (152 mg) as a white foam. (Yield: 73%)

Mass spectrum (FAB, m/z): 647 ($M^+$+1).

$^1$H-NMR spectrum (CDCl$_3$, δ ppm): 9.44 (dd, J=2.5, 1.2 Hz, 1H), 9.23 (dd, J=5.4, 1.2 Hz, 1H), 8.96 (dd, J=2.4, 0.8 Hz, 1H), 8.73 (dd, J=4.8, 1.7 Hz, 1H), 7.91 (ddd, J=8.0, 2.4, 1.7 Hz, 1H), 7.71 (d, J=8.4 Hz, 1H), 7.63 (dd, J=5.4, 2.5 Hz, 1H), 7.61-7.58 (m, 2H), 7.49 (dd, J=8.4, 7.3 Hz, 1H), 7.45-7.42 (m, 2H), 7.34 (ddd, J=8.0, 4.8, 0.8 Hz, 1H), 6.84 (dd, J=7.3, 0.6 Hz, 1H), 4.65 (s, 2H), 4.41 (s, 2H), 4.34 (s, 2H), 1.53 (s, 9H), 1.42 (s, 9H).

14-(b) (6-{[4-(Pyridazin-4-yl)benzyl](pyridin-3-ylsulfonyl)aminomethyl}pyridin-2-ylamino)acetic Acid Hydrochloride Reaction was carried out in the same manner as in Example 1-(c) except for using tert-butyl[tert-butoxycarbonyl(6-{[4-(pyridazin-4-yl)benzyl](pyridin-3-ylsulfonyl)aminomethyl}pyridin-2-yl)amino]acetate (150 mg, 0.232 mmol) obtained in Example 14-(a) in place of tert-butyl(tert-butoxycarbonyl{6-[(6-phenylpyridazin-3-ylmethyl)(pyridin-3-ylsulfonyl)aminomethyl]pyridin-2-yl}amino)acetate. After completion of the reaction, the reaction solution was concentrated under reduced pressure. Water and acetone were added to the resulting residue, followed by concentration again under reduced pressure to afford the title compound (137 mg) as a slightly yellow solid. (Yield: 98%)

Rf value: 0.38 (n-butanol:acetic acid:water=3:1:1).

Mass spectrum (FAB, m/z): 491 ($M^+$+1).

$^1$H-NMR spectrum (CD$_3$OD, δ ppm): 9.91 (dd, J=2.4, 0.9 Hz, 1H), 9.58 (dd, J=6.0, 0.9 Hz, 1H), 9.23 (d, J=2.0 Hz, 1H), 8.98 (dd, J=5.2, 1.5 Hz, 1H), 8.77 (dd, J=6.0, 2.4 Hz, 1H), 8.63 (dd, J=8.2, 2.0, 1.5 Hz, 1H), 7.99-7.95 (m, 2H), 7.92 (ddd, J=8.2, 5.2, 0.5 Hz, 1H), 7.71 (dd, J=8.9, 7.3 Hz, 1H), 7.61-7.57 (m, 2H), 6.83 (d, J=8.9 Hz, 1H), 6.76 (d, J=7.3 Hz, 1H), 4.69 (s, 2H), 4.69 (s, 2H), 4.17 (s, 2H).

Example 15

{6-[(6-Methoxybenzo[b]thiophen-2-ylmethyl)(pyridin-3-ylsulfonyl)aminomethyl]-pyridin-2-ylamino}acetic Acid Hydrochloride (Exemplified Compound No. 361)

15-(a) tert-Butyl(tert-butoxycarbonyl{6-[(6-methoxybenzo[b]thiophen-2-ylmethyl)(pyridin-3-ylsulfonyl)aminomethyl]pyridin-2-yl}amino)acetate Reaction was carried out in the same manner as in Example 2-(a) except for using tert-butyl(tert-butoxycarbonyl{6-[(pyridin-3-ylsulfonyl)aminomethyl]pyridin-2-yl}amino)acetate (69.4 mg, 0.145 mmol) obtained in Reference Example 12-(d) in place of N-[4-(thiazol-2-yl)benzyl]pyridin-3-ylsulfonamide, and using (6-methoxybenzo[b]-thiophen-2-yl)methanol (see WO 2006/106711A, 33.9 mg, 0.175 mmol) in place of tert-butyl [tert-butoxycarbonyl(6-hydroxymethylpyridin-2-yl)amino]acetate. After completion of the reaction, the reaction solution was concentrated under reduced pressure, and water was added to the residue, followed by extraction with toluene. The separated organic layer was dried over anhydrous magnesium sulfate, and concentrated under reduced pressure. The resulting residue was subjected to silica gel column chromatography (eluent; hexane:ethyl acetate=3:1→1:1 (V/V)) and then to reversed phase column chromatography (column; Megabond Elut™ C18 (manufactured by Varian, Inc.), eluent; acetonitrile:water=1:1→1:0 (V/V)), and fractions containing the desired compound were concentrated under reduced pressure to afford the title compound (73.8 mg) as a white foam. (Yield: 78%)

Mass spectrum (FAB, m/z): 655 (M$^+$+1).

$^1$H-NMR spectrum (CDCl$_3$, δ ppm): 8.99 (dd, J=2.3, 0.8 Hz, 1H), 8.69 (dd, J=4.8, 1.6 Hz, 1H), 7.91 (ddd, J=8.0, 2.3, 1.6 Hz, 1H), 7.76 (d, J=8.4 Hz, 1H), 7.57 (dd, J=8.4, 7.3 Hz, 1H), 7.54 (d, J=8.7 Hz, 1H), 7.28 (ddd, J=8.0, 4.8, 0.8 Hz, 1H), 7.20 (d, J=2.4 Hz, 1H), 7.01 (d, 0.7 Hz, 1H), 6.96 (dd, J=7.3, 0.6 Hz, 1H), 6.95 (dd, J=8.7, 2.4 Hz, 1H), 4.79 (s, 2H), 4.49 (s, 2H), 4.45 (s, 2H), 3.85 (s, 3H), 1.53 (s, 9H), 1.42 (s, 9H).

15-(b) {6-[(6-Methoxybenzo[b]thiophen-2-ylmethyl)(pyridin-3-ylsulfonyl)aminomethyl]pyridin-2-ylamino}acetic Acid Hydrochloride Reaction and post-treatment were carried out in the same manner as in Example 1-(c) except for using tert-butyl(tert-butoxycarbonyl{6-[(6-methoxybenzo[b]-thiophen-2-ylmethyl)(pyridin-3-ylsulfonyl)aminomethyl]pyridin-2-yl}amino)acetate (72.6 mg, 0.111 mmol) obtained in Example 15-(a) in place of tert-butyl(tert-butoxycarbonyl{6-[(6-phenylpyridazin-3-ylmethyl)(pyridin-3-ylsulfonyl)aminomethyl]-pyridin-2-yl}amino)acetate to afford the title compound (63.1 mg) as a white solid. (Yield: 99%)

Rf value: 0.59 (n-butanol:acetic acid:water=3:1:1).

Mass spectrum (FAB, m/z): 499 (M$^+$+1).

$^1$H-NMR spectrum (CD$_3$OD, δ ppm): 9.18 (dd, J=2.4, 0.8 Hz, 1H), 8.90 (dd, J=5.1, 1.5 Hz, 1H), 8.51 (ddd, J=8.1, 2.4, 1.5 Hz, 1H), 7.78 (ddd, J=8.1, 5.1, 0.8 Hz, 1H), 7.73 (dd, J=9.1, 7.3 Hz, 1H), 7.51 (d, J=8.7 Hz, 1H), 7.26 (d, J=2.3 Hz, 1H), 7.02 (s, 1H), 6.92 (dd, J=8.7, 2.3 Hz, 1H), 6.82 (dd, J=7.3, 0.8 Hz, 1H), 6.76 (d, J=9.1 Hz, 1H), 4.78 (s, 2H), 4.66 (s, 2H), 4.00 (s, 2H), 3.82 (s, 3H).

Example 16

(6-{(Pyridin-2-ylsulfonyl)[4-(thiazol-4-yl)benzyl]aminomethyl}pyridin-2-ylamino)acetic Acid (Exemplified Compound No. 1090)

16-(a) tert-Butyl[tert-butoxycarbonyl(6-{(pyridin-2-ylsulfonyl)[4-(thiazol-4-yl)benzyl]-aminomethyl}pyridin-2-yl)amino]acetate Reaction and post-treatment were carried out in the same manner as in Example 2-(a) except for using tert-butyl(tert-butoxycarbonyl{6-[(pyridin-2-ylsulfonyl)aminomethyl]pyridin-2-yl}amino)acetate (200 mg, 0.418 mmol) obtained in Reference Example 14 in place of N-[4-(thiazol-2-yl)benzyl]pyridin-3-ylsulfonamide, and using 4-(thiazol-4-yl)benzyl alcohol (79.9 mg, 0.418 mmol) obtained in Reference Example 15-(b) in place of tert-butyl[tert-butoxycarbonyl(6-hydroxymethylpyridin-2-yl)amino]acetate to afford the title compound (240 mg) as a white foam. (Yield: 88%)

Mass spectrum (FAB, m/z): 652 (M$^+$+1).

$^1$H-NMR spectrum (CDCl$_3$, δ ppm): 8.87 (d, J=2.0 Hz, 1H), 8.60 (ddd, J=4.7, 1.7, 0.9 Hz, 1H), 7.82 (ddd, J=7.7, 1.1, 0.9 Hz, 1H), 7.81-7.78 (m, 2H), 7.77 (ddd, J=7.7, 7.6, 1.7 Hz, 1H), 7.65 (d, J=8.4 Hz, 1H), 7.51 (d, J=2.0 Hz, 1H), 7.45 (dd, J=8.4, 7.3 Hz, 1H), 7.38 (ddd, J=7.6, 4.7, 1.1 Hz, 1H), 7.32-7.29 (m, 2H), 6.91 (d, J=7.3 Hz, 1H), 4.74 (s, 2H), 4.49 (s, 2H), 4.45 (s, 2H), 1.52 (s, 9H), 1.42 (s, 9H).

16-(b) (6-{(Pyridin-2-ylsulfonyl)[4-(thiazol-4-yl)benzyl]aminomethyl}pyridin-2-ylamino)acetic Acid Reaction and post-treatment were carried out in the same manner as in Example 3-(b) except for using tert-butyl[tert-butoxycarbonyl(6-{(pyridin-2-ylsulfonyl)[4-(thiazol-4-yl)benzyl]aminomethyl}pyridin-2-yl)amino]acetate (230 mg, 0.353 mmol) obtained in Example 16-(a) in place of tert-butyl [tert-butoxycarbonyl(6-{(pyridin-2-ylsulfonyl)[4-(thiazol-2-yl)benzyl]aminomethyl}pyridin-2-yl)amino]acetate to afford the title compound (93.5 mg) as a white solid. (Yield: 53%)

Rf value: 0.50 (n-butanol:acetic acid:water=3:1:1).

Mass spectrum (FAB, m/z): 496 (M$^+$+1).

$^1$H-NMR spectrum (DMSO-d$_6$, δ ppm): 12.42 (brs, 0.6H), 9.19 (d, J=1.8 Hz, 1H), 8.65 (ddd, J=4.7, 1.7, 0.8 Hz, 1H), 8.14 (d, J=1.8 Hz, 1H), 7.95 (ddd, J=7.8, 7.7, 1.7 Hz, 1H), 7.91-7.88 (m, 2H), 7.81 (ddd, J=7.8, 0.9, 0.8 Hz, 1H), 7.58 (ddd, J=7.7, 4.7, 0.9 Hz, 1H), 7.33-7.30 (m, 2H), 7.20 (dd, J=8.3, 7.2 Hz, 1H), 6.75 (t, J=5.6 Hz, 0.9H), 6.34 (d, J=8.3 Hz, 1H), 6.29 (d, J=7.2 Hz, 1H), 4.73 (s, 2H), 4.24 (s, 2H), 3.83 (d, J=5.6 Hz, 2H).

Example 17

{6-[(Biphenyl-4-ylmethyl)(pyridin-2-ylsulfonyl)aminomethyl]pyridin-2-ylamino}acetic Acid Hydrochloride (Exemplified Compound No. 538)

17-(a) tert-Butyl({6-[(biphenyl-4-ylmethyl)(pyridin-2-ylsulfonyl)aminomethyl]pyridin-2-yl}tert-butoxycarbonylamino)acetate Reaction and post-treatment were carried out in the same manner as in Example 2-(a) except for using tert-butyl(tert-butoxycarbonyl{6-[(pyridin-2-ylsulfonyl)aminomethyl]pyridin-2-yl}amino)acetate (100 mg, 0.209 mmol) obtained in Reference Example 14 in place of N-[4-(thiazol-2-yl)benzyl]

pyridin-3-ylsulfonamide, and using 4-biphenylmethanol (38.8 mg, 0.211 mmol) in place of tert-butyl[tertbutoxycarbonyl(6-hydroxymethylpyridin-2-yl)amino]acetate to afford the title compound (116 mg) as a white foam. (Yield: 86%)

Mass spectrum (FAB, m/z): 645 (M$^+$+1).

$^1$H-NMR spectrum (CDCl$_3$, δ ppm): 8.60 (ddd, J=4.7, 1.7, 1.0 Hz, 1H), 7.82 (ddd, J=7.8, 1.2, 1.0 Hz, 1H), 7.77 (ddd, J=7.8, 7.6, 1.7 Hz, 1H), 7.65 (d, J=7.5 Hz, 1H), 7.56-7.52 (m, 2H), 7.47-7.41 (m, 5H), 7.39 (ddd, J=7.6, 4.7, 1.2 Hz, 1H), 7.36-7.32 (m, 1H), 7.31-7.28 (m, 2H), 6.92 (d, J=7.3 Hz, 1H), 4.74 (s, 2H), 4.52 (s, 2H), 4.46 (s, 2H), 1.52 (s, 9H), 1.42 (s, 9H).

17-(b) {6-[(Biphenyl-4-ylmethyl)(pyridin-2-ylsulfonyl)aminomethyl]pyridin-2-ylamino}acetic Acid Hydrochloride Reaction and post-treatment were carried out in the same manner as in Example 14-(b) except for using tert-butyl({6-[(biphenyl-4-ylmethyl)(pyridin-2-ylsulfonyl)aminomethyl]pyridin-2-yl}tert-butoxycarbonylamino)acetate (113 mg, 0.175 mmol) obtained in Example 17-(a) in place of tert-butyl[tert-butoxycarbonyl(6-{[(4-pyridazin-4-yl)benzyl](pyridin-3-ylsulfonyl)aminomethyl}pyridin-2-yl)amino]acetate to afford the title compound (93.9 mg) substantially quantitatively as a white solid.

Rf value: 0.62 (n-butanol:acetic acid:water=3:1:1).

Mass spectrum (FAB, m/z): 489 (M$^+$+1).

$^1$H-NMR spectrum (CD$_3$OD, δ ppm): 8.76 (ddd, J=4.8, 1.7, 1.1 Hz, 1H), 8.10 (ddd, J=7.6, 7.6, 1.7 Hz, 1H), 8.06 (ddd, J=7.6, 1.2, 1.1 Hz, 1H), 7.71-7.66 (m, 2H), 7.54-7.50 (m, 2H), 7.46-7.39 (m, 4H), 7.35-7.31 (m, 1H), 7.31-7.28 (m, 2H), 6.76 (d, J=8.8 Hz, 1H), 6.73 (d, J=7.2 Hz, 1H), 4.74 (s, 2H), 4.56 (s, 2H), 4.00 (s, 2H).

Example 18

(6-{(Pyridin-2-ylsulfonyl)[4-(pyrimidin-2-yl)benzyl]aminomethyl}pyridin-2-ylamino)acetic Acid Hydrochloride (Exemplified Compound No. 1266)

18-(a) tert-Butyl[tert-butoxycarbonyl(6-{(pyridin-2-ylsulfonyl)[4-(pyrimidin-2-yl)benzyl]aminomethyl}pyridin-2-yl)amino]acetate Reaction and post-treatment were carried out in the same manner as in Example 2-(a) except for using tert-butyl(tert-butoxycarbonyl{6-[(pyridin-2-ylsulfonyl)aminomethyl]pyridin-2-yl}amino)acetate (157 mg, 0.328 mmol) obtained in Reference Example 14 in place of N-[4-(thiazol-2-yl)benzyl]pyridin-3-ylsulfonamide, and using 4-(pyrimidin-2-yl)benzyl alcohol (60.8 mg, 0.327 mmol) obtained in Reference Example 16 in place of tert-butyl[tert-butoxycarbonyl(6-hydroxymethylpyridin-2-yl)amino]acetate to afford the title compound (144 mg) as a white foam. (Yield: 68%)

Mass spectrum (FAB, m/z): 647 (M$^+$+1).

$^1$H-NMR spectrum (CDCl$_3$, δ ppm): 8.79 (d, J=4.8 Hz, 2H), 8.60 (ddd, J=4.7, 1.6, 0.9 Hz, 1H), 8.33-8.30 (m, 2H), 7.82 (ddd, J=7.7, 1.1, 0.9 Hz, 1H), 7.76 (ddd, J=7.7, 7.6, 1.6 Hz, 1H), 7.65 (d, J=8.3 Hz, 1H), 7.46 (dd, J=8.3, 7.4 Hz, 1H), 7.38 (ddd, J=7.6, 4.7, 1.1 Hz, 1H), 7.37-7.34 (m, 2H), 7.18 (t, J=4.8 Hz, 1H), 6.92 (d, J=7.4 Hz, 1H), 4.79 (s, 2H), 4.50 (s, 2H), 4.46 (s, 2H), 1.52 (s, 9H), 1.42 (s, 9H).

18-(b) (6-{(Pyridin-2-ylsulfonyl)[4-(pyrimidin-2-yl)benzyl]aminomethyl}pyridin-2-ylamino)acetic Acid Hydrochloride Reaction and post-treatment were carried out in the same manner as in Example 14-(b) except for using tert-butyl[tert-butoxycarbonyl(6-{(pyridin-2-ylsulfonyl)[4-(pyrimidin-2-yl)benzyl]aminomethyl}pyridin-2-yl)amino]acetate (142 mg, 0.220 mmol) obtained in Example 18-(a) in place of tert-butyl[tert-butoxycarbonyl(6-{[(4-pyridazin-4-yl)benzyl](pyridin-3-ylsulfonyl)aminomethyl}pyridin-2-yl)amino]-acetate to afford the title compound (136 mg) substantially quantitatively as a slightly yellow solid.

Rf value: 0.45 (n-butanol:acetic acid:water=3:1:1).

Mass spectrum (FAB, m/z): 491 (M$^+$+1).

$^1$H-NMR spectrum (CD$_3$OD, δ ppm): 8.86 (d, J=5.0 Hz, 2H), 8.78 (ddd, J=4.7, 1.6, 1.0 Hz, 1H), 8.21-8.18 (m, 2H), 8.14-8.07 (m, 2H), 7.72 (dd, J=9.1, 7.4, Hz, 1H), 7.70 (ddd, J=7.1, 4.7, 1.8 Hz, 1H), 7.42 (t, J=5.0 Hz, 1H), 7.40-7.36 (m, 2H), 6.79 (d, J=7.4 Hz, 1H), 6.77 (d, J=9.1 Hz, 1H), 4.79 (s, 2H), 4.59 (s, 2H), 4.00 (s, 2H).

Example 19

(6-{[4-(Pyridin-2-yl)benzyl](pyridin-3-ylsulfonyl)aminomethyl}pyridin-2-ylamino)acetic Acid (Exemplified Compound No. 1158)

19-(a) tert-Butyl[tert-butoxycarbonyl(6-{[4-(pyridin-2-yl)benzyl](pyridin-3-ylsulfonyl)aminomethyl}pyridin-2-yl)amino]acetate Reaction and post-treatment were carried out in the same manner as in Example 2-(a) except for using tert-butyl(tert-butoxycarbonyl{6-[(pyridin-3-ylsulfonyl)aminomethyl]pyridin-2-yl}amino)acetate (934 mg, 1.95 mmol) obtained in Reference Example 12-(d) in place of N-[4-(thiazol-2-yl)benzyl]pyridin-3-ylsulfonamide, and using 4-(pyridin-2-yl)benzyl alcohol (397 mg, 2.14 mmol) in place of tert-butyl[tert-butoxycarbonyl(6-hydroxymethylpyridin-2-yl)amino]acetate to afford the title compound (1.76 g) (pure content 1.26 g) substantially quantitatively as a yellow oil.

Mass spectrum (FAB, m/z): 646 (M$^+$+1).

$^1$H-NMR spectrum (CDCl$_3$, δ ppm): 8.96 (dd, J=2.3, 0.9 Hz, 1H), 8.73-8.66 (m, 2H), 7.94-7.89 (m, 2H), 7.87 (ddd, J=8.1, 2.3, 1.7 Hz, 1H), 7.80-7.67 (m, 2H), 7.71 (d, J=8.4 Hz, 1H), 7.51 (dd, J=8.4, 7.4 Hz, 1H), 7.38-7.32 (m, 2H), 7.31 (ddd, J=8.1, 4.9, 0.9 Hz, 1H), 7.24 (ddd, J=7.1, 4.8, 1.5 Hz, 1H), 6.86 (dd, J=7.4, 0.6 Hz, 1H), 4.65 (s, 2H), 4.41 (s, 2H), 4.37 (s, 2H), 1.52 (s, 9H), 1.42 (s, 9H).

19-(b) (6-{[4-(Pyridin-2-yl)benzyl](pyridin-3-ylsulfonyl)aminomethyl}pyridin-2-ylamino)acetic Acid To a solution of tert-butyl[tert-butoxycarbonyl(6-{[4-(pyridin-2-yl)benzyl]-(pyridin-3-ylsulfonyl)aminomethyl}pyridin-2-yl)amino]acetate (1.76 g) (containing 1.95 mmol of a pure content) obtained in Example 19-(a) in tetrahydrofuran (5.6 ml) were added water (5.6 ml) and concentrated hydrochloric acid (2.3 ml), followed by stirring at 65° C. for 4.5 hours. After completion of the reaction, the reaction solution was concentrated under reduced pressure. After the concentrate was adjusted to pH 10.9 with a 1N aqueous sodium hydroxide solution, the insolubles were filtered off. The filtrate was then adjusted to pH 5.6 with 1N hydrochloric acid, followed by addition of ethyl acetate. A precipitated solid was collected by filtration, and then dried under reduced pressure to afford the title compound (553 mg) as a white solid. (Yield: 58%)

Rf value: 0.35 (n-butanol:acetic acid:water=3:1:1).

Mass spectrum (FAB, m/z): 490 (M$^+$+1).

$^1$H-NMR spectrum (CDCl$_3$, δ ppm): 9.11 (dd, J=2.2, 0.5 Hz, 1H), 8.79 (dd, J=4.8, 1.6 Hz, 1H), 8.67 (ddd, J=4.9, 1.6, 0.9 Hz, 1H), 8.08 (ddd, J=8.1, 2.2, 1.6 Hz, 1H), 7.81 (ddd, J=7.9, 7.8, 1.6 Hz, 1H), 7.75-7.69 (m, 2H), 7.64 (ddd, J=7.9, 1.0, 0.9 Hz, 1H), 7.43 (ddd, J=8.1, 4.8, 0.5 Hz, 1H), 7.34-7.27 (m, 2H), 7.23-7.17 (m, 2H), 6.58 (d, J=7.1 Hz, 1H), 6.29 (d, J=8.3 Hz, 1H), 4.58 (s, 2H), 4.28 (s, 2H), 3.86 (s, 2H).

Example 20

(6-{(Pyridin-3-ylsulfonyl)[4-(1,2,4-triazol-1-yl)benzyl]aminomethyl}pyridin-2-ylamino)acetic Acid (Exemplified Compound No. 1461)

20-(a) tert-Butyl[tert-butoxycarbonyl(6-{(pyridin-3-ylsulfonyl)[4-(1,2,4-triazol-1-yl)benzyl]aminomethyl}pyridin-2-yl)amino]acetate Reaction and post-treatment were carried out in the same manner as in Example 2-(a) except for using tert-butyl(tert-butoxycarbonyl{6-[(pyridin-3-ylsulfonyl)aminomethyl]pyridin-2-yl}amino)acetate (840 mg, 1.76 mmol) obtained in Reference Example 12-(d) in place of N-[4-(thiazol-2-yl)benzyl]pyridin-3-ylsulfonamide, and using 4-(triazol-1-yl)benzyl alcohol (342 mg, 1.95 mmol) in place of tert-butyl [tert-butoxycarbonyl(6-hydroxymethylpyridin-2-yl)amino]acetate to afford the title compound (938 mg) as a white foam. (Yield: 84%)

Mass spectrum (FAB, m/z): 636 (M$^+$+1).

$^1$H-NMR spectrum (CDCl$_3$, δ ppm): 8.96 (dd, J=2.3, 0.7 Hz, 1H), 8.73 (dd, J=4.9, 1.7 Hz, 1H), 8.56 (s, 1H), 8.10 (s, 1H), 7.90 (ddd, J=8.0, 2.3, 1.7 Hz, 1H), 7.70 (d, J=8.3 Hz, 1H), 7.62-7.57 (m, 2H), 7.49 (dd, J=8.3, 7.4 Hz, 1H), 7.42-7.38 (m, 2H), 7.34 (ddd, J=8.0, 4.9, 0.7 Hz, 1H), 6.83 (d, J=7.4 Hz, 1H), 4.63 (s, 2H), 4.39 (s, 2H), 4.33 (s, 2H), 1.53 (s, 9H), 1.42 (s, 9H).

20-(b) (6-{(Pyridin-3-ylsulfonyl)[4-(1,2,4-triazol-1-yl)benzyl]aminomethyl}pyridin-2-ylamino)acetic Acid Reaction was carried out in the same manlier as in Example 19-(b) except for using tert-butyl[tert-butoxycarbonyl(6-{(pyridin-3-ylsulfonyl)[4-(1,2,4-triazol-1-yl)benzyl]aminomethyl}pyridin-2-yl)amino]acetate (936 mg, 1.47 mmol) obtained in Example 20-(a) in place of tert-butyl[tert-butoxycarbonyl(6-{[4-(pyridin-2-yl)benzyl]-(pyridin-3-ylsulfonyl)aminomethyl}pyridin-2-yl)amino]acetate. After completion of the reaction, the reaction solution was concentrated under reduced pressure. The concentrate was adjusted to pH 4.5 with a 6N aqueous sodium hydroxide solution, and a precipitated solid was collected by filtration. Acetone (1.3 ml) was added to the crude product, followed by stirring at 50° C. for 1 hour, and then at room temperature for 1 hour. A precipitated solid was collected by filtration, and then dried under reduced pressure to afford the title compound (618 mg) as a white solid. (Yield: 88%)

Rf value: 0.36 (n-butanol:acetic acid:water=3:1:1).

Mass spectrum (FAB, m/z): 480 (M$^+$+1).

$^1$H-NMR spectrum (DMSO-d$_6$, δ ppm): 9.27 (s, 1H), 8.85 (dd, J=2.4, 0.8 Hz, 1H), 8.73 (dd, J=4.8, 1.7 Hz, 1H), 8.24 (s, 1H), 8.05 (ddd, J=8.1, 2.4, 1.7 Hz, 1H), 7.84-7.79 (m, 2H), 7.49 (ddd, J=8.1, 4.8, 0.8 Hz, 1H), 7.47-7.43 (m, 2H), 7.24 (dd, J=8.3, 7.1 Hz, 1H), 6.75 (t, J=5.6 Hz, 1H), 6.36 (d, J=8.3 Hz, 1H), 6.33 (d, J=7.1 Hz, 1H), 4.71 (s, 2H), 4.21 (s, 2H), 3.69 (d, J=5.6 Hz, 2H).

Example 21

(6-{[4-(Pyrazol-1-yl)benzyl](pyridin-2-ylsulfonyl)aminomethyl}pyridin-2-ylamino)acetic Acid (Exemplified Compound No. 876)

21-(a) tert-Butyl[tert-butoxycarbonyl(6-{[4-(pyrazol-1-yl)benzyl](pyridin-2-ylsulfonyl)aminomethyl}pyridin-2-yl)amino]acetate Reaction and post-treatment were carried out in the same manner as in Example 2-(a) except for using tert-butyl(tert-butoxycarbonyl{6-[(pyridin-2-ylsulfonyl)aminomethyl]pyridin-2-yl}amino)acetate (622 mg, 1.30 mmol) obtained in Reference Example 14 in place of N-[4-(thiazol-2-yl)benzyl]pyridin-3-ylsulfonamide, and using 4-(pyrazol-1-yl)benzyl alcohol (225 mg, 1.29 mmol) in place of tert-butyl [tert-butoxycarbonyl(6-hydroxymethylpyridin-2-yl)amino]acetate to afford the title compound (757 mg) as a white foam. (Yield: 92%)

Mass spectrum (FAB, m/z): 635 (M$^+$+1).

$^1$H-NMR spectrum (CDCl$_3$, δ ppm): 8.61 (ddd, J=4.7, 1.7, 0.9 Hz, 1H), 7.90 (dd, J=2.4, 0.5 Hz, 1H), 7.83 (ddd, J=7.8, 1.6, 0.9 Hz, 1H), 7.78 (ddd, J=7.8, 7.4, 1.7 Hz, 1H), 7.71 (dd, J=1.8, 0.5 Hz, 1H), 7.65 (d, J=8.4 Hz, 1H), 7.60-7.53 (m, 2H), 7.44 (dd, J=8.4, 7.3 Hz, 1H), 7.39 (ddd, J=7.4, 4.7, 1.6 Hz, 1H), 7.36-7.30 (m, 2H), 6.90 (d, J=7.3 Hz, 1H), 6.46 (dd, J=2.4, 1.8 Hz, 1H), 4.74 (s, 2H), 4.48 (s, 2H), 4.45 (s, 2H), 1.52 (s, 9H), 1.42 (s, 9H).

21-(b) (6-{[4-(Pyrazol-1-yl)benzyl](pyridin-2-ylsulfonyl)aminomethyl}pyridin-2-ylamino)acetic Acid Reaction was carried out in the same manner as in Example 19-(b) except for using tert-butyl[tert-butoxycarbonyl(6-{[4-(pyrazol-1-yl)benzyl](pyridin-2-ylsulfonyl)aminomethyl}pyridin-2-yl)amino]acetate (440 mg, 0.611 mmol) obtained in Example 21-(a) in place of tert-butyl[tert-butoxycarbonyl(6-{[4-(pyridin-2-yl)benzyl]-(pyridin-3-yl-sulfonyl)aminomethyl}pyridin-2-yl)amino]acetate. After completion of the reaction, the reaction solution was adjusted to pH 4.5 with a 2N aqueous sodium hydroxide solution, followed by extraction with ethyl acetate. The separated organic layer was dried over anhydrous magnesium sulfate, and then concentrated under reduced pressure. To the resulting residue were added ethyl acetate (4 ml) and diisopropyl ether (16 ml), followed by sonication at 40° C. for 15 minutes. The solvent was distilled off under reduced pressure, and then dried under reduced pressure to afford the title compound (542 mg) as a white foam. (Yield: 97%)

Rf value: 0.48 (n-butanol:acetic acid:water=3:1:1).

Mass spectrum (FAB, m/z): 479 (M$^+$+1).

$^1$H-NMR spectrum (DMSO-d$_5$, δ ppm): 12.41 (brs, 0.8H), 8.65 (ddd, J=4.7, 1.7, 0.9 Hz, 1H), 8.45 (dd, J=2.5, 0.5 Hz, 1H), 7.96 (ddd, J=7.8, 7.7, 1.7 Hz, 1H), 7.82 (ddd, J=7.8, 1.1, 0.9 Hz, 1H), 7.76-7.72 (m, 3H), 7.58 (ddd, J=7.7, 4.7, 1.1 Hz, 1H), 7.37-7.33 (m, 2H), 7.20 (dd, J=8.2, 7.1 Hz, 1H), 6.76 (t, J=5.8 Hz, 1H), 6.54 (dd, J=2.5, 1.8 Hz, 1H), 6.34 (d, J=8.2 Hz, 1H), 6.29 (d, J=7.1 Hz, 1H), 4.72 (s, 2H), 4.24 (s, 2H), 3.83 (d, J=5.8 Hz, 2H).

Example 22

(6-{[4-(5-Methylthiazol-2-yl)benzyl](pyridin-2-ylsulfonyl)aminomethyl}pyridin-2-ylamino)acetic Acid (Exemplified Compound No. 1446)

22-(a) tert-Butyl({6-[(4-bromobenzyl)(pyridin-2-ylsulfonyl)aminomethyl]pyridin-2-yl}tert-butoxycarbonylamino)acetate Reaction and post-treatment were carried out in the same manner as in Example 2-(a) except for using tert-butyl(tert-butoxycarbonyl{6-[(pyridin-2-ylsulfonyl)aminomethyl]pyridin-2-yl}amino)acetate (3.00 g, 6.27 mmol) obtained in Reference Example 14 in place of N-[4-(thiazol-2-yl)benzyl]pyridin-3-ylsulfonamide, and using 4-bromobenzyl alcohol (1.29 g, 6.90 mmol) in place of tert-butyl[tert-butoxycarbonyl(6-hydroxymethylpyridin-2-yl)amino]acetate to afford the title compound (4.16 g) substantially quantitatively as a pale yellow oil.

Mass spectrum (CI, m/z): 647 ($M^+$+1).

$^1$H-NMR spectrum (CDCl$_3$, δ ppm): 8.59 (ddd, J=4.6, 1.6, 1.0 Hz, 1H), 7.83-7.74 (m, 2H), 7.68-7.62 (m, 1H), 7.48-7.32 (m, 4H), 7.15-7.10 (m, 2H), 6.87 (d, J=7.8 Hz, 1H), 4.66 (s, 2H), 4.44 (s, 2H), 4.43 (s, 2H), 1.52 (s, 9H), 1.42 (s, 9H).

22-(b) tert-Butyl[tert-butoxycarbonyl(6-{(pyridin-2-ylsulfonyl)[4-(4,4,5,5-tetramethyl-[1,3,2]dioxaborolan-2-yl)benzyl]aminomethyl}pyridin-2-yl)amino]acetate To a solution of tert-butyl({6-[(4-bromobenzyl)(pyridin-2-ylsulfonyl)aminomethyl]pyridin-2-yl}tert-butoxycarbonylamino)acetate (4.15 g, 6.41 mmol) obtained in Example 22-(a) in 1,4-dioxane (42 ml) were added bis(pinacolato)diboron (2.28 g, 8.98 mmol), 1,1'-bis(diphenylphosphino)ferrocenepalladium chloride.methylene chloride complex (105 mg, 0.129 mmol) and potassium acetate (1.88 g, 19.2 mmol), followed by stirring at 85° C. for 31 hours. After completion of the reaction, water was added to the reaction solution, followed by extraction with ethyl acetate. The separated organic layer was washed with a saturated aqueous sodium chloride solution, dried over anhydrous magnesium sulfate, and then concentrated under reduced pressure. The resulting residue was subjected to silica gel column chromatography (eluent; hexane:ethyl acetate=1:0→7:3 (V/V)), and fractions containing the desired compound were concentrated under reduced pressure to afford the title compound (3.76 g) as a white foam. (Yield: 84%)

Mass spectrum (CI, m/z): 695 ($M^+$+1).

$^1$H-NMR spectrum (CDCl$_3$, δ ppm): 8.59 (ddd, J=4.7, 1.7, 0.9 Hz, 1H), 7.80 (ddd, J=7.7, 1.6, 0.9 Hz, 1H), 7.75 (ddd, J=7.7, 7.3, 1.7 Hz, 1H), 7.71-7.61 (m, 3H), 7.45 (dd, J=8.4, 7.4 Hz, 1H), 7.37 (ddd, J=7.3, 4.7, 1.6 Hz, 1H), 7.25-7.20 (m, 2H), 6.89 (dd, J=7.4, 0.6 Hz, 1H), 4.73 (s, 2H), 4.44 (s, 2H), 4.44 (s, 2H), 1.52 (s, 9H), 1.42 (s, 9H), 1.33 (s, 12H).

22-(c) tert-Butyl[tert-butoxycarbonyl(6-{[4-(5-methylthiazol-2-yl)benzyl](pyridin-2-ylsulfonyl)aminomethyl}pyridin-2-yl)amino]acetate To tert-butyl[tert-butoxycarbonyl(6-{(pyridin-2-ylsulfonyl)[4-(4,4,5,5-tetramethyl-[1,3,2]dioxaborolan-2-yl)benzyl]aminomethyl}pyridin-2-yl)amino]acetate (404 mg) (containing 0.577 mmol of a pure content) obtained in Example 22-(b) were added 2-bromo-5-methylthiazole (212 mg, 1.19 mmol), a mixed solvent (toluene:ethanol=7:3 (V/V), 11.5 ml) and a 2M aqueous sodium carbonate solution (0.58 ml), which was deaerated under reduced pressure, followed by argon substitution. Tetrakis(triphenylphosphine)palladium (66.6 mg, 0.0576 mmol) was then added, followed by stirring at 90° C. for 24 hours under argon atmosphere. After completion of the reaction, water was added to the reaction solution, followed by extraction with toluene. The separated organic layer was washed with a saturated aqueous sodium chloride solution, dried over anhydrous magnesium sulfate, and then concentrated under reduced pressure. The resulting residue was subjected to silica gel column chromatography (eluent; hexane:ethyl acetate=1:0→3:2 (V/V)), and fractions containing the desired compound were concentrated under reduced pressure to afford the title compound (291 mg) as a yellow oil. (Yield: 76%)

Mass spectrum (CI, m/z): 666 ($M^+$+1).

$^1$H-NMR spectrum (CDCl$_3$, δ ppm): 8.59 (ddd, J=4.7, 1.7, 1.0 Hz, 1H), 7.81 (ddd, J=7.9, 1.6, 1.0 Hz, 1H), 7.80-7.72 (m, 3H), 7.65 (d, J=7.8 Hz, 1H), 7.51-7.42 (m, 2H), 7.38 (ddd, J=7.2, 4.7, 1.6 Hz, 1H), 7.32-7.26 (m, 2H), 6.91 (dd, J=7.3, 0.7 Hz, 1H), 4.74 (s, 2H), 4.49 (s, 2H), 4.45 (s, 2H), 2.51 (d, J=1.2 Hz, 3H), 1.52 (s, 9H), 1.42 (s, 9H).

22-(d) (6-{[4-(5-Methylthiazol-2-yl)benzyl](pyridin-2-ylsulfonyl)aminomethyl}pyridin-2-ylamino)acetic Acid Reaction was carried out in the same manner as in Example 19-(b) except for using tert-butyl[tert-butoxycarbonyl(6-{[4-(5-methylthiazol-2-yl)benzyl](pyridin-2-ylsulfonyl)aminomethyl}pyridin-2-yl)amino]acetate (269 mg, 0.404 mmol) obtained in Example 22-(c) in place of tert-butyl[tert-butoxycarbonyl(6-{[4-(pyridin-2-yl)benzyl]-(pyridin-3-ylsulfonyl)aminomethyl}pyridin-2-yl)amino]acetate. After completion of the reaction, water (20 ml) was added to the reaction solution, then it was adjusted to pH 10.9 with a 1N aqueous sodium hydroxide solution, and subsequently insolubles were filtered off. The filtrate was adjusted to pH 5.6 with 1N hydrochloric acid, followed by extraction with ethyl acetate. The separated organic layer was dried over anhydrous magnesium sulfate, and then concentrated under reduced pressure. To the resulting residue were added tert-butyl methyl ether (1 ml) and diisopropyl ether (10 ml), followed by sonication. A precipitated solid was collected by aeration, and then dried under reduced pressure to afford the title compound (113 mg) as a white solid. (Yield: 55%)

Rf value: 0.51 (n-butanol:acetic acid:water=3:1:1).

Mass spectrum (FAB, m/z): 510 ($M^+$+1).

$^1$H-NMR spectrum (DMSO-d$_6$, δ ppm): 8.64 (d, J=3.9 Hz, 1H), 7.95 (ddd, J=7.7, 7.7, 1.6 Hz, 1H), 7.83-7.74 (m, 3H), 7.61-7.54 (m, 2H), 7.38-7.32 (m, 2H), 7.18 (dd, J=8.2, 7.2 Hz, 1H), 6.72 (t, J=5.4 Hz, 0.9H), 6.33 (d, J=8.2 Hz, 1H), 6.28 (d, J=7.2 Hz, 1H), 4.74 (s, 2H), 4.24 (s, 2H), 3.81 (d, J=5.4 Hz, 2H), 2.49 (s, 3H).

Example 23

(6-{[4-(4,5-Dimethylthiazol-2-yl)benzyl](pyridin-2-ylsulfonyl)aminomethyl}pyridin-2-ylamino)acetic Acid (Exemplified Compound No. 1453)

23-(a) tert-Butyl[tert-butoxycarbonyl(6-{[4-(4,5-dimethylthiazol-2-yl)benzyl](pyridin-2-ylsulfonyl)aminomethyl}pyridin-2-yl)amino]acetate Reaction and post-treatment were carried out in the same manner as in Example 22-(c) except for using tert-butyl[tertbutoxycarbonyl(6-{(pyridin-2-ylsulfonyl)[4-(4,4,5,5-tetramethyl-[1,3,2]dioxaborolan-2-yl)benzyl]aminomethyl}pyridin-2-yl)amino]acetate (490 mg, containing 0.700 mmol of a pure content) obtained in Example 22-(b), and using 2-bromo-4,5-dimethylthiazole (282 mg, 1.47 mmol) in place of 2-bromo-5-methylthiazole to afford the title compound (392 mg) as a white foam. (Yield: 82%)

Mass spectrum (FAB, m/z): 678 (M$^-$−1).

$^1$H-NMR spectrum (CDCl$_3$, δ ppm): 8.59 (ddd, J=4.7, 1.7, 0.9 Hz, 1H), 7.81 (ddd, J=7.9, 1.6, 0.9 Hz, 1H), 7.80-7.69 (m, 3H), 7.65 (dd, J=8.4 Hz, 1H), 7.45 (dd, J=8.4, 7.4 Hz, 1H), 7.38 (ddd, J=7.1, 4.7, 1.6 Hz, 1H), 7.28-7.23 (m, 2H), 6.91 (dd, J=7.4, 0.5 Hz, 1H), 4.72 (s, 2H), 4.48 (s, 2H), 4.45 (s, 2H), 2.41-2.36 (m, 6H), 1.52 (s, 9H), 1.42 (s, 9H).

23-(b) (6-{[4-(4,5-Dimethylthiazol-2-yl)benzyl](pyridin-2-ylsulfonyl)aminomethyl}-pyridin-2-ylamino)acetic Acid Reaction and post-treatment were carried out in the same manner as in Example 21-(b) except for using tert-butyl[tert-butoxycarbonyl(6-{[4-(4,5-dimethylthiazol-2-yl)benzyl](pyridin-2-ylsulfonyl)aminomethyl}pyridin-2-yl)amino]acetate (385 mg, 0.566 mmol) obtained in Example 23-(a) in place of tert-butyl[tert-butoxycarbonyl(6-{[4-(pyrazol-1-yl)benzyl](pyridin-2-ylsulfonyl)aminomethyl}pyridin-2-yl)amino]-acetate to afford the title compound (266 mg) as a white solid. (Yield: 90%)

Rf value: 0.51 (n-butanol:acetic acid:water=3:1:1).

Mass spectrum (FAB, m/z): 522 (M$^-$−1).

$^1$H-NMR spectrum (DMSO-d$_6$, δ ppm): 8.64 (ddd, J=4.7, 1.7, 0.9 Hz, 1H), 7.95 (ddd, J=7.8, 7.7, 1.7 Hz, 1H), 7.80 (ddd, J=7.8, 1.1, 0.9 Hz, 1H), 7.77-7.71 (m, 2H), 7.58 (ddd, J=7.7, 4.7, 1.1 Hz, 1H), 7.36-7.30 (m, 2H), 7.18 (dd, J=8.3, 7.0 Hz, 1H), 6.72 (t, J=5.4 Hz, 0.9H), 6.33 (d, J=8.3 Hz, 1H), 6.27 (d, J=7.0 Hz, 1H), 4.73 (s, 2H), 4.23 (s, 2H), 3.80 (d, J=5.4 Hz, 2H), 2.38 (d, J=0.7 Hz, 3H), 2.31 (d, J=0.7 Hz, 3H).

Example 24

(6-{[4-(5-Chlorothiazol-2-yl)benzyl](pyridin-2-ylsulfonyl)aminomethyl}pyridin-2-ylamino)acetic Acid (Exemplified Compound No. 1439)

24-(a) tert-Butyl[tert-butoxycarbonyl(6-{[4-(5-chlorothiazol-2-yl)benzyl](pyridin-2-ylsulfonyl)aminomethyl}pyridin-2-yl)amino]acetate Reaction and post-treatment were carried out in the same manner as in Example 22-(c) except for using tert-butyl[tert-butoxycarbonyl(6-{(pyridin-2-ylsulfonyl)[4-(4,4,5,5-tetramethyl-[1,3,2]dioxaborolan-2-yl)benzyl]aminomethyl}pyridin-2-yl)amino]acetate (404 mg, containing 0.577 mmol of a pure content) obtained in Example 22-(b), and using 2-bromo-5-chlorothiazole (see US2007/300939A) (230 mg, 1.16 mmol) in place of 2-bromo-5-methylthiazole to afford the title compound (277 mg) as an orange foam. (Yield: 70%)

Mass spectrum (CI, m/z): 686 (M$^+$+1).

$^1$H-NMR spectrum (CDCl$_3$, δ ppm): 8.61-8.58 (m, 1H), 7.84-7.62 (m, 6H), 7.47-7.30 (m, 4H), 6.89 (d, J=7.8 Hz, 1H), 4.75 (s, 2H), 4.48 (s, 2H), 4.44 (s, 2H), 1.52 (s, 9H), 1.42 (s, 9H).

24-(b) (6-{[4-(5-Chlorothiazol-2-yl)benzyl](pyridin-2-ylsulfonyl)aminomethyl}pyridin-2-ylamino)acetic Acid Reaction and post-treatment were carried out in the same manner as in Example 22-(d) except for using tert-butyl[tert-butoxycarbonyl(6-{[4-(5-chlorothiazol-2-yl)benzyl](pyridin-2-ylsulfonyl)aminomethyl}pyridin-2-yl)amino]acetate (265 mg, 0.386 mmol) obtained in Example 24-(a) in place of tert-butyl[tert-butoxycarbonyl(6-{[4-(5-methylthiazol-2-yl)benzyl](pyridin-2-ylsulfonyl)aminomethyl}pyridin-2-yl)amino]acetate to afford the title compound (135 mg) as a slightly brown solid. (Yield: 66%)

Rf value: 0.55 (n-butanol:acetic acid:water=3:1:1).

Mass spectrum (FAB, m/z): 530 (M$^+$+1).

$^1$H-NMR spectrum (DMSO-d$_6$, δ ppm): 8.64 (ddd, J=4.7, 1.7, 0.9 Hz, 1H), 7.96 (ddd, J=7.8, 7.7, 1.7 Hz, 1H), 7.95 (s, 1H), 7.83-7.78 (m, 3H), 7.59 (ddd, J=7.7, 4.7, 1.1 Hz, 1H), 7.41-7.37 (m, 2H), 7.18 (dd, J=8.3, 7.0 Hz, 1H), 6.70 (brs, 0.8H), 6.33 (d, J=8.3 Hz, 1H), 6.27 (d, J=7.0 Hz, 1H), 4.75 (s, 2H), 4.24 (s, 2H), 3.79 (d, J=5.3 Hz, 2H).

Example 25

(6-{(Pyridin-2-ylsulfonyl)[4-(4-trifluoromethylthiazol-2-yl)benzyl]aminomethyl}-pyridin-2-ylamino)acetic Acid (Exemplified Compound No. 1024)

25-(a) tert-Butyl[tert-butoxycarbonyl(6-{(pyridin-2-ylsulfonyl)[4-(4-trifluoromethylthiazol-2-yl)benzyl]aminomethyl}pyridin-2-yl)amino]acetate Reaction and post-treatment were carried out in the same manner as in Example 22-(c) except for using tert-butyl[tert-butoxycarbonyl(6-{(pyridin-2-ylsulfonyl)[4-(4,4,5,5-tetramethyl-[1,3,2]dioxaborolan-2-yl)benzyl]aminomethyl}pyridin-2-yl)amino]acetate (490 mg, containing 0.700 mmol of a pure content) obtained in Example 22-(b), and using 2-bromo-4-trifluoromethylthiazole (see WO 2005/077912A) (341 mg, 1.47 mmol) in place of 2-bromo-5-methylthiazole to afford the title compound (454 mg) as a white foam. (Yield: 90%)

Mass spectrum (FAB, m/z): 718 (M$^-$−1).

$^1$H-NMR spectrum (CDCl$_3$, δ ppm): 8.63-8.60 (m, 1H), 7.87-7.82 (m, 3H), 7.79 (ddd, J=7.7, 7.7, 1.8 Hz, 1H), 7.74-7.72 (m, 1H), 7.65 (d, J=7.8 Hz, 1H), 7.47-7.38 (m, 2H), 7.37-7.32 (m, 2H), 6.90 (d, J=7.3 Hz, 1H), 4.76 (s, 2H), 4.47 (s, 2H), 4.44 (s, 2H), 1.52 (s, 9H), 1.42 (s, 9H).

25-(b) (6-{(Pyridin-2-ylsulfonyl)[4-(4-trifluoromethylthiazol-2-yl)benzyl]aminomethyl}pyridin-2-ylamino)acetic Acid Reaction and post-treatment were carried out in the same manlier as in Example 21-(b) except for using tert-butyl[tert-butoxycarbonyl(6-{(pyridin-2-ylsulfonyl)[4-(4-trifluoromethylthiazol-2-yl)benzyl]aminomethyl}pyridin-2-yl)amino]acetate (440 mg, 0.611 mmol) obtained in Example 25-(a) in place of tert-butyl[tert-butoxycarbonyl(6-{[4-(pyrazol-1-yl)benzyl](pyridin-2-ylsulfonyl)aminomethyl}pyridin-2-yl)amino]acetate to afford the title compound (293 mg) as a white solid. (Yield: 85%)

Rf value: 0.58 (n-butanol:acetic acid:water=3:1:1).

Mass spectrum (FAB, m/z): 562 (M$^-$−1).

$^1$H-NMR spectrum (DMSO-d$_6$, δ ppm): 8.65 (ddd, J=4.6, 1.6, 0.9 Hz, 1H), 8.57-8.54 (m, 1H), 7.96 (ddd, J=7.8, 7.7, 1.6 Hz, 1H), 7.93-7.87 (m, 2H), 7.82 (ddd, J=7.8, 1.0, 0.9 Hz, 1H), 7.59 (ddd, J=7.7, 4.6, 1.0 Hz, 1H), 7.46-7.38 (m, 2H), 7.18 (dd, J=8.2, 7.2 Hz, 1H), 6.74 (t, J=5.4 Hz, 0.9H), 6.33 (d, J=8.2 Hz, 1H), 6.28 (d, J=7.2 Hz, 1H), 4.77 (s, 2H), 4.24 (s, 2H), 3.81 (d, J=5.4 Hz, 2H).

Example 26

(6-{(4-Fluorobenzenesulfonyl)[4-(pyrazol-1-yl)benzyl]aminomethyl}pyridin-2-ylamino)acetic Acid (Exemplified Compound No. 856)

26-(a) tert-Butyl[tert-butoxycarbonyl(6-{(4-fluorobenzenesulfonyl)[4-(pyrazol-1-yl)benzyl]aminomethyl}pyridin-2-yl)amino]acetate Reaction and post-treatment were carried out in the same manner as in Example 2-(a) except for using tert-butyl(tert-butoxycarbonyl{6-[(4-fluorobenzenesulfonyl)aminomethyl]pyridin-2-yl}amino)acetate (644 mg, 1.30 mmol) obtained in Reference Example 17 in place of N-[4-(thiazol-2-yl)benzyl]pyridin-3-ylsulfonamide, and using 4-(pyrazol-1-yl)benzyl alcohol (226 mg, 1.30 mmol) in place of tert-butyl [tert-butoxycarbonyl(6-hydroxymethylpyridin-2-yl)amino]acetate to afford the title compound (806 mg) as a white foam. (Yield: 95%)

Mass spectrum (FAB, m/z): 652 ($M^+$+1).
$^1$H-NMR spectrum (CDCl$_3$, δ ppm): 7.91 (dd, J=2.4, 0.7 Hz, 1H), 7.75-7.66 (m, 4H), 7.63-7.56 (m, 2H), 7.49 (dd, J=8.4, 7.5 Hz, 1H), 7.33-7.27 (m, 2H), 7.15-7.05 (m, 2H), 6.83 (d, J=7.5 Hz, 1H), 6.47 (dd, J=2.4, 1.7 Hz, 1H), 4.54 (s, 2H), 4.37 (s, 2H), 4.35 (s, 2H), 1.52 (s, 9H), 1.42 (s, 9H).

26-(b) (6-{(4-Fluorobenzenesulfonyl)[4-(pyrazol-1-yl)benzyl]aminomethyl}pyridin-2-ylamino)acetic Acid Reaction and post-treatment were carried out in the same manner as in Example 21-(b) except for using tert-butyl[tert-butoxycarbonyl(6-{(4-fluorobenzenesulfonyl)[4-(pyrazol-1-yl)benzyl]aminomethyl}pyridin-2-yl)amino]acetate (794 mg, 1.22 mmol) obtained in Example 26-(a) in place of tert-butyl[tert-butoxycarbonyl(6-{[4-(pyrazol-1-yl)benzyl](pyridin-2-ylsulfonyl)aminomethyl}pyridin-2-yl)amino]-acetate to afford the title compound (517 mg) as a white solid. (Yield: 86%)

Rf value: 0.61 (n-butanol:acetic acid:water=3:1:1).
Mass spectrum (FAB, m/z): 496 ($M^+$+1).
$^1$H-NMR spectrum (DMSO-d$_6$, δ ppm): 12.43 (brs, 0.7H), 8.47 (dd, J=2.5, 0.5 Hz, 1H), 7.80-7.73 (m, 5H), 7.38-7.34 (m, 2H), 7.33-7.26 (m, 2H), 7.24 (dd, J=8.3, 7.2 Hz, 1H), 6.80 (t, J=5.8 Hz, 0.9H), 6.54 (dd, J=2.5, 1.8 Hz, 1H), 6.38 (d, J=8.3 Hz, 1H), 6.30 (d, J=7.2 Hz, 1H), 4.62 (s, 2H), 4.15 (s, 2H), 3.76 (d, J=5.8 Hz, 2H).

Example 27

Ethyl(6-{(pyridin-2-ylsulfonyl)[4-(thiazol-2-yl)benzyl]aminomethyl}pyridin-2-ylamino)acetate (Exemplified Compound No. 920)

To tert-butyl[tert-butoxycarbonyl(6-{(pyridin-2-ylsulfonyl)[4-(thiazol-2-yl)benzyl]aminomethyl}pyridin-2-yl)amino]acetate (120 mg, 0.184 mmol) obtained in Example 3-(a) was added a 6M hydrogen chloride/ethanol solution (1 ml), and the mixture was left at room temperature for 16 hours. After completion of the reaction, the reaction solution was concentrated under reduced pressure, and a saturated aqueous sodium hydrogencarbonate solution was added to the residue, followed by extraction with ethyl acetate. The separated organic layer was dried over anhydrous magnesium sulfate, and then concentrated under reduced pressure. The resulting residue was subjected to silica gel column chromatography (eluent; hexane:ethyl acetate=2:1 (V/V)), and fractions containing the desired compound were concentrated under reduced pressure to afford the title compound (81.0 mg) as a colorless oil. (Yield: 84%)

Rf value: 0.58 (ethyl acetate).
Mass spectrum (FAB, m/z): 524 ($M^+$+1).
$^1$H-NMR spectrum (CDCl$_3$, δ ppm): 8.62 (ddd, J=4.8, 1.7, 0.9 Hz, 1H), 7.87-7.82 (m, 4H), 7.77 (ddd, J=7.7, 7.7, 1.7 Hz, 1H), 7.39 (ddd, J=7.7, 4.8, 1.2 Hz, 1H), 7.39-7.35 (m, 2H), 7.33 (d, J=3.3 Hz, 1H), 7.23 (dd, J=8.3, 7.2 Hz, 1H), 6.50 (d, J=7.2 Hz, 1H), 6.23 (d, J=8.3 Hz, 1H), 4.80 (s, 2H), 4.70 (t, J=5.5 Hz, 1H), 4.40 (s, 2H), 4.23 (q, J=7.2 Hz, 2H), 3.95 (d, J=5.5 Hz, 2H), 1.29 (t, J=7.2 Hz, 3H).

Example 28

Isopropyl(6-{(pyridin-2-ylsulfonyl)[4-(thiazol-2-yl)benzyl]aminomethyl}pyridin-2-ylamino)acetate (Exemplified Compound No. 914)

To a solution of tert-butyl[tert-butoxycarbonyl(6-{(pyridin-2-ylsulfonyl)[4-(thiazol-2-yl)benzyl]aminomethyl}pyridin-2-yl)amino]acetate (200 mg, 0.307 mmol) obtained in Example 3-(a) in isopropanol (1.5 ml) was added a 4N hydrogen chloride/-1,4-dioxane solution (1.5 ml), followed by stirring at 40° C. for 9 hours. After completion of the reaction, a saturated aqueous sodium hydrogencarbonate solution was added to the reaction solution, followed by extraction with ethyl acetate. The separated organic layer was dried over anhydrous magnesium sulfate, and then concentrated under reduced pressure. The resulting residue was subjected to silica gel column chromatography (eluent; hexane:ethyl acetate=1:2 (V/V)), and fractions containing the desired compound were concentrated under reduced pressure to afford the title compound (132 mg) (pure content: 118 mg) as a colorless oil. (Yield: 80%)

Rf value: 0.62 (ethyl acetate).
Mass spectrum (FAB, m/z): 538 ($M^+$+1).
$^1$H-NMR spectrum (CDCl$_3$, δ ppm): 8.62 (ddd, J=4.7, 1.8, 0.9 Hz, 1H), 7.87-7.82 (m, 4H), 7.77 (ddd, J=7.7, 7.7, 1.8 Hz, 1H), 7.39 (ddd, J=7.7, 4.7, 1.2 Hz, 1H), 7.39-7.35 (m, 2H), 7.33 (d, J=3.1 Hz, 1H), 7.23 (dd, J=8.2, 7.2 Hz, 1H), 6.49 (d, J=7.2 Hz, 1H), 6.22 (d, J=8.2 Hz, 1H), 5.09 (heptet, J=6.3 Hz, 1H), 4.80 (s, 2H), 4.70 (t, J=5.3 Hz, 1H), 4.40 (s, 2H), 3.91 (d, J=5.3 Hz, 2H), 1.26 (d, J=6.3 Hz, 6H).

Example 29

Hexyl(6-{(pyridin-2-ylsulfonyl)[4-(thiazol-2-yl)benzyl]aminomethyl}pyridin-2-ylamino)acetate (Exemplified Compound No. 1433)

To a solution of (6-{(pyridin-2-ylsulfonyl)[4-(thiazol-2-yl)benzyl]aminomethyl}pyridin-2-ylamino)acetic acid (110 mg, 0.222 mmol) obtained in Example 3-(b) in 1-hexanol (0.83 ml) was added a 4N hydrogen chloride/1,4-dioxane solution (0.83 ml), followed by stirring at room temperature for 16 hours. After completion of the reaction, the reaction solution was concentrated under reduced pressure, and a saturated aqueous sodium hydrogencarbonate solution was added to the residue, followed by extraction with ethyl acetate. The separated organic layer was dried over anhydrous magnesium sulfate, and then concentrated under reduced pressure. The resulting residue was subjected to silica gel column chromatography (eluent; hexane:ethyl acetate=2:1→1:1 (V/V)), and fractions containing the desired compound were concentrated under reduced pressure to afford the title compound (119 mg) as a colorless oil. (Yield: 92%)

Mass spectrum (FAB, m/z): 580 ($M^+$+1).

Rf value: 0.67 (ethyl acetate).

$^1$H-NMR spectrum (CDCl$_3$, δ ppm): 8.62 (ddd, J=4.7, 1.7, 0.8 Hz, 1H), 7.87-7.82 (m, 4H), 7.77 (ddd, J=7.7, 7.7, 1.7 Hz, 1H), 7.39 (ddd, J=7.7, 4.7, 1.2 Hz, 1H), 7.38-7.34 (m, 2H), 7.33 (d, J=3.3 Hz, 1H), 7.23 (dd, J=8.2, 7.2 Hz, 1H), 6.50 (d, J=7.2 Hz, 1H), 6.22 (d, J=8.2 Hz, 1H), 4.80 (s, 2H), 4.70 (t, J=5.4 Hz, 1H), 4.40 (s, 2H), 4.15 (t, J=6.8 Hz, 2H), 3.95 (d, J=5.4 Hz, 2H), 1.68-1.57 (m, 2H), 1.36-1.23 (m, 6H), 0.87 (t, J=7.0 Hz, 3H).

Example 30

Ethyl(6-{[4-(pyrazol-1-yl)benzyl](pyridin-3-ylsulfonyl)aminomethyl}pyridin-2-ylamino)acetate (Exemplified Compound No. 1467)

Reaction was carried out in the same manner as in Example 27 except for using (6-{[4-(pyrazol-1-yl)benzyl](pyridin-3-ylsulfonyl)aminomethyl}pyridin-2-ylamino)acetic acid hydrochloride (21.6 mg, 0.0367 mmol) obtained in Example 7-(b) in place of tert-butyl[tert-butoxycarbonyl(6-{(pyridin-2-ylsulfonyl)[4-(thiazol-2-yl)benzyl]aminomethyl}pyridin-2-yl)amino]acetate. After completion of the reaction, the reaction solution was concentrated under reduced pressure, and a saturated aqueous sodium hydrogencarbonate solution was added to the residue, followed by extraction with ethyl acetate. The separated organic layer was dried over anhydrous magnesium sulfate, and then concentrated under reduced pressure to afford the title compound (17.6 mg) as a colorless oil. (Yield: 95%)

Rf value: 0.32 (ethyl acetate).

Mass spectrum (FAB, m/z): 507 ($M^+$+1).

$^1$H-NMR spectrum (CDCl$_3$, δ ppm): 8.98 (d, J=1.8 Hz, 1H), 8.71 (dd, J=5.0, 1.1 Hz, 1H), 7.97-7.91 (m, 1H), 7.92 (dd, J=2.5, 0.5 Hz, 1H), 7.72 (dd, J=1.8, 0.5 Hz, 1H), 7.66-7.62 (m, 2H), 7.42-7.38 (m, 2H), 7.35-7.26 (m, 2H), 6.47 (dd, J=2.5, 1.8 Hz, 1H), 6.45 (d, J=6.8 Hz, 1H), 6.28 (d, J=8.1 Hz, 1H), 4.78 (brs, 0.8H), 4.64 (s, 2H), 4.32 (s, 2H), 4.22 (q, J=7.1 Hz, 2H), 3.86 (d, J=5.3 Hz, 2H), 1.29 (t, J=7.1 Hz, 3H).

Example 31

Isopropyl(6-{[4-(pyrazol-1-yl)benzyl](pyridin-3-ylsulfonyl)aminomethyl}pyridin-2-ylamino)acetate (Exemplified Compound No. 1473)

Reaction was carried out in the same manner as in Example 29 except for using (6-{[4-(pyrazol-1-yl)benzyl](pyridin-3-ylsulfonyl)aminomethyl}pyridin-2-ylamino)acetic acid hydrochloride (25.8 mg, 0.0439 mmol) obtained in Example 7-(b) in place of (6-{(pyridin-2-ylsulfonyl)[4-(thiazol-2-yl)benzyl]aminomethyl}pyridin-2-ylamino)acetic acid, and using isopropanol (0.20 ml) in place of 1-hexanol. After completion of the reaction, the reaction solution was concentrated under reduced pressure, and a saturated aqueous sodium hydrogencarbonate solution was added to the residue, followed by extraction with ethyl acetate. The separated organic layer was dried over anhydrous magnesium sulfate, and then concentrated under reduced pressure to afford the title compound (20.6 mg) as a colorless oil. (Yield: 90%)

Rf value: 0.39 (ethyl acetate).

Mass spectrum (FAB, m/z): 521 ($M^+$+1).

$^1$H-NMR spectrum (CDCl$_3$, δ ppm): 8.98 (dd, J=2.3, 0.8 Hz, 1H), 8.71 (dd, J=4.9, 1.6 Hz, 1H), 7.95 (ddd, J=8.0, 2.3, 1.6 Hz, 1H), 7.92 (dd, J=2.5, 0.6 Hz, 1H), 7.72 (dd, 0.6 Hz, 1H), 7.66-7.62 (m, 2H), 7.42-7.38 (m, 2H), 7.32 (ddd, J=8.0, 4.9, 0.8 Hz, 1H), 7.28 (dd, 7.0 Hz, 1H), 6.47 (dd, J=2.5, 1.8 Hz, 1H), 6.43 (d, J=7.0 Hz, 1H), 6.27 (d, J=8.1 Hz, 1H), 5.09 (heptet, J=6.3 Hz, 1H), 4.74 (t, J=5.3 Hz, 1H), 4.64 (s, 2H), 4.32 (s, 2H), 3.82 (d, J=5.3 Hz, 2H), 1.26 (d, J=6.3 Hz, 6H).

Compounds used for Examples were synthesized as follows.

Reference Example 1 tert-Butyl[(5-bromo-6-bromomethylpyridin-2-yl)tert-butoxycarbonylamino]acetate 1-(a) tert-Butyl[tert-butoxycarbonyl(6-methylpyridin-2-yl)amino]acetate To a solution of 2-(tert-butoxycarbonylamino)-6-methylpyridine (723 mg, 3.47 mmol) in N,N-dimethylformamide (11.5 ml) was added sodium hydride (mineral oil 55% dispersion) (0.18 g, 4.2 mmol) in portions under ice cooling. After stirring at room temperature for 30 minutes, tert-butyl bromoacetate (0.62 ml, 4.2 mmol) was added dropwise under ice cooling, followed by stirring at room temperature for 2 hours. After completion of the reaction, water was added to the reaction solution, followed by extraction with ethyl acetate. The separated organic layer was washed with a saturated aqueous sodium chloride solution, dried over anhydrous sodium sulfate, and then concentrated under reduced pressure. The resulting residue was subjected to silica gel column chromatography (eluent; hexane:ethyl acetate=10:1→5:1 (V/V)), and fractions containing the desired compound were concentrated under reduced pressure to afford the title compound (1.14 g) substantially quantitatively as a colorless liquid.

Mass spectrum (EI, m/z): 322 ($M^+$).

$^1$H-NMR spectrum (CDCl$_3$, δ ppm): 7.58 (d, J=8.2 Hz, 1H), 7.51 (dd, 7.1 Hz, 1H), 6.86-6.81 (m, 1H), 4.56 (s, 2H), 2.43 (s, 3H), 1.51 (s, 9H), 1.45 (s, 9H).

1-(b) tert-Butyl[(5-bromo-6-methylpyridin-2-yl)tert-butoxycarbonylamino]acetate

To a solution of tert-butyl[tert-butoxycarbonyl(6-methylpyridin-2-yl)amino]-acetate (477 mg, 1.48 mmol) obtained in Reference Example 1-(a) in acetonitrile (3 ml) was added NBS (398 mg, 2.24 mmol), followed by stirring at 40° C. for 3 hours. After completion of the reaction, the reaction solution was concentrated under reduced pressure. The resulting residue was subjected to silica gel column chromatography (eluent; hexane:ethyl acetate=20:1→5:1 (V/V)), and fractions containing the desired compound were concentrated under reduced pressure to afford the title compound (565 mg) as a white solid. (Yield: 95%)

Mass spectrum (EI, m/z): 400 ($M^+$).

$^1$H-NMR spectrum (CDCl$_3$, δ ppm): 7.69 (d, J=8.9 Hz, 1H), 7.56 (d, J=8.9 Hz, 1H), 4.54 (s, 2H), 2.52 (s, 3H), 1.52 (s, 9H), 1.45 (s, 9H).

1-(c) tert-Butyl[(5-bromo-6-bromomethylpyridin-2-yl)tert-butoxycarbonylamino]-acetate To a solution of tert-butyl[(5-bromo-6-methylpyridin-2-yl)tert-butoxycarbonylamino]acetate (560 mg, 1.40 mmol)

obtained in Reference Example 1-(b) in 1,2-dichloroethane (4.7 ml) were added NBS (373 mg, 2.10 mmol) and 2,2'-azobis(2-methylbutyronitrile) (10 mg, 0.052 mmol), followed by stirring at 90° C. for 1 hour. After completion of the reaction, the reaction solution was concentrated under reduced pressure. The resulting residue was subjected to silica gel column chromatography (eluent; hexane:ethyl acetate=20:1→10:1 (V/V)), and fractions containing the desired compound were concentrated under reduced pressure to afford a mixture (355 mg) containing the title compound as a slightly yellow oil. (Yield: 38%)

Mass spectrum (EI, m/z): 478 ($M^+$).

$^1$H-NMR spectrum ($CDCl_3$, δ ppm): 7.75 (s, 2H), 4.58 (s, 2H), 4.56 (s, 2H), 1.52 (s, 9H), 1.47 (s, 9H).

Reference Example 2

N-(6-Phenylpyridazin-3-ylmethyl)pyridin-3-ylsulfonamide 2-(a) 3-Bromomethyl-6-phenylpyridazine To a solution of 3-methyl-6-phenylpyridazine (925 mg, 5.43 mmol) in 1,2-dichloroethane (28 ml) were added NBS (1.07 g, 6.01 mmol) and 2,2'-azobis(2,4-dimethylvaleronitrile) (67.3 mg, 0.271 mmol), followed by stirring at 80° C. for 1 hour. During the reaction, 2,2'-azobis(2,4-dimethylvaleronitrile)(134 mg, 0.540 mmol) was additionally added in two portions. After completion of the reaction, the reaction solution was concentrated under reduced pressure. The resulting residue was subjected to silica gel column chromatography (eluent; hexane:ethyl acetate=5:1→0:1 (V/V)), and fractions containing the desired compound were concentrated under reduced pressure to afford the title compound (449 mg) as a slightly brown solid. (Yield: 33%)

Mass spectrum (CI, m/z): 249 ($M^+$+1).

$^1$H-NMR spectrum ($CDCl_3$, δ ppm): 8.13-8.07 (m; 2H), 7.89 (d, J=8.9 Hz, 1H), 7.72 (d, J=8.9 Hz, 1H), 7.56-7.50 (m, 3H), 4.80 (s, 2H).

2-(b) 3-[Bis(tert-butoxycarbonyl)aminomethyl]-6-phenylpyridazine

To a solution of 3-bromomethyl-6-phenylpyridazine (120 mg, 0.482 mmol) obtained in Reference Example 2-(a) in N,N-dimethylformamide (1.57 ml) were added di-tert-butyl iminodicarboxylate (127 mg, 0.585 mmol) and potassium carbonate (134 mg, 0.970 mmol), followed by stirring at 50° C. for 2 hours. After completion of the reaction, water was added to the reaction solution, followed by extraction with ethyl acetate. The separated organic layer was dried over anhydrous sodium sulfate, and then concentrated under reduced pressure. The resulting residue was subjected to silica gel column chromatography (eluent; hexane:ethyl acetate=2:1→1:1 (V/V)), and fractions containing the desired compound were concentrated under reduced pressure to afford the title compound (180 mg) as a slightly yellow solid. (Yield: 97%)

Mass spectrum (FAB, m/z): 386 ($M^+$+1).

$^1$H-NMR spectrum ($CDCl_3$, δ ppm): 8.10-8.07 (m, 2H), 7.83 (d, J=8.8 Hz, 1H), 7.56-7.49 (m, 3H), 7.44 (d, J=8.8 Hz, 1H), 5.19 (s, 2H), 1.47 (s, 9H), 1.47 (s, 9H).

2-(c) (6-Phenylpyridazin-3-ylmethyl)amine Hydrochloride

To a solution of 3-[bis(tert-butoxycarbonyl)aminomethyl]-6-phenylpyridazine (178 mg, 0.462 mmol) obtained in Reference Example 2-(b) in methylene chloride (2.33 ml) was added a 4N hydrogen chloride/1,4-dioxane solution (2.33 ml, 9.32 mmol), followed by stirring at 30° C. for 1 hour. After completion of the reaction, the reaction solution was concentrated under reduced pressure to afford the title compound (122 mg) substantially quantitatively as a slightly brown solid.

Mass spectrum (CI, m/z): 186 ($M^+$+1).

$^1$H-NMR spectrum ($CD_3OD$, δ ppm): 8.35 (d, J=8.9 Hz, 1H), 8.12-8.07 (m, 2H), 7.96 (d, J=8.9 Hz, 1H), 7.63-7.59 (m, 3H), 4.57 (s, 2H).

2-(d) N-(6-phenylpyridazin-3-ylmethyl)pyridin-3-ylsulfonamide

To a solution of (6-phenylpyridazin-3-ylmethyl)amine hydrochloride (121 mg) (containing 0.458 mmol of a pure content) obtained in Reference Example 2-(c) in methylene chloride (1 ml) were added triethylamine (0.26 ml, 1.8 mmol) and 3-pyridylsulfonyl chloride (see The Journal of Organic Chemistry, 54, 389 (1989)) (83.2 mg, 0.468 mmol), followed by stirring at room temperature for 17 hours. After completion of the reaction, the reaction solution was concentrated under reduced pressure, and water was added to the residue, followed by extraction with ethyl acetate. The separated organic layer was washed with a saturated aqueous sodium chloride solution, dried over anhydrous sodium sulfate, and then concentrated under reduced pressure. The resulting residue was subjected to silica gel column chromatography (eluent; ethyl acetate:acetonitrile=1:0→0:1 (V/V), then chloroform), and fractions containing the desired compound were concentrated under reduced pressure to afford the title compound (130 mg) as a slightly brown solid. (Yield: 87%)

Mass spectrum (CI, m/z): 327 ($M^+$+1).

$^1$H-NMR spectrum ($CDCl_3$, δ ppm): 9.11 (dd, J=2.4, 0.9 Hz, 1H), 8.75 (dd, J=4.8, 1.6 Hz, 1H), 8.19 (ddd, J=8.1, 2.4, 1.6 Hz, 1H), 8.05-8.00 (m, 2H), 7.82 (d, J=8.8 Hz, 1H), 7.56-7.49 (m, 4H), 7.42 (ddd, J=8.1, 4.8, 0.9 Hz, 1H), 6.30 (brs, 1H), 4.57 (s, 2H).

Reference Example 3 tert-Butyl[tert-butoxycarbonyl(6-hydroxymethylpyridin-2-yl)amino]acetate 3-(a) tert-Butyl[tert-butoxycarbonyl(6-ethoxycarbonylpyridin-2-yl)amino]acetate To a solution of sodium hydride (mineral oil 55% dispersion) (15.7 g, 0.360 mol) in N,N-dimethylformamide (362 ml) was added dropwise a solution of ethyl 6-tert-butoxycarbonylaminopyridin-2-carboxylate (see WO 2006/074884A) (81.2 g, 0.305 mol) in N,N-dimethylformamide (300 ml) over 20 minutes under ice cooling in an argon atmosphere, followed by stirring at room temperature for 1 hour. tert-Butyl bromoacetate (54.0 ml, 0.366 mol) was then added dropwise over 10 minutes under ice cooling, followed by further stirring at room temperature for 1 hour. After completion of the reaction, to the reaction solution was added an aqueous solution in which ammonium chloride (1.77 g, 33.0 mmol) was dissolved in water (300 ml), followed by extraction with toluene. The separated organic layer was washed with a saturated aqueous sodium chloride solution, dried over anhydrous magnesium sulfate, and then concentrated under reduced pressure. The resulting residue was subjected to silica gel column chromatography (eluent; hexane:ethyl acetate=9:1→4:1 (V/V)), and fractions containing the desired compound were concentrated under reduced pressure to afford the title compound (108 g) as a pale yellow liquid. (Yield: 93%)

Mass spectrum (CI, m/z): 381 (M$^+$+1).

$^1$H-NMR spectrum (CDCl$_3$, δ ppm): 8.04 (d, J=7.8 Hz, 1H), 7.81 (dd, J=7.6, 1.5 Hz, 1H), 7.76 (dd, J=7.8, 7.6 Hz, 1H), 4.67 (s, 2H), 4.40 (q, J=7.1 Hz, 2H), 1.52 (s, 9H), 1.45 (s, 9H), 1.40 (t, J=7.1 Hz, 3H).

3-(b) tert-Butyl[tert-butoxycarbonyl(6-hydroxymethylpyridin-2-yl)amino]acetate To a solution of tert-butyl[tert-butoxycarbonyl(6-ethoxycarbonylpyridin-2-yl)amino]acetate (98.8 g, 0.260 mol) obtained in Reference Example 3-(a) in ethanol (195 ml), was added dropwise a solution of calcium chloride (34.6 g, 0.312 mol) in ethanol (195 ml) over 20 minutes under ice cooling. A 3M sodium borohydride/tetraethylene glycol dimethyl ether solution (105 ml, 0.315 mol) was then added dropwise over 20 minutes at 35° C. or lower, followed by further stirring at room temperature for 15 minutes. After completion of the reaction, the reaction solution was added dropwise to an aqueous solution of acetic acid (17.8 ml) in water (195 ml) over 10 minutes under ice cooling, followed by stirring at room temperature for 1 hour. Water (315 ml) was then added, followed by extraction with toluene. The separated organic layer was washed with a saturated aqueous sodium hydrogencarbonate solution, water and then a saturated aqueous sodium chloride solution, followed by concentration under reduced pressure. The resulting residue was subjected to silica gel column chromatography (eluent; hexane:ethyl acetate=4:1→3:2 (V/V)), and fractions containing the desired compound were concentrated under reduced pressure to afford the title compound (81.1 g) as a pale yellow liquid. (Yield: 92%)

Mass spectrum (CI, m/z): 339 (M$^+$+1).

$^1$H-NMR spectrum (CDCl$_3$, δ ppm): 7.74 (d, J=8.2 Hz, 1H), 7.63 (dd, J=8.2, 7.4 Hz, 1H), 6.93-6.98 (m, 1H), 4.68-4.65 (m, 2H), 4.54 (s, 2H), 3.39 (t, J=5.3 Hz, 1H), 1.54 (s, 9H), 1.46 (s, 9H).

Reference Example 4

N-[4-(Thiazol-2-yl)benzyl]pyridin-3-ylsulfonamide

4-(a) 4-(Thiazol-2-yl)benzyl Alcohol

To 4-(thiazol-2-yl)benzaldehyde (see JP 2001-519414A) (1.57 g, 8.30 mmol) were added ethanol (20 ml), tetrahydrofuran (0.46 ml), and then sodium borohydride (157 mg, 4.15 mmol), followed by stirring at room temperature for 1.5 hours. After completion of the reaction, water was added to the reaction solution, followed by extraction with ethyl acetate. The separated organic layer was dried over anhydrous sodium sulfate, and then concentrated under reduced pressure. The resulting residue was subjected to silica gel column chromatography (eluent; hexane:ethyl acetate=2:1→1:1 (V/V)), and fractions containing the desired compound were concentrated under reduced pressure to afford the title compound (1.49 g) as a white solid. (Yield: 94%)

Mass spectrum (CI, m/z): 192 (M$^+$+1).

$^1$H-NMR spectrum (CDCl$_3$, δ ppm): 7.94-7.89 (m, 2H), 7.84 (d, J=3.2 Hz, 1H), 7.44-7.38 (m, 2H), 7.32 (d, J=3.2 Hz, 1H), 4.72 (d, J=5.9 Hz, 2H), 2.41 (t, J=5.9 Hz, 1H).

4-(b) 4-(Thiazol-2-yl)benzyl Bromide

To a solution of 4-(thiazol-2-yl)benzyl alcohol (1.31 g, 6.85 mmol) obtained in 4-(a) in tetrahydrofuran (55.8 ml) were added triphenylphosphine (1.80 g, 8.90 mmol) and NBS (1.59 g, 8.93 mmol), followed by stirring at room temperature for 1.5 hours. After completion of the reaction, a saturated aqueous sodium hydrogencarbonate solution was added to the reaction solution, followed by extraction with ethyl acetate. The separated organic layer was washed with a saturated aqueous sodium chloride solution, dried over anhydrous sodium sulfate, and then concentrated under reduced pressure. The resulting residue was subjected to silica gel column chromatography (eluent; hexane:ethyl acetate=2:1 (V/V)), and fractions containing the desired compound were concentrated under reduced pressure to afford the title compound (1.26 g) as a slightly yellow solid. (Yield: 72%)

Mass spectrum (CI, m/z): 254 (M$^+$+1).

$^1$H-NMR spectrum (CDCl$_3$, δ ppm): 7.98-7.92 (m, 2H), 7.88 (d, J=3.3 Hz, 1H), 7.50-7.45 (m, 2H), 7.35 (d, J=3.3 Hz, 1H), 4.52 (s, 2H).

4-(c) 2-{4-[Bis(tert-butoxycarbonyl)aminomethyl]phenyl}thiazole

To a solution of 4-(thiazol-2-yl)benzyl bromide (1.25 g, 4.92 mmol) obtained in Reference Example 4-(b) in N,N-dimethylformamide (16 ml) were added di-tert-butyl iminodicarboxylate (1.28 g, 5.89 mmol) and potassium carbonate (1.35 g, 9.76 mmol), followed by stirring at room temperature for 3 hours. After completion of the reaction, water was added to the reaction solution, followed by extraction with ethyl acetate. The separated organic layer was washed with a saturated aqueous sodium chloride solution, dried over anhydrous sodium sulfate, and then concentrated under reduced pressure. The resulting residue was subjected to silica gel column chromatography (eluent; hexane:ethyl acetate=2:1 (V/V)), and fractions containing the desired compound were concentrated under reduced pressure to afford the title compound (2.05 g) substantially quantitatively as a colorless oil.

$^1$H-NMR spectrum (CDCl$_3$, δ ppm): 7.95-7.89 (m, 2H), 7.85 (d, J=3.4 Hz, 1H), 7.39-7:34 (m, 2H), 7.32 (d, J=3.4 Hz, 1H), 4.81 (s, 2H), 1.46 (s, 9H), 1.46 (s, 9H).

4-(d) 4-(Thiazol-2-yl)benzylamine Hydrochloride

Reaction and post-treatment were carried out in the same manner as in Reference Example 2-(c) except for using 2-{4-[bis(tert-butoxycarbonyl)aminomethyl]-phenyl}thiazole (1.91 g, 4.89 mmol) obtained in Reference Example 4-(c) in place of 3-[bis(tert-butoxycarbonyl)aminomethyl]-6-phenylpyridazine to afford a crude product (1.37 g) containing the title compound substantially quantitatively as a white solid.

$^1$H-NMR spectrum (DMSO-d$_6$, δ ppm): 8.56 (brs, 2H), 8.03-7.97 (m, 2H), 7.95 (d, J=3.2 Hz, 1H), 7.83 (d, J=3.2 Hz, 1H), 7.67-7.60 (m, 2H), 4.12-4.03 (m, 2H).

4-(e) N-[4-(Thiazol-2-yl)benzyl]pyridin-3-ylsulfonamide

Reaction and post-treatment were carried out in the same manner as in Reference Example 2-(d) except for using 3-pyridylsulfonyl chloride (495 mg, 2.79 mmol), and using 4-(thiazol-2-yl)benzylamine hydrochloride (687 mg, 2.61 mmol) obtained in Reference Example 4-(d) in place of (6-phenylpyridazin-3-ylmethyl)amine hydrochloride to afford the title compound (689 mg) as a white solid. (Yield: 80%)

Mass spectrum (CI, m/z): 332 (M$^+$+1).

$^1$H-NMR spectrum (DMSO-d$_6$, δ ppm): 8.92 (d, J=2.4 Hz, 1H), 8.77 (dd, J=4.9, 1.5 Hz, 1H), 8.17-8.12 (m, 1H), 7.91 (d, J=3.1 Hz, 1H), 7.87-7.82 (m, 2H), 7.77 (d, J=3.1 Hz, 1H), 7.61-7.55 (m, 1H), 7.39-7.32 (m, 2H), 4.13 (s, 2H).

Reference Example 5

N-[4-(Thiazol-2-yl)benzyl]pyridin-2-ylsulfonamide

Reaction and post-treatment were carried out in the same manner as in Reference Example 2-(d) except for using 2-pyridylsulfonyl chloride (see Heterocycles, 28, 1115 (1989)) (220 mg, 1.24 mmol) in place of 3-pyridylsulfonyl chloride, and using 4-(thiazol-2-yl)benzylamine hydrochloride (300 mg, 1.14 mmol) obtained in Reference Example 4-(d) in place of (6-phenylpyridazin-3-ylmethyl)amine hydrochloride to afford the title compound (284 mg) as a white solid. (Yield: 75%)

Mass spectrum (CI, m/z): 332 (M$^+$+1).

$^1$H-NMR spectrum (CDCl$_3$, δ ppm): 8.66 (ddd, J=4.6, 1.7, 1.0 Hz, 1H), 7.98 (ddd, J=7.9, 1.2, 1.0 Hz, 1H), 7.91-7.82 (m, 4H), 7.47 (ddd, J=7.6, 4.6, 1.2 Hz, 1H), 7.35-7.30 (m, 3H), 5.59 (t, J=6.5 Hz, 1H), 4.32 (d, J=6.5 Hz, 2H).

Reference Example 6

4-Fluoro-N-[4-(thiazol-2-yl)benzyl]benzenesulfonamide

Reaction and post-treatment were carried out in the same manner as in Reference Example 2-(d) except for using 4-fluorobenzenesulfonyl chloride (278 mg, 1.42 mmol) in place of 3-pyridylsulfonyl chloride, and using 4-(thiazol-2-yl)benzylamine hydrochloride (364 mg, 1.38 mmol) obtained in Reference Example 4-(d) in place of (6-phenylpyridazin-3-ylmethyl)amine hydrochloride to afford the title compound (411 mg) as a slightly yellow solid. (Yield: 85%)

Mass spectrum (CI, m/z): 349 (M$^+$+1).

$^1$H-NMR spectrum (DMSO-d$_6$, δ ppm): 8.29 (brs, 0.8H), 7.91 (d, J=3.2 Hz, 1H), 7.89-7.81 (m, 4H), 7.77 (d, J=3.2 Hz, 1H), 7.45-7.32 (m, 4H), 4.06 (s, 2H).

Reference Example 7

N-[4-(4,5-Dihydrothiazol-2-yl)benzyl]-4-fluorobenzenesulfonamide 7-(a) N-(4-Cyanobenzyl)-4-fluorobenzenesulfonamide Reaction was carried out in the same manner as in a Reference Example 2-(d) except for using 4-fluorobenzenesulfonyl chloride (1.18 g, 6.06 mmol) in place of 3-pyridylsulfonyl chloride, and using 4-cyanobenzylamine hydrochloride (1.00 g, 5.93 mmol) in place of (6-phenylpyridazin-3-ylmethyl)amine hydrochloride. After completion of the reaction, a saturated aqueous sodium chloride solution was added to the reaction solution, followed by extraction with ethyl acetate. The separated organic layer was dried over anhydrous magnesium sulfate, and then concentrated under reduced pressure. To the resulting residue dissolved in a small amount of methylene chloride was added hexane, and a precipitated solid was collected by filtration. The resulting solid was dried under reduced pressure at 60° C. to afford the title compound (1.54 g) as a slightly brown solid. (Yield: 89%)

Mass spectrum (CI, m/z): 291 (M$^+$+1).

$^1$H-NMR spectrum (CDCl$_3$, δ ppm): 7.92-7.83 (m, 2H), 7.62-7.55 (m, 2H), 7.40-7.33 (m, 2H), 7.24-7.15 (m, 2H), 5.07 (t, J=6.5 Hz, 1H), 4.22 (d, J=6.5 Hz, 2H).

7-(b) N-[4-(4,5-Dihydrothiazol-2-yl)benzyl]-4-fluorobenzenesulfonamide

To a solution of N-(4-cyanobenzyl)-4-fluorobenzenesulfonamide (1.23 g, 4.24 mmol) obtained in Reference Example 7-(a) in ethanol (5 ml) was added 2-aminoethanethiol (0.426 g, 5.52 mmol), which was deaerated under reduced pressure, followed by argon substitution. This reaction mixture was then heated to reflux for 6 hours. After completion of the reaction, a saturated aqueous sodium chloride solution was added to the reaction solution, followed by extraction with ethyl acetate. The separated organic layer was dried over anhydrous magnesium sulfate, and then concentrated under reduced pressure. The resulting residue was subjected to silica gel column chromatography (eluent; chloroform:ethyl acetate=7:3 (V/V)), and fractions containing the desired compound were concentrated under reduced pressure to afford the title compound (1.32 g) as a white solid. (Yield: 89%)

Mass spectrum (CI, m/z): 351 (M$^+$+1).

$^1$H-NMR spectrum (CDCl$_3$, δ ppm): 7.91-7.83 (m, 2H), 7.77-7.71 (m, 2H), 7.25-7.13 (m, 4H), 4.82 (t, J=6.2 Hz, 1H), 4.45 (t, J=8.4 Hz, 2H), 4.20 (d, J=6.2 Hz, 2H), 3.42 (t, J=8.4 Hz, 2H).

Reference Example 8

N-(Biphenyl-4-ylmethyl)pyridin-3-ylsulfonamide

Reaction was carried out in the same manner as in Reference Example 2-(d) except for using 3-pyridylsulfonyl chloride (890 mg, 5.01 mmol), and using (biphenyl-4-ylmethyl)amine (1.01 g, 5.51 mmol) in place of (6-phenylpyridazin-3-ylmethyl)amine hydrochloride. After completion of the reaction, water was added to the reaction solution, followed by extraction with ethyl acetate. The separated organic layer was washed with a saturated aqueous sodium chloride solution, dried over anhydrous sodium sulfate, and then concentrated under reduced pressure. The resulting residue was subjected to silica gel column chromatography (eluent; hexane:ethyl acetate=1:1 (V/V)→chloroform:ethyl acetate=1:1 (V/V)→ethyl acetate), and fractions containing the desired compound were concentrated under reduced pressure. To the resulting crude product were added methylene chloride (5 ml) and diisopropyl ether (10 ml), followed by being left for 1 hour. A precipitated solid was collected by filtration, and dried under reduced pressure at 35° C. to afford the title compound (1.49 g) as a white solid. (Yield: 92%)

Mass spectrum (CI, m/z): 325 (M$^+$+1).

$^1$H-NMR spectrum (CDCl$_3$, δ ppm): 9.09 (dd, J=2.3, 0.7 Hz, 1H), 8.78 (dd, J=4.9, 1.7 Hz, 1H), 8.10 (ddd, J=8.1, 2.3, 1.7 Hz, 1H), 7.57-7.31 (m, 8H), 7.29-7.23 (m, 2H), 4.96 (t, J=5.9 Hz, 1H), 4.27 (d, J=5.9 Hz, 2H).

Reference Example 9

N-[4-(Pyrazol-1-yl)benzyl]pyridin-3-ylsulfonamide 9-(a) 4-(Pyrazol-1-yl)benzylamine To 4-(pyrazol-1-yl)benzonitrile (see WO 2005/095343A) (1.46 g, 8.63 mmol) was added a solution of 1M borane.tetrahydrofuran complex in tetrahydrofuran (93 ml, 93 mmol), followed by heating to reflux for 16 hours. After completion of the reaction, methanol (14 ml) was added to the reaction solution, followed by concentration under reduced pressure. 6N Hydrochloric acid (265 ml) was added to the residue, followed by further heating to reflux for 3 hours. After this solution was concentrated under reduced pressure, a small amount of water was added. The resulting solution was adjusted to pH 11 with a 30% aqueous sodium hydroxide solution under ice cooling, followed by extraction with methylene chloride. The separated organic layer was dried over anhydrous sodium sulfate, and then concentrated under reduced pressure. The resulting residue was subjected to silica gel column chromatography (eluent; chloroform:methanol:28% aqueous ammonia=90:10:1 (V/V/V)), and fractions containing the desired compound were concentrated under reduced pressure to afford the title compound (1.24 g) as a pale yellow solid. (Yield: 83%)

Mass spectrum (CI, m/z): 174 ($M^+$+1).

$^1$H-NMR spectrum (CDCl$_3$, δ ppm): 7.91 (dd, J=2.5, 0.5 Hz, 1H), 7.72 (d, J=1.6 Hz, 1H), 7.69-7.63 (m, 2H), 7.44-7.37 (m, 2H), 6.46 (dd, J=2.5, 1.6 Hz, 1H), 3.91 (s, 2H).

9-(b) N-[4-(Pyrazol-1-yl)benzyl]pyridin-3-ylsulfonamide

Reaction and post-treatment were carried out in the same manner as in Reference Example 2-(d) except for using 3-pyridylsulfonyl chloride (150 mg, 0.845 mmol), and using 4-(pyrazol-1-yl)benzylamine (133 mg, 0.767 mmol) obtained in Reference Example 9-(a) in place of (6-phenylpyridazin-3-ylmethyl)amine hydrochloride to afford the title compound (186 mg) as a white solid. (Yield: 77%)

Mass spectrum (CI, m/z): 315 ($M^+$+1).

$^1$H-NMR spectrum (CDCl$_3$, δ ppm): 8.98 (dd, J=2.4, 0.9 Hz, 1H), 8.78 (dd, J=4.9, 1.7 Hz, 1H), 8.10 (ddd, J=8.0, 2.4, 1.7 Hz, 1H), 7.88 (dd, J=2.5, 0.5 Hz, 1H), 7.70 (dd, J=1.8, 0.5 Hz, 1H), 7.61-7.55 (m, 2H), 7.42 (1H, ddd, J=8.0, 4.9, 0.9 Hz, 1H), 7.30-7.24 (m, 2H), 6.46 (dd, J=2.5, 1.8 Hz, 1H), 5.72 (t, J=6.0 Hz, 1H), 4.23 (d, J=6.0 Hz, 2H).

Reference Example 10

N-(Benzofuran-2-ylmethyl)pyridin-3-ylsulfonamide 10-(a) 2-Benzofuran Carbaldehyde Oxime To a solution of 2-benzofuran carbaldehyde (1.00 g, 6.85 mmol) in methanol (20 ml) were added hydroxylammonium chloride (530 mg, 7.63 mmol) and pyridine (2.8 ml), followed by stirring at room temperature for 6.5 hours. After completion of the reaction, the reaction solution was concentrated under reduced pressure. Ethyl acetate was added to the resulting residue, followed by washing sequentially with a 5% aqueous potassium hydrogensulfate solution, a saturated aqueous sodium hydrogen carbonate solution and then a saturated aqueous sodium chloride solution. The resulting organic layer was dried over anhydrous magnesium sulfate, and then concentrated under reduced pressure to afford the title compound (1.07 g) as a white solid. (Yield: 97%)

$^1$H-NMR spectrum (CDCl$_3$, δ ppm): 8.47 & 7.81 (brs, total 1H), 8.14 & 7.67 (s, total 1H), 7.69 & 6.96 (d, J=0.9 Hz, total 1H), 7.67 & 7.60 (ddd, J=7.7, 1.2, 0.9 Hz, total 1H), 7.55-7.49 (m, 1H), 7.43-7.22 (m, 2H).

10-(b) (Benzofuran-2-ylmethyl)amine

To a solution of 2-benzofuran carbaldehyde oxime (1.07 g, 6.64 mmol) obtained in Reference Example 10-(a) in ethanol (30 ml) was added 10% palladium-active carbon (50% hydrate) (0.75 g), followed by stirring at room temperature for 4.5 hours under hydrogen atmosphere at 1 atm. After completion of the reaction, insolubles were filtered off, and the filtrate was concentrated under reduced pressure. The resulting residue was subjected to silica gel column chromatography (eluent; chloroform:methanol:28% aqueous ammonia=190:10:1 (V/V/V)), and fractions containing the desired compound were concentrated under reduced pressure to afford the title compound (0.21 g) as a pale yellow oil. (Yield: 21%)

Mass spectrum (CI, m/z): 147 ($M^+$).

$^1$H-NMR spectrum (CDCl$_3$, δ ppm): 7.54-7.49 (m, 1H), 7.46-7.41 (m, 1H), 7.28-7.16 (m, 2H), 6.54-6.51 (m, 1H), 3.98 (d, J=0.8 Hz, 2H).

10-(c) N-(Benzofuran-2-ylmethyl)pyridin-3-ylsulfonamide

Reaction and post-treatment were carried out in the same manner as in Reference Example 2-(d) except for using 3-pyridylsulfonyl chloride (154 mg, 0.867 mmol), and using (benzofuran-2-ylmethyl)amine (128 mg, 0.870 mmol) obtained in Reference Example 10-(b) in place of (6-phenylpyridazin-3-ylmethyl)amine hydrochloride to afford the title compound (239 mg) as a white solid. (Yield: 96%)

$^1$H-NMR spectrum (DMSO-d$_6$, δ ppm): 8.92 (d, J=1.8 Hz, 1H), 8.67 (dd, J=5.1, 1.7 Hz, 1H), 8.13 (ddd, J=8.0, 1.8, 1.7 Hz, 1H), 7.56-7.45 (m, 2H), 7.35 (d, J=8.0 Hz, 1H), 7.29-7.14 (m, 2H), 6.67 (s, 1H), 4.30 (s, 2H).

Reference Example 11

N-(4-Bromobenzyl)pyridin-3-ylsulfonamide

Reaction and post-treatment were carried out in the same manner as in Reference Example 2-(d) except for using 3-pyridylsulfonyl chloride (300 mg, 1.69 mmol), and using 4-bromobenzylamine hydrochloride (342 mg, 1.54 mmol) in place of (6-phenylpyridazin-3-ylmethyl)amine hydrochloride to afford the title compound (422 mg) as a white solid. (Yield: 84%)

Mass spectrum (CI, m/z): 327 ($M^+$+1).

$^1$H-NMR spectrum (CDCl$_3$, δ ppm): 9.05 (dd, J=2.3, 0.7 Hz, 1H), 8.79 (dd, J=4.9, 1.7 Hz, 1H), 8.07 (ddd, J=8.0, 2.3, 1.7 Hz, 1H), 7.46-7.37 (m, 3H), 7.11-7.05 (m, 2H), 5.09 (t, J=5.9 Hz, 1H), 4.18 (d, J=5.9 Hz, 2H).

Reference Example 12 tert-Butyl(tert-butoxycarbonyl{6-[(pyridin-3-ylsulfonyl)aminomethyl]pyridin-2-yl}-amino)acetate 12-(a) tert-Butyl[tert-butoxycarbonyl(6-formylpyridin-2-yl)amino]acetate To a solution of Dess-martin reagent (12.9 g, 30.4 mmol) in methylene chloride (130 ml) was added dropwise a solution of tert-butyl[tert-butoxycarbonyl(6-hydroxymethylpyridin-2-yl)amino]acetate (10.0 g, 29.6 mmol) obtained in Reference Example 3-(b) in methylene chloride (50 ml) over 20 minutes under ice cooling in argon atmosphere. After completion of the dropwise addition, the mixture was stirred at room temperature for 2 hours. After completion of the reaction, a 0.1% aqueous sodium thiosulfate solution (305 ml) was added to the reaction solution, followed by extraction with methylene chloride. The separated organic layer was washed sequentially with a 0.5N aqueous sodium hydroxide solution and a saturated aqueous sodium chloride solution, dried over anhydrous magnesium sulfate, and then concentrated under reduced pressure to afford the title compound (9.61 g) substantially quantitatively as a slightly yellow oil.

Mass spectrum (CI, m/z): 336 ($M^+$).

$^1$H-NMR spectrum (DMSO-$d_6$, δ ppm): 9.82 (s, 1H), 8.11-7.99 (m, 2H), 7.68 (dd, J=6:6, 1.5 Hz, 1H), 4.58 (s, 2H), 1.48 (s, 9H), 1.42 (s, 9H).

12-(b) tert-Butyl[tert-butoxycarbonyl(6-hydroxyiminomethylpyridin-2-yl)amino]-acetate To a solution of tert-butyl[tert-butoxycarbonyl(6-formylpyridin-2-yl)amino]-acetate (2.88 g, 8.56 mmol) obtained in Reference Example 12-(a) in methanol (28.5 ml) were added hydroxylammonium chloride (0.650 g, 9.35 mmol) and pyridine (3.5 ml), followed by stirring at room temperature for 1 hour. After completion of the reaction, the reaction solution was concentrated under reduced pressure. Ethyl acetate was added to the concentrate, which was washed sequentially with a 5% aqueous potassium hydrogensulfate solution, a saturated aqueous sodium hydrogencarbonate solution and a saturated aqueous sodium chloride solution, then dried over anhydrous magnesium sulfate, and subsequently concentrated under reduced pressure. The resulting residue was subjected to silica gel column chromatography (eluent; hexane:ethyl acetate=3:2 (V/V)), and fractions containing the desired compound were concentrated under reduced pressure to afford the title compound (2.76 g) as a colorless oil. (Yield: 92%)

Mass spectrum (EI, m/z): 351 ($M^+$).

$^1$H-NMR spectrum (CDCl$_3$, δ ppm): 8.06 (s, 1H), 7.91 (s, 1H), 7.85 (d, J=8.2 Hz, 1H), 7.65 (dd, J=8.2, 7.6 Hz, 1H), 7.47 (dd, J=7.6, 0.7 Hz, 1H), 4.59 (s, 2H), 1.53 (s, 9H), 1.45 (s, 9H).

12-(c) tert-Butyl[(6-aminomethylpyridin-2-yl)tert-butoxycarbonylamino]acetate To a solution of tert-butyl[tert-butoxycarbonyl(6-hydroxyiminomethylpyridin-2-yl)amino]acetate (2.75 g, 7.83 mmol) obtained in Reference Example 12-(b) in ethanol (49 ml) was added 10% palladium-active carbon (50% hydrate) (0.98 g), followed by stirring at room temperature for 1 hour under hydrogen atmosphere at 1 atm. After completion of the reaction, insolubles were filtered off, and the filtrate was concentrated under reduced pressure to afford the title compound (2.48 g) as a colorless oil. (Yield: 94%)

Mass spectrum (CI, m/z): 338 ($M^+$+1).

$^1$H-NMR spectrum (CDCl$_3$, δ ppm): 7.68 (d, J=8.3 Hz, 1H), 7.58 (dd, J=8.3, 7.4 Hz, 1H), 6.91 (d, J=7.4 Hz, 1H), 4.57 (s, 2H), 3.85 (s, 2H), 1.53 (s, 9H), 1.46 (s, 9H).

12-(d) tert-Butyl(tert-butoxycarbonyl{6-[(pyridin-3-ylsulfonyl)aminomethyl]pyridin-2-yl}amino)acetate To a solution of 3-pyridylsulfonyl chloride (640 mg, 3.60 mmol) in methylene chloride (14 ml) were added tert-butyl [(6-aminomethylpyridin-2-yl)tert-butoxycarbonylamino]acetate (1.20 g, 3.56 mmol) obtained in Reference Example 12-(c) and triethylamine (2.24 ml, 16.2 mmol), followed by stirring at room temperature for 1 hour. After completion of the reaction, a 5% aqueous potassium hydrogensulfate solution was added to the reaction solution, followed by extraction with chloroform. The separated organic layer was washed sequentially with a saturated aqueous sodium hydrogencarbonate solution and a saturated aqueous sodium chloride solution, dried over anhydrous magnesium sulfate, and then concentrated under reduced pressure. The resulting residue was subjected to silica gel column chromatography (eluent; hexane:ethyl acetate=1:1→1:2 (V/V)), and fractions containing the desired compound were concentrated under reduced pressure to afford the title compound (1.45 g) as a colorless oil. (Yield: 85%)

Mass spectrum (CI, m/z): 479 ($M^+$+1).

$^1$H-NMR spectrum (CDCl$_3$, δ ppm): 9.06 (d, J=2.2 Hz, 1H), 8.71 (dd, J=4.6, 1.5 Hz, 1H), 8.13-8.08 (m, 1H), 7.68 (d, J=8.2 Hz, 1H), 7.52 (dd, J=8.2, 7.4 Hz, 1H), 7.38-7.32 (m, 1H), 6.77 (d, J=7.4 Hz, 1H), 5.80 (t, J=5.1 Hz, 1H), 4.40 (s, 2H), 4.24 (d, J=5.1 Hz, 2H), 1.53 (s, 9H), 1.46 (s, 9H).

Reference Example 13

4-(Pyridazin-4-yl)benzyl alcohol

To a solution of 4-bromopyridazine (131 mg, 0.824 mmol) in 1,2-dimethoxyethane (16.4 ml) were added 4-hydroxymethylphenylboronic acid (189 mg, 1.24 mmol), potassium carbonate (517 mg, 3.74 mmol) and water (8.2 ml), which was deaerated under reduced pressure, followed by argon substitution. Tetrakis(triphenylphosphine)palladium (73.5 mg, 0.0636 mmol) was then added, followed by heating to reflux for 5 hours under argon atmosphere. After completion of the reaction, the reaction solution was concentrated under reduced pressure. The resulting residue was subjected to reversed phase column chromatography (column; Megabond Elut™ C18 (manufactured by Varian, Inc.), eluent; acetonitrile:water=0:1→1:4 (V/V), then methanol), and fractions containing the desired compound were concentrated under reduced pressure to afford the title compound (97.7 mg) as a slightly brown solid. (Yield: 64%)

Mass spectrum (CI, m/z): 187 ($M^+$+1).

$^1$H-NMR spectrum (CD$_3$OD, δ ppm): 9.55 (dd, J=2.4, 1.2 Hz, 1H), 9.19 (dd, J=5.5, 1.2 Hz, 1H), 8.01 (dd, J=5.5, 2.4 Hz, 1H), 7.88-7.83 (m, 2H), 7.60-7.54 (m, 2H), 4.70 (s, 2H).

Reference Example 14 tert-Butyl(tert-butoxycarbonyl{6-[(pyridin-2-ylsulfonyl)aminomethyl]pyridin-2-yl}-amino)acetate Reaction and post-treatment were carried out in the same manner as in Reference Example 12-(d) except for using tert-butyl[(6-aminomethylpyridin-2-yl)tert-butoxycarbonylamino]acetate (1.20 g, 3.56 mmol) obtained in Reference Example 12-(c), and using 2-pyridylsulfonyl chloride (640 mg, 3.60 mmol) in place of 3-pyridylsulfonyl chloride to afford the title compound (1.46 g) as a white solid. (Yield: 86%)

Mass spectrum (APCI, m/z): 479 ($M^+$+1).

$^1$H-NMR spectrum (CDCl$_3$, δ ppm): 8.56 (ddd, J=4.7, 1.7, 0.9 Hz, 1H), 7.97 (ddd, J=7.8, 1.1, 0.9 Hz, 1H), 7.84 (ddd, J=7.8, 7.7, 1.7 Hz, 1H), 7.68 (d, J=8.4 Hz, 1H), 7.52 (dd, J=8.4, 7.4 Hz, 1H), 7.40 (ddd, J=7.7, 4.7, 1.1 Hz, 1H), 6.84 (dd, J=7.4, 0.5 Hz, 1H), 5.86 (t, J=5.6 Hz, 1H), 4.48 (s, 2H), 4.36 (d, J=5.6 Hz, 2H), 1.53 (s, 9H), 1.45 (s, 9H).

Reference Example 15

4-(Thiazol-4-yl)benzyl Alcohol

15-(a) 4-(Thiazol-4-yl)benzaldehyde

To a solution of 4-bromothiazole (see The Journal of Organic Chemistry, 71, 3754 (2006)) (1.31 g, 7.98 mmol) in 1,2-dimethoxyethane (38.0 ml) were added 4-formylphenylboronic acid (1.45 g, 9.67 mmol), sodium hydrogencarbonate (2.00 g, 23.8 mmol) and water (19 ml), which was deaerated under reduced pressure, followed by argon substitution. Tetrakis(triphenylphosphine)palladium (270 mg, 0.234 mmol) was then added, followed by heating to reflux for 16 hours under argon atmosphere. After completion of the reaction, a saturated aqueous sodium chloride solution was added to the reaction solution, followed by extraction with chloroform. The separated organic layer was dried over anhydrous magnesium sulfate, and then concentrated under reduced pressure. The resulting residue was subjected to silica gel column chromatography (eluent; hexane:ethyl acetate-4:1 (V/V)), and fractions containing the desired compound were concentrated under reduced pressure to afford the title compound (1.29 g) as a slightly yellow solid. (Yield: 85%)

Mass spectrum (CI, m/z): 190 ($M^+$+1).

$^1$H-NMR spectrum (CDCl$_3$, δ ppm): 10.05 (s, 1H), 8.93 (d, J=2.0 Hz, 1H), 8.14-8.10 (m, 2H), 7.99-7.94 (m, 2H), 7.73 (d, J=2.0 Hz, 1H).

15-(b) 4-(Thiazol-4-yl)benzyl Alcohol

Reaction and post-treatment were carried out in the same manner as in Reference Example 4-(a) except for using 4-(thiazol-4-yl)benzaldehyde (1.28 g, 6:76 mmol) obtained in Reference Example 15-(a) in place of 4-(thiazol-2-yl)benzaldehyde to afford the title compound (1.07 g) as a white solid. (Yield: 83%)

Mass spectrum (CI, m/z): 192 ($M^+$+1).

$^1$H-NMR spectrum (CDCl$_3$, δ ppm): 8.88 (d, J=2.0 Hz, 1H), 7.95-7.90 (m, 2H), 7.54 (d, J=2.0 Hz, 1H), 7.46-7.41 (m, 2H), 4.74 (d, J=5.9 Hz, 2H), 1.85 (t, J=5.9 Hz, 1H).

Reference Example 16

4-(Pyrimidin-2-yl)benzyl Alcohol

Reaction and post-treatment were carried out in the same manlier as in Reference Example 13 except for using 4-hydroxymethylphenylboronic acid (144 mg, 0.948 mmol), and using 2-bromopyrimidine (101 mg, 0.635 mmol) in place of 4-bromopyridazine to afford the title compound (119 mg) substantially quantitatively as a slightly yellow solid.

Mass spectrum (CI, m/z): 187 ($M^+$+1).

$^1$H-NMR spectrum (CDCl$_3$, δ ppm): 8.81 (d, J=4.7 Hz, 2H), 8.47-8.42 (m, 2H), 7.52-7.47 (m, 2H), 7.19 (t, J=4.7 Hz, 1H), 4.79 (d, J=6.0 Hz, 2H), 1.75 (t, J=6.0 Hz, 1H).

Reference Example 17 tert-Butyl(tert-butoxycarbonyl{6-[(4-fluorobenzenesulfonyl)aminomethyl]pyridin-2-yl}amino)acetate Reaction and post-treatment were carried out in the same manner as in Reference Example 12-(d) except for using tert-butyl[(6-aminomethylpyridin-2-yl)tert-butoxycarbonylamino]acetate (7.00 g, 20.7 mmol) obtained in Reference Example 12-(c), and using 4-fluorobenzenesulfonyl chloride (4.00 g, 20.6 mmol) in place of 3-pyridylsulfonyl chloride to afford the title compound (4.91 g) as a white solid. (Yield: 48%)

Mass spectrum (FAB, m/z): 496 ($M^+$+1).

$^1$H-NMR spectrum (CDCl$_3$, δ ppm): 7.90-7.81 (m, 2H), 7.69 (d, J=8.3 Hz, 1H), 7.52 (dd, J=8.3, 7.4 Hz, 1H), 7.14-7.05 (m, 2H), 6.76 (dd, J=7.4, 0.6 Hz, 1H), 5.60 (t, J=5.3 Hz, 0.9H), 4.42 (s, 2H), 4.18 (d, J=5.3 Hz, 2H), 1.53 (s, 9H), 1.46 (s, 9H).

Test Example 1

Measurement of EP2 Receptor Binding Affinity

Measurement of EP2 receptor binding affinity was carried out according to the method of Abramovitz et al. (Biochimica et Biophysica Acta, 1483, 285 (2000)). A test compound dissolved in dimethylsulfoxide and [$^3$H]PGE$_2$ (NET-428, available from PerkinElmer Inc.) (final concentration: 10 nM) were added to a buffer solution (10 mM MES-KOH (pH 6.0), 10 mM MgCl$_2$, 1 mM EDTA) in which 10 μg of a membrane fraction (ES-562-M, available from Euroscreen S.A.) of HEK293 cells expressing human EP2 receptor had been suspended, followed by incubation at 30° C. for 60 minutes. The membrane fraction was recovered on glass fiber filter paper (GF/B, available from Whatman PLC) using a cell harvester (M30R, available from Brandel Inc.), and after washing with a buffer solution (10 mM MES-KOH (pH 6.0), 10 mM MgCl$_2$), radioactivity was measured with a liquid scintillation analyzer (2000CA, available from Packard). The concentration (IC$_{50}$ value) of the test compound necessary for substituting 50% of the [$^3$H]PGE$_2$ bound to the receptor was calculated by using EXSAS (version 7.1.6, available from Arm Systex Co., Ltd.), and the inhibition constant (Ki value) was obtained from the following formula. The dissociation constant (Kd value) was calculated by Scatchard analysis.

$$Ki=IC_{50}/(1+([^3H]PGE_2 \text{ concentration}/Kd))$$

The test results are shown in Table 2. Incidentally, Compound A shown in the table is a sodium salt of {3-[(4-tert-butylbenzyl)(pyridin-3-ylsulfonyl)aminomethyl]phenoxy}-acetic acid (CP-533,536), which is a compound of Example 14e of WO 99/19300A, and is a control compound having EP2 receptor binding affinity.

TABLE 2

| Test compound Example No. | Ki value of EP2 receptor binding affinity (nM) |
|---|---|
| Example 3 | 1.9 |
| Example 4 | 2.8 |
| Example 5 | 7.0 |
| Example 6 | 3.8 |
| Example 9 | 4.4 |
| Example 11 | 3.8 |
| Example 12 | 1.1 |
| Example 13 | 13 |
| Example 15 | 9.4 |
| Example 16 | 3.1 |
| Example 17 | 1.5 |
| Example 18 | 9.2 |
| Compound A | 16 |

In this test, compounds of the present invention showed excellent EP2 receptor binding affinity as compared with the control compound.

Test Example 2

Measurement of EP2 Agonist Activity

Measurement of EP2 agonist activity was carried out according to the method of Wilson et al. (European Journal of Pharmacology, 501, 49 (2004)). HEK 293 cells (ES-562-C, available from Euroscreen S.A.) expressed human EP2 receptor were cultured in a MEM medium containing 10% FBS and seeded at $2\times10^4$ cells per each well of a 96-well plate. On the next day, the medium was replaced with serum-free MEM medium containing 3-isobutyl-1-methylxanthine (final concentration: 500 μM) and after culturing for 30 minutes, a test compound dissolved in dimethylsulfoxide was added followed by allowing to stand undisturbed in a carbon dioxide gas incubator. After 30 minutes, an amount of cAMP in the cells was measured with a cAMP Biotrak EIA System kit (available from GE Healthcare Bioscience). The concentration ($EC_{50}$ value) of the test compound necessary for increasing the amount of cAMP to 50% of the maximum increased amount was calculated by non-linear regression of the concentration of the test compound and the amount of cAMP using EXSAS.

The test results are shown in Table 3.

TABLE 3

| Test compound Example No. | $EC_{50}$ value of EP2 agonist activity (nM) |
|---|---|
| Example 3 | 0.45 |
| Example 4 | 0.29 |
| Example 5 | 1.8 |
| Example 6 | 2.0 |
| Example 7 | 2.8 |
| Example 8 | 5.6 |
| Example 11 | 0.42 |
| Example 12 | 0.49 |
| Example 13 | 3.4 |
| Example 15 | 0.96 |
| Example 16 | 0.62 |
| Example 17 | 1.8 |
| Example 18 | 5.0 |
| Example 19 | 2.0 |
| Example 21 | 1.1 |
| Example 25 | 7.9 |
| Example 26 | 0.78 |
| Compound A | 17 |

In this test, compounds of the present invention showed excellent EP2 agonist activity as compared with the control compound.

Test Example 3

Measurement of $PGE_2$ Receptor Selectivity

With regard to EP3 and EP4 receptors, measurements of receptor binding affinity were carried out according to the following methods in the same manner as in Test example 1.

1) Measurement of EP3 Receptor Binding Affinity

Measurement of EP3 receptor binding affinity was carried out according to the method described in the data sheet of Millipore Corp. The test compound dissolved in dimethylsulfoxide and $[^3H]PGE_2$ (NET-428, available from PerkinElmer Inc.) (final concentration: 2 nM) were added to a buffer solution (50 mM Tris-HCl (pH 7.4), 10 mM $MgCl_2$, 1 mM EDTA) in which 10 μg of a membrane fraction (HTS092M, available from Millipore Corp.) of Chem-1 cells expressing human EP3 receptor had been-suspended, followed by incubation at 30° C. for 60 minutes. The membrane fraction was recovered on glass fiber filter paper (GF/B, available from Whatman PLC) pretreated with 0.3% polyethyleneimine by using a cell harvester (M30R, available from Brandel Inc.), and after washing with a buffer solution (50 mM Tris-HCl (pH 7.4)), radioactivity was measured with a liquid scintillation analyzer (2000CA, available from Packard). A concentration ($IC_{50}$ value) of the test compound necessary for substituting 50% of the $[^3H]PGE_2$ bound to the receptor was calculated by using EXSAS (version 7.1.6, available from Arm Systex Co., Ltd.), and the inhibition constant (Ki value) was obtained by the following formula. The dissociation constant (Kd value) was calculated by Scatchard analysis.

$Ki=IC_{50}/(1+([^3H]PGE_2 \text{ concentration}/Kd))$

2) Measurement of EP4 Receptor Binding Affinity

Measurement of EP4 receptor binding affinity was carried out according to the method described in the data sheet of Millipore Corp. The test compound dissolved in dimethylsulfoxide and $[^3H]PGE_2$ (NET-428, available from PerkinElmer Inc.) (final concentration: 1 nM) were added to a buffer solution (50 mM HEPES-NaOH (pH 7.4), 5 mM $MgCl_2$, 1 mM $CaCl_2$, 0.2% BSA) in which 20 μg of a membrane fraction (HTS142M, available from Millipore Corp.) of Chem-1 cells expressing human EP4 receptor had been suspended, followed by incubation at 30° C. for 60 minutes. The membrane fraction was recovered on glass fiber filter paper (GF/B, available from Whatman PLC) pretreated with 0.3% polyethyleneimine by using a cell harvester (M30R, available from Brandel Inc.), and after washing with a buffer solution (50 mM HEPES-NaOH (pH 7.4), 500 mM NaCl, 0.1% BSA), radioactivity was measured with a liquid scintillation analyzer (2000CA, available from Packard). A concentration ($IC_{50}$ value) of the test compound necessary for substituting 50% of the $[^3H]PGE_2$ bound to the receptor was calculated by using EXSAS (version 7.1.6, available from Arm Systex Co., Ltd.), and the inhibition constant (Ki value) was obtained by the following formula. The dissociation constant (Kd value) was calculated by Scatchard analysis.

$Ki=IC_{50}/(1+([^3H]PGE_2 \text{ concentration}/Kd))$

3) PGE2 Receptor Selectivity

From the receptor binding affinity measurement test of 1) and 2) in [Test example 1] and [Test example 3], PGE2 receptor selectivities of the representative compounds of the present invention except EP1 are shown in Table 4. Incidentally, as a comparative control, $PGE_2$ which is an endogeneous ligand was used.

TABLE 4

| Test compound Example No. | EP2 receptor binding affinity Ki value (nM) | EP3 receptor binding affinity Ki value (nM) | EP4 receptor binding affinity Ki value (nM) |
|---|---|---|---|
| Example 3 | 1.9 | >10000 | 4800 |
| Example 4 | 2.8 | >10000 | 2900 |
| Example 11 | 3.8 | >10000 | 2800 |
| $PGE_2$ | 7.1 | 2.8 | 1.4 |

The compounds of the present invention have weak binding affinity to EP3 and EP4 receptors as compared with $PGE_2$ and showed selective EP2 agonist activity.

Representative Preparation examples to be used in the present invention are shown below.

Preparation Example 1

Ophthalmic Solutions

To sterile purified water were added 2.5 g of conc. glycerin and 200 mg of polysorbate 80, then, 10 mg of the compound of Example 6 was added to the mixture to dissolve the compound, and the total amount was made 100 mL with sterile purified water, passing through a membrane filter for sterilization, then, filled in a predetermined container to prepare an ophthalmic solution.

In the same manner as in Preparation example 1, ophthalmic solutions, etc., containing 5 mg, 25 mg or 100 mg of the compound of Example 6 in 100 mL of the solution can be prepared. Also, in place of the compound of Example 6, other EP2 agonists of the present invention can be used.

UTILIZABILITY IN INDUSTRY

The pyridylaminoacetic acid compound represented by the formula (1) which is an effective ingredient of a medical composition of the present invention or a pharmaceutically acceptable salt thereof has an ocular hypotensive effect due to high EP2 receptor selectivity and potent EP2 agonistic action, and further, has excellent properties in terms of tissue distribution, fast-acting pharmacological effect, sustained pharmacological effect, toxicity, etc., so that it is effective for glaucoma. Accordingly, a medical composition containing the pyridylaminoacetic acid compound represented by the formula (1) of the present invention or a pharmaceutically acceptable salt thereof as an effective ingredient is useful as a medicine for the treatment and/or prophylaxis of glaucoma.

The invention claimed is:
1. A medical composition for treatment or prophylaxis of glaucoma which comprises pyridylaminoacetic acid compound represented by the formula (1):

[Formula 1]

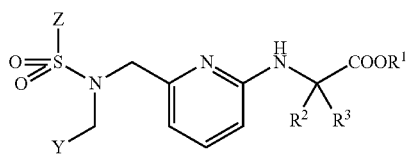

(1)

wherein $R^1$, $R^2$ and $R^3$ each independently represent a hydrogen atom or a $C_1$-$C_6$ alkyl group,
Y represents a bicyclic heteroaromatic ring group or group -$Q^1$-$Q^2$ each of which may be substituted by a group(s) selected from the group consisting of a halogen atom, $C_1$-$C_6$ alkyl group, halogeno $C_1$-$C_6$ alkyl group, $C_1$-$C_6$ alkoxyl group, halogeno $C_1$-$C_6$ alkoxyl group and $C_1$-$C_6$ alkylthio group,
wherein $Q^1$ represents an arylene group or a 5- to 6-membered heteroarylene group, $Q^2$ represents an aromatic group or 5- to 6-membered ring heterocyclic group each of which may be substituted by a group(s) selected from the group consisting of a halogen atom, hydroxyl group, $C_1$-$C_6$ alkyl group, halogeno $C_1$-$C_6$ alkyl group, $C_1$-$C_6$ alkoxyl group and halogeno $C_1$-$C_6$ alkoxyl group,
Z represents an aromatic group or a 5- to 6-membered heteroaromatic ring group each of which may be substituted by a group(s) selected from the group consisting of a halogen atom, $C_1$-$C_6$ alkyl group, halogeno $C_1$-$C_6$ alkyl group, $C_1$-$C_6$ alkoxyl group and halogeno $C_1$-$C_6$ alkoxyl group,
or a pharmaceutically acceptable salt thereof as an effective ingredient, and a pharmaceutically acceptable carrier therefor.
2. The medical composition according to claim 1, wherein $R^2$ and $R^3$ each independently represent a hydrogen atom or a $C_1$-$C_4$ alkyl group.
3. The medical composition according to claim 1 or 2, wherein Y represents a bicyclic heteroaromatic ring group or a group -$Q^1$-$Q^2$ each of which may be substituted by a group(s) selected from the group consisting of a halogen atom, $C_1$-$C_4$ alkyl group, halogeno $C_1$-$C_4$ alkyl group, $C_1$-$C_4$ alkoxyl group, halogeno $C_1$-$C_4$ alkoxyl group and $C_1$-$C_4$ alkylthio group,
wherein $Q^1$ represents an arylene group or a 5- to 6-membered heteroarylene group, $Q^2$ represents an aromatic group or a 5- to 6-membered ring heterocyclic group each of which may be substituted by a group(s) selected from the group consisting of a halogen atom, hydroxyl group, $C_1$-$C_4$ alkyl group, halogeno $C_1$-$C_4$ alkyl group, $C_1$-$C_4$ alkoxyl group and halogeno $C_1$-$C_4$ alkoxyl group.
4. The medical composition according to claim 1, wherein Z represents an aromatic group or a completely unsaturated 5- to 6-membered heteroaromatic ring group each of which may be substituted by a group(s) selected from the group consisting of a halogen atom, $C_1$-$C_4$ alkyl group, halogeno $C_1$-$C_4$ alkyl group, $C_1$-$C_4$ alkoxyl group and halogeno alkoxyl group.
5. The medical composition according to claim 1, wherein Y represents a benzofuryl group, benzothienyl group, benzoxazolyl group or benzothiazolyl group, or group -$Q^1$-$Q^2$ each of which may be substituted by a group(s) selected from the group consisting of a halogen atom, $C_1$-$C_4$ alkyl group, halogeno $C_1$-$C_4$ alkyl group, $C_1$-$C_4$ alkoxyl group, halogeno $C_1$-$C_4$ alkoxyl group and $C_1$-$C_4$ alkylthio group,
wherein $Q^1$ represents a phenylene group, thienylene group, pyridazinylene group or pyrimidinylene group, $Q^2$ represents a phenyl group, thienyl group, pyrazolyl group, oxazolyl group, thiazolyl group, 1,2,4-triazolyl group, pyridyl group, pyridazinyl group, pyrimidinyl group, 4,5-dihydrothiazolyl group, pyrrolidinyl group or piperidinyl group which may be substituted by a group(s) selected from the group consisting of a halogen atom, hydroxyl group, $C_1$-$C_4$ alkyl group, halogeno $C_1$-$C_4$ alkyl group, $C_1$-$C_4$ alkoxyl group and halogeno alkoxyl group.
6. The medical composition according to claim 5, wherein Y represents a benzofuryl group, benzothienyl group, benzoxazolyl group or benzothiazolyl group each of which may be substituted by a group(s) selected from the group consisting of a fluorine atom, chlorine atom, bromine atom, methyl group, ethyl group, propyl group, isopropyl group, tert-butyl group, trifluoromethyl group, difluoromethyl group, trichloromethyl group, dichloromethyl group, 2,2,2-trifluoroethyl group, 2,2,2-trichloroethyl group, methoxy group, ethoxy group, propoxy group, isopropoxy group, tert-butoxy group, trifluoromethoxy group, difluoromethoxy group, trichloromethoxy group, dichloromethoxy group, methylthio group, ethylthio group, propylthio group, isopropylthio group and tert-butylthio group.
7. The medical composition according to claim 5, wherein Y is a group -$Q^1$-$Q^2$
wherein $Q^1$ represents a phenylene group, thienylene group, pyridazinylene group or pyrimidinylene group, $Q^2$ represents a phenyl group, thienyl group, pyrazolyl group, oxazolyl group, thiazolyl group, 1,2,4-triazolyl group, pyridyl group, pyridazinyl group, pyrimidinyl group, 4,5-dihydrothiazolyl group, pyrrolidinyl group or piperidinyl group each of which may be substituted by a group(s) selected from the group consisting of a fluorine atom, chlorine atom, bromine atom, hydroxyl group, methyl group, ethyl group, propyl group, isopropyl group, tert-butyl group, trifluoromethyl group, difluoromethyl group, trichloromethyl group, dichloromethyl group, 2,2,2-trifluoroethyl group, 2,2,2-trichloroethyl group, methoxy group, ethoxy group, propoxy group, isopropoxy group, tert-butoxy group, trifluoromethoxy group, difluoromethoxy group, trichloromethoxy group and dichloromethoxy group.

8. The medical composition according to claim 1, wherein Z represents a phenyl group, thienyl group, imidazolyl group, thiazolyl group, pyridyl group or pyrimidinyl group each of which may be substituted by a group(s) selected from the group consisting of a halogen atom, $C_1$-$C_4$ alkyl group, halogeno $C_1$-$C_4$ alkyl group, $C_1$-$C_4$ alkoxyl group and halogeno $C_1$-$C_4$ alkoxyl group.

9. The medical composition according to claim 8, wherein Z represents a phenyl group, thienyl group, imidazolyl group, thiazolyl group, pyridyl group or pyrimidinyl group each of which may be substituted by a group(s) selected from the group consisting of a fluorine atom, chlorine atom, bromine atom, methyl group, ethyl group, propyl group, isopropyl group, tert-butyl group, trifluoromethyl group, difluoromethyl group, trichloromethyl group, dichloromethyl group, 2,2,2-trifluoroethyl group, 2,2,2-trichloroethyl group, methoxy group, ethoxy group, propoxy group, isopropoxy group, tert-butoxy group, trifluoromethoxy group, difluoromethoxy group, trichloromethoxy group and dichloromethoxy group.

10. The medical composition according to claim 1, wherein $R^2$ and $R^3$ each independently represent a hydrogen atom or a methyl group.

11. The medical composition according to claim 1, wherein Y represents a benzofuryl group or benzothienyl group each of which may be substituted by a group(s) selected from the group consisting of a halogen atom and a $C_1$-$C_4$ alkoxyl group.

12. The medical composition according to claim 1, wherein Y represents a group -$Q^1$-$Q^2$
wherein $Q^1$ represents a phenylene group or pyridazinylene group, $Q^2$ represents a phenyl group, pyrazolyl group, thiazolyl group, 1,2,4-triazolyl group, pyridyl group, pyridazinyl group, pyrimidinyl group or 4,5-dihydrothiazolyl group each of which may be substituted by a group(s) selected from the group consisting of a halogen atom, $C_1$-$C_4$ alkyl group and halogeno $C_1$-$C_4$ alkyl group.

13. The medical composition according to claim 1, wherein Z represents a phenyl group or pyridyl group each of which may be substituted by a group(s) selected from the group consisting of a halogen atom and a $C_1$-$C_4$ alkoxyl group.

14. The medical composition according to claim 1, wherein $R^1$ represents a hydrogen atom, methyl group, ethyl group, propyl group, isopropyl group, butyl group, isobutyl group, sec-butyl group, tert-butyl group, pentyl group or hexyl group,
$R^2$ and $R^3$ each independently represent a hydrogen atom or methyl group,
Y represents a benzofuran-2-yl group, 6-fluorobenzofuran-2-yl group, 6-chlorobenzofuran-2-yl group, 6-methoxybenzofuran-2-yl group, benzo[b]thiophen-2-yl group, 6-fluorobenzo[b]thiophen-2-yl group, 5,6-difluorobenzo[b]thiophen-2-yl group, 6-chlorobenzo[b]thiophen-2-yl group, 6-chloro-5-fluorobenzo[b]thiophen-2-yl group, 6-methylbenzo[b]thiophen-2-yl group, 5-fluoro-6-methylbenzo[b]thiophen-2-yl group, 6-ethylbenzo[b]thiophen-2-yl group, 6-ethyl-5-fluorobenzo[b]thiophen-2-yl group, 6-trifluoromethylbenzo[b]thiophen-2-yl group, 5-fluoro-6-trifluoromethylbenzo[b]thiophen-2-yl group, 6-methoxybenzo[b]thiophen-2-yl group, 5-fluoro-6-methoxybenzo[b]thiophen-2-yl group, 6-difluoromethoxybenzo[b]thiophen-2-yl group, 6-difluoromethoxy-5-fluorobenzo[b]thiophen-2-yl group, 6-methylthiobenzo[b]thiophen-2-yl group, 5-fluoro-6-methylthiobenzo[b]thiophen-2-yl group, biphenyl-4-yl group, 2'-fluorobiphenyl-4-yl group, 3'-fluorobiphenyl-4-yl group, 4'-fluorobiphenyl-4-yl group, 2',4'-difluorobiphenyl-4-yl group, 3',4'-difluorobiphenyl-4-yl group, 2'-chlorobiphenyl-4-yl group, 3'-chlorobiphenyl-4-yl group, 4'-chlorobiphenyl-4-yl group, 4'-chloro-2'-fluorobiphenyl-4-yl group, 4'-chloro-3'-fluorobiphenyl-4-yl group, 4'-hydroxybiphenyl-4-yl group, 3'-methylbiphenyl-4-yl group, 3'-ethylbiphenyl-4-yl group, 3'-trifluoromethylbiphenyl-4-yl group, 3'-methoxybiphenyl-4-yl group, 3'-difluoromethoxybiphenyl-4-yl group, 4-(thiophen-2-yl)phenyl group, 4-(thiophen-3-yl)phenyl group, 4-(pyrazol-1-yl)phenyl group, 4-(oxazol-2-yl)phenyl group, 4-(oxazol-4-yl)phenyl group, 4-(thiazol-2-yl)phenyl group, 4-(4-fluorothiazol-2-yl)phenyl group, 4-(4-chlorothiazol-2-yl)phenyl group, 4-(5-chlorothiazol-2-yl)phenyl group, 4-(5-methylthiazol-2-yl)phenyl group, 4-(4,5-dimethylthiazol-2-yl)phenyl group, 4-(4-trifluoromethylthiazol-2-yl)phenyl group, 4-(thiazol-4-yl)phenyl group, 4-(2-fluorothiazol-4-yl)phenyl group, 4-(2-chlorothiazol-4-yl)phenyl group, 4-(thiazol-5-yl)phenyl group, 4-(1,2,4-triazol-1-yl)phenyl group, 4-(pyridin-2-yl)phenyl group, 4-(pyridazin-3-yl)phenyl group, 4-(pyridazin-4-yl)phenyl group, 4-(pyrimidin-2-yl)phenyl group, 4-(5-hydroxypyrimidin-2-yl)phenyl group, 4-(pyrimidin-4-yl)phenyl group, 4-(pyrimidin-5-yl)phenyl group, 4-(4,5-dihydrothiazol-2-yl)phenyl group, 6-phenylpyridazin-3-yl group, 6-(thiazol-2-yl)pyridazin-3-yl group or 6-(thiazol-4-yl)pyridazin-3-yl group, and
Z represents a phenyl group, 2-fluorophenyl group, 3-fluorophenyl group, 4-fluorophenyl group, 3,4-difluorophenyl group, 3,5-difluorophenyl group, 3,4,5-trifluorophenyl group, 2-chlorophenyl group, 3-chlorophenyl group, 4-chlorophenyl group, 2,6-dichlorophenyl group, 4-chloro-3-fluorophenyl group, 4-chloro-3,5-difluorophenyl group, 4-bromophenyl group, 4-methylphenyl group, 3-fluoro-4-methylphenyl group, 4-ethylphenyl group, 4-ethyl-3-fluorophenyl group, 4-propylphenyl group, 4-isopropylphenyl group, 4-tert-butylphenyl group, 4-trifluoromethylphenyl group, 3-fluoro-4-trifluoromethylphenyl group, 4-difluoromethylphenyl group, 4-trichloromethylphenyl group, 4-dichloromethylphenyl group, 4-(2,2,2-trifluoroethyl)phenyl group, 4-(2,2,2-trichloroethyl)phenyl group, 4-methoxyphenyl group, 3-fluoro-4-methoxyphenyl group, 4-ethoxyphenyl group, 4-propoxyphenyl group, 4-isopropoxyphenyl group, 4-tert-butoxyphenyl group, 4-trifluoromethoxyphenyl group, 4-difluoromethoxyphenyl group, 4-difluoromethoxy-3-fluorophenyl group, 4-trichloromethoxyphenyl group, 4-dichloromethoxyphenyl group, thiophen-2-yl group, thiophen-3-yl group, 5-chloro thiophen-2-yl group, 1-methyl-1H-imidazol-4-yl group, thiazol-2-yl group, pyridin-2-yl group, 5-fluoropyridin-2-yl group, 5-chloropyridin-2-yl group, 5-methylpyridin-2-yl group, 5-ethylpyridin-2-yl group, 5-trifluoromethylpyridin-2-yl group, 5-methoxypyridin-2-yl group, 5-difluoromethoxypyridin-2-yl group, pyridin-3-yl group, 6-fluoropyridin-3-yl group, 6-chloropyridin-3-yl group, 6-methylpyridin-3-yl group, 6-ethylpyridin-3-yl group, 6-trifluoromethylpyridin-3-yl group, 6-methoxypyridin-3-yl group, 6-difluoromethoxypyridin-3-yl group, pyridin-4-yl group or pyrimidin-2-yl group.

15. The medical composition according to claim 1, wherein R¹ represents a hydrogen atom, methyl group, ethyl group, propyl group, isopropyl group, tert-butyl group or hexyl group, R² and R³ each independently represent a hydrogen atom or methyl group, Y represents a benzofuran-2-yl group, 6-fluorobenzofuran-2-yl group, 6-chlorobenzofuran-2-yl group, 6-methoxybenzofuran-2-yl group, benzo[b]thiophen-2-yl group, 6-fluorobenzo[b]thiophen-2-yl group, 6-chlorobenzo[b]thiophen-2-yl group, 6-methoxybenzo[b]thiophen-2-yl group, biphenyl-4-yl group, 2'-fluorobiphenyl-4-yl group, 3'-fluorobiphenyl-4-yl group, 4'-fluorobiphenyl-4-yl group, 2'-chlorobiphenyl-4-yl group, 3'-chlorobiphenyl-4-yl group, 4'-chlorobiphenyl-4-yl group, 3'-methylbiphenyl-4-yl group, 3'-trifluoromethylbiphenyl-4-yl group, 4-(thiophen-2-yl)phenyl group, 4-(thiophen-3-yl)phenyl group, 4-(pyrazol-1-yl)phenyl group, 4-(oxazol-2-yl)phenyl group, 4-(oxazol-4-yl)phenyl group, 4-(thiazol-2-yl)phenyl group, 4-(4-fluorothiazol-2-yl)phenyl group, 4-(4-chlorothiazol-2-yl)phenyl group, 4-(5-chlorothiazol-2-yl)phenyl group, 4-(5-methylthiazol-2-yl)phenyl group, 4-(4,5-dimethylthiazol-2-yl)phenyl group, 4-(4-trifluoromethylthiazol-2-yl)phenyl group, 4-(thiazol-4-yl)phenyl group, 4-(2-fluorothiazol-4-yl)phenyl group, 4-(2-chlorothiazol-4-yl)phenyl group, 4-(thiazol-5-yl)phenyl group, 4-(1,2,4-triazol-1-yl)phenyl group, 4-(pyridin-2-yl)phenyl group, 4-(pyridazin-3-yl)phenyl group, 4-(pyridazin-4-yl)phenyl group, 4-(pyrimidin-2-yl)phenyl group, 4-(pyrimidin-4-yl)phenyl group, 4-(pyrimidin-5-yl)phenyl group, 4-(4,5-dihydrothiazol-2-yl)phenyl group or 6-phenylpyridazin-3-yl group, and Z represents a phenyl group, 2-fluorophenyl group, 3-fluorophenyl group, 4-fluorophenyl group, 3,4-difluorophenyl group, 3,5-difluorophenyl group, 2-chlorophenyl group, 3-chlorophenyl group, 4-chlorophenyl group, 2,6-dichlorophenyl group, 4-chloro-3-fluorophenyl group, 4-methylphenyl group, 3-fluoro-4-methylphenyl group, 4-ethylphenyl group, 4-ethyl-3-fluorophenyl group, 4-trifluoromethylphenyl group, 3-fluoro-4-trifluoromethylphenyl group, 4-methoxyphenyl group, 3-fluoro-4-methoxyphenyl group, 4-difluoromethoxyphenyl group, 4-difluoromethoxy-3-fluorophenyl group, thiophen-2-yl group, thiophen-3-yl group, pyridin-2-yl group, 5-fluoropyridin-2-yl group, 5-chloropyridin-2-yl group, 5-methoxypyridin-2-yl group, pyridin-3-yl group, 6-fluoropyridin-3-yl group, 6-chloropyridin-3-yl group, 6-methoxypyridin-3-yl group or pyridin-4-yl group.

16. The medical composition according to claim 1, wherein R¹ represents a hydrogen atom, methyl group, ethyl group, isopropyl group or hexyl group, R² and R³ each represent a hydrogen atom, Y represents a benzofuran-2-yl group, 6-fluorobenzofuran-2-yl group, 6-chlorobenzofuran-2-yl group, 6-methoxybenzofuran-2-yl group, benzo[b]thiophen-2-yl group, 6-fluorobenzo[b]thiophen-2-yl group, 6-chlorobenzo[b]thiophen-2-yl group, 6-methoxybenzo[b]thiophen-2-yl group, biphenyl-4-yl group, 2'-fluorobiphenyl-4-yl group, 3'-fluorobiphenyl-4-yl group, 4'-fluorobiphenyl-4-yl group, 2'-chlorobiphenyl-4-yl group, 3'-chlorobiphenyl-4-yl group, 4'-chlorobiphenyl-4-yl group, 3'-methylbiphenyl-4-yl group, 3'-trifluoromethylbiphenyl-4-yl group, 4-(thiophen-2-yl)phenyl group, 4-(thiophen-3-yl)phenyl group, 4-(pyrazol-1-yl)phenyl group, 4-(oxazol-2-yl)phenyl group, 4-(oxazol-4-yl)phenyl group, 4-(thiazol-2-yl)phenyl group, 4-(4-fluorothiazol-2-yl)phenyl group, 4-(4-chlorothiazol-2-yl)phenyl group, 4-(5-chlorothiazol-2-yl)phenyl group, 4-(5-methylthiazol-2-yl)phenyl group, 4-(4,5-dimethylthiazol-2-yl)phenyl group, 4-(4-trifluoromethylthiazol-2-yl)phenyl group, 4-(thiazol-4-yl)phenyl group, 4-(2-fluorothiazol-4-yl)phenyl group, 4-(2-chlorothiazol-4-yl)phenyl group, 4-(thiazol-5-yl)phenyl group, 4-(1,2,4-triazol-1-yl)phenyl group, 4-(pyridin-2-yl)phenyl group, 4-(pyridazin-3-yl)phenyl group, 4-(pyridazin-4-yl)phenyl group, 4-(pyrimidin-2-yl)phenyl group, 4-(pyrimidin-4-yl)phenyl group, 4-(pyrimidin-5-yl)phenyl group, 4-(4,5-dihydrothiazol-2-yl)phenyl group or 6-phenylpyridazin-3-yl group, and Z represents a phenyl group, 2-fluorophenyl group, 3-fluorophenyl group, 4-fluorophenyl group, 2-chlorophenyl group, 3-chlorophenyl group, 4-chlorophenyl group, 2,6-dichlorophenyl group, 4-methoxyphenyl group, pyridin-2-yl group or pyridin-3-yl group.

17. The medical composition according to claim 1, wherein R¹ represents a hydrogen atom, methyl group, ethyl group, isopropyl group or hexyl group, R² and R³ each represent a hydrogen atom, Y represents a benzofuran-2-yl group, benzo[b]thiophen-2-yl group, 6-chlorobenzo-[b]thiophen-2-yl group, 6-methoxybenzo[b]thiophen-2-yl group, biphenyl-4-yl group, 4'-fluorobiphenyl-4-yl group, 4'-chlorobiphenyl-4-yl group, 4-(pyrazol-1-yl)phenyl group, 4-(thiazol-2-yl)phenyl group, 4-(5-chlorothiazol-2-yl)phenyl group, 4-(5-methylthiazol-2-yl)phenyl group, 4-(4,5-dimethylthiazol-2-yl)phenyl group, 4-(4-trifluoromethylthiazol-2-yl)phenyl group, 4-(thiazol-4-yl)phenyl group, 4-(1,2,4-triazol-1-yl)phenyl group, 4-(pyridin-2-yl)phenyl group, 4-(pyridazin-4-yl)phenyl group, 4-(pyrimidin-2-yl)phenyl group, 4-(4,5-dihydrothiazol-2-yl)phenyl group or 6-phenylpyridazin-3-yl group, and Z represents a phenyl group, 2-fluorophenyl group, 3-fluorophenyl group, 4-fluorophenyl group, 2-chlorophenyl group, 3-chlorophenyl group, 4-chlorophenyl group, 2,6-dichlorophenyl group, 4-methoxyphenyl group, pyridin-2-yl group or pyridin-3-yl group.

18. The medical composition according to claim 1, wherein the pyridylaminoacetic acid compound is
{6-[(benzofuran-2-ylmethyl)(pyridin-3-ylsulfonyl)aminomethyl]pyridin-2-ylamino}-acetic acid,
{6-[(benzo[b]thiophen-2-ylmethyl)(pyridin-3-ylsulfonyl)aminomethyl]pyridin-2-ylamino}acetic acid,
{6-[(6-chlorobenzo[b]thiophen-2-ylmethyl)(pyridin-3-ylsulfonyl)aminomethyl]pyridin-2-ylamino}acetic acid,
{6-[(6-methoxybenzo[b]thiophen-2-ylmethyl)(pyridin-3-ylsulfonyl)aminomethyl]-pyridin-2-ylamino}acetic acid,
{6-[(biphenyl-4-ylmethyl)(pyridin-2-ylsulfonyl)aminomethyl]pyridin-2-ylamino}acetic acid,
{6-[(biphenyl-4-ylmethyl)(pyridin-3-ylsulfonyl)aminomethyl]pyridin-2-ylamino}acetic acid,
{6-[(4'-fluorobiphenyl-4-ylmethyl)(pyridin-3-ylsulfonyl)aminomethyl]pyridin-2-ylamino}acetic acid,
{6-[(4'-chlorobiphenyl-4-ylmethyl)(pyridin-3-ylsulfonyl)aminomethyl]pyridin-2-ylamino}acetic acid,
(6-{(4-fluorobenzenesulfonyl)[4-(pyrazol-1-yl)benzyl]aminomethyl}pyridin-2-ylamino)acetic acid,
(6-{[4-(pyrazol-1-yl)benzyl](pyridin-2-ylsulfonyl)aminomethyl}pyridin-2-ylamino)acetic acid,
(6-{[4-(pyrazol-1-yl)benzyl](pyridin-3-ylsulfonyl)aminomethyl}pyridin-2-ylamino)acetic acid, isopropyl(6-{(pyridin-2-ylsulfonyl)[4-(thiazol-2-yl)benzyl]aminomethyl}pyridin-2-ylamino)acetate,
ethyl(6-{(pyridin-2-ylsulfonyl)[4-(thiazol-2-yl)benzyl]aminomethyl}pyridin-2-ylamino)acetate,
(6-{(4-fluorobenzenesulfonyl)[4-(thiazol-2-yl)benzyl]aminomethyl}pyridin-2-ylamino)acetic acid,
(6-{(pyridin-2-ylsulfonyl)[4-(thiazol-2-yl)benzyl]aminomethyl}pyridin-2-ylamino)acetic acid,
(6-{(pyridin-3-ylsulfonyl)[4-(thiazol-2-yl)benzyl]aminomethyl}pyridin-2-ylamino)acetic acid,
(6-{(pyridin-2-ylsulfonyl)[4-(4-trifluoromethylthiazol-2-yl)benzyl]aminomethyl}pyridin-2-ylamino)acetic acid,
(6-{(pyridin-2-ylsulfonyl)[4-(thiazol-4-yl)benzyl]aminomethyl}pyridin-2-ylamino)acetic acid,
(6-{[4-(pyridin-2-yl)benzyl](pyridin-3-ylsulfonyl)aminomethyl}pyridin-2-ylamino)acetic acid,
(6-{[4-(pyridazin-4-yl)benzyl](pyridin-3-ylsulfonyl)aminomethyl}pyridin-2-ylamino)-acetic acid,
(6-{(pyridin-2-ylsulfonyl)[4-(pyrimidin-2-yl)benzyl]aminomethyl}pyridin-2-ylamino)-acetic acid,
(6-{[4-(4,5-dihydrothiazol-2-yl)benzyl](4-fluorobenzenesulfonyl)aminomethyl}pyridin-2-ylamino)acetic acid,
{6-[(6-phenylpyridazin-3-ylmethyl)(pyridin-3-ylsulfonyl)aminomethyl]pyridin-2-ylamino}acetic acid,
hexyl(6-{(pyridin-2-ylsulfonyl)[4-(thiazol-2-yl)benzyl]aminomethyl}pyridin-2-ylamino)acetate,
(6-{[4-(5-chlorothiazol-2-yl)benzyl](pyridin-2-ylsulfonyl)aminomethyl}pyridin-2-ylamino)acetic acid,
(6-{[4-(5-methylthiazol-2-yl)benzyl](pyridin-2-ylsulfonyl)aminomethyl}pyridin-2-ylamino)acetic acid,
(6-{[4-(4,5-dimethylthiazol-2-yl)benzyl](pyridin-2-ylsulfonyl)aminomethyl}pyridin-2-ylamino)acetic acid,
(6-{(pyridin-3-ylsulfonyl)[4-(1,2,4-triazol-1-yl)benzyl]aminomethyl}pyridin-2-ylamino)acetic acid,
(6-{[4-(pyrazol-1-yl)benzyl](pyridin-3-ylsulfonyl)aminomethyl}pyridin-2-ylamino)ethyl acetate or
(6-{[4-(pyrazol-1-yl)benzyl](pyridin-3-ylsulfonyl)aminomethyl}pyridin-2-ylamino)-isopropyl acetate.

\* \* \* \* \*